US009539300B2

(12) United States Patent
Fogelman et al.

(10) Patent No.: US 9,539,300 B2
(45) Date of Patent: Jan. 10, 2017

(54) MODULATING DISEASE THROUGH GENETIC ENGINEERING OF PLANTS

(71) Applicant: The Regents of the University of California, Oakland, CA (US)

(72) Inventors: Alan M. Fogelman, Los Angeles, CA (US); Srinivasa T. Reddy, Cerritos, CA (US); Mohamad Navab, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 828 days.

(21) Appl. No.: 13/789,513

(22) Filed: Mar. 7, 2013

(65) Prior Publication Data

US 2013/0344173 A1   Dec. 26, 2013

Related U.S. Application Data

(60) Provisional application No. 61/618,753, filed on Mar. 31, 2012, provisional application No. 61/716,322, filed on Oct. 19, 2012.

(51) Int. Cl.
| | |
|---|---|
| *A61K 38/10* | (2006.01) |
| *C12N 15/63* | (2006.01) |
| *C07K 14/775* | (2006.01) |
| *A61K 36/81* | (2006.01) |
| *C12N 15/82* | (2006.01) |

(52) U.S. Cl.
CPC ............... *A61K 38/10* (2013.01); *A23K 10/30* (2016.05); *A23L 19/00* (2016.08); *A23L 33/10* (2016.08); *A23L 33/185* (2016.08); *A61K 36/81* (2013.01); *C07K 14/775* (2013.01); *C12N 15/8247* (2013.01); *C12N 15/8257* (2013.01)

(58) Field of Classification Search
None
See application file for complete search history.

(56) References Cited

U.S. PATENT DOCUMENTS

| | | | |
|---|---|---|---|
| 6,118,049 A * | 9/2000 | Bestwick ........... | C12N 15/8222 435/320.1 |
| 6,664,230 B1 | 12/2003 | Fogelman et al. | |
| 6,930,085 B2 | 8/2005 | Fogelman et al. | |
| 6,933,279 B2 | 8/2005 | Fogelman et al. | |
| 7,144,862 B2 | 12/2006 | Fogelman et al. | |
| 7,148,197 B2 | 12/2006 | Fogelman et al. | |
| 7,166,578 B2 | 1/2007 | Fogelman et al. | |
| 7,199,102 B2 | 4/2007 | Fogelman et al. | |
| 7,531,514 B2 | 5/2009 | Fogelman et al. | |
| 7,579,319 B2 | 8/2009 | Fogelman | |
| 7,638,494 B2 | 12/2009 | Fogelman et al. | |
| 7,723,303 B2 | 5/2010 | Fogelman et al. | |
| 7,786,352 B2 * | 8/2010 | Moloney ........... | C12N 15/8257 800/287 |
| 7,807,640 B2 | 10/2010 | Fogelman et al. | |
| 7,820,784 B2 | 10/2010 | Fogelman et al. | |
| 7,994,132 B2 | 8/2011 | Fogelman et al. | |
| 8,048,851 B2 | 11/2011 | Fogelman et al. | |
| 8,084,423 B2 | 12/2011 | Anantharamiah et al. | |
| 8,236,754 B2 | 8/2012 | Fogelman | |
| 8,404,635 B2 | 3/2013 | Fogelman et al. | |
| 2003/0045460 A1 | 3/2003 | Fogelman et al. | |
| 2003/0171277 A1 | 9/2003 | Fogelman et al. | |
| 2003/0191057 A1 | 10/2003 | Fogelman et al. | |
| 2003/0229015 A1 | 12/2003 | Fogelman et al. | |
| 2004/0254120 A1 | 12/2004 | Fogelman et al. | |
| 2004/0266671 A1 | 12/2004 | Fogelman et al. | |
| 2005/0164950 A1 | 7/2005 | Fogelman et al. | |
| 2005/0172359 A1 | 8/2005 | Moloney et al. | |
| 2006/0205669 A1 | 9/2006 | Fogelman et al. | |
| 2006/0234908 A1 | 10/2006 | Fogelman et al. | |
| 2006/0258839 A1 | 11/2006 | Fogelman et al. | |
| 2007/0032430 A1 | 2/2007 | Fogelman et al. | |
| 2007/0060527 A1 | 3/2007 | Fogelman et al. | |
| 2007/0136896 A1 * | 6/2007 | Takaiwa ............ | A23L 1/10 800/288 |
| 2007/0254839 A1 | 11/2007 | Fogelman et al. | |
| 2008/0045459 A1 | 2/2008 | Fogelman et al. | |
| 2008/0095821 A1 | 4/2008 | Fogelman et al. | |
| 2008/0096814 A1 | 4/2008 | Fogelman et al. | |
| 2008/0096815 A1 | 4/2008 | Fogelman et al. | |

(Continued)

FOREIGN PATENT DOCUMENTS

| | | |
|---|---|---|
| WO | WO 02/15923 | 2/2002 |
| WO | WO 03/086326 | 10/2003 |

(Continued)

OTHER PUBLICATIONS

Navab et al (Arterioscler Thromb Vasc Biol,. 2005, 25: 1325-1331).*
Getz et al (Current Atherosclerosis Reports, Feb. 2010, 12(2):96-104).*
Poitou et al (Obes Surg., 2006, 16(11): 1475-1481).*
Su et al (PNAS, 2010, 107(46):19997-20002).*
U.S. Appl. No. 10/269,755, Oct. 11, 2002, Fogelman et al.
U.S. Appl. No. 11/541,481, Sep. 26, 2006, Fogelman et al.
U.S. Appl. No. 11/541,482, Sep. 26, 2006, Fogelman et al.
U.S. Appl. No. 11/541,494, Sep. 26, 2006, Fogelman et al.

(Continued)

*Primary Examiner* — John S Brusca
*Assistant Examiner* — Stephen Uyeno
(74) *Attorney, Agent, or Firm* — Tom Hunter; Weaver Austin Villeneuve & Sampson LLP

(57) ABSTRACT

In certain embodiments transgenic plants (e.g., transgenic tomatoes) are provided that comprise cells that express a peptide one or more domains of which comprise the amino acid sequence of an apolipoprotein or apolipoprotein mimetic peptide where the peptide has biological activity (e.g., lowers SAA, and/or increases paroxonase activity, and/or improves HDL inflammatory index, etc.) when the plant and/or the peptide is fed to a mammal.

22 Claims, 77 Drawing Sheets

(56) References Cited

U.S. PATENT DOCUMENTS

| | | |
|---|---|---|
| 2008/0096816 A1 | 4/2008 | Fogelman et al. |
| 2008/0293639 A1 | 11/2008 | Fogelman et al. |
| 2009/0286741 A1 | 11/2009 | Fogelman |
| 2010/0168006 A1 | 7/2010 | Fogher et al. |
| 2010/0227825 A1 | 9/2010 | Fogelman et al. |
| 2012/0004720 A1 | 1/2012 | Fogelman et al. |
| 2012/0035095 A1 | 2/2012 | Fogelman et al. |

FOREIGN PATENT DOCUMENTS

| | | |
|---|---|---|
| WO | WO 2004/034977 | 4/2004 |
| WO | WO 2004/043403 | 5/2004 |
| WO | WO 2005/016280 | 2/2005 |
| WO | WO 2006/034056 | 3/2006 |
| WO | WO 2006/063132 | 6/2006 |
| WO | WO 2006/118805 | 11/2006 |
| WO | WO 2008/017906 | 2/2008 |
| WO | WO 2009/073725 | 6/2009 |
| WO | WO 2011/159771 | 12/2011 |
| WO | WO 2013/148214 | 10/2013 |

OTHER PUBLICATIONS

PCT International Search Report dated Jan. 3, 2002 issued in PCT US01/26497 (WO 2002/015923).

PCT International Written Opinion dated May 20, 2002 issued in PCT US01/26497 (WO 2002/015923).

PCT International Preliminary Examination Report dated Oct. 25, 2002 issued in PCT/US01/26497 (WO 2002/015923).

PCT International Search Report dated Sep. 8, 2004 issued in PCT/US03/32442 (WO 2004/034977).

PCT International Search Report dated Oct. 21, 2003 issued in PCT/US2003/009988 (WO 2003/086326).

PCT International Search Report and Written Opinion dated Nov. 18, 2005 issued in PCT/US04/26288 (WO 2005/016280).

PCT International Preliminary Report on Patentability dated Mar. 29, 2006 issued in PCT/US04/26288 (WO 2005/016280).

PCT International Search Report dated Apr. 19, 2006 issued in PCT/US2005/033205 (WO 2006/034056).

PCT International Preliminary Report on Patentability and Written Opinion dated Mar. 20, 2007 issued in PCTUS2005/033205 (WO 2006/034056).

PCT International Search Report dated Jun. 21, 2006 issued in PCT/US2005/044422 (WO 2006/063132).

PCT International Preliminary Report on Patentability and Written Opinion dated Jun. 13, 2007 issued in PCT/US2005/044422 (WO 2006/063132).

PCT International Search Report dated Apr. 18, 2007 issued in PCT/US/2006/014839 (WO 2006/118805).

PCT International Preliminary Report on Patentability and Written Opinion dated Oct. 30, 2007 issued in PCT/US/2006/014839 (WO 2006/118805).

PCT International Search Report [Declaration of Non-Establishment of ISR] and Written Opinion dated Apr. 24, 2009 issued in PCT/US2008/085409 (WO 2009/073725).

PCT International Search Report and Written Opinion dated Aug. 21, 2013 issued in PCT/US2013/031037.

PCT International Preliminary Report on Patentability and Written Opinion dated Oct. 9, 2014 issued in PCT/US2013/031037.

Chebolu et al., (2009) "Chloroplast-Derived Vaccine Antigens and Biopharmaceuticals: Expression, Folding, Assembly and Functionality," *Curr Top Microbiol Immunol.*, 332:33-54.

Cheung et al., (2011) "Glucose lowering effect of transgenic human insulin-like growth factor-I from rice: in vitro and in vivo studies," *BMC Biotechnology*, 11:37, 10pp.

Chiaiese et al., (Jan. 2011) "Expression of human apolipoprotein A-I in *Nicotiana tabacum*," *Biotechnology Letters* 33(1):159-165.

Deng et al., (Dec. 2011) "Bcl-2 suppresess hydrogen peroxide-induced programmed cell death via *OsVPE2* and *OsVPE3* but not via *OsVPE1* and *OsVPE4*, in rice," *FEBS Journal*,278(24):4797-4810.

Desai et al., (Jul.-Aug. 2010) "Production of heterologous proteins in plants: Strategies for optimal expression," *Biotechnology Advances*, 28(4):427-435.

Dreesen et al., (2010) "Heat stable oral alga-vaccine protects mice from *Staphylococcus aureus* infection," *Journal of Biotechnology*, 145(3):273-280.

Elias-López et al., (Oct. 2008) "Transgenic tomato expressing interleukin-12 has a therapeutic effect in a murine model of progressive pulmonary tuberculosis," *Clinical and Experimental Immunology*, 154(1):123-133.

Fu et al., (2011) "High Levels of Expression of Fibroblast Growth Factor 21 in Transgenic Tobacco (*Nicotiana benthamiana*)," *Appl Biochem Biotechnol*, 165:465-475.

Gisby et al., (Jun. 2011) "A synthetic gene increases TGFβ3 accumulation by 75-fold in tobacco cholorplasts enabling rapid purification and folding into a biologically active molecule," *Plant Biotechnology Journal*, 9(5):618-628.

Gomord et al., (2004) "Postranslational modification of therapeutic proteins in plants," *Current Opinion in Plant Biology*, 7:171-181.

Gutiérrez-Ortega et al. (2005) "Expression of functional interleukin-12 from mouse in transgenic tomato plants," *Transgenic Research*, 14(6):877-885.

Kwon et al., (Jan. 2013) "Oral delivery of bioencapsulated exendin-4 expressed in chloroplasts lowers blood glucose level in mice and stimulates insulin secretion in beta-TC6 cells," *Plant Biotechnology Journal*,11(1):77-86.

Larrick et al., (Aug. 2001) "Producing proteins in transgenic plants and animals," *Current Opinion in Biotechnology*,12(4):411-418.

Luchakivskaya et al., (Mar. 2011) "High level expression of human interferon alpha-2b in transgenic carrot (*Daucus carota* L.) plants," *Plant Cell Rep.*,30(3):407-415.

Maruyama et al., (2011) "The development of transgenic crops to improve human health by advanced utilization of seed storage proteins," *Biosci. Biotechnol. Biochem.*, 75(5):823-828.

Medrano et al., (2009) "Rapid system for evaluating bioproduction capacity of complex pharmaceutical proteins in plants," *Methods in Molecular Biology*, 483:51-67.

Medrano et al., (2010) "Efficient plant-based production of chicken interleukin-12 yields a strong immunostimulatory cytokine," *J Interferon Cyokine Res.*, 30:143-154.

Morandini et al., (Oct. 2011) "Non-food/feed seeds as biofactories for the high-yield production of recombinant pharmaceuticals," *Plant Biotechnology Journal*, 9(8):911-921.

Nykiforuk et al., (2011) "Expression and recovery of biologically active recombinant Apolipoprotein $AI_{Milano}$ from transgenic safflower (Carthamus tinctorius) seeds" *Plant Biotechnology Journal*, 9(2):250-263.

Rojas-Anaya et al., (2009) "Expression of rabies virus G protein in carrots (*Daucus carota*)," *Transgenic Res.*, 18(6):911-919.

Sperb et al., (2011) "Molecular Cloning and Transgenic Expression of a Synthetic Human Erythropoietin Gene in Tobacco," *Appl Biochem Biotechnol*, 165(2):652-665.

Terakami et al., (2007) "Agrobacterium-mediated transformation of the dwarf pomegranate (*Punica granatum* L. var. nana)" *Plant Cell Rep* 26:1243-1251.

Tran et al., (Nov. 1, 2009) "Synthesis and assembly of a full-length human monoclonal antibody in algal chloroplasts," *Biotechnol Bioeng.*, 104(4):663-673.

Wally et al., (2009) "Broad-spectrum disease resistance to necrotrophic and biotrophic pathogens in transgenic carrots (*Daucus carota* L.) expressing an Arabidopsis $NPR_1$ gene," *Planta*, 231:131-141.

Yoshida et al., (2000) "Transgene expression systems in plant, a natural bioreactor," *Journal of Bioscience and Bioengineering*, 90(4):353-362.

Yoshida et al., (2011) "Transgenic Rice Expressing Amyloid β-peptide for Oral Immunization," *International Journal of Biological Sciences*, 7(3):301-307.

Zhang et al., (Feb. 2010) "Oral immunogenicity and protective efficacy in mice of a carrot-derived vaccine candidate expressing UreB subunit against Helicobacter pylori," *Protein Expression and Purification*, 69(2):127-131.

(56) References Cited

OTHER PUBLICATIONS

European Extended Search Report dated Dec. 17, 2015 issued in EP 13 769 821.3.

Chattopadhyay et al., (2015) "Efficacy of tomato concentrates in mouse models of dyslipidemia and cancer," *Pharmacology Research & Perspectives*, 3(4): e00154, 13 pp.

Chattopadhyay et al., (2016) "Tomatoes expressing the 6F Peptide Ameliorate the Increase in Oxidized Phospholipids in the Jejunum of Mice Fed Unsaturated Lysophosphatidylcholine or Western Diet," JLR 2015/064352 Revision #1, *Journal of Lipid Research*, [Retrieved on Mar. 11, 2016 at www.jlr.org at UCLA Biomedical Lib/Serials], 77 pp.

Navab et al., (2013) "Transgenic 6F tomatoes act on the small intestine to prevent systemic inflammation and dyslipidemia caused by Western diet and intestinally derived lysophosphatidic acid," *Journal of Lipid Research*, 54:3403-3418.

Navab et al., (2015) "Overcoming the high cost of production of chemically synthesized ApoA-I mimetic peptides," p. 20 In: *Apolipoprotein mimetics in the management of human disease*, Anantharamaiah and Goldberg, eds. Springer, 2015.

Navab et al., (2015) "Source and role of intestinally derived lysophosphatidic acid in dyslipidemia and atherosclerosis," *Journal of Lipid Research*, 56:871-887.

Navab et al., (2012) "High-Density Lipoprotein and 4F Peptide Reduce Systemic Inflammation by Modulating Intestinal Oxidized Lipid Metabolism: Novel Hypotheses and Review of Literature," *Arterioscler Thromb Vasc Biol.*,32(11):2553-2560 [NIH Public Access Author Manuscript, 16 pp].

Nykiforuk et al., (2011) "Expression and recovery of biologically active recombinant Apolipoprotein $A1_{Milano}$ from transgenic safflower (*Carthamus tinctorius*) seeds," *Plant Biotechnology Journal*, 9:250-263.

Reddy et al., (2014) "Searching for a successful HDL-based treatment strategy," *Biochimica et Biophysica Acta*, 1841:162-167.

Reddy et al., (Aug. 2014) "Apolipoprotein A-1 mimetics," *Current Opinion Lipidol*, 25(4):304-308.

Van Lenten et al., (2007) "Lipoprotein inflammatory properties and serum amyloid A levels but not cholesterol levels predict lesion area in cholesterol-fed rabbits," *Journal of Lipid Research*, 48:2344-2353.

\* cited by examiner

Plant Expression

Peptide (6F) DWLKAFYDKFFEKFKEFF

Codon usage for tomato   http://www.kazusa.or.jp/codon/
cgi-bin/showcodon.cgi?
species=4081

DNA(6F) after addition of signal peptide   (MIMASSKLLSLALFLALLSHANS)
*ALPHA-AI1-Phaseolus vulgaris*

TCTAGAATGATTATGGCTTCTTCTAAACTTCTTTCTCTTGCTCT
TTTTCTTGCTCTTCTTTCTCATGCTAATTCTGATGGCTTAAA
GCTTTTTATGATAAATTTTTTGAAAAATTTAAAGAATTTTTTT
GAGAGCTC

*Fig. 4*

Transformed Agrobacterium LBA4404 with 6F overexpression vector

*Agrobacterium tumefaciens* strain with
pBI121only and pBI121+6F

*Fig. 5*

```
tccctaatga tattgttcat gtaattaagt tttgtggaag tgagagagtc caattttga
aagaaaagag tcagaaaacg taatatttta aaagtctaaa tctttctaca aataagagca
aatttattta ttttttaatc caataaatat taatggagga caaattcaat tcactttggt
tgtaaaataa acttaaacca ataaccaaag aactaataaa tcctgaagtg gaattattaa
ggataaatgt acatagacga tgaagaaata ataggttcga tgaattaata ataattaagg
atgttacaat catcatgtgc caagtatata cacaatattc tatgggattt ataatttcgt
tacttcactt aacttttgcg taaataaaac gaattatctg atattttata ataaaacagt
taattaagaa ccatcatttt taacaacata gatatattat ttctaatagt ttaatgatac
ttttaaatct tttaaatttt atgtttcttt tagaaaataa aaattcaaaa aattaaatat
atttacaaaa actacaatca aacacaactt catatattaa aagcaaaata tattttgaaa
atttcaagtg tcctaacaaa taagacaaga ggaaaatgta cgatgagaga cataaagaga
actaataatt gaggagtcct ataatatata ataaagttta ttagtaaact taattattaa
ggactcctaa aatatatgat aggagaaaat gaatggtgag agatattgga aaacttaata
attaaggatt ttaaaatata tggtaaaaga taggcaaagt atccattatc ccctttttaac
ttgaagtcta ctaggcgcat gtgaaagttg attttttgtc acgtcatata gctataacgt
aaaaaaagaa agtaaaattt ttaatttttt ttaatatatg acatatttta aacgaaatat
aggacaaaat gtaaatgaat agtaaaggaa acaaagatta atacttactt tgtaagaatt
taagataaat ttaaaattta atagatcaac tttacgtcta gaaagaccca tatctagaag
gaatttcacg aaatcggccc ttattcgaaa ataacttttta aataatgaat tttaaatttt
aagaaataat atccaatgaa taaatgacat gtagcatttt acctaaatat ttcaactatt
ttaatccaat attaatttgt tttattccca acaatagaaa gtcttgtgca gacatttaat
ctgactttc cagtactaaa tattaatttt ctgaagattt tcgggtttag tccacaagtt
ttagtgagaa gttttgctca aattttaggt gagaaggttt gatatttatc ttttgttaaa
ttaatttatc taggtgacta ttatttattt aagtagaaat tcatatcatt acttttgcca
acttgtagtc ataataggag taggtgtata tgatgaagga ataaacaagt tcagtgaagt
gattaaaata aaatataatt taggtgtaca tcaaataaaa accttaaagt ttagaaaggc
accgaataat tttgcataga agatattagt aaatttataa aaataaaaga aatgtagttg
tcaagttgtc ttctttttt tggataaaaa tagcagttgg cttatgtcat tcttttacaa
cctccatgcc acttgtccaa ttattgacac ttaactaatt agtttgattc atgtatgaat
actaaataat tttttaggac tgactcaaat attttttatat tatcatagta atatttatct
aattttttagg accacttatt acttaataat aaattaacta caactatatt attgttgtga
aacaacaacg ttttggttgt tatgatgaaa cgtacactat atcagtatga aaaattcaaa
acgattagta taaattatat tgaaaatttg atatttttct attcttaatc agacgtattg
ggtttcatat tttaaaaagg gactaaactt agaagagaag tttgtttgaa actacttttg
tctctttctt gttcccattt ctctcttaga tttcaaaaag tgaactactt tatctctttc
tttgttcaca ttttattta ttctattata aatatggcat cctcatattg agatttttag
aaattattct aatcattcac agtgcaaaag a
```

*Fig. 35*

← Sequence Verified as E8 promoter

PCR FRAGMENT of E8 promoter

MODULATING DISEASE THROUGH GENETIC ENGINEERING OF PLANTS

CROSS-REFERENCE TO RELATED APPLICATIONS

This application claims benefit of and priority to U.S. Ser. No. 61/618,753, filed on Mar. 31, 2012 and to U.S. Ser. No. 61/716,322, filed on Oct. 19, 2012, both of which are incorporated herein by reference in their entirety for all purposes.

STATEMENT OF GOVERNMENTAL SUPPORT

This invention was made with Government support under Grant Nos. HL030568, HL034343 awarded by the National Institutes of Health. The Government has certain rights in this invention.

BACKGROUND

High density lipoprotein (HDL), its main protein, apolipoprotein A-I (apoA-I), and mimetics of apoA-I have been shown in a number of laboratories to reduce inflammation in animal models of disease (Getz and Reardon (2011) *J. Inflamm. Res.* 4: 83-92; Navab et al. (2012) *Arterioscler. Thromb. Vasc. Biol.* 32: 2553-2560; Degoma and Rader (2011) *Nat. Rev. Cardiol.* 8: 266-277; Yao et al. (2012) *Front. Pharmacol.,* 3: 37; Navab et al. (2010) *Arterioscler. Thromb. Vasc. Biol.* 30: 164-168).

In particular, the use of such ApoA-I mimetic peptides such as 4F to modulate diseases has been demonstrated in a wide variety of contexts including, but not limited to animal models of arthritis (Charles-Schoeman (2008) *Clin. Immunol.* 127: 234-244) asthma (Nandedkar et al. (2011) *J. Lipid Res.,* 52: 499-508) atherosclerosis (Navab et al. (2011) *J. Lipid Res.* 52: 1200-1210), Alzheimer's disease (Handattu et al. (2009) *Neurobiol. Dis.* 34: 525-534), cancer (Su et al. (2010) *Proc. Natl. Acad. Sci. USA,* 107: 19997-20002; Gao et al. (2011) *Integr. Biol. (Camb).* 3: 479-489; Ganaphthy et al. (2012) *Int. J. Cancer,* 130: 1071-1081), diabetes (Morgantini et al. (2010) *Diabetes.* 59: 3223-3228), hepatic fibrosis (DeLeve et al. (2008) *Am. J. Pathol.* 173: 993-1001), kidney disease (Vaziri et al. (2009) *Kidney Int.* 76: 437-444; Vaziri et al. (2010) *Nephrol. Dial. Transplant.* 25: 3525-3534), obesity (Peterson et al. (2009) *J. Lipid Res.* 50: 1293-1304), osteoporosis (Sage et al. (2011) *J. Bone Miner. Res.* 26: 1197-1206), scleroderma (Weihrauch et al. (2007) *Am. J Physiol. Heart Circ. Physiol.* 293: H1432-H1441), systemic lupus erythematosus (Woo et al. (2010) *Arthritis Res. Ther.,* 12: R93), transplant vasculopathy (Hsieh et al. (2007) *Transplantation* 27:84:238-243), and vascular dementia (Buga et al. (2006) *J. Lipid Res.* 47: 2148-2160). Thus, the potential benefit of such peptides is great.

The apoA-I mimetic peptide 4F showed great promise in a variety of mouse models of disease (Navab et al. (2010) *Arterioscler. Thromb. Vasc. Biol.* 30: 164-168) leading to a phase I/II study in humans with high risk cardiovascular disease (Bloedon et al. (2008) *J. Lipid Res.* 49: 1344-1352). In this study the 4F peptide synthesized from all D-amino acids (D-4F) was administered orally at doses that ranged from 0.43-7.14 mg/kg. The resulting plasma peptide levels were low (Cmax 15.9±6.5 ng/mL). Despite these very low plasma levels, doses of 4.3 and 7.14 mg/kg significantly improved the HDL inflammatory index (HII), which is a measure of the ability of a test HDL to inhibit LDL-induced monocyte chemoattractant protein-1 (MCP-1) production by cultured human artery wall cells; doses of 0.43 and 1.43 mg/kg were not effective (Id.). A second clinical trial focused on achieving high plasma peptide levels using low doses (0.042-1.43 mg/kg) of the 4F peptide synthesized from all L-amino acids (L-4F) delivered by intravenous (IV) or subcutaneous (SQ) administration (Watson et al. (2011) *J. Lipid Res.* 52: 361-373). Very high plasma levels were in fact achieved (e.g., Cmax 3,255±630 ng/mL in the IV study), but there was no improvement in HII (Id.).

To resolve this paradox, new studies were conducted in mice that led to the surprising discovery that the major site of action for the peptide may be in the intestine, even when the peptide is administered SQ (Navab et al. (2011) *J. Lipid Res.* 52: 1200-1210). Moreover, the dose administered, not the plasma level, was the major determinant of efficacy (Id.). Efficacy was the same at the same dose when the peptide was administered orally or SQ suggesting that in the compartment controlling peptide efficacy, peptide concentrations should be similar; the peptide concentration was similar only in the feces (Id.). In a subsequent study, this compartment was further identified as the small intestine (Navab et al. (2012) *J. Lipid Res.* 53: 437-445). Additionally, metabolites of arachidonic and linoleic acids in the enterocytes of the small intestine were found to be ~10-fold higher than in the liver, but the percent reduction in these metabolites after oral 4F peptide administration was significantly greater in the liver compared to the small intestine strongly suggesting that the small intestine is a major site for peptide action (Id.). As a result of these studies (Navab et al. (2011) *J. Lipid Res.* 52: 1200-1210; Navab et al. (2012) *J. Lipid Res.* 53: 437-445), it was concluded that doses of peptide ranging between 40-100 mg/kg/day would be required instead of doses of 0.42-1.43 mg/kg/day as was used in the studies of Watson et al. (Watson et al. (2011) *J. Lipid Res.* 52: 361-373).

The 4F peptide (Ac-D-W-F-K-A-F-Y-D-K-V-A-E-K-F-K-E-A-F-NH$_2$, (SEQ ID NO:1)) has end blocking groups (Ac— and —NH$_2$) that stabilize the class A amphipathic helix and dramatically increase efficacy (Venkatachalapathi et al. (1993) *Proteins Structure Function Genet.* 15: 349-359; Yancey et al. (1995) *Biochemistry.* 34: 7955-7965; Datta et al. (2001) *J. Lipid Res.* 42: 1096-1104; Ananthara-maiah et al. (2007) *J. Lipid Res.,* 48: 1915-1923). In unpublished studies in mice, it was found that in the absence of these end groups the 4F peptide is 25,000-fold less effective in vivo. The required end (protecting) groups for 4F and for a number of other apoA-I mimetic peptides (Navab et al. (2010) *Arterioscler. Thromb. Vasc. Biol.* 30: 164-168) can only be added by chemical synthesis; living organisms cannot be engineered to make a molecule containing these end groups. Thus, the production of peptide for clinical use at these doses would not be practical because of the cost of producing this amount of peptide by solid phase synthesis.

SUMMARY

In certain embodiments a transgenic plant is provided that comprises cells that express a peptide one or more domains of which comprise or consist of the amino acid sequence of an apolipoprotein or apolipoprotein mimetic peptide (e.g., a peptide that comprises or consists of one or more copies of an amino acid sequence of an apolipoprotein or apolipoprotein mimetic peptide, e.g., as described herein). In certain embodiments the transgenic plant or a portion thereof and/or the peptide has biological activity (e.g., lowers plasma SAA levels, and/or increases paraoxonase activity, and/or reduces levels of lysophosphatidic acid, and/or reduces levels of metabolites of arachidonic and linoleic acids, and/or improves HDL inflammatory index, and/or inhibits LDL-induced monocyte chemotaxis in culture, etc.). In certain embodiments peptide expressed in the transgenic plant comprises one domain that comprises the amino acid sequence of the apolipoprotein or apolipoprotein mimetic peptide). In certain embodiments peptide expressed in the transgenic plant comprises at least two domains that comprise the amino acid sequence of the apolipoprotein or apolipoprotein mimetic peptide. In certain embodiments the amino acid sequence comprises an ApoA-I mimetic amino acid sequence and/or a G* peptide amino acid sequence, and/or an ApoE peptide sequence. In certain embodiments the amino acid sequence comprises an amino acid sequence selected from Table 1 Table 2, or Table 3. In certain embodiments the amino acid sequence comprises an amino acid sequence selected from the group consisting of DWLKAFYDKFFEKFKEFF (6F, SEQ ID NO:17), FFEKFKEFFKDYFAKLWD (rev6F, SEQ ID NO: 25), DWFKAFYDKVAEKFKEAF (4F, SEQ ID NO:15), FAEKFKEAVKDYFAKFWD (rev4F, SEQ ID NO: 23), LLEQLNEQFNWVSRLANL (SEQ ID NO:609), and LVGRQLEEFL (SEQ ID NO:612). In certain embodiments the amino acid sequence comprises the amino sequence DWLKAFYDKFFEKFKEFF (6F, SEQ ID NO:17) or the reverse thereof. In certain embodiments the peptide is effective to decrease plasma levels of lyophosphatidic acid (LPA) in a mammal, and/or to decrease SAA levels in the mammal, and/or to increase plasma paraoxonase activity in the mammal when fed to the mammal without substantial purification from the transgenic plant. In certain embodiments the peptide is effective to decrease plasma levels of lyophosphatidic acid (LPA) in a mammal when at least a portion of the plant is fed to the mammal (e.g., alone or as a component of a food, food supplement, and/or diet). In certain embodiments the peptide is effective to significantly decrease SAA levels in a in a mouse model of atherosclerosis when at least a portion of the plant is fed to the mouse. In certain embodiments the peptide is effective to increase plasma paraoxonase activity in a mammal, when at least a portion of the plant is fed to the mammal. In certain embodiments the peptide is expressed by a nucleic acid construct stably integrated into the plant genome. In certain embodiments the plant is transformed by an *agrobacterium* comprising a construct encoding the peptide. In certain embodiments at least a portion of the plant is edible. In certain embodiments at least a portion of the plant, when processed is edible. In certain embodiments the plant is selected from the group consisting of tomato, rice, tobacco, turnip, maize, corn, soybean, grape, apple, pear, plum, peach, orange, kiwi, payaya, pineapple, guava, lilikoi, starfruit, lychee, mango, pomegranate, fig, plum, potato, carrot, mustard greens, chard, kale, lettuce, broccoli, and safflower seeds. In certain embodiments at least a portion of the plant is dried or lyophilized, and/or ground. In certain embodiments all of the plant is dried or lyophilized, and/or ground.

In various embodiments a seed of a transgenic plant (e.g., a plant that expresses a peptide comprising or consisting of an apolipoprotein domain as described herein) is provided (e.g., a seed that expresses/contains a recombinantly expressed peptide that comprises or consists of one or more copies of an amino acid sequence of an apolipoprotein or apolipoprotein mimetic peptide, e.g., as described herein). In certain embodiments the seed capable of generating a transgenic plant as described herein when grown. In certain embodiments the seed when fed to a mammal in an effective amount is effective to decrease plasma levels of lyophosphatidic acid (LPA) in a mammal, and/or to decrease SAA levels in the mammal, and/or to increase plasma paraoxonase activity in the mammal.

In various embodiments a fruit of a transgenic plant (e.g., a plant that expresses a peptide comprising or consisting of an apolipoprotein domain as described herein) is provided (e.g., a fruit that expresses/contains a recombinantly expressed peptide that comprises or consists of one or more copies of an amino acid sequence of an apolipoprotein or apolipoprotein mimetic peptide, e.g., as described herein). In certain embodiments the fruit is a fresh fruit, while in other embodiments, the fruit is a dried and/or processed fruit. In certain embodiments the fruit is a tomato, an apple, a peach, a pear, or a plum. In certain embodiments the fruit when fed to a mammal in an effective amount is effective to decrease plasma levels of lyophosphatidic acid (LPA) in a mammal, and/or to decrease SAA levels in the mammal, and/or to increase plasma paraoxonase activity in the mammal, and/or to improve HDL inflammatory index of HDL in the mammal.

In various embodiments a leaf of a transgenic plant (e.g., a plant that expresses a peptide comprising or consisting of an apolipoprotein domain as described herein) is provided (e.g., a leaf that expresses/contains a recombinantly expressed peptide that comprises or consists of one or more copies of an amino acid sequence of an apolipoprotein or apolipoprotein mimetic peptide, e.g., as described herein). In certain embodiments the leaf when fed to a mammal in an effective amount is effective to decrease plasma levels of lyophosphatidic acid (LPA) in a mammal, and/or to decrease SAA levels is the mammal, and/or to increase plasma paraoxonase activity in the mammal.

In various embodiments a root or tuber of a transgenic plant (e.g., a plant that expresses a peptide comprising or consisting of an apolipoprotein domain as described herein) is provided (e.g., a root or tuber that expresses/contains a recombinantly expressed peptide that comprises or consists of one or more copies of an amino acid sequence of an apolipoprotein or apolipoprotein mimetic peptide, e.g., as described herein). In certain embodiments the root or tuber when fed to a mammal in an effective amount is effective to decrease plasma levels of lyophosphatidic acid (LPA) in a mammal, and/or to decrease SAA levels is the mammal, and/or to increase plasma paraoxonase activity in the mammal.

In various embodiments a cutting of a transgenic plant (e.g., a plant that expresses a peptide comprising or consisting of an apolipoprotein domain as described herein) is provided (e.g., a cutting that expresses/contains a recombinantly expressed peptide that comprises or consists of one or more copies of an amino acid sequence of an apolipoprotein or apolipoprotein mimetic peptide, e.g., as described herein). In certain embodiments the cutting is capable of generating a transgenic plant as described herein when propagated or generating at least a portion of a plant that is transgenic when grafted onto a host plant. In certain embodiments tissue generated from the cutting, when fed to a mammal in an effective amount, is effective to decrease plasma levels of lyophosphatidic acid (LPA) in a mammal, and/or to decrease SAA levels is the mammal, and/or to increase plasma paraoxonase activity in the mammal.

In various embodiments a clone of a transgenic plant (e.g., a plant that expresses a peptide comprising or consisting of an apolipoprotein domain as described herein) is provided (e.g., a clone that expresses/contains a recombinantly expressed peptide that comprises or consists of one or more copies of an amino acid sequence of an apolipoprotein or apolipoprotein mimetic peptide, e.g., as described herein).

In various embodiments the transgenic plant, seed, fruit, root and/or tuber, cutting, clone, or other components and/or cells, and/or tissues of the plant do not express ApoA-I and/or do not express ApoA-I Milano, and/or do not express a protein comprising ApoA-I, and/or ApoA-I Milano.

In various embodiments a peptide is provided where the peptide is expressed in a plant where at least one domain of the peptide comprises an apolipoprotein mimetic and where the neither the peptide nor a domain thereof comprises or consists of the amino acid sequence of ApoA-I or apoA-I milano. In certain embodiments the peptide comprises one domain that comprises the amino acid sequence of the apolipoprotein mimetic peptide. In certain embodiments the peptide comprises at least two domains that comprise the amino acid sequence of the apolipoprotein mimetic peptide. In certain embodiments the amino acid sequence of the peptide (or domain thereof) comprises an amino acid sequence selected from Table 1 Table 2, or Table 3. In certain embodiments the amino acid sequence comprises an amino acid sequence selected from the group consisting of DWLKAFYDKFFEKFKEFF (6F, SEQ ID NO:17), FFEK-FKEFFKDYFAKLWD (rev6F, SEQ ID NO: 25), DWFKA-FYDKVAEKFKEAF (4F, SEQ ID NO:15), FAEK-FKEAVKDYFAKFWD (rev4F, SEQ ID NO: 23), LLEQLNEQFNWVSRLANL (SEQ ID NO:609), and LVGRQLEEFL (SEQ ID NO:612). In certain embodiments the amino acid sequence comprises the amino sequence DWLKAFYDKFFEKFKEFF (6F, SEQ ID NO:17) or the reverse thereof. In certain embodiments the peptide is effective to decrease plasma levels of lyophosphatidic acid (LPA) in a mammal, and/or to decrease SAA levels in the mammal, and/or to increase plasma paraoxonase activity in the mammal when fed to the mammal. In certain embodiments the peptide is present in a tissue of the plant. In certain embodiments the peptide is effective to decrease plasma levels of lyophosphatidic acid (LPA) in a mammal when fed to the mammal without substantial isolation from the tissues of the plant. In certain embodiments the peptide is effective to significantly decrease SAA levels in a mouse model of atherosclerosis when fed to the mouse without substantial isolation from tissues of the plant. In certain embodiments the peptide is effective to increase plasma paraoxonase activity in a mammal, when fed to the mammal without substantial isolation from tissues of the plant. In certain embodiments the peptide is expressed by a nucleic acid construct stably integrated into the genome of the plant. In certain embodiments at least a portion of the plant is edible. In certain embodiments at least a portion of the plant, when processed is edible. In certain embodiments the plant is selected from the group consisting of tomato, rice, tobacco, turnip, maize, corn, soybean, grape, fig, plum, potato, carrot, apple, pear, plum, peach, orange, kiwi, payaya, pineapple, guava, lilikoi, starfruit, lychee, mango, pomegranate, mustard greens, chard, kale, lettuce, broccoli, and safflower seeds. In certain embodiments the peptide is expressed in a tomato. In certain embodiments the peptide is contained in a tissue of a dried and/or lyophilized plant and/or a ground plant. In certain embodiments the peptide is stored in a seed or fruit of the plant. In certain embodiments the peptide is purified.

In various embodiments a food is provided where the food is comprised of at least a portion of a transgenic plant (e.g., a plant that expresses a peptide comprising or consisting of an apolipoprotein domain as described herein) capable of being ingested for its nutritional value. In certain embodiments the food is a component of a diet optimized for a mammal for the treatment and/or prophylaxis of atherosclerosis. In certain embodiments the food is a component of a diet optimized for a mammal for the treatment and/or prophylaxis of a pathology characterized by an inflammatory response. In certain embodiments the food is a component of a diet optimized for a mammal for the treatment and/or prophylaxis of a cancer. In certain embodiments the diet provides the nutritional requirements of a human. In certain embodiments the diet is a prepared fixed diet for a human. In certain embodiments the diet provides the nutritional requirements of a non-human mammal. In certain embodiments the diet provides nutritional requirements of a non-human mammal selected from the group consisting of a canine, a feline, an equine, a porcine, a bovine, and a lagomorph. In certain embodiments the diet provides the nutritional requirements of a canine. In certain embodiments the diet is a prepackaged animal food, or a prepackaged human food or meal. In certain embodiments diet is a prepared fixed diet for the non-human mammal. In certain embodiments the plant portion of the food includes a portion of the plant selected from the group consisting of the fruit, leaves, stems, roots, and seeds.

In various embodiments a protein powder is provided where at least a portion of the protein powder comprises an apolipoprotein or apolipoprotein mimetic peptide or a peptide comprising an apolipoprotein or apolipoprotein mimetic domain as described herein. In certain embodiments the remainder of the protein powder comprises a plant derived protein. In certain embodiments the plant derived protein comprises a protein derived from a plant selected from the group consisting of soy, and hemp. In certain embodiments the remainder of the protein powder comprises an animal-derived protein powder (e.g., a protein powder derived from milk or eggs).

In various embodiments a nutritional supplement is provided. The nutritional supplement typically comprises a transgenic plant (e.g., a plant that expresses a peptide comprising or consisting of an apolipoprotein domain, an apolipoprotein mimetic domain, an apolipoprotein, or an apolipoprotein mimetic, e.g., as described herein), and/or a portion of the plant; and/or an apolipoprotein or apolipoprotein mimetic peptide according to any one of as described herein. In certain embodiments the nutritional supplement further comprises one or more vitamin supplements (e.g., one or omega 3 fatty acid supplements, and/or one or more dietary antioxidants, and/or one or more vitamins (e.g., B vitamins, vitamin C, vitamin D, vitamin E, and the like).

Also provided are methods for the treatment or prophylaxis of a pathology characterized by an inflammatory response. The methods typically involve administering to a mammal in need thereof an effective amount of at least a portion of a transgenic plant as described herein; and/or an apolipoprotein or apolipoprotein mimetic peptide as described herein; and/or a food as described herein; and/or a protein powder as described herein; and/or a nutritional supplement and/or protein bar/power bar as described herein. In certain embodiments the mammal is administered at least a portion of a transgenic plant as described herein. In certain embodiments the transgenic plant expresses a 6F peptide or a peptide comprising a 6F domain. In certain embodiments the pathology is atherosclerosis. In certain embodiments the mammal is diagnosed with atherosclerosis and the administering comprises administering a sufficient amount of the plant, and/or peptide, and/or food, and/or protein powder, and/or nutritional supplement to ameliorate one or more symptoms of atherosclerosis and/or to reduce one or more markers of an atherosclerotic pathology. In certain embodiments the mammal is at risk for atherosclerosis and the administering comprises administering a sufficient amount of the plant, and/or peptide, and/or food, and/or protein powder, and/or nutritional supplement to reduce the risk for atherosclerosis, and/or to improve a risk marker for atherosclerosis, and/or to slow the progression of atherosclerosis. In certain embodiments the risk marker is HDL/LDL, CRP, triglycerides, SAA, paraoxonase activity, Lp(a), oxidized LDL or antibodies to oxidized LDL, or sPLA$_2$. In certain embodiments the pathology is macular degeneration. In certain embodiments the pathology is cancer (e.g., ovarian cancer, breast cancer, colon cancer, prostate cancer, brain cancer, and the like). In certain embodiments the plant, a portion of the plant and/or an extract of the plant and/or the peptide described herein is applied topically to a skin cancer (e.g., a melanoma, a carcinoma, etc.). In certain embodiments the plant, plant portion, and/or extract thereof is administered alone, in combination with an excipient, or in combination with another topical anticancer agent (e.g., SFU, imiquimod). In certain embodiments the plant or plant portion, and/or peptide, and/or food, and/or protein powder, and/or nutritional supplement is administered in an amount sufficient to reduce lyophosphatidic acid (LPA) levels in the mammal. In certain embodiments the mammal is a human. In certain embodiments the mammal is a non-human mammal (e.g., a canine, a feline, an equine, a porcine, a bovine, a largomorph, and the like). In certain embodiments the mammal is administered at least a portion of a transgenic plant that expresses a peptide comprising or consisting of an amino acid sequence selected from Table 1 Table 2, or Table 3. In certain embodiments the amino acid sequence comprises an amino acid sequence selected from the group consisting of DWLKAFYDKFFEKFKEFF (6F, SEQ ID NO:17), FFEKFKEFFKDYFAKLWD (rev6F, SEQ ID NO: 25), DWFKAFYDKVAEKFKEAF (4F, SEQ ID NO:15), FAEKFKEAVKDYFAKFWD (rev4F, SEQ ID NO: 23), LLEQLNEQFNWVSRLANL (SEQ ID NO:609), and LVGRQLEEFL (SEQ ID NO:612). In certain embodiments the amino acid sequence comprises the amino sequence DWLKAFYDKFFEKFKEFF (6F, SEQ ID NO:17) or the reverse thereof. In certain embodiments the mammal is administered at least a portion of a transgenic tomato that comprising cells that express a peptide comprising the amino acid sequence DWLKAFYDKFFEKFKEFF (6F, SEQ ID NO:17) or the reverse thereof. In certain embodiments the peptide is not substantially purified from tissue of the tomato. In certain embodiments the plant (e.g., the tomato) is dried and/or lyophilized.

In certain embodiments a method of preventing or reducing the uptake of one or more dietary pro-inflammatory micro-lipid components in a mammal is provided where the method comprises administering to the mammal an effective amount of at least a portion of a transgenic plant as described and/or claimed herein; and/or an apolipoprotein or apolipoprotein mimetic peptide according as described and/or claimed herein; and/or a food or food ingredient as described and/or claimed herein; and/or a protein powder as described and/or claimed herein; and/or a nutritional supplement as described and/or claimed herein. In certain embodiments the mammal is administered at least a portion of a transgenic plant as described and/or claimed herein. In certain embodiments the mammal is administered a fruit or part of a fruit of the transgenic plant. In certain embodiments the fruit is selected from the group consisting of a tomato, an apple, a pear, a plum, a peach, an orange, a kiwi, a payaya, a pineapple, a guava, a lilikoi, a starfruit, a lychee, a mango, a pomegranate, and a plum. In certain embodiments the fruit is a tomato. In certain embodiments the mammal is administered a peptide as described and/or claimed herein. In certain embodiments the mammal is administered a food as described and/or claimed herein. In certain embodiments the mammal has or is at at risk for atherosclerosis. In certain embodiments the mammal is diagnosed with atherosclerosis. In certain embodiments the mammal is determined to be at risk for atherosclerosis. In certain embodiments the mammal is determined to be at risk by measurement of a marker selected from the group consisting of HDL/LDL, CRP, triglycerides, SAA, paraoxonase activity, Lp(a), oxidized LDL or antibodies to oxidized LDL, or sPLA$_2$. In certain embodiments the plant or plant portion, and/or peptide, and/or food, and/or protein powder, and/or nutritional supplement is administered in an amount sufficient to reduce lyophosphatidic acid (LPA) levels in the mammal. In certain embodiments the plant or plant portion, and/or peptide, and/or food, and/or protein powder, and/or nutritional supplement is administered in an amount sufficient to reduce lyophosphatidic acid (LPA) levels in the intestine (e.g., in the small intestine) of the mammal. In certain embodiments the mammal is a human. In certain embodiments the mammal is a non-human mammal (e.g., a canine, a feline, an equine, a porcine, a bovine, a largomorph, etc In certain embodiments the mammal is administered at least a portion of a transgenic plant that expresses a peptide comprising or consisting of an amino acid sequence selected from Table 1 Table 2, or Table 3. In certain embodiments the amino acid sequence comprises an amino acid sequence selected from the group consisting of DWLKAFYDKFFEKFKEFF (6F, SEQ ID NO:17), FFEKFKEFFKDYFAKLWD (rev6F, SEQ ID NO: 25), DWFKAFYDKVAEKFKEAF (4F, SEQ ID NO:15), FAEKFKEAVKDYFAKFWD (rev4F, SEQ ID NO: 23), LLEQLNEQFNWVSRLANL (SEQ ID NO:609), and LVGRQLEEFL (SEQ ID NO:612). In certain embodiments the amino acid sequence comprises the amino sequence DWLKAFYDKFFEKFKEFF (6F, SEQ ID NO:17) or the reverse thereof. In certain embodiments the mammal is administered at least a portion of a transgenic tomato that comprising cells that express a peptide comprising the amino acid sequence DWLKAFYDKFFEKFKEFF (6F, SEQ ID NO:17) or the reverse thereof. In certain embodiments the peptide is not substantially purified from tissue of the tomato. In certain embodiments the plant (e.g., the tomato) is dried and/or lyophilized.

In various embodiments an isolated nucleic acid that encodes a peptide one or more domains of which comprise the amino acid sequence of an apolipoprotein mimetic peptide, where the codons of the nucleic acid are optimized for expression in a plant. In certain embodiments the nucleic acid does not encode the amino acid sequence of ApoA-I and/or ApoA-I Milano. In certain embodiments the peptide comprises one domain that comprises the amino acid sequence of the apolipoprotein mimetic peptide. In certain embodiments the peptide comprises at least two domains that comprise the amino acid sequence of the apolipoprotein mimetic peptide. In certain embodiments the amino acid sequence comprises an amino acid sequence selected from Table 1 Table 2, or Table 3. In certain embodiments the amino acid sequence comprises an amino acid sequence selected from the group consisting of DWLKAFYDKFFEKFKEFF (6F, SEQ ID NO:17), FFEKFKEFFKDYFAKLWD (rev6F, SEQ ID NO: 25), DWFKAFYDKVAEKFKEAF (4F, SEQ ID NO:15), FAEKFKEAVKDYFAKFWD (rev4F, SEQ ID NO: 23), LLEQLNEQFNWVSRLANL (SEQ ID NO:609), and LVGRQLEEFL (SEQ ID NO:612). In certain embodiments the amino acid sequence comprises the amino sequence DWLKAFYDKFFEKFKEFF (6F, SEQ ID NO:17) or the reverse thereof. In certain embodiments the codons are optimized for expression in a plant a least a portion of which is edible. In certain embodiments at least a portion of the plant, when processed is edible. In certain embodiments the codons are optimized for expression in a plant is selected from the group consisting of tomato, rice, tobacco, turnip, maize, corn, soybean, grape, fig, plum, apple, pear, peach, orange, kiwi, payaya, pineapple, guava, lilikoi, starfruit, lychee, mango, pomegranate, potato, carrot, pomegranate, mustard greens, chard, kale, lettuce, broccoli, and safflower seeds. In certain embodiments the codons are optimized for expression in a tomato.

Also provided is a vector that expresses an apolipoprotein mimetic peptide at an effective concentration/amount when transfected into a plant, the vector comprising a nucleic acid according encoding an apolipoprotein (or mimetic) or an apoprotein (or mimetic) domain as described herein. In certain embodiments the vector does not encode an ApoA-I peptide or an ApoA-I Milano peptide. In certain embodiments the vector when transfected into a plant expresses the peptide at levels sufficient so that the plant or a portion thereof has biological activity (e.g., as described herein) when fed to a mammal. In certain embodiments the vector further comprises a promoter effective in a plant cell. In certain embodiments the vector comprises a CaMV 35S promoter. In certain embodiments the vector further comprises a terminator. In certain embodiments the vector comprises a Nopaline synthase terminator (NOS term). In certain embodiments the vector further encodes a plant derived signal peptide. In certain embodiments the signal peptide comprises the amino acid sequence M-I-M-A-S-S-K-L-L-S-L-A-L-F-L-A-L-L-S-H-A-N-S (SEQ ID NO:2). In certain embodiments the vector is a plasmid vector. In certain embodiments the vector is a binary vector. In certain embodiments the vector is an integrative vector. In certain embodiments the vector is in an *Agrobacterium tumefaciens*.

Also provided is a plant cell transfected with a nucleic acid as described herein where the plant cell expresses the peptide one or more domains of which comprise the amino acid sequence of an apolipoprotein mimetic peptide as described herein. In certain embodiments the plant cell does not express an ApoA-I or an ApoA-I Milano peptide. In certain embodiments the plant cell is a cell of a plant at least a portion of which is edible. In certain embodiments the plant cell is a cell of a plant at least a portion of which, when processed, is edible. In certain embodiments the cell is a cell of a plant selected from the group consisting of tomato, rice, tobacco, turnip, maize, corn, soybean, grape, fig, plum, apple, pear, plum, peach, orange, kiwi, payaya, pineapple, guava, lilikoi, starfruit, lychee, mango, pomegranate, potato, carrot, pomegranate, mustard greens, chard, kale, lettuce, broccoli, and safflower seeds. In certain embodiments the cell is a cell of a plant protoplast.

Also provided are methods for producing a transgenic plant that expresses a peptide comprising at least one domain that encodes an apolipoprotein mimetic as described herein. The method typically involves providing a vector or a nucleic acid as described herein; transforming a plant cell with the vector or DNA fragment; and propagating a plant from the cell. In certain embodiments the method further comprises recovering all or a portion of the plant for use in a therapeutic or prophylactic method. In certain embodiments the recovering comprises harvesting at least a portion of the plant. In certain embodiments the recovering comprises obtaining an extract of a plant cell or tissue. In certain embodiments the recovering comprises drying and/or lyophilizing at least a portion of the plant. In certain embodiments the plant cell is transformed utilizing an *Agrobacterium* system. In certain embodiments the plant cell is transformed using a method selected from the group consisting of microparticle bombardment, polyethylene glycol mediated uptake, and electroporation. In certain embodiments the plant cell is a cell of a dicotyledon. In certain embodiments the cell is a cell of a monocotyledon. In certain embodiments the cell is a cell of a food plant, e.g., a plant a least a portion of which is edible. In certain embodiments the cell is a cell of a plant that at least a portion of which, when processed is edible. In certain embodiments the cell is a cell of a plant selected from the group consisting of tomato, rice, tobacco, turnip, maize, corn, soybean, grape, fig, plum, apple, pear, peach, orange, kiwi, payaya, pineapple, guava, lilikoi, starfruit, lychee, mango, pomegranate, potato, carrot, pomegranate, mustard greens, chard, kale, lettuce, broccoli, and safflower seeds. In certain embodiments the cell is a cell of a tomato.

In certain embodiments a food or food ingredient is provided comprising at least a portion of a transgenic plant capable of being ingested for its nutritional value and/or taste, where a tissue of the plant comprising the food or food ingredient comprises a peptide recombinantly expressed in cells comprising the tissue where the peptide comprises or consists of one or more copies of the amino acid sequence of an apolipoprotein or apolipoprotein mimetic peptide (e.g., a peptide as shown in Table 1 Table 2, or Table 3) where the transgenic plant or a portion thereof when fed to a mammal has biological activity (e.g., decreases plasma levels of lyophosphatidic acid (LPA), and/or decreases SAA levels, and/or increases plasma paraoxonase activity, and/or reduces atherosclerotic lesion(s)). In certain embodiments the peptide comprises or consists of one domain (e.g., one copy of) the amino acid sequence of the apolipoprotein or apolipoprotein mimetic peptide. In certain embodiments the peptide comprises at least two domains that each comprise or consist of the amino acid sequence of the apolipoprotein or apolipoprotein mimetic peptide (e.g., the peptide comprises or consists of at least two copies of the amino acid sequence of the apolipoprotein or apolipoprotein mimetic). In certain embodiments the peptide comprises or consists of an ApoA-I mimetic amino acid sequence and/or a G* peptide amino acid sequence, and/or an ApoE peptide sequence. In certain embodiments the peptide comprises or consists of the amino acid sequence DWLKAFYDKFFEK-FKEFF (6F, SEQ ID NO:17). In certain embodiments the peptide comprises or consists of an amino acid sequence comprises an amino acid sequence selected from the group consisting of DWLKAFYDKFFEKFKEFF (6F, SEQ ID NO: 17), FFEKFKEFFKDYFAKLWD (rev6F, SEQ ID NO:25), DWFKAFYDKVAEKFKEAF (4F, SEQ ID NO:15), FAEKFKEAVKDYFAKFWD (rev4F, SEQ ID NO:23), LLEQLNEQFNWVSRLANL (SEQ ID NO:609), and LVGRQLEEFL (SEQ ID NO:612). In certain embodiments the peptide comprises or consists of an amino acid sequence selected from the group consisting of DWLKA-FYDKVAEKLKEAF (SEQ ID NO:11), DWLKAFYDK-VAEKLKEAF (SEQ ID NO:12), DWFKAFYDK-VAEKLKEAF (SEQ ID NO:13), DWLKAFYDKVAEKFKEAF (SEQ ID NO:14), DWFKA-FYDKVAEKFKEAF (SEQ ID NO:15), DWLKAFYDK-VFEKFKEFF (SEQ ID NO:16), DWLKAFYDKFFEKFK-EFF (SEQ ID NO:17), DWFKAFYDKFFEKFKEFF (SEQ ID NO:18), DWLKAFYDKVAEKLKEFF (SEQ ID NO:19), FAEKLKEAVKDYFAKLWD (SEQ ID NO:20), FAEKLKEAVKDYFAKLWD (SEQ ID NO:21), FAEKLKEAVKDYFAKFWD (SEQ ID NO:22), FAEKFKEAVKDYFAKFWD (SEQ ID NO:23), FFEKFKEFVKDYFAKLWD (SEQ ID NO:24), FFEKFKEFFKDYFAKLWD (SEQ ID NO:25), FFEKFKEFFKDYFAKFWD (SEQ ID NO:26), DWLKAFYDKVFEKFKEAF (SEQ ID NO:27), DWLKAFYDKVFEKLKEFF (SEQ ID NO:28), DWLKAFYDKVAEKFKEFF (SEQ ID NO:29), DWLKAFYDKVFEKFKEFF (SEQ ID NO:30), EWLKLFYEKVLEKFKEAF (SEQ ID NO:31), EWLKAFYDKVAEKFKEAF (SEQ ID NO:32), EWLKAFYDKVAEKLKEFF (SEQ ID NO:33), EWLKAFYDKVFEKFKEAF (SEQ ID NO:34), EWLKAFYDKVFEKLKEFF (SEQ ID NO:35), EWLKAFYDKVAEKFKEFF (SEQ ID NO:36), EWLKAFYDKVFEKFKEFF (SEQ ID NO:37), AFYDKVAEKLKEAF (SEQ ID NO:38), AFYDKVAEKFKEAF (SEQ ID NO:39), AFYDKVAEKFKEAF (SEQ ID NO:40), AFYDKFFEKFKEFF (SEQ ID NO:41), AFYDKFFEKFKEFF (SEQ ID NO:42), AFYDKVAEKFKEAF (SEQ ID NO:43), AFYDKVAEKLKEFF (SEQ ID NO:44), AFYDKVFEKFKEAF (SEQ ID NO:45), AFYDKVFEKLKEFF (SEQ ID NO:46), AFYDKVAEKFKEFF (SEQ ID NO:47), KAFYDKVFEKFKEF (SEQ ID NO:48), LFYEKVLEKFKEAF (SEQ ID NO:49), AFYDKVAEKFKEAF (SEQ ID NO:50), AFYDKVAEKLKEFF (SEQ ID NO:51), AFYDKVFEKFKEAF (SEQ ID NO:52), AFYDKVFEKLKEFF (SEQ ID NO:53), AFYDKVAEKFKEFF (SEQ ID NO:54), AFYDKVFEKFKEFF (SEQ ID NO:55), DWLKALYDKVAEKLKEAL (SEQ ID NO:56), DWFKAFYEKVAEKLKEFF (SEQ ID NO:57), DWFKAFYEKFFEKFKEFF (SEQ ID NO:58), EWLKALYEKVAEKLKEAL (SEQ ID NO:59), EWLKAFYEKVAEKLKEAF (SEQ ID NO:60), EWFKAFYEKVAEKLKEFF (SEQ ID NO:61), EWLKAFYEKVFEKFKEFF (SEQ ID NO:62), EWLKAFYEKFFEKFKEFF (SEQ ID NO:63), EWFKAFYEKFFEKFKEFF (SEQ ID NO:64), DFLKAWYDKVAEKLKEAW (SEQ ID NO:65), EFLKAWYEKVAEKLKEAW (SEQ ID NO:66), DFWKAWYDKVAEKLKEWW (SEQ ID NO:67), EFWKAWYEKVAEKLKEWW (SEQ ID NO:68), DKLKAFYDKVFEWAKEAF (SEQ ID NO:69), DKWKAVYDKFAEAFKEFL (SEQ ID NO:70), EKLKAFYEKVFEWAKEAF (SEQ ID NO:71), EKWKAVYEKFAEAFKEFL (SEQ ID NO:72), DWLKAFVDKFAEKFKEAY (SEQ ID NO:73), EKWKAVYEKFAEAFKEFL (SEQ ID NO:74), DWLKAFVYDKVFKLKEFF (SEQ ID NO:75), EWLKAFVYEKVFKLKEFF (SEQ ID NO:76), DWLRAFYDKVAEKLKEAF (SEQ ID NO:77), EWLRAFYEKVAEKLKEAF (SEQ ID NO:78), DWLKAFYDRVAEKLKEAF (SEQ ID NO:79), EWLKAFYERVAEKLKEAF (SEQ ID NO:80), DWLKAFYDKVAERLKEAF (SEQ ID NO:81), EWLKAFYEKVAERLKEAF (SEQ ID NO:82), DWLKAFYDKVAEKLREAF (SEQ ID NO:83), EWLKAFYEKVAEKLREAF (SEQ ID NO:84), DWLKAFYDRVAERLKEAF (SEQ ID NO:85), EWLKAFYERVAERLKEAF (SEQ ID NO:86), DWLRAFYDKVAEKLREAF (SEQ ID NO:87), EWLRAFYEKVAEKLREAF (SEQ ID NO:88), DWLRAFYDRVAEKLKEAF (SEQ ID NO:89), EWLRAFYERVAEKLKEAF (SEQ ID NO:90), DWLKAFYDKVAERLREAF (SEQ ID NO:91), EWLKAFYEKVAERLREAF (SEQ ID NO:92), DWLRAFYDKVAERLREAF (SEQ ID NO:93), EWLRAFYEKVAERLREAF (SEQ ID NO:94), DWLKAFYDKVAEKLKEAFPDWLKAFYDKVAEKLKEAF (SEQ ID NO:95), DWLKAFYDKVAEKLKEFFPDWLKAFYDKVAEKLKEFF (SEQ ID NO:96), DWFKAFYDKVAEKLKEAFPDWFKAFYDKVAEKLKEAF (SEQ ID NO:97), DKLKAFYDKVFEWAKEAFPDKLKAFYDKVFEWLKEAF (SEQ ID NO:98), DKWKAVYDKFAEAFKEFLPDKWKAVYDKFAEAFKEFL (SEQ ID NO:99), DWFKAFYDKVAEKFKEAFPDWFKAFYDKVAEKFKEAF (SEQ ID NO:100), DWLKAFVYDKVFKLKEFFPDWLKAFVYDKVFKLKEFF (SEQ ID NO:101), DWLKAFYDKFAEKFKEFFPDWLKAFYDKFAEKFKEFF (SEQ ID NO:102), EWFKAFYEKVAEKFKEAF (SEQ ID NO:103), DWFKAFYDKVAEKF (SEQ ID NO:104), FKAFYDKVAEKFKE (SEQ ID NO:105), FKAFYEKVAEKFKE (SEQ ID NO:106), FKAFYDKVAEKFKE (SEQ ID NO:107), FKAFYEKVAEKFKE (SEQ ID NO:108), DWFKAFYDKVAEKFKEAF (SEQ ID NO:109), EWFKAFYEKVAEKFKEAF (SEQ ID NO:110), AFYDKVAEKFKEAF (SEQ ID NO:111), DWFKAFYDKVAEKF (SEQ ID NO:112), DWLKAFYDKVFEKFKEFF (SEQ ID NO:113), EWLKAFYEKVFEKFKEFF (SEQ ID NO:114), AFYDKVFEKFKEFF (SEQ ID NO:115), AFYEKVFEKFKEFF (SEQ ID NO:116), DWLKAFYDKVFEKF (SEQ ID NO:117), EWLKAFYEKVFEKF (SEQ ID NO:118), LKAFYDKVFEKFKE (SEQ ID NO:119), LKAFYEKVFEKFKE (SEQ ID NO:120), EWFKAFYEKVADKFKDAF (SEQ ID NO:121), EWFKAFYDKVADKFKEAF (SEQ ID NO:122), DWFKAFYEKVADKFKEAF (SEQ ID NO:123), DWFKAFYEKVAEKFKDAF (SEQ ID NO:124), DFWKAFYDKVAEKFKEAF (SEQ ID NO:125), EFWKAFYEKVADKFKDAF (SEQ ID NO:126), EFWKAFYDKVADKFKEAF (SEQ ID NO:127), DFWKAFYEKVADKFKEAF (SEQ ID NO:128), DFWKAFYEKVAEKFKDAF (SEQ ID NO:129), DWFKAYFDKVAEKFKEAF (SEQ ID NO:130), EWFKAYFEKVADKFKDAF (SEQ ID NO:131), EWFKAYFDKVADKFKEAF (SEQ ID NO:132), DWFKAYFEKVADKFKEAF (SEQ ID NO:133), DWFKAYFEKVAEKFKDAF (SEQ ID NO:134), DWFKAFVDKYAEKFKEAF (SEQ ID NO:135), EWFKAFVEKYADKFKDAF (SEQ ID NO:136), EWFKAFVDKYADKFKEAF (SEQ ID NO:137), DWFKAFVEKYADKFKEAF (SEQ ID NO:138), DWFKAFVEKYAEKFKDAF (SEQ ID NO:139), DWFKAFYDKAVEKFKEAF (SEQ ID NO:140), EWFKAFYEKAVDKFKDAF (SEQ ID NO:141), EWFKAFYDKAVDKFKEAF (SEQ ID NO:142), DWFKAFYEKAVDKFKEAF (SEQ ID NO:143), DWFKAFYEKAVEKFKDAF (SEQ ID NO:144), DWFKAFYDKVFEKAKEAF (SEQ ID NO:145), EWFKAFYEKVFDKAKDAF (SEQ ID NO:146), EWFKAFYDKVFDKAKEAF (SEQ ID NO:147), DWFKAFYEKVFDKAKEAF (SEQ ID NO:148), DWFKAFYEKVFEKAKDAF (SEQ ID NO:149), DWFKAFYDKVAEKAKEFF (SEQ ID NO:150), EWFKAFYEKVADKAKDFF (SEQ ID NO:151), EWFKAFYDKVADKAKEFF (SEQ ID NO:152), DWFKAFYEKVADKAKEFF (SEQ ID NO:153), DWFKAFYEKVAEKAKDFF (SEQ ID NO:154), DWFKAFYDKVAEKFKEFA (SEQ ID NO:155), EWFKAFYEKVADKFKDFA (SEQ ID NO:156), EWFKAFYDKVADKFKEFA (SEQ ID NO:157), DWFKAFYEKVADKFKEFA (SEQ ID NO:158), DWFKAFYEKVAEKFKDFA (SEQ ID NO:159), DAFKAFYDKVAEKFKEWF (SEQ ID NO:160), EAFKAFYEKVADKFKDWF (SEQ ID NO:161), EAFKAFYDKVADKFKEWF (SEQ ID NO:162), DAFKAFYEKVADKFKEWF (SEQ ID NO:163), DAFKAFYEKVAEKFKDWF (SEQ ID NO:164), DAFKAFYDKVWEKFKEAF (SEQ ID NO:165), EAFKAFYEKVWDKFKDAF (SEQ ID NO:166), EAFKAFYDKVWDKFKEAF (SEQ ID NO:167), DAFKAFYEKVWDKFKEAF (SEQ ID NO:168), DAFKAFYEKVWEKFKDAF (SEQ ID NO:169), DYFKAFWDKVAEKFKEAF (SEQ ID NO:170), EYFKAFWEKVADKFKDAF (SEQ ID NO:171), EYFKAFWDKVADKFKEAF (SEQ ID NO:172), DYFKAFWEKVADKFKEAF (SEQ ID NO:173), DYFKAFWEKVAEKFKDAF (SEQ ID NO:174), DWAKAFYDKVAEKFKEFF (SEQ ID NO:175), EWAKAFYEKVADKFKDFF (SEQ ID NO:176), EWAKAFYDKVADKFKEFF (SEQ ID NO:177), DWAKAFYEKVADKFKEFF (SEQ ID NO:178), DWAKAFYEKVAEKFKDFF (SEQ ID NO:179), DWFKAAYDKVAEKFKEFF (SEQ ID NO:180), EWFKAAYEKVADKFKDFF (SEQ ID NO:181), EWFKAAYDKVADKFKEFF (SEQ ID NO:182), DWFKAAYEKVADKFKEFF (SEQ ID NO:183), DWFKAAYEKVAEKFKDFF (SEQ ID NO:184), DWFKAFADKVAEKFKEYF (SEQ ID NO:185), EWFKAFAEKVADKFKDYF (SEQ ID NO:186), EWFKAFADKVADKFKEYF (SEQ ID NO:187), DWFKAFAEKVADKFKEYF (SEQ ID NO:188), DWFKAFAEKVAEKFKDYF (SEQ ID NO:189), DWFKAFYDKAAEKFKEVF (SEQ ID NO:190), EWFKAFYEKAADKFKDVF (SEQ ID NO:191), EWFKAFYDKAADKFKEVF (SEQ ID NO:192), DWFKAFYEKAADKFKEVF (SEQ ID NO:193), DWFKAFYEKAAEKFKDVF (SEQ ID NO:194), DWYKAFFDKVAEKFKEAF (SEQ ID NO:195), EWYKAFFEKVADKFKDAF (SEQ ID NO:196), EWYKAFFDKVADKFKEAF (SEQ ID NO:197), DWYKAFFEKVADKFKEAF (SEQ ID NO:198), DWYKAFFEKVAEKFKDAF (SEQ ID NO:199), DWVKAFYDKFAEKFKEAF (SEQ ID NO:200), EWVKAFYEKFADKFKDAF (SEQ ID NO:201), EWVKAFYDKFADKFKEAF (SEQ ID NO:202), DWVKAFYEKFADKFKEAF (SEQ ID NO:203), DWVKAFYEKFAEKFKDAF (SEQ ID NO:204), DWFKAFFDKVAEKYKEAF (SEQ ID NO:205), EWFKAFFEKVADKYKDAF (SEQ ID NO:206), EWFKAFFDKVADKYKEAF (SEQ ID NO:207), DWFKAFFEKVADKYKEAF (SEQ ID NO:208), DWFKAFFEKVADKYKEAF (SEQ ID NO:209), DWFKAFFDKVAEKFKEAY (SEQ ID NO:210), EWFKAFFEKVADKFKDAY (SEQ ID NO:211), EWFKAFFDKVADKFKEAY (SEQ ID NO:212), DWFKAFFEKVADKFKEAY (SEQ ID NO:213), DWFKAFFEKVAEKFKDAY (SEQ ID NO:214), DWFKAFYDKFAEKFKEAV (SEQ ID NO:215), EWFKAFYEKFADKFKDAV (SEQ ID NO:216), EWFKAFYDKFADKFKEAV (SEQ ID NO:217), DWFKAFYEKFADKFKEAV (SEQ ID NO:218), DWFKAFYEKFAEKFKDAV (SEQ ID NO:219), DKFKAFYDKVAEKFWEAF (SEQ ID NO:220), EKFKAFYEKVADKFWDAF (SEQ ID NO:221), EKFKAFYDKVADKFWEAF (SEQ ID NO:222), DKFKAFYEKVADKFWEAF (SEQ ID NO:223), DKFKAFYEKVAEKFWDAF (SEQ ID NO:224), DKWKAFYDKVAEKFFEAF (SEQ ID NO:225), EKWKAFYEKVADKFFDAF (SEQ ID NO:226), EKWKAFYDKVADKFFEAF (SEQ ID NO:227), DKWKAFYEKVADKFFEAF (SEQ ID NO:228), DKWKAFYEKVAEKFFDAF (SEQ ID NO:229), DKFKAFYDKWAEVFKEAF (SEQ ID NO:230), EKFKAFYEKWADVFKDAF (SEQ ID NO:231), EKFKAFYDKWADVFKEAF (SEQ ID NO:232), DKFKAFYEKWADVFKEAF (SEQ ID NO:233), DKFKAFYEKWAEVFKDAF (SEQ ID NO:234), DKFKAFYDKVAEFWKEAF (SEQ ID NO:235), EKFKAFYEKVADFWKDAF (SEQ ID NO:236), EKFKAFYDKVADFWKEAF (SEQ ID NO:237), DKFKAFYEKVADFWKEAF (SEQ ID NO:238), DKFKAFYEKVAEFWKDAF (SEQ ID NO:239), FAEKFKEAVKDYFAKFWD (SEQ ID NO:240), FADKFKDAVKEYFAKFWE (SEQ ID NO:241), FADKFKEAVKDYFAKFWE (SEQ ID NO:242), FAEKFKDAVKEYFAKFWD (SEQ ID NO:243), FAEKFKDAVKDYFAKFWE (SEQ ID NO:244), FWEKFKEAVKDYFAKFAD (SEQ ID NO:245), FWDKFKDAVKEYFAKFAE (SEQ ID NO:246), FADKFKEAVKDYFAKFWE (SEQ ID NO:247), FAEKFKDAVKEYFAKFWD (SEQ ID NO:248), FAEKFKDAVKDYFAKFWE (SEQ ID NO:249), FFEKFKEAVKDYFAKAWD (SEQ ID NO:250), FFDKFKDAVKEYFAKAWE (SEQ ID NO:251), FFDKFKEAVKDYFAKAWE (SEQ ID NO:252), FFEKFKDAVKEYFAKAWD (SEQ ID NO:253), FFEKFKDAVKDYFAKAWE (SEQ ID NO:254), FAEKAKEFVKDYFAKFWD (SEQ ID NO:255), FADKAKDFVKEYFAKFWE (SEQ ID NO:256), FADKAKEFVKDYFAKFWE (SEQ ID NO:257), FAEKAKDFVKEYFAKFWD (SEQ ID NO:258), FAEKAKDFVKDYFAKFWE (SEQ ID NO:259), FAEKFKEVAKDYFAKFWD (SEQ ID NO:260), FADKFKDVAKEYFAKFWE (SEQ ID NO:261), FADKFKEVAKDYFAKFWE (SEQ ID NO:262), FAEKFKDVAKEYFAKFWD (SEQ ID NO:263), FAEKFKDVAKDYFAKFWE (SEQ ID NO:264), FAEKFKEAYKDVFAKFWD (SEQ ID NO:265), FADKFKDAYKEVFAKFWE (SEQ ID NO:266), FADKFKEAYKDVFAKFWE (SEQ ID NO:267), FAEKFKDAYKEVFAKFWD (SEQ ID NO:268), FAEKFKDAYKDVFAKFWE (SEQ ID NO:269), FAEKFKEAVKDYFAKFWD (SEQ ID NO:270), FADKFKDAVKEFYAKFWE (SEQ ID NO:271), FADKFKEAVKDFYAKFWE (SEQ ID NO:272), FAEKFKDAVKEFYAKFWD (SEQ ID NO:273), FAEKFKDAVKDFYAKFWE (SEQ ID NO:274), FAEKFWEAVKDYFAKFKD (SEQ ID NO:275), FADKFWDAVKEYFAKFKE (SEQ ID NO:276), FADKFWEAVKDYFAKFKE (SEQ ID NO:277), FAEKFWDAVKEYFAKFKD (SEQ ID NO:278), FAEKFWDAVKDYFAKFKE (SEQ ID NO:279), AFEKFKEAVKDYFAKFWD (SEQ ID NO:280), AFDKFKDAVKEYFAKFWE (SEQ ID NO:281), AFDKFKEAVKDYFAKFWE (SEQ ID NO:282), AFEKFKDAVKEYFAKFWD (SEQ ID NO:283), AFEKFKDAVKDYFAKFWE (SEQ ID NO:284), VAEKFKEAFKDYFAKFWD (SEQ ID NO:285), VADKFKDAFKEYFAKFWE (SEQ ID NO:286), VADKFKEAFKDYFAKFWE (SEQ ID NO:287), VAEKFKDAFKEYFAKFWD (SEQ ID NO:288), VAEKFKDAFKDYFAKFWE (SEQ ID NO:289), YAEKFKEAVKDFFAKFWD (SEQ ID NO:290), YADKFKDAVKEFFAKFWE (SEQ ID NO:291), YADKFKEAVKDFFAKFWE (SEQ ID NO:292), YAEKFKDAVKEFFAKFWD (SEQ ID NO:293), YAEKFKDAVKDFFAKFWE (SEQ ID NO:294), AAEKFKEFVKDYFAKFWD (SEQ ID NO:295), AADKFKDFVKEYFAKFWE (SEQ ID NO:296), AADKFKEFVKDYFAKFWE (SEQ ID NO:297), AAEKFKDFVKEYFAKFWD (SEQ ID NO:298), AAEKFKDFVKDYFAKFWE (SEQ ID NO:299), FFEKAKEAVKDYFAKFWD (SEQ ID NO:300), FFDKAKDAVKEYFAKFWE (SEQ ID NO:301), FFDKAKEAVKDYFAKFWE (SEQ ID NO:302), FFEKAKDAVKEYFAKFWD (SEQ ID NO:303), FFEKAKDAVKDYFAKFWE (SEQ ID NO:304), FYEKFKEAVKDAFAKFWD (SEQ ID NO:305), FYDKFKDAVKEAFAKFWE (SEQ ID NO:306), FYDKFKEAVKDAFAKFWE (SEQ ID NO:307), FYEKFKDAVKEAFAKFWD (SEQ ID NO:308), FYEKFKDAVKDAFAKFWE (SEQ ID NO:309), FVEKFKEAAKDYFAKFWD (SEQ ID NO:310), FVDK- FKDAAKEYFAKFWE (SEQ ID NO:311), FVDKFKEAAKDYFAKFWE (SEQ ID NO:312), FVEKFKDAAKEYFAKFWD (SEQ ID NO:313), FVEKFKDAAKDYFAKFWE (SEQ ID NO:314), FAEKYKEAVKDFFAKFWD (SEQ ID NO:315), FADKYKDAVKEFFAKFWE (SEQ ID NO:316), FADKYKEAVKDFFAKFWE (SEQ ID NO:317), FAEYKDAVKEFFAKFWD (SEQ ID NO:318), FAEKYKDAVKDFFAKFWE (SEQ ID NO:319), FAEKVKEAFKDYFAKFWD (SEQ ID NO:320), FADKVKDAFKEYFAKFWE (SEQ ID NO:321), FADKVKEAFKDYFAKFWE (SEQ ID NO:322), FAEKVKDAFKEYFAKFWD (SEQ ID NO:323), FAEKVKDAFKDYFAKFWE (SEQ ID NO:324), FAEKFKEYVKDAFAKFWD (SEQ ID NO:325), FADKFKDYVKEAFAKFWE (SEQ ID NO:326), FADKFKEYVKDAFAKFWE (SEQ ID NO:327), FAEKFKDYVKEAFAKFWD (SEQ ID NO:328), FAEKFKDYVKDAFAKFWE (SEQ ID NO:329), FAEKFKEAFKDYVAKFWD (SEQ ID NO:330), FADKFKDAFKEYVAKFWE (SEQ ID NO:331), FADKFKEAFKDYVAKFWE (SEQ ID NO:332), FAEKFKDAFKEYVAKFWE (SEQ ID NO:333), FAEKFKDAFKDYVAKFWE (SEQ ID NO:334), FAEKFKEAFKDYFAKVWD (SEQ ID NO:335), FADKFKDAFKEYFAKVWE (SEQ ID NO:336), FADKFKEAFKDYFAKVWE (SEQ ID NO:337), FAEKFKDAFKEYFAKVWD (SEQ ID NO:338), FAEKFKDAFKDYFAKVWE (SEQ ID NO:339), FAEKFKEAVKDFFAKYWD (SEQ ID NO:340), FADKFKDAVKEFFAKYWE (SEQ ID NO:341), FADKFKEAVKDFFAKYWE (SEQ ID NO:342), FAEKFKDAVKEFFAKYWD (SEQ ID NO:343), FAEKFKDAVKDFFAKYWE (SEQ ID NO:344), WAEKFFEAVKDYFAKFKD (SEQ ID NO:345), WADKFFDAVKEYFAKFKE (SEQ ID NO:346), WADKFFEAVKDYFAKFKE (SEQ ID NO:347), WAEKFFDAVKEYFAKFKD (SEQ ID NO:348), WAEKFFDAVKDYFAKFKE (SEQ ID NO:349), FAEKWFEAVKDYFAKFKD (SEQ ID NO:350), FADKWFDAVKEYFAKFKE (SEQ ID NO:351), FADKWFEAVKDYFAKFKE (SEQ ID NO:352), FAEKWFDAVKEYFAKFKD (SEQ ID NO:353), FAEKWFDAVKDYFAKFKE (SEQ ID NO:354), FAEKFVEAWKDYFAKFKD (SEQ ID NO:355), FADKFVDAWKEYFAKFKE (SEQ ID NO:356), FADKFVEAWKDYFAKFKE (SEQ ID NO:357), FAEKFVDAWKEYFAKFKD (SEQ ID NO:358), FAEKFVDAWKDYFAKFKE (SEQ ID NO:359), FYEKFAEAVKDWFAKFKD (SEQ ID NO:360), FYDKFADAVKEWFAKFKE (SEQ ID NO:361), FYDKFAEAVKDWFAKFKE (SEQ ID NO:362), FYEKFADAVKEWFAKFKD (SEQ ID NO:363), FYEKFADAVKDWFAKFKE (SEQ ID NO:364), DWFKHFYDKVAEKFKEAF (SEQ ID NO:365), EWFKHFYEKVADKFKDAF (SEQ ID NO:366), EWFKHFYDKVAEKFKEAF (SEQ ID NO:367), DWFKHFYEKVAEKFKEAF (SEQ ID NO:368), DWFKHFYDKVADKFKEAF (SEQ ID NO:369), DWFKHFYDKVAEKFKDAF (SEQ ID NO:370), DWHKFFYDKVAEKFKEAF (SEQ ID NO:371), EWHKFFYEKVADKFKDAF (SEQ ID NO:372), EWHKFFYDKVAEKFKEAF (SEQ ID NO:373), DWHKFFYEKVAEKFKEAF (SEQ ID NO:374), DWHKFFYDKVADKFKEAF (SEQ ID NO:375), DWHKFFYDKVAEKFKDAF (SEQ ID NO:376), DWFKFHYDKVAEKFKEAF (SEQ ID NO:377), EWFKFHYEKVADKFKDAF (SEQ ID NO:378), EWFKFHYDKVAEKFKEAF (SEQ ID NO:379), DWFKFHYEKVAEKFKEAF (SEQ ID NO:380), DWFKFHYDKVADKFKEAF (SEQ ID NO:381), DWFKFHYDKVAEKFKDAF (SEQ ID NO:382), DWFKVFYDKHAEKFKEAF (SEQ ID NO:383), EWFKVFYEKHADKFKDAF (SEQ ID NO:384), EWFKVFYDKHAEKFKEAF (SEQ ID NO:385), DWFKVFYEKHAEKFKEAF (SEQ ID NO:386), DWFKVFYDKHADKFKEAF (SEQ ID NO:387), DWFKVFYDKHAEKFKDAF (SEQ ID NO:388), DWFKAFYDKVAEKFKEHF (SEQ ID NO:389), EWFKAFYEKVADKFKDHF (SEQ ID NO:390), EWFKAFYDKVAEKFKEHF (SEQ ID NO:391), DWFKAFYEKVAEKFKEHF (SEQ ID NO:392), DWFKAFYDKVADKFKEHF (SEQ ID NO:393), DWFKAFYDKVAEKFKDHF (SEQ ID NO:394), DWFKAFYDKVAEKFKEFH (SEQ ID NO:395), EWFKAFYEKVADKFKDFH (SEQ ID NO:396), EWFKAFYDKVAEKFKEFH (SEQ ID NO:397), DWFKAFYDKVAEKFKEFH (SEQ ID NO:398), DWFKAFYEKVAEKFKEFH (SEQ ID NO:399), DWFKAFYDKVAEKFKEFH (SEQ ID NO:400), DWFKAFYDKVAEKFKDFH (SEQ ID NO:401), FAEKFKEAVKDYFAKFWD (SEQ ID NO:402), FHEKFKEAVKDYFAKFWD (SEQ ID NO:403), FHEKFKEAVKEYFAKFWE (SEQ ID NO:404), FHDKFKDAVKDYFAKFWD (SEQ ID NO:405), FHDKFKDAVKEYFAKFWE (SEQ ID NO:406), FHDKFKEAVKDYFAKFWD (SEQ ID NO:407), FHEKFKDAVKDYFAKFWD (SEQ ID NO:408), FHEKFKEAVKEYFAKFWD (SEQ ID NO:409), FHEKFKEAVKDYFAKFWE (SEQ ID NO:410), HFEKFKEAVKDYFAKFWD (SEQ ID NO:411), HFDKFKDAVKEYFAKFWE (SEQ ID NO:412), HFEKFKEAVKEYFAKFWE (SEQ ID NO:413), HFDKFKEAVKDYFAKFWD (SEQ ID NO:414), HFEKFKDAVKDYFAKFWD (SEQ ID NO:415), HFEKFKEAVKEYFAKFWD (SEQ ID NO:416), HFEKFKEAVKDYFAKFWE (SEQ ID NO:417), FFEKHKEAVKDYFAKFWD (SEQ ID NO:418), FFDKHKDAVKEYFAKFWE (SEQ ID NO:419), FFEKHKEAVKEYFAKFWE (SEQ ID NO:420), FFDKHKDAVKDYFAKFWD (SEQ ID NO:421), FFDKHKEAVKDYFAKFWD (SEQ ID NO:422), FFEKHKEAVKEYFAKFWD (SEQ ID NO:423), FFEKHKEAVKDYFAKFWE (SEQ ID NO:424), FVEKFKEAHKDYFAKFWD (SEQ ID NO:425), FVDKFKDAHKEYFAKFWE (SEQ ID NO:426), FVEKFKEAHKEYFAKFWE (SEQ ID NO:427), FVDKFKDAHKDYFAKFWD (SEQ ID NO:428), FVDKFKEAHKDYFAKFWD (SEQ ID NO:429), FVEKFKDAHKDYFAKFWD (SEQ ID NO:430), FVEKFKEAHKEYFAKFWD (SEQ ID NO:431), FVEKFKEAHKDYFAKFWE (SEQ ID NO:432), FAEKFKEHVKDYFAKFWD (SEQ ID NO:433), FADKFKDHVKEYFAKFWE (SEQ ID NO:434), FAEKFKEHVKEYFAKFWE (SEQ ID NO:435), FADKFKDHVKDYFAKFWD (SEQ ID NO:436), FADKFKEHVKDYFAKFWD (SEQ ID NO:437), FAEKFKDHVKDYFAKFWD (SEQ ID NO:438), FAEKFKEHVKEYFAKFWD (SEQ ID NO:439), FAEKFKEHVKDYFAKFWE (SEQ ID NO:440), FAEKFKEFVKDYHAKFWD (SEQ ID NO:441), FADKFKDFVKEYHAKFWE (SEQ ID NO:442), FADKFKEFVKDYHAKFWD (SEQ ID NO:443), FAEKFKDFVKDYHAKFWD (SEQ ID NO:444), FADKFKDFVKDYHAKFWD (SEQ ID NO:445), FAEKFKEFVKEYHAKFWE (SEQ ID NO:446), FAEKFKEFVKEYHAKFWD (SEQ ID NO:447), FAEKFKEFVKDYHAKFWE (SEQ ID NO:448), FAEKFKEFVKDYFAKHWD (SEQ ID NO:449), FADKFKD- FVKEYFAKHWE (SEQ ID NO:450), FAEKFKEFVKEYFAKHWE (SEQ ID NO:451), FADKFKDFVKDYFAKHWD (SEQ ID NO:452), FADKFKEFVKDYFAKHWD (SEQ ID NO:453), FAEKFKDFVKDYFAKHWD (SEQ ID NO:454), FAEKFKEFVKEYFAKHWD (SEQ ID NO:455), FAEKFKEFVKDYFAKHWE (SEQ ID NO:456), FAEKFKEAVKEYFAKFWE (SEQ ID NO:457), FADKFKDAVKDYFAKFWD (SEQ ID NO:458), FAERFREAVKDYFAKFWD (SEQ ID NO:459), FAEKFREAVKDYFAKFWD (SEQ ID NO:460), FAEKFKEAVRDYFAKFWD (SEQ ID NO:461), FAEKFKEAVKDYFARFWD (SEQ ID NO:462), FAEKFKEAVKEYFAKFWE (SEQ ID NO:463), FADKFKDAVKDYFAKFWD (SEQ ID NO:464), FAERFREAVKDYFAKFWD (SEQ ID NO:465), FAEKFREAVKDYFAKFWD (SEQ ID NO:466), FAEKFKEAVRDYFAKFWD (SEQ ID NO:467), FAEKFKEAVKDYFARFWD (SEQ ID NO:468), FAEKFKEAVKEYFAKFWE (SEQ ID NO:469), FADKFKDAVKDYFAKFWD (SEQ ID NO:470), FAERFREAVKDYFAKFWD (SEQ ID NO:471), FAEKFREAVKDYFAKFWD (SEQ ID NO:472), FAEKFKEAVRDYFAKFWD (SEQ ID NO:473), FAEKFKEAVKDYFARFWD (SEQ ID NO:474), FAERFREAVKDYFAKFWD (SEQ ID NO:475), FAEKFREAVKDYFAKFWD (SEQ ID NO:476), FAEKFKEAVRDYFAKFWD (SEQ ID NO:477), FAEKFKEAVKDYFARFWD (SEQ ID NO:478), FAEKFKEAVKEYFAKFWE (SEQ ID NO:479), FADKFKDAVKDYFAKFWD (SEQ ID NO:480), FAERFREAVKDYFAKFWD (SEQ ID NO:481), FAEKFREAVKDYFAKFWD (SEQ ID NO:482), FAEKFKEAVRDYFAKFWD (SEQ ID NO:483), FAEKFKEAVKDYFARFWD (SEQ ID NO:484), LFEKFAEAFKDYVAKWKD (SEQ ID NO:485), LFERFAEAFKDYVAKWKD (SEQ ID NO:486), LFEKFAEAFRDYVAKWKD (SEQ ID NO:487), LFEKFAEAFKDYVARWKD (SEQ ID NO:488), LFEKFAEAFKDYVAKWRD (SEQ ID NO:489), LFEKFAEAFKEYVAKWKE (SEQ ID NO:490), LFDKFADAFKDYVAKWKD (SEQ ID NO:491), LFDKFAEAFKDYVAKWKD (SEQ ID NO:492), LFEKFADAFKDYVAKWKD (SEQ ID NO:493), LFEKFAEAFKEYVAKWKD (SEQ ID NO:494), LFEKFAEAFKDYVAKWKE (SEQ ID NO:495), FAEKAWEFVKDYFAKLKD (SEQ ID NO:496), FAERAWEFVKDYFAKLKD (SEQ ID NO:497), FAEKAWEFVKDYFAKLKD (SEQ ID NO:498), FAEKAWEFVKDYFAKLKD (SEQ ID NO:499), FAEKAWEFVKDYFAKLRD (SEQ ID NO:500), FAEKAWEFVKEYFAKLKE (SEQ ID NO:501), FADKAWDFVKDYFAKLKD (SEQ ID NO:502), FADKAWEFVKDYFAKLKD (SEQ ID NO:503), FAEKAWDFVKDYFAKLKD (SEQ ID NO:504), FAEKAWEFVKEYFAKLKD (SEQ ID NO:505), FAEKAWEFVKDYFAKLKE (SEQ ID NO:506), FFEKFKEFVKDYFAKLWD (SEQ ID NO:507), FFEKFKEFVKEYFAKLWE (SEQ ID NO:508), FFDKFKDFVKDYFAKLWD (SEQ ID NO:509), FFERFKEFVKDYFAKLWD (SEQ ID NO:510), FFEKFREFVKDYFAKLWD (SEQ ID NO:511), FFEKFKEFVRDYFAKLWD (SEQ ID NO:512), FFEKFKEFVKDYFARLWD (SEQ ID NO:513), FFEKFKEFVKDYFAKLWD (SEQ ID NO:514), FFEKFKDFVKDYFAKLWD (SEQ ID NO:515), FFEKFKEFVKEYFAKLWD (SEQ ID NO:516), FFEKFKEFVKDYFAKLWE (SEQ ID NO:517), FLEKFKEFVKDYFAKFWD (SEQ ID NO:518), FLEKFKEFVKEYFAKFWE (SEQ ID NO:519), FLDKFKEFVKDYFAKFWD (SEQ ID NO:520), FLDKFKEFVKDYFAKFWD (SEQ ID NO:521), FLEKFKDFVKDYFAKFWD (SEQ ID NO:522), FLEKFKEFVKEYFAKFWD (SEQ ID NO:523), FLEKFKEFVKDYFAKFWE (SEQ ID NO:524), FLERFKEFVKDYFAKFWD (SEQ ID NO:525), FLEKFREFVKDYFAKFWD (SEQ ID NO:526), FLEKFKEFVRDYFAKFWD (SEQ ID NO:527), FLEKFKEFVKDYFARFWD (SEQ ID NO:528), FFEKFKEFFKDYFAKLWD (SEQ ID NO:529), FFEKFKEFFKEYFAKLWE (SEQ ID NO:530), FFDKFKDFFKDYFAKLWD (SEQ ID NO:531), FFERFKEFFKDYFAKLWD (SEQ ID NO:532), FFEKFREFFKDYFAKLWD (SEQ ID NO:533), FFEKFKEFFRDYFAKLWD (SEQ ID NO:534), FFERFKEFFKDYFARLWD (SEQ ID NO:535), FFDKFKEFFKDYFAKLWD (SEQ ID NO:536), FFEKFKDFFKDYFAKLWD (SEQ ID NO:537), FFEKFKEFFKEYFAKLWD (SEQ ID NO:538), FFEKFKEFFKDYFAKLWE (SEQ ID NO:539), FAEKFKEAVKDYFAKFWD (SEQ ID NO:540), FAEKFKEAVKEYFAKFWE (SEQ ID NO:541), FADKFKDAVKDYFAKFWD (SEQ ID NO:542), FAERFREAVKDYFAKFWD (SEQ ID NO:543), FAEKFREAVKDYFAKFWD (SEQ ID NO:544), FAEKFKEAVRDYFAKFWD (SEQ ID NO:545), FAEKFKEAVKDYFARFWD (SEQ ID NO:546), DKWKAVYDKFAEAFKEFF (SEQ ID NO:547), EKWKAVYEKFAEAFKEFF (SEQ ID NO:548), DKWKAVYDKFADAFKDFF (SEQ ID NO:549), DRWKAVYDKFAEAFKEFF (SEQ ID NO:550), DKWRAVYDKFAEAFKEFF (SEQ ID NO:551), DKWKAVYDRFAEAFKEFF (SEQ ID NO:552), DKWKAVYDKFAEAFREFF (SEQ ID NO:553), FFEKFAEAFKDYVAKWKD (SEQ ID NO:554), FFEKFAEAFKEYVAKWKE (SEQ ID NO:555), FFDKFADAFKDYVAKWKD (SEQ ID NO:556), FFERFAEAFKDYVAKWKD (SEQ ID NO:557), FFEKFAEAFRDYVAKWKD (SEQ ID NO:558), FFEKFAEAFKDYVARWKD (SEQ ID NO:559), FFERFAEAFKDYVAKWRD (SEQ ID NO:560), FFDKFAEAFKDYVAKWKD (SEQ ID NO:561), FFEKFADAFKDYVAKWKD (SEQ ID NO:562), FFERFAEAFKEYVAKWKD (SEQ ID NO:563), FFERFAEAFKDYVAKWKE (SEQ ID NO:564), FFEKFKEFFKDYFAKFWD (SEQ ID NO:565), FFDKFKDFFKDYFAKFWD (SEQ ID NO:566), FFEKFKEFFKEYFAKFWE (SEQ ID NO:567), FFERFKEFFKDYFAKFWD (SEQ ID NO:568), FFEKFREFFKDYFAKFWD (SEQ ID NO:569), FFEKFKEFFRDYFAKFWD (SEQ ID NO:570), FFEKFKEFFKDYFARFWD (SEQ ID NO:571), FFDKFKEFFKDYFAKFWD (SEQ ID NO:572), FFEKFKDFFKDYFAKFWD (SEQ ID NO:573), FFEKFKEFFKEYFAKFWD (SEQ ID NO:574), FFEKFKEFFKDYFAKFWE (SEQ ID NO:575), EVRAKLEEQAQQIRLQAEAFQARLKSWFEPLVE (SEQ ID NO:576), EVRAKLEEQAQQIRLQAEAFQARLKSWFE (SEQ ID NO:577), EVRSKLEEWFAAFREFAEEFLARLKS (SEQ ID NO:578), PVLDLFRELLNELLEALKQKLK (SEQ ID NO:579), DWLKAFYDKVAEKLKEAF-P-DWAKAAYDKAAEKAKEAA (SEQ ID NO:580), EELKEKLEELKEKLEEKL-P-EELKEKLEELKEKLEEKL (SEQ ID NO:581), EELKAKLEELKAKLEEKL-P-EELKAKLEELKAKLEEKL (SEQ ID NO:582), EKLKALLEKLLAKLKELL P-EKLKALLEKLLAKLKELL (SEQ ID NO:583), EWLKELLEKLLEKLKELL-P-EWLKELLEKLLEKLKELL (SEQ ID NO:584), EKFKELLEKFLEKFKELL-P-EKFKELLE-KFLEKFKELL (SEQ ID NO:585), EKLKELLEKL-LELLKKLL-P-EKLKELLEKLLELLKKLL (SEQ ID NO:586), EKLKELLEKLKAKLEELL-P-EKLKELLE-KLKAKLEELL (SEQ ID NO:587), EKLKELLEKLLAK-LKELL-P-EKLKELLEKLLAKLKELL (SEQ ID NO:588), EKFKELLEKLLEKLKELL-P-EKFKELLEKLLE-KLKELL (SEQ ID NO:589), EKLKAKLEELKAKLEELL-P-EKLKAKLEELKAKLEELL (SEQ ID NO:590), EELKELLKELLKKLEKLL-P-ELKELLKELLKKLEKLL (SEQ ID NO:591), EELKKLLEELLKKLKELL-P-EELK-KLLEELLKKLKELL (SEQ ID NO:592), EKLKELLE-KLLEKLKELL-A-EKLKELLEKLLEKLKELL (SEQ ID NO:593), EKLKELLEKLLEKLKELL-AA-EKLKELLE-KLLEKLKELL (SEQ ID NO:594), EKLKAKLEELKAK-LEELL-P-EKAKAALEEAKAKAEELA (SEQ ID NO:595), EKLKAKLEELKAKLEELL-P-EHAKAALEE-AKCKAEELA (SEQ ID NO:596), DHLKAFYDKVACK-LKEAF-P-DWAKAAYDKAAEKAKEAA (SEQ ID NO:597), DWLKAFYDKVAEKLKEAF-P-DHAKAAYD-KAACKAKEAA (SEQ ID NO:598), DWLKAFYDK-VACKLKEAF-P-DWAKAAYNKAAEKAKEAA (SEQ ID NO:599), DHLKAFYDKVAEKLKEAF-P-DWAKAAYD-KAAEKAKEAA (SEQ ID NO:600), VLESFKVSFLSAL-EEYTKKLNTQ (SEQ ID NO:601), DKWKAVYDK-FAEAFKEFL (SEQ ID NO:602), DKLKAFYDKVFEWAKEAF (SEQ ID NO:603), DQYYL-RVTTVA (SEQ ID NO:605), ECKPCLKQTCMKF-YARVCR (SEQ ID NO:606), FSRASSIIDELFQD (SEQ ID NO:607), IQNAVNGVKQIKTLIEKTNEE (SEQ ID NO:608), LLEQLNEQFNWVSRLANL (SEQ ID NO:609), LLEQLNEQFNWVSRLANLTEGE (SEQ ID NO:610), LLEQLNEQFNWVSRLANLTQGE (SEQ ID NO:611), LVGRQLEEFL (SEQ ID NO:612), MNGDRIDSLLEN (SEQ ID NO:613), NELQEMSNQGSKYVNKEIQ-NAVNGV (SEQ ID NO:614), PCLKQTCMKFYARVCR (SEQ ID NO:615), PFLEMIHEAQQAMDI (SEQ ID NO:616), PGVCNETMMALWEECK (SEQ ID NO:617), PKFMETVAEKALQEYRKKHRE (SEQ ID NO:618), PSGVTEVVVKLFDS (SEQ ID NO:619), PSQAKLR-RELDESLQVAERLTRKYNELLKSYQ (SEQ ID NO:620), PTEFIREGDDD (SEQ ID NO:621), QQTHMLDVMQD (SEQ ID NO:622), RKTLLSNLEEAKKKKEDALNETRE-SETKLKEL (SEQ ID NO:623), RMKDQCDKCREILSV (SEQ ID NO:624), GIKKFLGSIWKFIKAFVG (SEQ ID NO:626), GFKKFLGSWAKIYKAFVG (SEQ ID NO:627), GFRRFLGSWARIYRAFVG (SEQ ID NO:628), TEEL-RVRLASHLRKLRKRLL (SEQ ID NO:629), TEELRVR-LASHLRKLRK (SEQ ID NO:630), LRVRLASHLRKL-RKRLL (SEQ ID NO:631), RLASHLRKLRKRLL (SEQ ID NO:632), SHLRKLRKRLL (SEQ ID NO:633), LRKL-RKRLL (SEQ ID NO:634), LRKLRKRLLLRKLRKRLL (SEQ ID NO:635), LRKLRKRLLLRKLRKRLLLRKL-RKRLL (SEQ ID NO:636), RQIKIWFQNRRMKWKKCL-RVRLASHLRKLRKRLL (SEQ ID NO:637), LRVR-LASHLRKLRKRLL (SEQ ID NO:638), EELRVRLASHLRKLRKRLLRDADDLQKRLAVY-EEQAQQIRLQAEAFQARLKSWFE PLVEDM (SEQ ID NO:639), CEELRVRLASHLRKLRKRLLRDADDLQKR-LAVY (SEQ ID NO:640), LRKLRKRLLRDADDLLRKL-RKRLLRDADDL (SEQ ID NO:641), TEELRVRLASHL-RKLRKRLL (SEQ ID NO:642), TEELRVRLASHLEKLRKRLL (SEQ ID NO:643), TEEL-RVRLASHLRELRKRLL (SEQ ID NO:644), LREKKL-RVSALRTHRLELRL (SEQ ID NO:645), LRKLRKRLL-RDWLKAFYDKVAEKLKEAF (SEQ ID NO:646), LRRLRRRLLRDWLKAFYDKVAEKLKEAF (SEQ ID NO:647), and RRRRRRRRRDWLKAFYDK-VAEKLKEAF (SEQ ID NO:648). In certain embodiments the food or food ingredient is effective to decrease plasma levels of lyophosphatidic acid (LPA) in a mammal, and/or to decrease SAA levels in said mammal, and/or to increase plasma paraoxonase activity in said mammal when said food or food ingredient is fed to said mammal. In certain embodiments the food or food ingredient is effective to decrease plasma levels of lyophosphatidic acid (LPA) in a mammal when said food or food ingredient is fed to said mammal. In certain embodiments the food or food ingredient is effective to significantly decrease SAA levels in a in a mouse model of atherosclerosis when said food or food ingredient is fed to said mouse. In certain embodiments the food or food ingredient is effective to increase plasma paraoxonase activity in a mammal, when said food or food ingredient is fed to said mammal. In certain embodiments the peptide in the transgenic plant comprising the food or food ingredient is expressed by a nucleic acid construct stably integrated into the genome of said plant. In certain embodiments the plant is a plant transformed by an *agrobacterium* comprising a construct encoding the peptide. In certain embodiments at least a portion of the plant is edible without processing. In certain embodiments at least a portion of the plant, when processed, is edible. In certain embodiments the plant comprising the food or food ingredient is a tomato. In certain embodiments the plant comprising the food or food ingredient is selected from the group consisting of tomatoes, carrots, potatoes, apples, pears, plums, peaches, oranges, kiwis, papayas, pineapples, guava, lilikoi, starfruit, lychee, mango, grape, pomegranate, mustard greens, kale, chard, lettuce, soybean, rice, corn and other grains (e.g., wheat, rice, barley, bulgur, faro, kamut, kaniwa, millet, oats, quinoa, rice, rye, sorghum, spelt, teff, triticale, and the like), berries such as strawberries, blueberries, blackberries, goji berries, and raspberries, banana, rice, turnip, maize, grape, fig, plum, potato, safflower seeds, nuts (e.g., almond, walnut, pecan, peanut, cashew, macademia, hazelnut, etc.), legumes (e.g., alfalfa, clover, peas, beans (including black beans), lentils, lupins, mesquite, carob, soybeans, and the like). In certain embodiments the plant comprising the food or food ingredient is selected from the group consisting of tomato, rice, tobacco, turnip, maize, corn, soybean, grape, fig, plum, potato, carrot, pomegranate, mustard greens, chard, kale, lettuce, broccoli, and safflower seeds. In certain embodiments the portion of a transgenic plant comprising the food or food ingredient comprises one or more plant parts selected from the group consisting of a fruit, a seed, a nut, a leafy green, a tuber, a stem, a flower, and a root. In certain embodiments the peptide expressed in the plant is expressed under the control of a CaMV promoter or an E8 promoter, or a hybrid E4/E8 promoter. In certain embodiments at least a portion of the plant comprising the food or food ingredient is dried and/or lyophilized, and/or ground. In certain embodiments all of the plant comprising the food or food ingredient is dried and/or lyophilized, and/or ground. In certain embodiments the food or food ingredient is a component of a diet optimized for a mammal for the treatment and/or prophylaxis of atherosclerosis. In certain embodiments the food or food ingredient is a component of a diet optimized for a mammal for the treatment and/or prophylaxis of a pathology characterized by an inflammatory response. In certain embodiments the food or food ingredient is a component of a diet optimized for a mammal for the treatment and/or prophylaxis of a cancer. In certain embodiments the diet provides the nutritional requirements of a human. In certain embodiments the diet is a prepared fixed diet for a human. In certain embodiments the diet provides the nutritional requirements of a non-human mammal. In certain embodiments the diet provides the nutritional requirements of a non-human mammal selected from the group consisting of a canine, a feline, an equine, a porcine, a bovine, and a lagomorph. In certain embodiments the diet is a prepared fixed diet for the non-human mammal. In certain embodiments the food or food ingredient is formulated as a nutritional supplement. In certain embodiments the food or food ingredient comprises a dried fruit. In certain embodiments the food or food ingredient comprises a dried or lyophilized and powdered fruit. In certain embodiments the food or food ingredient comprises a tomato. In certain embodiments the food or food ingredient comprises a fruit selected from the group consisting of an apple, a pear, a peach, and a plum.

In certain embodiments the constructs described herein expressly exclude ApoA-I$_{Milano}$. In certain embodiments the constructs described herein expressly exclude safflower seeds.

Definitions

The HDL inflammatory index refers to the ability of HDL to inhibit LDL-induced monocyte chemotactic activity. In certain embodiments the HDL-inflammatory index is calculated by comparing the monocyte chemotactic activity generated by a standard control LDL in the absence and presence of the test HDL. In the absence of the test HDL the monocyte chemotactic activity is normalized to 1.0. If the monocyte chemotactic activity increases upon addition of the test HDL the HDL-inflammatory index is >1.0 and the test HDL is classified as pro-inflammatory. If the monocyte chemotactic activity decreases upon addition of the test HDL the HDL-inflammatory index is <1.0 and the HDL is classified as anti-inflammatory. A reduction in HDL inflammatory index is considered an improvement in HDL inflammatory index.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers, however a recombinantly expressed peptide typically consists of amino acids that are all found in the host organism (e.g., naturally occurring amino acids).

The term "an amphipathic helical peptide" refers to a peptide comprising at least one amphipathic helix (amphipathic helical domain). Certain amphipathic helical peptides contemplated herein can comprise two or more (e.g., 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) Proteins: Structure, Function, and Genetics 8: 103-117).

"Apolipoprotein J" (apo J) is known by a variety of names including clusterin, TRPM2, GP80, and SP 40 (see, e.g., Fritz (1995) Pp 112 In: Clusterin: Role in Vertebrate Development, Function, and Adaptation (Harmony JAK Ed.), R. G. Landes, Georgetown, Tex.). It was first described as a heterodimeric glycoprotein and a component of the secreted proteins of cultured rat Sertoli cells (see, e.g., Kissinger et al. (1982) Biol. Reprod.; 27: 233240). The translated product is a single-chain precursor protein that undergoes intracellular cleavage into a disulfide-linked 34 kDa α subunit and a 47 kDa β subunit (see, e.g., Collard and Griswold (1987) Biochem., 26: 3297-3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) Biochem., 40: 11828-11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, e.g., Segrest et al. (1990) Proteins: Structure, Function, and Genetics. 8: 103-117; Erratum (1991) Proteins: Structure, Function and Genetics, 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see, e.g., Segrest et al. (1992) J. Lipid Res., 33: 141-166; Anantharamaiah et al. (1993) Pp. 109-142 In: The Amphipathic Helix, Epand, R. M. Ed CRC Press, Boca Raton, Fla.). Computer programs to identify and classify amphipathic helical domains have been described by Jones et al. (1992) J. Lipid Res. 33: 287-296) and include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "treat" when used with reference to treating, e.g. a pathology or disease refers to the mitigation and/or elimination of one or more symptoms of that pathology or disease, and/or a reduction in the rate of onset or severity of one or more symptoms of that pathology or disease, and/or the prevention of that pathology or disease.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

A "transgenic plant" is a plant that expresses in at least some of the cells of the plant a heterologous peptide. In certain embodiments the heterologous peptide consists of, or comprises the amino acid sequence of one or more apolipoprotein(s) or apolipoprotein mimetics, e.g., an apoA-I mimetic, and/or a G* peptide, and/or an apoE peptide, e.g., as described herein. In certain embodiments the transgenic plant is a plant that at least a portion of which is edible by a human and/or by a non-human mammal.

The term "biological activity" when used with respect to an apolipoprotein peptide, an apolipoprotein peptide mimetic, a peptide/protein comprising one or more apolipoprotein and/or apolipoprotein mimetic domains indicates that the peptide, when fed to a mammal lowers plasma SAA levels, and/or increases paraoxonase activity, and/or reduces levels of lysophosphatidic acid, and/or reduces levels of metabolites of arachidonic and linoleic acids. A transgenic plant or portion thereof having biological activity indicates that the plant or portion thereof when fed to a mammal lowers plasma SAA levels, and/or increases paraoxonase activity, and/or reduces levels of lysophosphatidic acid, and/or reduces levels of metabolites of arachidonic and linoleic acids.

The term, "recombinant nucleic acid" as used herein refers to nucleic acid, originally formed in vitro, in general, in a form not normally found in nature.

A "heterologous" DNA coding sequence is a structural coding sequence that is not native to the plant being transformed, or a coding sequence that has been engineered for improved characteristics of its protein product. Heterologous, with respect to the promoter, refers to a coding sequence that does not exist in nature in the same gene with the promoter to which it is currently attached.

A "heterologous promoter" is a promoter manipulated so that it controls the transcription of a nucleic acid that is not a nucleic acid typically under regulation of that promoter.

A "regulatable promoter" is any promoter whose activity is affected by a cis or trans acting factor (e.g., an ethylene-inducible promoter such as the tomato E8 promoter).

A "constitutive promoter" is any promoter that directs RNA transcription in many or all tissues of a plant transformant at most times.

A "tissue-specific promoter" is any promoter that directs RNA transcription at higher levels in particular types of cells and tissues (e.g., a fruit specific promoter).

By "promoter" or "promoter segment" (e.g., a tomato E8 promoter or E4 promoter or hybrid E4/E8 promoter) is meant a sequence of DNA that functions alone as a promoter or as a component of a promoter herein to direct transcription of a downstream gene, and can include promoter or promoter regions derived by means of ligation with operator regions, random or controlled mutagenesis, addition or duplication of enhancer sequences, addition or modification with synthetic linkers, and the like.

By an E8 or an E4 gene promoter is meant a promoter obtained from an E8 or E4 gene considered to share sequence identity with the tomato E8 or E4 gene sequences (e.g., as described in U.S. Pat. No. 6,118,049), or a particular region or regions thereof, or from a gene having at least about 70%, preferably at least about 80%, more preferably at least about 85%, even more preferably at least about 90% sequence identify, or at least about 95% sequence identity, or at least about 98% sequence identity over a length of polynucleotide sequence corresponding to the tomato E8 or tomato E4 gene sequences.

The term "conservative substitution" is used in reference to proteins or peptides to reflect amino acid substitutions that do not substantially alter the activity (e.g., ability to reduce SAA, and/or ability to increase paroxonase in a mammal. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A "macro-lipid component of the diet" refers to a lipid component of a mammal's diet that is typically present in milligram amounts per gram of diet. In a Western diet such macro-lipid components typically include, but are not limited to phospholipids such as phosphatidylcholine and sterols such as cholesterol. Even lysophosphatidylcholine is likely to be present in milligram quantities after phosphatidylcholine is acted upon in the Duodenum by $PLA_2$ and hence, in various embodiments, can be regarded as a macro-lipid component.

A "micro-lipid component of the diet" refers to a lipid component of a mammal's diet that is typically present in microgram (or lower) amounts per gram of diet. Illustrative microlipid components typically include, but are not limited to lysophosphatidic acid, phosphatidic acid, and the like.

BRIEF DESCRIPTION OF THE DRAWINGS

FIG. 4 illustrates plant expression of the 6F peptide. Basically a nucleic acid (SEQ ID NO:4) is produced that encodes the 6F peptide (SEQ ID NO:17) attached to a signal peptide (SEQ ID NO:2). The nucleic acid is codon optimized for expression in a tomato plant.

FIG. 5. *Agrobacterium tumefaciens* LBA4404 was transformed with the vector shown in FIG. 15 with or without the sequence for 6F shown in FIG. 4. Plasmid p6F was electroporated into *Agrobacterium tumefaciens* strain LBA4404, and four colonies harboring the binary vector were sequence verified (UCLA GeneSeq Core) and further used for plant transformation.

FIG. 13 shows the appearance of Western Diet containing lyophilized material from ripened wild-type or 6F transgenic tomatoes.

FIG. 16A: Groups of female apoE$^{-/-}$ mice (n=20) 16-18 months of age were maintained on rodent chow that did not contain peptide (Chow) or contained 1.2 mg of the 6F peptide without ending blocking groups per 4 grams of chow (Chow+L-6F) providing a dose of ~60 mg/kg/day peptide. The mice in both groups consumed approximately 4 grams of the chow per mouse per day. The peptide constituted ~0.03% of the diet by weight. After 10 days the mice were bled and SAA levels were determined by ELISA as described in the Materials and Methods in Example 3. FIG. 16B: Groups of female apoE$^{-/-}$ mice 4-6 months of age were fed a western diet (WD) that did not contain or which contained L-6F without end blocking groups (WD+6F) at a dose of 60 mg/kg/day of peptide. After 6 weeks the mice were bled and plasma SAA levels were determined by ELISA as described in Materials and Methods in Example 3. FIG. 16C: Groups of female apoE$^{-/-}$ mice 6-8 months of age (n=30 per group) were fed WD that did not contain peptide (No Peptide) or contained L-6F without end blocking groups (L-6F) at a dose of 60 mg/kg/day of peptide. After 7 weeks the percent of the aorta with atherosclerotic lesions was determined by en face analysis as described in Materials and Methods in Example 3.

FIG. 18A demonstrates that the bands migrating similarly to authentic 6F (arrow in the inset) exhibited the ESI-MS signature for 6F while the same region from those lanes without bands in this region of the gel (arrow in the inset) did not (FIG. 18B). In the inset EV=an empty vector tomato line (the control tomato); 1A=a tomato line transgenic for 6F; M=molecular markers.

FIG. 19A: Serum Amyloid A (SAA); FIG. 19B: paraoxonase-1 activity (PON); FIG. 19C: lysophosphatidic acid 16:0 (LPA 16:0); FIG. 19D: lysophosphatidic acid 18:0 (LPA 18:0); FIG. 19E: lysophosphatidic acid 18:1 (LPA 18:1); FIG. 19F: lysophosphatidic acid 20:4 (LPA 20:4); FIG. 19G: free 5-HETE levels; FIG. 19H: free 15-HETE levels; FIG. 19I: Free PGD2 levels; FIG. 19J: Free PGE2 levels; FIG. 19K: HDL-cholesterol. Measurements were made as described in Materials and Methods in Example 3 (LPA levels were determined by LC-ESI-MS/MS).

FIG. 21A: Serum Amyloid A (SAA); FIG. 21B: Total Cholesterol; FIG. 21C: Triglycerides; FIG. 21D: Paraoxonase-1 activity (PON); FIG. 21E: HDL-cholesterol; FIG. 21F: Lysophosphatidic acid (LPA) 18:1; FIG. 21G: LPA 18:2; FIG. 21H: LPA 20:4; FIG. 21I: Body Weight.

FIG. 22B: Free 5-HETE; FIG. 22C: Free 15-HETE; FIG. 22D: Free DHA; FIG. 22E: Free EPA.

FIG. 24A: Plasma Total Cholesterol; FIG. 24B: Plasma Triglycerides; FIG. 24C: Plasma HDL cholesterol levels; FIG. 24D: Plasma PON activity; FIG. 24E: Body Weight.

FIG. 25A: LPA 18:2 in the duodenum. FIG. 25B: LPA 20:4 in the duodenum. FIG. 25C: LPA 18:2 in the jejunum. FIG. 25D: LPA 20:4 in the jejunum. FIG. 25E: LPA 18:2 in the ileum. FIG. 25F: LPA 20:4 in the ileum.

FIG. 26A: LPA 18:2 duodenum. FIG. 26B: LPA 20:4 duodenum. FIG. 26C: LPA 18:2 jejunum. FIG. 26D: LPA 20:4 jejunum. FIG. 26E: LPA 18:2 ileum. FIG. 26F: LPA 20:4 ileum.

PGE2 levels were determined in the plasma of the mice described in FIG. 30A as described in Materials and Methods of Example 3.

FIG. 35 shows the nucleic acid sequence of the E8 promoter and 5'UTR partial sequence (2191 bp DNA, SEQ ID NO:5) from *Lycopersicon esculentum* ethylene-responsive fruit ripening gene.

DETAILED DESCRIPTION

Figure 1:
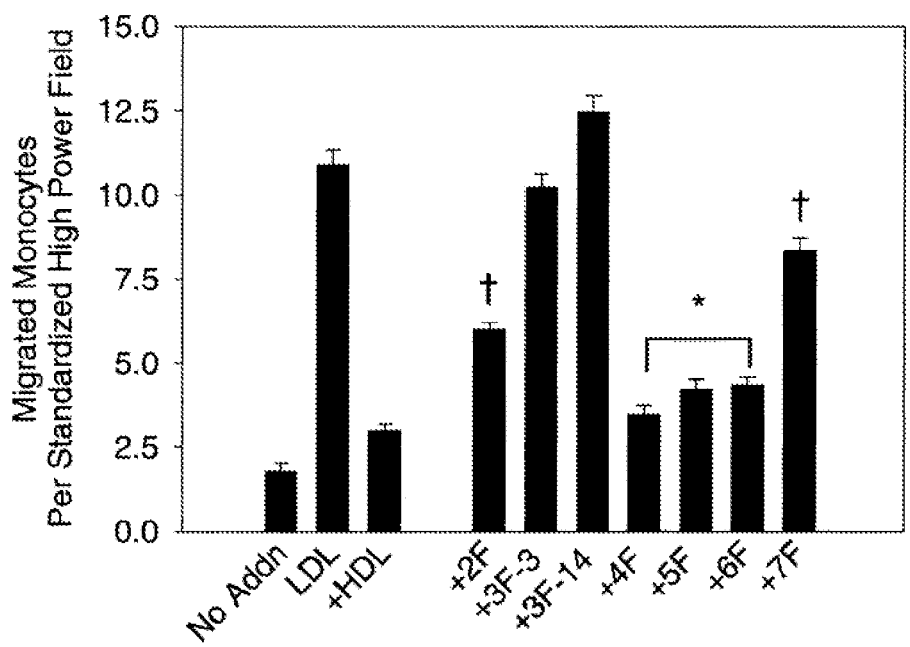
FIG. 1 shows the activity of various peptides in inhibition of monocyte chemotactic activity, a measure of peptide activity. This figure has been adapted from FIG. 5 in Datta et al. (2001) *J. Lipid Res.* 42: 1096-1104, and it demonstrates the equivalent efficacy of the peptides 4F, 5F and 6F in an in vitro assay.

It was a surprising discovery that the small intestine is an important site of action for various apoA-I mimetic peptides such as 4F, 6F, and the like. It was also determined that high dosages of such peptides are desirable to achieve optimum efficacy. However, because these peptides are typically administered daily and the daily cost of producing them would cost thousands of dollars per day per person, prior to the discoveries described herein, these peptides are not likely to find therapeutic use.

It was a surprising discovery that it was possible to produce stable transgenic plant lines that express therapeutic peptides (e.g., apolipoprotein peptides and apolipoprotein mimetic peptides), especially ApoA-I mimetic peptides, and related peptides described herein, that have desired biological activities (e.g., a reduction in SAA, an increase in plasma paraoxonase activity, and the like). It was also a surprising discovery that successfully transfected plants (or portions thereof) can simply be incorporated into the diet of the subject to be "treated" and the expressed peptide(s), when consumed as a food additive, show therapeutic and/or prophylactic activity in the subject (e.g., as evidenced using appropriate biomarkers, e.g., decrease in SAA levels, and/or increase in plasma paraoxonase activity, etc.). It is believed that such a discovery is contrary to the prevailing dogma that therapeutic peptides expressed in plants must be purified (e.g., isolated from the plant tissue) to be utilized as a relevant therapeutic and/or prophylactic agent.

In particular, it was demonstrated that mice fed lyophilized tissue of a transgenic tomato expressing the 6F peptide showed a decrease in SAA levels and an increases in plasma paraoxonase activity. Also, it was demonstrated that about 2 hours after the mice finished eating a high-fat high-cholesterol Western diet supplemented with the 6F expressing transgenic plant, intact 6F peptide was detected in the small intestine of the mice, but was not found in their blood. This strongly suggests that the peptide acts in the small intestine and is then degraded before it is absorbed as component amino acids. This indicates that the peptides act in the intestine and should not have direct effects in organs other than the intestine and suggests that administration of the transgenic plants described herein (or parts/tissues thereof) has a high degree of safety. It was also observed that the tissue content of lysophosphatidic acid (18:2 and 20:4) significantly decreased in the small intestine after feeding the transgenic 6F tomatoes but not after feeding control tomatoes. The tissue levels of lysophosphatidic acid in the small intestine (but not the cholesterol levels in the small intestine) significantly correlated with the percent of aorta with atherosclerotic lesions suggesting that a major beneficial effect of the transgenic 6F tomatoes is mediated by decreasing the levels of lysophosphatidic acid in the small intestine. Again it is a surprising discovery that consumption of the transgenic plant (or part/tissue(s) thereof) could produce such effects as the prevailing approach is to purify (e.g., isolate from the plant tissue) the desired peptide(s) to be utilized as a relevant therapeutic and/or prophylactic agents.

Accordingly, in various embodiments, transgenic plants are provided comprising cells that express a peptide that consists of or that comprises, one or more domains of or comprising the amino acid sequence of an apolipoprotein or apolipoprotein mimetic, e.g., an ApoA-I mimetic peptide and/or a G* peptide, and/or an apoE peptide, and/or any other therapeutic peptide described herein. In various embodiments the peptide is expressed in levels sufficient to decrease SAA levels in a mammal and/or to decrease the tissue content of lysophosphatidic acid (18:2 and 20:4) in the small intestine, when the plant or a portion/part thereof is fed to the mammal (e.g., to a mouse model of atherosclerosis), and/or to increase plasma paroxonase activity when the plant, or a portion thereof, is fed to the mammal. Illustrative transgenic plants include, but are not limited to transgenic tomatoes, transgenic carrot, transgenic potato, transgenic apple, transgenic pear, transgenic plum, transgenic peach, transgenic orange, transgenic kiwi, transgenic payaya, transgenic pineapple, transgenic guava, transgenic lilikoi, transgenic starfruit, transgenic lychee, transgenic mango, transgenic grape, transgenic pomegranate, transgenic mustard greens, transgenic kale, transgenic chard, transgenic lettuce, transgenic soybean, transgenic rice, transgenic corn and other grains (e.g., wheat, rice, barley, bulgur, faro, kamut, kañiwa, millet, oats, quinoa, rice, rye, sorghum, spelt, teff, triticale, and the like), transgenic berries such as strawberries, blueberries, blackberries, goji berries, and raspberries, transgenic banana, transgenic rice, transgenic turnip, transgenic maize, transgenic grape, transgenic fig, transgenic plum, transgenic potato, transgenic safflower seeds, transgenic nuts (e.g., almond, walnut, pecan, peanut, cashew, macademia, hazelnut, etc.), transgenic legumes (e.g., alfalfa, clover, peas, beans (including black beans), lentils, lupins, mesquite, carob, soybeans, and the like), and transgenic tobacco.

In certain embodiments the peptide that is expressed comprises a single apolipoprotein sequence or apolipoprotein mimetic sequence, e.g., an ApoA-I mimetic peptide amino acid sequence (see, e.g., Table 1), or a single G* peptide amino acid sequence (see, e.g., Table 2), and/or a single ApoE peptide amino acid sequence (see, e.g., Table 3), or a single other therapeutic peptide described herein. In various embodiments the peptide comprises two or more domains each of which comprises or consists of an apolipoprotein or apolipoprotein mimetic sequence, e.g., an ApoA-I mimetic peptide amino acid sequence (see, e.g., Table 1), and/or a G* peptide amino acid sequence (see, e.g., Table 2), and/or an apoE peptide amino acid sequence (see, e.g., Table 3), and/or another therapeutic peptide described herein. In certain embodiments the peptide that is expressed comprise at least 2, at least 3, at least 4, at least 5, at least 6, at least 7, at least 8, at least 9, or at 10, at least 15, at least 20, at least 25, such domains. The domains can be the same of different or any combination of an ApoA-I mimetic peptide amino acid sequence (see, e.g., Table 1), and/or a G* peptide amino acid sequence (see, e.g., Table 2), and/or an apoE peptide amino acid sequence (see, e.g., Table 3), and/or another therapeutic peptide described herein. The various domains can be directly linked to each other or they can be separated by one or more amino acids. In certain embodiments the domains are separated by a single proline (P), or by two prolines (PP), or by three prolines (PPP), or by a single alanine (A) or by two alanines (AA), or by three alanines (AAA). In certain embodiments the domains are separated by a KVEPLRA (SEQ ID NO:6) linker region, GGG linker region, or by a GGGG (SEQ ID NO:7) linker region, or by a GGGGS (SEQ ID NO:8) linker region or a (GGGGS)$_2$ (SEQ ID NO:9) linker region, or by a (GGGGS)$_3$ (SEQ ID NO:10) linker region. In certain embodiments the domains are separated from each other by 1 amino acid, or by 2 amino acids, or by 3 amino acids, or by 4 amino acids, or by 5 amino acids, or by 6 amino acids, or by 7 amino acids, or by 8 amino acids, or by 9 amino acids, or by 10 or more amino acids, or by 15 or more amino acids, or by 20 or more amino acids, or by 25 or more amino acids, or by 30 or more amino acids, or by 35 or more amino acids, or by 40 or more amino acids, or by 45 or more amino acids, or by 55 or more amino acids. In certain embodiments the expressed peptide ranges in length from about 5 amino acids, or about 6 amino acids, or about 7 amino acids, or about 8 amino acids, or about 9 amino acids, or about 10 amino acids, or about 12 amino acids, up to a length of about 15 amino acids, or up to a length of about 18, or up to a length of about 20 amino acids, or up to a length of about 30 amino acids, or up to a length of about 36 amino acids, or up to a length of about 37 amino acids, or up to a length of about 40 amino acids, or up to a length of about 50 amino acids, or up to a length of about 60 amino acids, or up to a length of about 70 amino acids, or up to a length of about 80 amino acids, or up to a length of about 90 amino acids, or up to a length of about 100 amino acids, or up to a length of about 110 amino acids, or up to a length of about 120 amino acids, or up to a length of about 130 amino acids, or up to a length of about 140 amino acids, or up to a length of about 150 amino acids, or up to a length of about 160 amino acids, or up to a length of about 170 amino acids, or up to a length of about 180 amino acids, or up to a length of about 190 amino acids, or up to a length of about 200 amino acids. In any case the peptide composition is selected such that when fed to an animal (as an isolated peptide, or more preferably when the plant tissue is fed to a mammal) SAA levels in the mammal decrease and/or plasma paroxonase activity increases.

In addition to such transgenic plants, in various embodiments, parts of such plants are also provided. Illustrative parts of such transgenic plants include seeds of such plants, fruits of such plants, leaves of such plants, roots of such plants, cuttings of such plants. In addition cuttings, grafts, and clones of such plants are also contemplated. With respect to grafts, it is contemplated that a wild-type (or other plant) can be grafted with elements of a transgenic plant so that a portion of the plant comprises cells of the transgenic plant as described above.

In certain embodiments, a food and/or food product is provided that comprise at least a portion of a transgenic plant (as described herein) capable of being ingested for its taste and/or nutritional value. The transgenic plant expresses a peptide comprising an amino acid sequence comprises an ApoA-I mimetic peptide amino acid sequence, and/or a G* peptide amino acid sequence, and/or another therapeutic as described herein, and in certain embodiments, the food and/or food product comprises sufficient amount of the plant (and the plant comprises a sufficient amount of the active peptide) that ingestion of the food provides a desirable prophylactic and/or therapeutic activity (e.g., lowering of SAA, and/or increasing plasma paraoxonase activity, etc.) as described herein.

The transgenic plants described herein and/or peptides isolated therefrom, also find use in the manufacture of protein powders and other nutritional supplements. For example, in certain embodiments, a protein powder is contemplated where at least a portion of the protein powder comprises a peptide as described herein (e.g., an ApoA-I mimetic peptide, and/or a G* peptide, and/or an apoE peptide, and or another therapeutic peptide as described herein) and/or a transgenic plant or part thereof comprising such a peptide. Similarly, in certain embodiments, nutritional supplements are contemplated. Illustrative supplements include, but are not limited to vitamin supplements comprising a peptide as described herein (e.g., an ApoA-I mimetic peptide, and/or a G* peptide, and/or an apoE peptide, and/or another therapeutic peptide as described herein) and/or a transgenic plant or part thereof comprising such a peptide.

Also contemplated are "power bars" or other food products comprising a peptide as described herein (e.g., an ApoA-I mimetic peptide, and/or a G* peptide, and/or an apoE peptide, and/or another therapeutic peptide as described herein) and/or a transgenic plant or part (e.g., tissue) thereof comprising such a peptide. Such power bars include for example, dietary supplement bars, protein bars, energy bars, and other sports and/or nutrition bars.

In various embodiments methods of prophylaxis and/or treatment are also provided. Such methods include a method for the treatment or prophylaxis of a pathology characterized by an inflammatory response (e.g., atherosclerosis). The methods typically involve administering (or causing to be administered) to a mammal in need thereof an effective amount of at least a portion of a transgenic plant (e.g., transgenic plant tissue) as described herein, and/or a peptide derived from such a plant, and/or a food comprising at least a portion of such a plant; and/or a protein powder nutritional supplement, or power bar (or other food product) as described herein. Illustrative pathologies include, but are not limited to Alzheimer's disease, atherosclerosis, arthritis, cancer, diabetes, hepatic fibrosis, macular degeneration, kidney disease, metabolic syndrome, obesity, osteoporosis, scleroderma, systemic lupus erythematosus, transplant vasculopathy, and vascular dementia.

ApoA-I Mimetic Peptides, G* Peptides, apoE Peptides, and Other Therapeutic Peptides.

Activity of ApoA-I Mimetic Peptides.

To determine if the dose of peptide administered or the plasma level was more important, doses of 0.15, 0.45, 4.5, or 45 mg/kg/day of the synthetic peptide D-4F were administered orally or subcutaneously (SQ) to apolipoprotein (apo)E null mice. Plasma levels of peptide were 1,000-fold higher when administered SQ compared with orally. Regardless of the route of administration, doses of 4.5 and 45 mg/kg significantly reduced plasma serum amyloid A (SAA) levels and the HDL inflammatory index (P<0.0001), while doses of 0.15 or 0.45 mg/kg did not. A dose of 45 mg/kg/day administered to apoE null mice on a Western diet reduced aortic atherosclerosis by ~50% (P<0.0009) whether administered orally or SQ and also significantly reduced plasma levels of SAA (P<0.002) and lysophosphatidic acid (P<0.0009).

The data showed that the dose of the apoA-I mimetic peptide 4F administered to apoE null (apoE−/−) mice determined efficacy, but plasma and hepatic levels of peptide did not (see, e.g., Navab et al. (2011) J. Lipid Res. 52: 1200-1210). Since efficacy was similar at the same doses, but plasma and hepatic levels were dramatically higher when the peptide was administered by subcutaneous injection (SQ) compared to oral administration, it was suspected that there might be a compartment outside of the liver or plasma where peptide concentration would be similar. It was found that the concentration of D-4F in the feces was the same regardless of whether the peptide was administered SQ or orally suggesting that the intestine maybe a major site of action for the peptide regardless of the route of administration (Id.).

The concentration of free 15-HETE and 13-HODE in the plasma of apoE−/− mice was significantly higher than that of wild-type mice (Imaizumi et al. (2010) Drug Metab. Lett. 4: 139-148). After administration of the 4F peptide, plasma levels of free oxidized fatty acids that bound with higher affinity to the mimetic peptide compared to apoA-I (e.g. 5-HETE, 15-HETE, 9-HODE, 13-HODE) significantly decreased but the levels of 20-HETE which bound with equal low affinity to apoA-1 and 4F did not decrease (see, e.g., Imaizumi et al. supra.). These studies focused on the plasma levels of free oxidized fatty acids, which are only a small fraction (<10%) of the total plasma oxidized fatty acids. Interestingly, only the free oxidized fatty acid plasma levels decreased after the administration of the apoA-I mimetic peptide; esterified oxidized fatty acid levels were unchanged (Id.).

In other studies, apoE−/− mice were made diabetic, resulting in a significant increase in the hepatic content of free arachidonic acid and free 12-HETE, 15-HETE, 13-HODE, PGD2 and PGE2. This was associated with a significant increase in aortic atherosclerosis. Oral administration of D-4F significantly decreased the hepatic content of free arachidonic acid and free oxidized fatty acids derived from arachidonic and linoleic acids, and significantly decreased aortic atherosclerosis, without affecting other plasma lipid or lipoprotein levels (Morgantini et al. (2010) Diabetes. 59: 3223-3228).

It was also determined that HDL from type 2 diabetics contained significantly more free 5-HETE, 12-HETE, 15-HETE, 9-HODE and 13-HODE than HDL from healthy volunteers. The type 2 diabetic HDL was also pro-inflammatory in a cell-based assay and was abnormal in a cell-free assay. The HDL content of free 5-HETE, 12-HETE, 15-HETE, 9-HODE and 13-HODE significantly correlated with the values obtained in the cell-free assay (Morgantini et al. (2011) Diabetes; 60: 2617-2623).

To test the hypothesis that intestine is a major site of action for D-4F, LDLR−/− mice were fed a Western Diet (WD) and administered the peptide subcutaneously (SQ) or orally at 900 μg peptide/mouse/day (~45 mg/kg/day). Plasma and liver D-4F levels were 298-fold and 96-fold higher, respectively, after SQ administration, while peptide levels in small intestine only varied by 1.66±0.33-fold. Levels of free metabolites of arachidonic and linoleic acids known to bind with high affinity to D-4F were significantly reduced in intestine, liver and hepatic bile to a similar degree whether administered SQ or orally. However, levels of 20-HETE, which is known to bind with low affinity, were unchanged. D-4F treatment reduced plasma SAA and triglyceride levels (p<0.03) and increased HDL-cholesterol (p<0.04) similarly after SQ or oral administration. Plasma levels of metabolites of arachidonic and linoleic acids significantly correlated with SAA levels (p<0.0001). Feeding 15-HETE in chow (without WD) significantly increased plasma SAA and triglyceride levels and decreased HDL-cholesterol and paroxonase activity (p<0.05), all of which were significantly ameliorated by SQ D-4F (p<0.05).

Without being bound to a particular theory, it is believed that the 4F peptide, 6F peptide, (and other ApoA-I mimetic peptides, and/or other peptides described herein) reduce levels of metabolites of arachidonic and linoleic acids in the small intestine and this is associated with decreased inflammation in LDLR−/− mice (Navab et al. (2012) *J. Lipid Res.* 53: 437-445). Moreover, as indicated above it is believed that such peptides find use in the treatment and/or prophylaxis of atherosclerosis. Such peptides are also believed to be useful in the treatment and/or prevention of cancer, and or in the treatment and/or prevention of a number of other pathologies, e.g., arthritis, atherosclerosis, cancer, diabetes, hepatic fibrosis, macular degeneration, kidney disease, obesity, osteoporosis, scleroderma, systemic lupus erythematosus, transplant vasculopathy, vascular dementia, and the like. Other pathologies include, but are not limited to any of the pathologies disclosed in PCT/US2006/014839 (WO/2006/118805) which is incorporated herein by reference for the pathologies and peptides disclosed therein. Illustrative conditions are shown in Table 5 below.

While the foregoing discussion focuses on ApoA-I mimetic peptides, it is noted that similar activities have been demonstrated for G* (ApoJ peptides), ApoE, peptides, combined ApoA-ApoE peptides, and the like (see, e.g., U.S. Pat. Nos. 6,930,085, and 7,638,494, PCT Publication PCT/US03/09988 (WO 2003/086326), U.S. Pat. No. 7,148,197, Publication PCT/US2004/026288 (WO/2005/016280), U.S. Pat. Nos. 6,933,279, 7,144,862, 7,166,578, 7,199,102, 7,531,514, 7,820,784, and 7,994,132, and PCT Publications PCT/US2001/026497 (WO 02/15923), PCT/US03/32442 (WO 2004/034977), and PCT/US2006/014839 (WO/2006/118805).

In view of the showing herein that transgenic plants that express the 6F peptide can provide a desirable (therapeutic or prophylactic) physiological effect, e.g., to decrease SAA levels and/or to increase plasma paroxonase activity when the plant, or a portion thereof, is fed to a mammal, and the demonstration of the similar activity profiles of other peptides described herein, it is believed that transgenic plants expressing a peptide consisting of or comprising one or more domains the amino acid sequence of which is an ApoA-I peptide (or mimetic), and/or an ApoJ peptide (or mimetic) and/or an ApoE peptide (or mimetic thereof), or combined ApoA-ApoE peptides and various concatamers thereof are contemplated.

ApoA-I Mimetics and Other Peptides for Expression in Plants.

As indicated above, having demonstrated that the 6F peptide when expressed in a plant (e.g., a tomato) shows significant biological activity when the plant or plant part is fed to a mammal without purification of the peptide away from the plant tissue, it is believed that a similar result can be obtained with any of a number of other therapeutic peptides or peptides/proteins comprising domains that are therapeutic peptide sequences and these results can be obtained by expression of the peptide(s) in other plants, e.g., as described herein.

In certain embodiments these peptides include, but are not limited to class A amphipathic helical peptides, class A amphipathic helical peptide mimetics of apoA-I having aromatic or aliphatic residues in the non-polar face, Apo-J (G* peptides), apoE peptides, and the like, and peptide mimetics, e.g., as described below.

ApoA-I Mimetic Peptides.

In certain embodiments the peptides expressed in a transgenic plant comprise or consist of apoA-I mimetic peptides. In certain embodiments such peptides include, but are not limited to, class A amphipathic helical peptides, e.g. as described in U.S. Pat. No. 6,664,230, and PCT Publications WO 02/15923 and WO 2004/034977, which are incorporated herein by reference for the peptide sequences disclosed therein. It was discovered that peptides comprising a class A amphipathic helix ("class A peptides"), in addition to being capable of mitigating one or more symptoms of atherosclerosis are also useful in the treatment of one or more of the other indications described herein.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) *Meth. Enzymol,* 128: 626-668). It is noted that the fourth exon of apo A-I, when folded into 3.667 residues/turn produces a class A amphipathic helical structure.

Significant biological activity has been demonstrated for various apoA-I mimetic peptides including, but not limited to the peptides designated 4F, retro (reverse 4F), 5F, 6F, and the like. Various class A peptides inhibited lesion development in atherosclerosis-susceptible mice. In addition, the peptides show varying, but significant degrees of efficacy in mitigating one or more symptoms of the various pathologies described herein. A number of such peptides described in PCT patent application Nos: PCT/US2001/026497 (WO 02/15923), PCT/US03/32442 (WO 2004/034977), PCT/US2008/085409, and in Bielicki et al. (2010) *J. Lipid Res.* 51: 1496-1503, Zheng et al. (2011) *Biochemistry* 50: 4068-4076, Di Bartolo et al. (2011) *Lipids in Health and Disease* 10: 224. In certain embodiments the peptides expressed in the transgenic plants comprise one or more domains that have an amino acid sequence shown in Table 1 or the reverse sequence.

TABLE 1

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| 18A | DWLKAFYDKVAEKLKEAF | 11 |
| 2F | DWLKAFYDKVAEKLKEAF | 12 |
| 3F | DWFKAFYDKVAEKLKEAF | 13 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| 3F14 | DWLKAFYDKVAEKFKEAF | 14 |
| 4F | DWFKAFYDKVAEKFKEAF | 15 |
| 5F | DWLKAFYDKVFEKFKEFF | 16 |
| 6F | DWLKAFYDKFFEKFKEFF | 17 |
| 7F | DWFKAFYDKFFEKFKEFF | 18 |
|  | DWLKAFYDKVAEKLKEFF | 19 |
| Rev18A | FAEKLKEAVKDYFAKLWD | 20 |
| Rev2F | FAEKLKEAVKDYFAKLWD | 21 |
| Ref3F | FAEKLKEAVKDYFAKFWD | 22 |
| Rev4F | FAEKFKEAVKDYFAKFWD | 23 |
| Rev5F | FFEKFKEFVKDYFAKLWD | 24 |
| Rev6F | FFEKFKEFFKDYFAKLWD | 25 |
| Rev7F | FFEKFKEFFKDYFAKFWD | 26 |
|  | DWLKAFYDKVFEKFKEAF | 27 |
|  | DWLKAFYDKVFEKLKEFF | 28 |
|  | DWLKAFYDKVAEKFKEFF | 29 |
|  | DWLKAFYDKVFEKFKEFF | 30 |
|  | EWLKLFYEKVLEKFKEAF | 31 |
|  | EWLKAFYDKVAEKFKEAF | 32 |
|  | EWLKAFYDKVAEKLKEFF | 33 |
|  | EWLKAFYDKVFEKFKEAF | 34 |
|  | EWLKAFYDKVFEKLKEFF | 35 |
|  | EWLKAFYDKVAEKFKEFF | 36 |
|  | EWLKAFYDKVFEKFKEFF | 37 |
|  | AFYDKVAEKLKEAF | 38 |
|  | AFYDKVAEKFKEAF | 39 |
|  | AFYDKVAEKFKEAF | 40 |
|  | AFYDKFFEKFKEFF | 41 |
|  | AFYDKFFEKFKEFF | 42 |
|  | AFYDKVAEKFKEAF | 43 |
|  | AFYDKVAEKLKEFF | 44 |
|  | AFYDKVFEKFKEAF | 45 |
|  | AFYDKVFEKLKEFF | 46 |
|  | AFYDKVAEKFKEFF | 47 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| | KAFYDKVFEKFKEF | 48 |
| | LFYEKVLEKFKEAF | 49 |
| | AFYDKVAEKFKEAF | 50 |
| | AFYDKVAEKLKEFF | 51 |
| | AFYDKVFEKFKEAF | 52 |
| | AFYDKVFEKLKEFF | 53 |
| | AFYDKVAEKFKEFF | 54 |
| | AFYDKVFEKFKEFF | 55 |
| | DWLKALYDKVAEKLKEAL | 56 |
| | DWFKAFYEKVAEKLKEFF | 57 |
| | DWFKAFYEKFFEKFKEFF | 58 |
| | EWLKALYEKVAEKLKEAL | 59 |
| | EWLKAFYEKVAEKLKEAF | 60 |
| | EWFKAFYEKVAEKLKEFF | 61 |
| | EWLKAFYEKVFEKFKEFF | 62 |
| | EWLKAFYEKFFEKFKEFF | 63 |
| | EWFKAFYEKFFEKFKEFF | 64 |
| | DFLKAWYDKVAEKLKEAW | 65 |
| | EFLKAWYEKVAEKLKEAW | 66 |
| | DFWKAWYDKVAEKLKEWW | 67 |
| | EFWKAWYEKVAEKLKEWW | 68 |
| | DKLKAFYDKVFEWAKEAF | 69 |
| | DKWKAVYDKFAEAFKEFL | 70 |
| | EKLKAFYEKVFEWAKEAF | 71 |
| | EKWKAVYEKFAEAFKEFL | 72 |
| | DWLKAFVDKFAEKFKEAY | 73 |
| | EKWKAVYEKFAEAFKEFL | 74 |
| | DWLKAFVYDKVFKLKEFF | 75 |
| | EWLKAFVYEKVFKLKEFF | 76 |
| | DWLRAFYDKVAEKLKEAF | 77 |
| | EWLRAFYEKVAEKLKEAF | 78 |
| | DWLKAFYDRVAEKLKEAF | 79 |
| | EWLKAFYERVAEKLKEAF | 80 |
| | DWLKAFYDKVAERLKEAF | 81 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| | EWLKAFYEKVAERLKEAF | 82 |
| | DWLKAFYDKVAEKLREAF | 83 |
| | EWLKAFYEKVAEKLREAF | 84 |
| | DWLKAFYDRVAERLKEAF | 85 |
| | EWLKAFYERVAERLKEAF | 86 |
| | DWLRAFYDKVAEKLREAF | 87 |
| | EWLRAFYEKVAEKLREAF | 88 |
| | DWLRAFYDRVAEKLREAF | 89 |
| | EWLRAFYERVAEKLREAF | 90 |
| | DWLKAFYDKVAERLREAF | 91 |
| | EWLKAFYEKVAERLREAF | 92 |
| | DWLRAFYDKVAERLKEAF | 93 |
| | EWLRAFYEKVAERLKEAF | 94 |
| | DWLKAFYDKVAEKLKEAFPDWLKAFYDKVAEKLKEAF | 95 |
| | DWLKAFYDKVAEKLKEFFPDWLKAFYDKVAEKLKEFF | 96 |
| | DWFKAFYDKVAEKLKEAFPDWFKAFYDKVAEKLKEAF | 97 |
| | DKLKAFYDKVFEWAKEAFPDKLKAFYDKVFEWLKEAF | 98 |
| | DKWKAVYDKFAEAFKEFLPDKWKAVYDKFAEAFKEFL | 99 |
| | DWFKAFYDKVAEKFKEAFPDWFKAFYDKVAEKFKEAF | 100 |
| | DWLKAFVYDKVFKLKEFFPDWLKAFVYDKVFKLKEFF | 101 |
| | DWLKAFYDKFAEKFKEFFPDWLKAFYDKFAEKFKEFF | 102 |
| | EWFKAFYEKVAEKFKEAF | 103 |
| | DWFKAFYDKVAEKF | 104 |
| | FKAFYDKVAEKFKE | 105 |
| | FKAFYEKVAEKFKE | 106 |
| | FKAFYDKVAEKFKE | 107 |
| | FKAFYEKVAEKFKE | 108 |
| | DWFKAFYDKVAEKFKEAF | 109 |
| | EWFKAFYEKVAEKFKEAF | 110 |
| | AFYDKVAEKFKEAF | 111 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| | DWFKAFYDKVAEKF | 112 |
| | DWLKAFYDKVFEKFKEFF | 113 |
| | EWLKAFYEKVFEKFKEFF | 114 |
| | AFYDKVFEKFKEFF | 115 |
| | AFYEKVFEKFKEFF | 116 |
| | DWLKAFYDKVFEKF | 117 |
| | EWLKAFYEKVFEKF | 118 |
| | LKAFYDKVFEKFKE | 119 |
| | LKAFYEKVFEKFKE | 120 |
| [Switch D-E]-1-4F | EWFKAFYEKVADKFKDAF | 121 |
| [Switch D-E]-2-4F | EWFKAFYDKVADKFKEAF | 122 |
| [Switch D-E]-3-4F | DWFKAFYEKVADKFKEAF | 123 |
| [Switch D-E]-4-4F | DWFKAFYEKVAEKFKDAF | 124 |
| 4F-2 | DFWKAFYDKVAEKFKEAF | 125 |
| [Switch D-E]-1-4F-2 | EFWKAFYEKVADKFKDAF | 126 |
| [Switch D-E]-2-4F-2 | EFWKAFYDKVADKFKEAF | 127 |
| [Switch D-E]-3-4F-2 | DFWKAFYEKVADKFKEAF | 128 |
| [Switch D-E]-4-4F-2 | DFWKAFYEKVAEKFKDAF | 129 |
| 4F-3 | DWFKAYFDKVAEKFKEAF | 130 |
| [Switch D-E]-1-4F-5 | EWFKAYFEKVADKFKDAF | 131 |
| [Switch D-E]-2-4F-5 | EWFKAYFDKVADKFKEAF | 132 |
| [Switch D-E]-3-4F-5 | DWFKAYFEKVADKFKEAF | 133 |
| [Switch D-E]-4-4F-5 | DWFKAYFEKVAEKFKDAF | 134 |
| 4F-4 | DWFKAFVDKYAEKFKEAF | 135 |
| [Switch D-E]-1-4F-4 | EWFKAFVEKYADKFKDAF | 136 |
| [Switch D-E]-2-4F-4 | EWFKAFVDKYADKFKEAF | 137 |
| [Switch D-E]-3-4F-4 | DWFKAFVEKYADKFKEAF | 138 |
| [Switch D-E]-4-4F | DWFKAFVEKYAEKFKDAF | 139 |
| 4-F-5 | DWFKAFYDKAVEKFKEAF | 140 |
| [Switch D-E]-1-4F-5 | EWFKAFYEKAVDKFKDAF | 141 |
| [Switch D-E]-2-4F-5 | EWFKAFYDKAVDKFKEAF | 142 |
| [Switch D-E]-3-4F-5 | DWFKAFYEKAVDKFKEAF | 143 |
| [Switch D-E]-4-4F-5 | DWFKAFYEKAVEKFKDAF | 144 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| 4F-6 | DWFKAFYDKVFEKAKEAF | 145 |
| [Switch D-E]-1-4F-6 | EWFKAFYEKVFDKAKDAF | 146 |
| [Switch D-E]-2-4F-6 | EWFKAFYDKVFDKAKEAF | 147 |
| [Switch D-E]-3-4F-6 | DWFKAFYEKVFDKAKEAF | 148 |
| [Switch D-E]-4-4F-6 | DWFKAFYEKVFEKAKDAF | 149 |
| 4F-7 | DWFKAFYDKVAEKAKEFF | 150 |
| [Switch D-E]-1-4F-7 | EWFKAFYEKVADKAKDFF | 151 |
| [Switch D-E]-2-4F-7 | EWFKAFYDKVADKAKEFF | 152 |
| [Switch D-E]-3-4F-7 | DWFKAFYEKVADKAKEFF | 153 |
| [Switch D-E]-4-4F-7 | DWFKAFYEKVAEKAKDFF | 154 |
| 4F-8 | DWFKAFYDKVAEKFKEFA | 155 |
| [Switch D-E]-1-4F-8 | EWFKAFYEKVADKFKDFA | 156 |
| [Switch D-E]-2-4F-8 | EWFKAFYDKVADKFKEFA | 157 |
| [Switch D-E]-3-4F-8 | DWFKAFYEKVADKFKEFA | 158 |
| [Switch D-E]-4-4F-8 | DWFKAFYEKVAEKFKDFA | 159 |
| 4F-9 | DAFKAFYDKVAEKFKEWF | 160 |
| [Switch D-E]-1-4F-9 | EAFKAFYEKVADKFKDWF | 161 |
| [Switch D-E]-2-4F-9 | EAFKAFYDKVADKFKEWF | 162 |
| [Switch D-E]-3-4F-9 | DAFKAFYEKVADKFKEWF | 163 |
| [Switch D-E]-4-4F-9 | DAFKAFYEKVAEKFKDWF | 164 |
| 4F-10 | DAFKAFYDKVWEKFKEAF | 165 |
| [Switch D-E]-1-4F-10 | EAFKAFYEKVWDKFKDAF | 166 |
| [Switch D-E]-2-4F-10 | EAFKAFYDKVWDKFKEAF | 167 |
| [Switch D-E]-3-4F-10 | DAFKAFYEKVWDKFKEAF | 168 |
| [Switch D-E]-4-4F-10 | DAFKAFYEKVWEKFKDAF | 169 |
| 4F-11 | DYFKAFWDKVAEKFKEAF | 170 |
| [Switch D-E]-1-4F-11 | EYFKAFWEKVADKFKDAF | 171 |
| [Switch D-E]-2-4F-11 | EYFKAFWDKVADKFKEAF | 172 |
| [Switch D-E]-3-4F-11 | DYFKAFWEKVADKFKEAF | 173 |
| [Switch D-E]-4-4F-11 | DYFKAFWEKVAEKFKDAF | 174 |
| 4F-12 | DWAKAFYDKVAEKFKEFF | 175 |
| [Switch D-E]-1-4F-12 | EWAKAFYEKVADKFKDFF | 176 |
| [Switch D-E]-2-4F-12 | EWAKAFYDKVADKFKEFF | 177 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| [Switch D-E]-3-4F-12 | DWAKAFYEKVADKFKEFF | 178 |
| [Switch D-E]-4-4F-12 | DWAKAFYEKVAEKFKDFF | 179 |
| 4F-13 | DWFKAAYDKVAEKFKEFF | 180 |
| [Switch D-E]-1-4F-13 | EWFKAAYEKVADKFKDFF | 181 |
| [Switch D-E]-2-4F-13 | EWFKAAYDKVADKFKEFF | 182 |
| [Switch D-E]-3-4F-13 | DWFKAAYEKVADKFKEFF | 183 |
| [Switch D-E]-4-4F-13 | DWFKAAYEKVAEKFKDFF | 184 |
| 4F-14 | DWFKAFADKVAEKFKEYF | 185 |
| [Switch D-E]-1-4F-14 | EWFKAFAEKVADKFKDYF | 186 |
| [Switch D-E]-2-4F-14 | EWFKAFADKVADKFKEYF | 187 |
| [Switch D-E]-3-4F-14 | DWFKAFAEKVADKFKEYF | 188 |
| [Switch D-E]-4-4F | DWFKAFAEKVAEKFKDYF | 189 |
| 4F-15 | DWFKAFYDKAAEKFKEVF | 190 |
| [Switch D-E]-1-4F-15 | EWFKAFYEKAADKFKDVF | 191 |
| [Switch D-E]-2-4F-15 | EWFKAFYDKAADKFKEVF | 192 |
| [Switch D-E]-3-4F-15 | DWFKAFYEKAADKFKEVF | 193 |
| [Switch D-E]-4-4F-15 | DWFKAFYEKAAEKFKDVF | 194 |
| 4F-16 | DWYKAFFDKVAEKFKEAF | 195 |
| [Switch D-E]-1-4F-16 | EWYKAFFEKVADKFKDAF | 196 |
| [Switch D-E]-2-4F-16 | EWYKAFFDKVADKFKEAF | 197 |
| [Switch D-E]-3-4F-16 | DWYKAFFEKVADKFKEAF | 198 |
| [Switch D-E]-4-4F-16 | DWYKAFFEKVAEKFKDAF | 199 |
| 4F-17 | DWVKAFYDKFAEKFKEAF | 200 |
| [Switch D-E]-1-4F-17 | EWVKAFYEKFADKFKDAF | 201 |
| [Switch D-E]-2-4F-17 | EWVKAFYDKFADKFKEAF | 202 |
| [Switch D-E]-3-4F-17 | DWVKAFYEKFADKFKEAF | 203 |
| [Switch D-E]-4-4F-17 | DWVKAFYEKFAEKFKDAF | 204 |
| 4F-18 | DWKAFFDKVAEKYKEAF | 205 |
| [Switch D-E]-1-4F-18 | EWFKAFFEKVADKYKDAF | 206 |
| [Switch D-E]-2-4F-18 | EWFKAFFDKVADKYKEAF | 207 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| [Switch D-E]-3-4F-18 | DWFKAFFEKVADKYKEAF | 208 |
| [Switch D-E]-3-4F-18 | DWFKAFFEKVADKYKEAF | 209 |
| 4F-19 | DWFKAFFDKVAEKFKEAY | 210 |
| [Switch D-E]-1-4F-19 | EWFKAFFEKVADKFKDAY | 211 |
| [Switch D-E]-2-4F-19 | EWFKAFFDKVADKFKEAY | 212 |
| [Switch D-E]-3-4F-19 | DWFKAFFEKVADKFKEAY | 213 |
| [Switch D-E]-4-4F-19 | DWFKAFFEKVAEKFKDAY | 214 |
| 4F-20 | DWFKAFYDKFAEKFKEAV | 215 |
| [Switch D-E]-1-4F-20 | EWFKAFYEKFADKFKDAV | 216 |
| [Switch D-E]-2-4F-20 | EWFKAFYDKFADKFKEAV | 217 |
| [Switch D-E]-3-4F-20 | DWFKAFYEKFADKFKEAV | 218 |
| [Switch D-E]-4-4F-20 | DWFKAFYEKFAEKFKDAV | 219 |
| 4F-21 | DKFKAFYDKVAEKFWEAF | 220 |
| [Switch D-E]-1-4F-21 | EKFKAFYEKVADKFWDAF | 221 |
| [Switch D-E]-2-4F-21 | EKFKAFYDKVADKFWEAF | 222 |
| [Switch D-E]-3-4F-21 | DKFKAFYEKVADKFWEAF | 223 |
| [Switch D-E]-4-4F-21 | DKFKAFYEKVAEKFWDAF | 224 |
| 4F-22 | DKWKAFYDKVAEKFFEAF | 225 |
| [Switch D-E]-1-4F-22 | EKWKAFYEKVADKFFDAF | 226 |
| [Switch D-E]-2-4F-22 | EKWKAFYDKVADKFFEAF | 227 |
| [Switch D-E]-3-4F-22 | DKWKAFYEKVADKFFEAF | 228 |
| [Switch D-E]-4-4F-22 | DKWKAFYEKVAEKFFDAF | 229 |
| 4F-23 | DKFKAFYDKWAEVFKEAF | 230 |
| [Switch D-E]-1-4F-23 | EKFKAFYEKWADVFKDAF | 231 |
| [Switch D-E]-2-4F-23 | EKFKAFYDKWADVFKEAF | 232 |
| [Switch D-E]-3-4F-23 | DKFKAFYEKWADVFKEAF | 233 |
| [Switch D-E]-4-4F-23 | DKFKAFYEKWAEVFKDAF | 234 |
| 4F-24 | DKFKAFYDKVAEFWKEAF | 235 |
| [Switch D-E]-1-4F-24 | EKFKAFYEKVADFWKDAF | 236 |
| [Switch D-E]-2-4F-24 | EKFKAFYDKVADFWKEAF | 237 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
| --- | --- | --- |
| [Switch D-E]-3-4F-24 | DKFKAFYEKVADFWKEAF | 238 |
| [Switch D-E]-4-4F-24 | DKFKAFYEKVAEFWKDAF | 239 |
| Rev-4F | FAEKFKEAVKDYFAKFWD | 240 |
| [Switch D-E]-1-Rev-4F | FADKFKDAVKEYFAKFWE | 241 |
| [Switch D-E]-2-Rev-4F | FADKFKEAVKDYFAKFWE | 242 |
| [Switch D-E]-3-Rev-4F | FAEKFKDAVKEYFAKFWD | 243 |
| [Switch D-E]-4-Rev-4F | FAEKFKDAVKDYFAKFWE | 244 |
| Rev-4F-1 | FWEKFKEAVKDYFAKFAD | 245 |
| [Switch D-E]-1-Rev-4F-1 | FWDKFKDAVKEYFAKFAE | 246 |
| [Switch D-E]-2-Rev-4F-1 | FADKFKEAVKDYFAKFWE | 247 |
| [Switch D-E]-3-Rev-4F-1 | FAEKFKDAVKEYFAKFWD | 248 |
| [Switch D-E]-4-Rev-4F-1 | FAEKFKDAVKDYFAKFWE | 249 |
| Rev-4F-2 | FFEKFKEAVKDYFAKAWD | 250 |
| [Switch D-E]-1-Rev-4F-2 | FFDKFKDAVKEYFAKAWE | 251 |
| [Switch D-E]-2-Rev-4F-2 | FFDKFKEAVKDYFAKAWE | 252 |
| [Switch D-E]-3-Rev-4F-2 | FFEKFKDAVKEYFAKAWD | 253 |
| [Switch D-E]-4-Rev-4F-2 | FFEKFKDAVKDYFAKAWE | 254 |
| Rev-4F-3 | FAEKAKEFVKDYFAKFWD | 255 |
| [Switch D-E]-1-Rev-4F-3 | FADKAKDFVKEYFAKFWE | 256 |
| [Switch D-E]-2-Rev-4F-3 | FADKAKEFVKDYFAKFWE | 257 |
| [Switch D-E]-3-Rev-4F-3 | FAEKAKDFVKEYFAKFWD | 258 |
| [Switch D-E]-4-Rev-4F-3 | FAEKAKDFVKDYFAKFWE | 259 |
| Rev-4F-4 | FAEKFKEVAKDYFAKFWD | 260 |
| [Switch D-E]-1-Rev-4F-4 | FADKFKDVAKEYFAKFWE | 261 |
| [Switch D-E]-2-Rev-4F-4 | FADKFKEVAKDYFAKFWE | 262 |
| [Switch D-E]-3-Rev-4F-4 | FAEKFKDVAKEYFAKFWD | 263 |
| [Switch D-E]-4-Rev-4F-4 | FAEKFKDVAKDYFAKFWE | 264 |
| Rev-4F-5 | FAEKFKEAYKDVFAKFWD | 265 |
| [Switch D-E]-1-Rev-4F-5 | FADKFKDAYKEVFAKFWE | 266 |
| [Switch D-E]-2-Rev-4F-5 | FADKFKEAYKDVFAKFWE | 267 |
| [Switch D-E]-3-Rev-4F-5 | FAEKFKDAYKEVFAKFWD | 268 |
| [Switch D-E]-4-Rev-4F-5 | FAEKFKDAYKDVFAKFWE | 269 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
| --- | --- | --- |
| Rev-4F-6 | FAEKFKEAVKDFYAKFWD | 270 |
| [Switch D-E]-1-Rev-4F-6 | FADKFKDAVKEFYAKFWE | 271 |
| [Switch D-E]-2-Rev-4F-6 | FADKFKEAVKDFYAKFWE | 272 |
| [Switch D-E]-3-Rev-4F-6 | FAEKFKDAVKEFYAKFWD | 273 |
| [Switch D-E]-4-Rev-4F-6 | FAEKFKDAVKDFYAKFWE | 274 |
| Rev-4F-7 | FAEKFWEAVKDYFAKFKD | 275 |
| [Switch D-E]-1-Rev-4F-7 | FADKFWDAVKEYFAKFKE | 276 |
| [Switch D-E]-2-Rev-4F-7 | FADKFWEAVKDYFAKFKE | 277 |
| [Switch D-E]-3-Rev-4F-7 | FAEKFWDAVKEYFAKFKD | 278 |
| [Switch D-E]-4-Rev-4F-7 | FAEKFWDAVKDYFAKFKE | 279 |
| Rev-4F-8 | AFEKFKEAVKDYFAKFWD | 280 |
| [Switch D-E]-1-Rev-4F-8 | AFDKFKDAVKEYFAKFWE | 281 |
| [Switch D-E]-2-Rev-4F-8 | AFDKFKEAVKDYFAKFWE | 282 |
| [Switch D-E]-3-Rev-4F-8 | AFEKFKDAVKEYFAKFWD | 283 |
| [Switch D-E]-4-Rev-4F-8 | AFEKFKDAVKDYFAKFWE | 284 |
| Rev-F-9 | VAEKFKEAFKDYFAKFWD | 285 |
| [Switch D-E]-1-Rev-4F-9 | VADKFKDAFKEYFAKFWE | 286 |
| [Switch D-E]-2-Rev-4F-9 | VADKFKEAFKDYFAKFWE | 287 |
| [Switch D-E]-3-Rev-4F-9 | VAEKFKDAFKEYFAKFWD | 288 |
| [Switch D-E]-4-Rev-4F-9 | VAEKFKDAFKDYFAKFWE | 289 |
| Rev-4F-10 | YAEKFKEAVKDFFAKFWD | 290 |
| [Switch D-E]-1-Rev-4F-10 | YADKFKDAVKEFFAKFWE | 291 |
| [Switch D-E]-2-Rev-4F-10 | YADKFKEAVKDFFAKFWE | 292 |
| [Switch D-E]-3-Rev-4F-10 | YAEKFKDAVKEFFAKFWD | 293 |
| [Switch D-E]-4-Rev-4F-10 | YAEKFKDAVKDFFAKFWE | 294 |
| Rev-4F-11 | AAEKFKEFVKDYFAKFWD | 295 |
| [Switch D-E]-1-Rev-4F-11 | AADKFKDFVKEYFAKFWE | 296 |
| [Switch D-E]-2-Rev-4F-11 | AADKFKEFVKDYFAKFWE | 297 |
| [Switch D-E]-3-Rev-4F-11 | AAEKFKDFVKEYFAKFWD | 298 |
| Switch D-E]-4-Rev-4F-11 | AAEKFKDFVKDYFAKFWE | 299 |
| Rev-4F-12 | FFEKAKEAVKDYFAKFWD | 300 |
| [Switch D-E]-1-Rev-4F-12 | FFDKAKDAVKEYFAKFWE | 301 |
| [Switch D-E]-2-Rev-4F-12 | FFDKAKEAVKDYFAKFWE | 302 |
| [Switch D-E]-3-Rev-4F-12 | FFEKAKDAVKEYFAKFWD | 303 |

TABLE 1-continued

Certain ApoA-I mimetic peptides that can be expressed in transgenic plants, e.g., as described herein. The TABLE 1-continued Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| [Switch D-E]-3-Rev-4F-19 | FAEKFKDAFKEYFAKVWD | 338 |
| Switch D-E]-4-Rev-4F-19 | FAEKFKDAFKDYFAKVWE | 339 |
| Rev-4F-20 | FAEKFKEAVKDFFAKYWD | 340 |
| [Switch D-E]-1-Rev-4F-20 | FADKFKDAVKEFFAKYWE | 341 |
| [Switch D-E]-2-Rev-4F-20 | FADKFKEAVKDFFAKYWE | 342 |
| [Switch D-E]-3-Rev-4F-20 | FAEKFKDAVKEFFAKYWD | 343 |
| [Switch D-E]-4-Rev-4F-20 | FAEKFKDAVKDFFAKYWE | 344 |
| Rev-4F-21 | WAEKFFEAVKDYFAKFKD | 345 |
| [Switch D-E]-1-Rev-4F-7 | WADKFFDAVKEYFAKFKE | 346 |
| [Switch D-E]-2-Rev-4F-7 | WADKFFEAVKDYFAKFKE | 347 |
| [Switch D-E]-3-Rev-4F-7 | WAEKFFDAVKEYFAKFKD | 348 |
| Switch D-E]-4-Rev-4F-7 | WAEKFFDAVKDYFAKFKE | 349 |
| Rev-4F-22 | FAEKWFEAVKDYFAKFKD | 350 |
| [Switch D-E]-1-Rev-4F-22 | FADKWFDAVKEYFAKFKE | 351 |
| [Switch D-E]-2-Rev-4F-22 | FADKWFEAVKDYFAKFKE | 352 |
| [Switch D-E]-3-Rev-4F-22 | FAEKWFDAVKEYFAKFKD | 353 |
| [Switch D-E]-4-Rev-4F-22 | FAEKWFDAVKDYFAKFKE | 354 |
| Rev-4F-23 | FAEKFVEAWKDYFAKFKD | 355 |
| [Switch D-E]-1-Rev-4F-23 | FADKFVDAWKEYFAKFKE | 356 |
| [Switch D-E]-2-Rev-4F-23 | FADKFVEAWKDYFAKFKE | 357 |
| [Switch D-E]-3-Rev-4F-23 | FAEKFVDAWKEYFAKFKD | 358 |
| [Switch D-E]-4-Rev-4F-23 | FAEKFVDAWKDYFAKFKE | 359 |
| Rev-4F-24 | FYEKFAEAVKDWFAKFKD | 360 |
| [Switch D-E]-1-Rev-4F-24 | FYDKFADAVKEWFAKFKE | 361 |
| [Switch D-E]-2-Rev-4F-24 | FYDKFAEAVKDWFAKFKE | 362 |
| [Switch D-E]-3-Rev-4F-24 | FYEKFADAVKEWFAKFKD | 363 |
| [Switch D-E]-4-Rev-4F-24 | FYEKFADAVKDWFAKFKE | 364 |
| [A-5 > H]4F | DWFKHFYDKVAEKFKEAF | 365 |
| [A-5 > H, D-E switched]4F | EWFKHFYEKVADKFKDAF | 366 |
| [A-5 > H, D-1 > E]4F | EWFKHFYDKVAEKFKEAF | 367 |
| [A-5 > H, D-8 > E]4-F | DWFKHFYEKVAEKFKEAF | 368 |
| [A-5 > H, E-12 > D]4F | DWFKHFYDKVADKFKEAF | 369 |
| [A-5 > H, E-16 > D]4F | DWFKHFYDKVAEKFKDAF | 370 |
| [F-3 > H,A-5 > F]-4F | DWHKFFYDKVAEKFKEAF | 371 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| [F-3 > H, A-5 > F, D-E switched]-4F | EWHKFFYEKVADKFKDAF | 372 |
| [F-3 > H, A-5 > F, D-1 > E]-4F | EWHKFFYDKVAEKFKEAF | 373 |
| [F-3 > H, A-5 > F, D-8 > E]-4F | DWHKFFYEKVAEKFKEAF | 374 |
| [F-3 > H, A-5 > F, E-12 > D]-4F | DWHKFFYDKVADKFKEAF | 375 |
| [F-3 > H, A-5 > F, E-16 > D]-4F | DWHKFFYDKVAEKFKDAF | 376 |
| [A-5 > F, F-6 > H]4F | DWFKFHYDKVAEKFKEAF | 377 |
| [A-5 > F, F-6 > H, D-E switched]4F | EWFKFHYEKVADKFKDAF | 378 |
| [[A-5 > F, F-6 > H, D-1 > E]4F | EWFKFHYDKVAEKFKEAF | 379 |
| [A-5 > F, F-6 > H, D-8 > E]4F | DWFKFHYEKVAEKFKEAF | 380 |
| [A-5 > F, F-6 > H, E-12 > D]4F | DWFKFHYDKVADKFKEAF | 381 |
| [A-5 > F, F-6 > H, E-16 > D]4F | DWFKFHYDKVAEKFKDAF | 382 |
| [A-5 > V, V-10 > H]4F | DWFKVFYDKHAEKFKEAF | 383 |
| [A-5 > V, V-10 > H, D-E switched]4F | EWFKVFYEKHADKFKDAF | 384 |
| [A-5 > V, V-10 > H, D-1 > E]4F | EWFKVFYDKHAEKFKEAF | 385 |
| [A-5 > V, V-10 > H, D-8 > E]4F | DWFKVFYEKHAEKFKEAF | 386 |
| [A-5 > V, V-10 > H, E-12 > D]4F | DWFKVFYDKHADKFKEAF | 387 |
| [A-5 > V, V-10 > H, E16 > D]4F | DWFKVFYDKHAEKFKDAF | 388 |
| [[A-17 > H]4F | DWFKAFYDKVAEKFKEHF | 389 |
| [A-17 > H, D-E switched]4F | EWFKAFYEKVADKFKDHF | 390 |
| [[A-17 > H,D-1 > E]4F | EWFKAFYDKVAEKFKEHF | 391 |
| [[A-17 > H, D-8 > E]4F | DWFKAFYEKVAEKFKEHF | 392 |
| [[A-17 > H,E-12 > D]4F | DWFKAFYDKVADKFKEHF | 393 |
| [[A-17 > H, E16 > D]4F | DWFKAFYDKVAEKFDHKF | 394 |
| [A-17 > F, F-18 > H]4F | DWFKAFYDKVAEKFKEFH | 395 |
| [A-17 > F, F-18 > H, D-E switched]4F | EWFKAFYEKVADKFKDFH | 396 |
| [A-17 > F, F-18 > H, D-1 > E]-4F | EWFKAFYDKVAEKFKEFH | 397 |
| [A-17 > F, F-18 > H]4F | DWFKAFYDKVAEKFKEFH | 398 |
| [A-17 > F, F-18 > H, D-8 > E]-4F | DWFKAFYEKVAEKFKEFH | 399 |
| [A-17 > F, F-18 > H, E-12 > D]4F | DWFKAFYDKVAEKFKEFH | 400 |
| [A-17 > F, F-18 > H], E-16 > D]-4F | DWFKAFYDKVAEKFKDFH | 401 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| Rev-4F | FAEKFKEAVKDYFAKFWD | 402 |
| [A-2 > H]Rev4F | FHEKFKEAVKDYFAKFWD | 403 |
| Rev-[A-2 > H, D > E]-4F | FHDKFKDAVKEYFAKFWE | 404 |
| Rev-[A-2 > H, E > D]4F | FHDKFKDAVKDYFAKFWD | 405 |
| [A-2 > H, D-E switched]Rev-4F | FHDKFKDAVKEYFAKFWE | 406 |
| [A-2 > H, E-3 > D]Rev-4F | FHDKFKEAVKDYFAKFWD | 407 |
| [A-2 > H, E-7 > D]Rev-4F | FHEKFKDAVKDYFAKFWD | 408 |
| [A-2 > H, D-11 > E]Rev-4F | FHEKFKEAVKEYFAKFWD | 409 |
| [A-2 > H, D-18 > E]Rev-4F | FHEKFKEAVKDYFAKFWE | 410 |
| [F-1 > H, A-2 > F]Rev-4F | HFEKFKEAVKDYFAKFWD | 411 |
| [F-1 > H, A-2 > F,D-E switched]Rev-4F | HFDKFKDAVKEYFAKFWE | 412 |
| [F-1 > H, A-2 > F, D > E]Rev-4F | HFEKFKEAVKEYFAKFWE | 413 |
| [F-1 > H, A-2 > F,E-3 > D]Rev-4F | HFDKFKEAVKDYFAKFWD | 414 |
| [F-1 > H, A-2 > F,E-7 > D]Rev-4F | HFEKFKDAVKDYFAKFWD | 415 |
| [F-1 > H, A-2 > F,D-11 > E]Rev4F- | HFEKFKEAVKEYFAKFWD | 416 |
| [F-1 > H, A-2 > F, D-18 > E]Rev-4F | HFEKFKEAVKDYFAKFWE | 417 |
| [A-2 > F, F-5 > H]Rev D-4F | FFEKHKEAVKDYFAKFWD | 418 |
| [A-2 > F, F-5 > H,D-E switched] Rev D-4F | FFDKHKDAVKEYFAKFWE | 419 |
| [A-2 > F, F-5 > H, D > E]Rev D-4F | FFEKHKEAVKEYFAKFWE | 420 |
| [A-2 > F, F-5 > H,E > D]Rev D-4F | FFDKHKDAVKDYFAKFWD | 421 |
| [A-2 > F, F-5 > H,E-3 > D]Rev D-4F | FFDKHKEAVKDYFAKFWD | 422 |
| [A-2 > F, F-5 > H,D-11 > E]Rev D-4F | FFEKHKEAVKEYFAKFWD | 423 |
| [A-2 > F, F-5 > H,D-18 > E]Rev D-4F | FFEKHKEAVKDYFAKFWE | 424 |
| [A-2 > V, V-9 > H]Rev D-4F | FVEKFKEAHKDYFAKFWD | 425 |
| [A-2 > V, V-9 > H,D-E switched]Rev D-4F | FVDKFKDAHKEYFAKFWE | 426 |
| [A-2 > V, V-9 > H,D > E]Rev D-4F | FVEKFKEAHKEYFAKFWE | 427 |
| [A-2 > V, V-9 > H,E > D]Rev D-4F | FVDKFKDAHKDYFAKFWD | 428 |
| [A-2 > V, V-9 > H,E-3 > D]Rev D-4F | FVDKFKEAHKDYFAKFWD | 429 |
| [A-2 > V, V-9 > H,E-7 > D]Rev D-4F | FVEKFKDAHKDYFAKFWD | 430 |
| [A-2 > V, V-9 > H,D-11 > E]Rev D-4F | FVEKFKEAHKEYFAKFWD | 431 |
| [A-2 > V, V-9 > H,D-18 > E]Rev D-4F | FVEKFKEAHKDYFAKFWE | 432 |
| [A-8 > H]Rev-4F | FAEKFKEHVKDYFAKFWD | 433 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| [A-8 > H,D-E switched]Rev-4F | FA<u>D</u>KFK<u>DH</u>VK<u>E</u>YFAKFW<u>E</u> | 434 |
| [A-8 > H,D > E]Rev-4F | FAEKFKE<u>H</u>VK<u>E</u>YFAKFW<u>E</u> | 435 |
| [A-8 > H,E > D]Rev-4F | FA<u>D</u>KFK<u>DH</u>VKDYFAKFWD | 436 |
| [A-8 > H,E-3 > D]Rev-4F | FA<u>D</u>KFKE<u>H</u>VKDYFAKFWD | 437 |
| [A-8 > H, E-7 > D]Rev-4F | FAEKFK<u>DH</u>VKDYFAKFWD | 438 |
| [A-8 > H, D-11 > E]Rev-4F | FAEKFKE<u>H</u>VK<u>E</u>YFAKFWD | 439 |
| [A-8 > H, D-18 > E]Rev-4F | FAEKFKE<u>H</u>VKDYFAKFW<u>E</u> | 440 |
| [A-8 > F,F-13 > H]Rev-4F | FAEKFKE<u>F</u>VKDY<u>H</u>AKFWD | 441 |
| [A-8 > F,F-13 > H,D-E switched]Rev-4F | FA<u>D</u>KFK<u>DF</u>VK<u>E</u>Y<u>H</u>AKFW<u>E</u> | 442 |
| [A-8 > F,F-13 > H, E-3 > D]Rev-4F | FA<u>D</u>KFKE<u>F</u>VKDY<u>H</u>AKFWD | 443 |
| [A-8 > F,F-13 > H, E-7 > D]Rev-4F | FAEKFK<u>DF</u>VKDY<u>H</u>AKFWD | 444 |
| [A-8 > F,F-13 > H, E > D]Rev-4F | FA<u>D</u>KFK<u>DF</u>VKDY<u>H</u>AKFWD | 445 |
| [A-8 > F,F-13 > H,D > E]Rev-4F | FAEKFKE<u>F</u>VK<u>E</u>Y<u>H</u>AKFW<u>E</u> | 446 |
| [A-8 > F,F-13 > H,D-11 > E]Rev-4F | FAEKFKE<u>F</u>VK<u>E</u>Y<u>H</u>AKFWD | 447 |
| [A-8 > F,F-13 > H, D-18 > E]Rev-4F | FAEKFKE<u>F</u>VKDY<u>H</u>AKFW<u>E</u> | 448 |
| [A-8 > F, F16 > H]Rev.-4F | FA<u>D</u>KFK<u>DF</u>VKDYFAK<u>H</u>WD | 449 |
| [A-8 > F, F16 > H,D-E switched]Rev.-4F | FA<u>D</u>KFK<u>DF</u>VK<u>E</u>YFAK<u>H</u>W<u>E</u> | 450 |
| [A-8 > F, F16 > H,D > E]Rev.-4F | FAEKFKE<u>F</u>VK<u>E</u>YFAK<u>H</u>W<u>E</u> | 451 |
| [A-8 > F, F16 > H, E > D]Rev.-4F | FA<u>D</u>KFK<u>DF</u>VKDYFAK<u>H</u>WD | 452 |
| [A-8 > F, F16 > H,E-3 > D]Rev.-4F | FA<u>D</u>KFKE<u>F</u>VKDYFAK<u>H</u>WD | 453 |
| [A-8 > F, F16 > H,E-7 > D]Rev.-4F | FAEKFK<u>DF</u>VKDYFAK<u>H</u>WD | 454 |
| [A-8 > F, F16 > H,D-11 > E]Rev.-4F | FAEKFKE<u>F</u>VK<u>E</u>YFAK<u>H</u>WD | 455 |
| [A-8 > F, F16 > H,D-18 > E]Rev.-4F | FAEKFKE<u>F</u>VKDYFAK<u>H</u>W<u>E</u> | 456 |
| Rev-[D > E]-4F | FAEKFKEAVK<u>E</u>YFAKFW<u>E</u> | 457 |
| Rev-[E > D]4F | FA<u>D</u>KFK<u>D</u>AVKDYFAKFWD | 458 |
| Rev-R4-4F | FAE<u>R</u>FKEAVKDYFAKFWD | 459 |
| Rev-R6-4F | FAEKF<u>R</u>EAVKDYFAKFWD | 460 |
| Rev-R10-4F | FAEKFKEAV<u>R</u>DYFAKFWD | 461 |
| Rev-R14 -4F | FAEKFKEAVKDYFA<u>R</u>FWD | 462 |
| Rev-[D > E]-4F | FAEKFKEAVK<u>E</u>YFAKFW<u>E</u> | 463 |
| Rev-[E > D]4F | FA<u>D</u>KFK<u>D</u>AVKDYFAKFWD | 464 |
| Rev-R4-4F | FAE<u>R</u>FKEAVKDYFAKFWD | 465 |
| Rev-R6-4F | FAEKF<u>R</u>EAVKDYFAKFWD | 466 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| Rev-R10-4F | FAEKFKEAVRDYFAKFWD | 467 |
| Rev-R14 -4F | FAEKFKEAVKDYFARFWD | 468 |
| Rev-[D > E]-4F | FAEKFKEAVKEYFAKFWE | 469 |
| Rev-[E > D]4F | FADKFKDAVKDYFAKFWD | 470 |
| Rev-R4-4F | FAERFREAVKDYFAKFWD | 471 |
| Rev-R6-4F | FAEKFREAVKDYFAKFWD | 472 |
| Rev-R10-4F | FAEKFKEAVRDYFAKFWD | 473 |
| Rev-R14 -4F | FAEKFKEAVKDYFARFWD | 474 |
| Rev-R4-4F | FAERFREAVKDYFAKFWD | 475 |
| Rev-R6-4F | FAEKFREAVKDYFAKFWD | 476 |
| Rev-R10-4F | FAEKFKEAVRDYFAKFWD | 477 |
| Rev-R14 -4F | FAEKFKEAVKDYFARFWD | 478 |
| Rev-[D > E]-4F | FAEKFKEAVKEYFAKFWE | 479 |
| Rev-[E > D]4F | FADKFKDAVKDYFAKFWD | 480 |
| Rev-R4-4F | FAERFREAVKDYFAKFWD | 481 |
| Rev-R6-4F | FAEKFREAVKDYFAKFWD | 482 |
| Rev-R10-4F | FAEKFKEAVRDYFAKFWD | 483 |
| Rev-R14 -4F | FAEKFKEAVKDYFARFWD | 484 |
| Rev3F-2 | LFEKFAEAFKDYVAKWKD | 485 |
| RevR4-3F-2 | LFERFAEAFKDYVAKWKD | 486 |
| RevR10-3F2 | LFEKFAEAFRDYVAKWKD | 487 |
| RevR15-3F-2 | LFEKFAEAFKDYVARWKD | 488 |
| Rev R17-3F-2 | LFEKFAEAFKDYVAKWRD | 489 |
| Rev[D > E]3F2 | LFEKFAEAFKEYVAKWKE | 490 |
| Rev[E > D]3F-2 | LFDKFADAFKDYVAKWKD | 491 |
| Rev-[E3 > D]-3F-2 | LFDKFADAFKDYVAKWKD | 492 |
| Rev-[E7 > D]-3F-2 | LFDKFADAFKDYVAKWKD | 493 |
| Rev[D11 > N3F-2 | LFEKFAEAFKEYVAKWKD | 494 |
| Rev-[D18 > N3F-2 | LFEKFAEAFKDYVAKWKE | 495 |
| Rev3F-1 | FAEKAWEFVKDYFAKLKD | 496 |
| RevR4-3F-1 | FAERAWEFVKDYFAKLKD | 497 |
| RevR10-3F-1 | FAEKAWEFVKDYFAKLKD | 498 |
| RevR15-3F-1 | FAEKAWEFVKDYFAKLKD | 499 |
| RevR17-3F-1 | FAEKAWEFVKDYFAKLRD | 500 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| Rev[D > N3F-1 | FAEKAWEFVKEYFAKLKE | 501 |
| Rev[E > D}F-1 | FADKAWDFVKDYFAKLKD | 502 |
| Rev[E3 > D]-3F-1 | FADKAWEFVKDYFAKLKD | 503 |
| Rev[E7 > D]3F-1 | FAEKAWDFVKDYFAKLKD | 504 |
| Rev-[D11 > N3F-1 | FAEKAWEFVKEYFAKLKD | 505 |
| Rev-[D18 > N3F-1 | FAEKAWEFVKDYFAKLKE | 506 |
| Rev-5F | FFEKFKEFVKDYFAKLWD | 507 |
| Rev-[D > E]5F | FFEKFKEFVKEYFAKLWE | 508 |
| Rev- [E > D]5F | FFDKFKDFVKDYFAKLWD | 509 |
| Rev-R4-5F | FFERFKEFVKDYFAKLWD | 510 |
| Rev-R6-5F | FFEKFREFVKDYFAKLWD | 511 |
| Rev-R10-5F | FFEKFKEFVRDYFAKLWD | 512 |
| Rev-R15-5F | FFEKFKEFVKDYFARLWD | 513 |
| Rev-[E3 > D]-5F | FFDKFKEFVKDYFAKLWD | 514 |
| Rev-[E7 > D]5F | FFEKFKDFVKDYFAKLWD | 515 |
| Rev-[D11 > E]-5F | FFEKFKEFVKEYFAKLWD | 516 |
| Rev-[D18 > E]-5F | FFEKFKEFVKDYFAKLWE | 517 |
| Rev-5F-2 | FLEKFKEFVKDYFAKFWD | 518 |
| Rev-[D > E]-5F-2 | FLEKFKEFVKEYFAKFWE | 519 |
| Rev-[E > D]-5F-2 | FLDKFKEFVKDYFAKFWD | 520 |
| Rev-[E3 > D]-5F-2 | FLDKFKEFVKDYFAKFWD | 521 |
| Rev-[E7 > D]-5F-2 | FLEKFKDFVKDYFAKFWD | 522 |
| Rev-[D11 > E]-5F-2 | FLEKFKEFVKEYFAKFWD | 523 |
| Rev-[D18 > E]-5F-2 | FLEKFKEFVKDYFAKFWE | 524 |
| Rev-R4-5F-2 | FLERFKEFVKDYFAKFWD | 525 |
| Rev-R6-5F-2 | FLEKFREFVKDYFAKFWD | 526 |
| RevR10-5F-2 | FLEKFKEFVRDYFAKFWD | 527 |
| Rev-R16-5F-2 | FAEKFKEAVKDYFARFWD | 528 |
| Rev-6F | FFEKFKEFFKDYFAKLWD | 529 |
| Rev-[D > E]-6F | FFEKFKEFFKEYFAKLWE | 530 |
| Rev-[E > D]-6F | FFDKFKDFFKDYFAKLWD | 531 |
| Rev-R4-6F | FFE RFKEFFKDYFAKLWD | 532 |
| Rev-R6-6F | FFEKFREFFKDYFAKLWD | 533 |
| Rev-R10-6F | FFEKFKEFFRDYFAKLWD | 534 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| Rev-R14-6F | FFERFKEFFKDYFARLWD | 535 |
| Rev-[E3 > D]-6F | FFDKFKEFFKDYFAKLWD | 536 |
| Rev-[E7 > D]-6F | FFEKFKDFFKDYFAKLWD | 537 |
| Rev-[D11 > E]-6F | FFEKFKEFFKEYFAKLWD | 538 |
| Rev-[D18 > E]-6F | FFEKFKEFFKDYFAKLWE | 539 |
| Rev-4F | FAEKFKEAVKDYFAKFWD | 540 |
| Rev-[D > E]-4F | FAEKFKEAVKEYFAKFWE | 541 |
| Rev-[E > D]4F | FADKFKDAVKDYFAKFWD | 542 |
| Rev-R4-4F | FAERFREAVKDYFAKFWD | 543 |
| Rev-R6-4F | FAEKFREAVKDYFAKFWD | 544 |
| Rev-R10-4F | FAEKFKEAVRDYFAKFWD | 545 |
| Rev-R14-4F | FAEKFKEAVKDYFARFWD | 546 |
| 4F-2 | DKWKAVYDKFAEAFKEFF | 547 |
| [D > E]-4F-2 | EKWKAVYEKFAEAFKEFF | 548 |
| [E > D]-4F-2 | DKWKAVYDKFADAFKDFF | 549 |
| R2-4F-2 | DRWKAVYDKFAEAFKEFF | 550 |
| R4-4F-2 | DKWRAVYDKFAEAFKEFF | 551 |
| R9-4F-2 | DKWKAVYDRFAEAFKEFF | 552 |
| R14-4F-2 | DKWKAVYDKFAEAFREFF | 553 |
| Rev4F-2 | FFEKFAEAFKDYVAKWKD | 554 |
| Rev-[D > E]-4F-2 | FFEKFAEAFKEYVAKWKE | 555 |
| Rev-[E > D]-3F-2 | FFDKFADAFKDYVAKWKD | 556 |
| Rev-R4-4F-2 | FFERFAEAFKDYVAKWKD | 557 |
| Rev-R10-4F-2 | FFERFAEAFRDYVAKWKD | 558 |
| Rev-R15-4F-2 | FFEKFAEAFKDYVARWKD | 559 |
| Rev-R17-4F-2 | FFERFAEAFKDYVAKWRD | 560 |
| Rev-[E3 > D]-4F-2 | FFDKFAEAFKDYVAKWKD | 561 |
| Rev-[E7 > D]-4F-2 | FFEKFADAFKDYVAKWKD | 562 |
| Rev-[D11 > E]-4F-2 | FFERFAEAFKEYVAKWKD | 563 |
| Rev-[D18 > E]-4F-2 | FFERFAEAFKDYVAKWKE | 564 |
| Rev-7F | FFEKFEFFKDYFAKFWD | 565 |
| Rev-[E > D]-7F | FFDKFKDFFKDYFAKFWD | 566 |
| Rev-[D > E]-7F | FFEKFKEFFKEYFAKFWE | 567 |
| Rev-R4-7F | FFERFKEFFKDYFAKFWD | 568 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
|---|---|---|
| Rev-R6-7F | FFEKFREFFKDYFAKFWD | 569 |
| Rev-R10-7F | FFEKFKEFFRDYFAKFWD | 570 |
| Rev-R14-7F | FFEKFKEFFKDYFARFWD | 571 |
| Rev-[E3 > D]-7F | FFDKFKEFFKDYFAKFWD | 572 |
| Rev-[E7 > D]7F | FFEKFKDFFKDYFAKFWD | 573 |
| Rev-[D11 > E]-7F | FFEKFKEFFKEYFAKFWD | 574 |
| Rev-[D18 > E]-7F | FFEKFKEFFKDYFAKFWE | 575 |
|  | EVRAKLEEQAQQIRLQAEAFQARLKSWFEPLVE | 576 |
|  | EVRAKLEEQAQQIRLQAEAFQARLKSWFE | 577 |
|  | EVRSKLEEWFAAFREFAEEFLARLKS | 578 |
|  | PVLDLFRELLNELLEALKQKLK | 579 |
|  | DWLKAFYDKVAEKLKEAF- P-DWAKAAYDKAAEKAKEAA | 580 |
|  | EELKEKLEELKEKLEEKL-P-EELKEKLEELKEKLEEKL | 581 |
|  | EELKAKLEELKAKLEEKL-P-EELKAKLEELKAKLEEKL | 582 |
|  | EKLKALLEKLLAKLKELL-P-EKLKALLEKLLAKLKELL | 583 |
|  | EWLKELLEKLLEKLKELL-P-EWLKELLEKLLEKLKELL | 584 |
|  | EKFKELLEKFLEKFKELL-P-EKFKELLEKFLEKFKELL | 585 |
|  | EKLKELLEKLLELLKKLL-P-EKLKELLEKLLELLKKLL | 586 |
|  | EKLKELLEKLKAKLEELL-P-EKLKELLEKLKAKLEELL | 587 |
|  | EKLKELLEKLLAKLKELL-P-EKLKELLEKLLAKLKELL | 588 |
|  | EKFKELLEKLLEKLKELL-P-EKFKELLEKLLEKLKELL | 589 |
|  | EKLKAKLEELKAKLEELL-P-EKLKAKLEELKAKLEELL | 590 |
|  | EELKELLKELLKKLEKLL-P-ELKELLKELLKKLEKLL | 591 |
|  | EELKKLLEELLKKLKELL-P-EELKKLLEELLKKLKELL | 592 |
|  | EKLKELLEKLLEKLKELL-A-EKLKELLEKLLEKLKELL | 593 |
|  | EKLKELLEKLLEKLKELL-AA-EKLKELLEKLLEKLKELL | 594 |

TABLE 1-continued

Certain ApoA-I mimetic peptides that can be expressed in transgenic plants, e.g., as described herein. The table includes various class A and/or class Y peptide analogs. For each sequence listed in this table, the retro form of the sequence is also contemplated. Thus, for example where the 6F peptide sequence DWLKAFYDKFFEKFKEFF (SEQ ID NO: 17) is shown, the retro amino acid sequence FFEKFKEFFKDYFAKLWD (SEQ ID NO: 25) is also contemplated.

| Peptide Name | Amino Acid Sequence | SEQ ID NO. |
| --- | --- | --- |
| | EKLKAKLEELKAKLEELL-P-EKAKAALEEAKAKAEELA | 595 |
| | EKLKAKLEELKAKLEELL-P-EHAKAALEEAKCKAEELA | 596 |
| | DHLKAFYDKVACKLKEAF-P-DWAKAAYDKAAEKAKEAA | 597 |
| | DWLKAFYDKVAEKLKEAF-P-DHAKAAYDKAACKAKEAA | 598 |
| | DWLKAFYDKVACKLKEAF-P-DWAKAAYNKAAEKAKEAA | 599 |
| | DHLKAFYDKVAEKLKEAF-P-DWAKAAYDKAAEKAKEAA | 600 |
| | VLESFKVSFLSALEEYTKKLNTQ | 601 |
| (3F$^{Cπ}$) | DKWKAVYDKFAEAFKEFL | 602 |
| (3F$^{Iπ}$) | DKLKAFYDKVFEWAKEAF | 603 |

Apo-J (G* Peptides).

It was also discovered that peptides that mimic the amphipathic helical domains of apoJ are also capable of mitigating one or more symptoms of atherosclerosis and/or other pathologies described herein. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A number of suitable G* amphipathic peptides are described U.S. Pat. Nos. 6,930,085, and 7,638,494, and in PCT Publication No: PCT/US03/09988 (WO 2003/086326) which are incorporated herein by reference for the peptides described therein. In certain embodiments the G* (apoJ) peptides expressed in the transgenic plants comprise one or more domains that have an amino acid sequence shown in Table 2 or the reverse sequence.

TABLE 2

Certain peptides related to G* amphipathic helical domains of apo J that can be expressed in transgenic plants, e.g., as described herein. For each sequence listed in this table, the retro form of the sequence is also contemplated. Thus, for example where the sequence DQYYLRVTTVA (SEQ ID NO: 605) is shown, the amino acid sequence AVTTVRLYYQD (SEQ ID NO: 604) is also contemplated.

| Amino Acid Sequence | SEQ ID NO |
| --- | --- |
| DQYYLRVTTVA | 605 |
| ECKPCLKQTCMKFYARVCR | 606 |
| FSRASSIIDELFQD | 607 |
| IQNAVNGVKQIKTLIEKTNEE | 608 |
| LLEQLNEQFNWVSRLANL | 609 |
| LLEQLNEQFNWVSRLANLTEGE | 610 |
| LLEQLNEQFNWVSRLANLTQGE | 611 |
| LVGRQLEEFL | 612 |
| MNGDRIDSLLEN | 613 |
| NELQEMSNQGSKYVNKEIQNAVNGV | 614 |
| PCLKQTCMKFYARVCR | 615 |
| PFLEMIHEAQQAMDI | 616 |
| PGVCNETMMALWEECK | 617 |

TABLE 2-continued

Certain peptides related to G* amphipathic helical domains of apo J that can be expressed in transgenic plants, e.g., as described herein. For each sequence listed in this table, the retro form of the sequence is also contemplated. Thus, for example where the sequence DQYYLRVTTVA (SEQ ID NO: 605) is shown, the amino acid sequence AVTTVRLYYQD (SEQ ID NO: 604) is also contemplated.

| Amino Acid Sequence | SEQ ID NO |
|---|---|
| PKFMETVAEKALQEYRKKHRE | 618 |
| PSGVTEVVVKLFDS | 619 |
| PSQAKLRRELDESLQVAERLTRKYNELLKSYQ | 620 |
| PTEFIREGDDD | 621 |
| QQTHMLDVMQD | 622 |
| RKTLLSNLEEAKKKKEDALNETRESETKLKEL | 623 |
| RMKDQCDKCREILSV | 624 |

ApoE Mimetic Peptides

ApoE mimetic peptides have also been demonstrated to have activities similar to those described above for ApoA-I mimetic peptides, particularly with respect to neurological and/or ocular dysfunction (see, e.g., Handattu et al. (2010) *J. Lipid Res.* 51: 3491-3499; Laskowitz et al. (2001) *Experimental Neurology* 167: 74-85; Minami et al. (2010) *Molecular Neurodegeneration,* 5:16; Bhattacharjee et al. (2008) *Invest Ophthalmol Vis Sci.* 49: 4263-4268; Li et al. 92010) *J. Pharmacol. and Experimental Therapeutics* 334: 106-115; Klein and Yakel (2004) *Neurosci.,* 127: 563-567; Laskowitz et al. (2007) *J. of Neurotrauma* 24: 1093-1107; Christensen et al. (2011) *J. Immunol.,* 186: 2535-2542; Croy et al. 92004) *Biochemistry* 43: 7328-7335). In certain embodiments the peptides expressed in the transgenic plants comprise one or more domains that have an apoE amino acid sequence or a dual ApoE/ApoA-I sequence shown in Table 3 or the reverse sequence.

TABLE 3

Certain ApoE peptides that can be expressed in transgenic plants, e.g., as described herein. For each sequence listed in this table, the retro form of the sequence is also contemplated. Thus, for example where the sequence GIKKFLGSIWKFIKAFVG (SEQ ID NO: 626) is shown, the amino acid sequence GVFAKIFKWISGLFKKIG (SEQ ID NO: 625) is also contemplated.

| Amino Acid Sequence | SEQ ID NO |
|---|---|
| ApoE peptides: | |
| GIKKFLGSIWKFIKAFVG | 626 |
| GFKKFLGSWAKIYKAFVG | 627 |
| GFRRFLGSWARIYRAFVG | 628 |
| TEELRVRLASHLRKLRKRLL | 629 |
| TEELRVRLASHLRKLRK | 630 |
| LRVRLASHLRKLRKRLL | 631 |
| RLASHLRKLRKRLL | 632 |
| SHLRKLRKRLL | 633 |
| LRKLRKRLL | 634 |
| LRKLRKRLLLRKLRKRLL | 635 |
| LRKLRKRLLLRKLRKRLLLRKLRKRLL | 636 |
| RQIKIWFQNRRMKWKKCLRVRLASHLRKLRKRLL | 637 |
| LRVRLASHLRKLRKRLL | 638 |

TABLE 3-continued

Certain ApoE peptides that can be expressed in transgenic plants, e.g., as described herein. For each sequence listed in this table, the retro form of the sequence is also contemplated. Thus, for example where the sequence GIKKFLGSIWKFIKAFVG (SEQ ID NO: 626) is shown, the amino acid sequence GVFAKIFKWISGLFKKIG (SEQ ID NO: 625) is also contemplated.

| Amino Acid Sequence | SEQ ID NO |
|---|---|
| EELRVRLASHLRKLRKRLLRDADDLQKRLAVYEEQAQQIRLQA EAFQARLKSWFEPLVEDM | 639 |
| CEELRVRLASHLRKLRKRLLRDADDLQKRLAVY | 640 |
| LRKLRKRLLRDADDLLRKLRKRLLRDADDL | 641 |
| TEELRVRLASHLRKLRKRLL | 642 |
| TEELRVRLASHLRKLRKRLL | 643 |
| TEELRVRLASHLRKLRKRLL | 644 |
| LREKKLRVSALRTHRLELRL | 645 |
| Dual ApoE and ApoA-I mimetic peptides: | |
| LRKLRKRLLRDWLKAFYDKVAEKLKEAF | 646 |
| LRRLRRRLLRDWLKAFYDKVAEKLKEAF | 647 |
| RRRRRRRRRDWLKAFYDKVAEKLKEAF | 648 |

It has been demonstrated that in certain embodiments, linking the receptor binding domain of apolipoprotein E (apoE) to a class A amphipathic helix can enhance internalization and degradation of LDL by fibroblasts and can lower plasma cholesterol and restore endothelial function (see, e.g., Datta et al. (2000) *Biochemistry* 39: 213-220; Gupta et al. (2005) *Circulation* 111: 3112-3118).

Accordingly in certain embodiments, any of the peptides described herein, when expressed in a transgenic plant, can be expressed as a peptide also comprising an apoE receptor binding domain (see, e.g., SEQ ID NOs:646-648 for illustrative examples).

In various embodiments, peptides comprising an oxpholipin domain such as Arg-Glu-Dpa-Thr-Gly-Leu-Ala-Trp-Glu-Trp-Trp-Arg-Thr-Val (SEQ ID NO:649), where Dpa (3,3'-diphenyl alanine) is substituted with Trp, Phe, or Ala) are also contemplated. Oxpholipin peptides are described by Ruchala et al. (2010) *PLoS ONE* 5(4): e10181) and in PCT Publication No: PCT/US2010/046534 (WO/2011/031460), which are incorporated herein by reference for the peptides described therein and where such peptides incorporate 3,3'-diphenylalanine, this residue is substituted with Trp, Phe, or Ala.

In addition to the sequences listed in Tables 1, 2, and 3 amino acid sequences comprising 1 conservative substitution, 2 conservative substitutions, 3 conservative substitutions, 4 conservative substitutions, 5 conservative substitutions, 6 conservative substitutions, 7 conservative substitutions, 8 conservative substitutions, 9 conservative substitutions, or 10 conservative substitutions are contemplated.

The foregoing peptides are intended to be illustrative and not limiting. In view of the surprising discovery that ApoA-I mimetic peptides and other related peptides can be expressed in a transgenic plant and can be effective when plant parts are administered to a mammal, one of skill in the art will recognized that numerous other such peptides can also be expressed in such plants and fed to a mammal to afford a similar utility.

Construction and Propagation of Transgenic Plants.

Nucleic Acids and Vectors Expressing the Peptide(s) of Interest.

In various embodiments methods for constructing transgenic plant cells are provided. The methods typically involve constructing a vector (e.g., a plasmid vector) or a DNA fragment by operably linking a DNA sequence encoding the peptide(s) of interest (e.g., peptides comprising ApoA-I, and/or G*, and/or ApoE domain(s)) to a plant-functional promoter capable of directing the expression of the peptide in the plant and then transforming a plant cell with the plasmid vector or DNA fragment. Where preferred, the method may be extended to produce transgenic plants from the transformed cells by including a step of regenerating a transgenic plant from the transgenic plant cell.

Typically, the codon usage of the nucleic acid that is to express the desired amino acid sequence(s) is selected to reflect the optimal codon usage in that plant. Methods of optimizing codon usage for expression of a nucleic acid in a particular host organism are known to those of skill in the art, and numerous software tools are available for such optimization. For example, codon tables are available from the Codon Usage Database, maintained by the Department of Plant Gene Research in Kazusa, Japan (see, e.g., www.kazusa.or.jp/codon/).

In certain embodiments the codon optimized nucleic acid sequence is incorporated into an expression vector (e.g., a plasmid). Typically the nucleic acid sequence is operably linked (put under control of) a promoter capable of directing expression of the nucleic acid sequence in the host plant.

Promoters

Promoters that are known or found to cause transcription of a foreign gene in plant cells are well known to those of skill in the art. Such promoters include, for example, promoters of viral origin and promoters of plant origin. The promoters can be constitutive or inducible, and in various embodiments, are tissue-specific promoters. In various embodiments any of these promoters are contemplated for the expression of a peptide described herein in a plant/plant tissue.

The most common promoters used for constitutive overexpression in plants are derived from plant virus sources, such as the cauliflower mosaic (CaMV) 35S promoter (Odell et al. (1985) *Nature,* 313: 810-812). This promoter, like similar virally derived promoters used in plant systems, is harvested from double-stranded DNA viral genomes, which use host nuclear RNA polymerase and do not appear to depend on any trans-acting viral gene products. The CaMV 35S promoter delivers high expression in virtually all regions of the transgenic plant, is readily obtainable in research and academic settings, and available in plant transformation vector cassettes that allow for easy subcloning of the transgene of interest. The CaMV 35S promoter can drive high levels of transgene expression in both dicots and monocots (Battraw and Hall (1990) *Plant Mol. Biol.* 15: 527-538; Benfey et al. (1990) *EMBO J.* 9: 1677-1684). In various embodiments the full-sized 35S promoter (−941 to +9 bp) (Odell et al. (1985) *Nature,* 313: 810-812) or various fragments such as a 2343 bp fragment can be used. Other viral promoters are also well known to those of skill in the art. These include, but are not limited to the cassava vein mosaic virus (CsVMV) promoter (see, e.g., Verdaguer et al. (1996) *Plant Mol. Biol.* 31: 1129-1139; Verdaguer et al. (1998) *Plant Mol. Biol.* 37: 1055-1067; Li et al. (2001) *Plant Sci.* 160: 877-887), Australian banana streak virus (BSV) promoters (see, e.g., Schenk et al. (2001) *Plant Mol. Biol.* 47: 399-412), mirabilis mosaic virus (MMV) promoter (see, e.g., Dey and Maiti (1999) *Plant Mol. Biol.* 40: 771-782), the figwort mosaic virus (FMV) promoter (see, e.g., Sanger et al. (1990) *Plant Mol. Biol.* 14: 433-443; Maiti et al. (1997) *Transgenic Res.* 6: 143-156) and the like.

Endogenous plant promoters are also used regularly to drive high constitutive levels of transgene expression (Gupta et al. (2001) *Plant Biotechnol.* 18: 275-282; Dhankher et al. (2002) *Nature Biotechnol.* 20:1-6). A number of these strong constitutive promoters are derived from actin and ubiquitin genes. For example, the Act2 promoter was developed from the actin gene family in *Arabidopsis* (An et al. (1996) *Plant J.* 10: 107-121). The rice actin 1 gene promoter has also been developed for use in cereal systems (McElroy et al. (1991); Zhang et al. (1991) *Plant Cell* 3: 1155-1165) and drives expression in virtually all tissues except xylem when transformed back into rice. Ubiquitin promoters, for example the maize ubiquitin 1 promoter (pUbi) has provided high expression in of heterologous genes in maize protoplasts. The maize Ubi1 promoter: GUS fusion has been used in rice (Cornejo et al. (1993) *Plant Mol. Biol.* 23: 567-581). The Ubi.U4 gene promoter has also been shown to drive high expression activity (Garbarino et al. (1995) *Plant Physiol.* 109: 1371-1378).

A number of tissue-specific (e.g., specific to fruit, seed/grain, tubers/root storage systems, florets/flowers, Leaves/green tissue, anthers/pollen, and the like) are known. Illustrative, but non-limiting fruit-specific promoters include, for example promoters from the 1-aminocyclopropane-1-carboxylate (ACC) oxidase gene, the E8 gene, and polygalacturonase (PG) genes have been characterized in apple (Atkinson et al. (1998) *Plant Mol. Biol.* 38: 449-460) and tomato (Montgomery et al. (1993) *Plant Cell* 5: 1049-1062; Nicholass et al. (1995) *Plant Mol. Biol.* 28: 423-435; Deikman and Fischer (1988) *EMBO J.* 7: 3315-3320). The promoter of the tomato E8 gene has been used successfully in a number of instances to target transgene expression to fruit. The promoter of the tomato polygalacturonase gene (PG gene product accumulates during ripening and is associated with fruit softening) has been used to drive expression of heterologous genes (Fraser et al. (2002) *Eur. J. Biochem.* 270: 1365-1380). In tomato, a single gene encodes PG, and analysis of a 1.4 kb promoter fragment shows that it also directs ripening-specific expression (Montgomery et al. (1993) *Plant Cell* 5: 1049-1062). Phytoene desaturase (Pds) is the second dedicated enzyme in carotenoid biosynthesis and is also encoded by a single gene in tomato (Giuliano et al. (1993) *Plant Cell* 5: 379-387). Because carotenoids accumulate in the chloroplasts and chromoplasts, the tomato Pds promoter (2.0 kb from start of translation) drives high levels of expression in organs and developing tissues where chromoplasts are found (fruits, petals, anthers) (Corona et al. (1996) *Plant J.* 9: 505-512).

Seed-specific transgene expression has been used for a number of genetic engineering applications. Illustrative seed specific promoters include, but are not limited to the promoters of various seed storage proteins. Other seed specific promoters include for example, those from the soybean β-conglycinin (Chen et al. (1989) *Dev. Genet.* 10: 112-122; Chamberland et al. (1992) *Plant Mol. Biol.* 19: 937-949; Lessard et al. (1993) *Plant Mol. Biol.* 5: 873-885), the sunflower helianthinin genes (Nunberg et al. (1994) *Plant Cell* 6: 473-486), and the like. One of the best-characterized and most commonly used seed-specific promoters is the French bean β-phaseolin gene (see, e.g., Bustos et al. (1989) *Plant Cell* 1: 839-853; van der Geest and Hall (1997) *Plant J.* 6: 413-423). Another useful seed specific promoter is the cotton α-globulin promoter (Sunilkumar et al. (2002) *Trans-* genic Res. 11: 347-359) and has been characterized in cotton, *Arabidopsis*, and tobacco. In monocots, several promoters of storage proteins include, but are not limited to the endosperm-specific hordein promoters in barley (Forde et al. (1985) *Nucleic Acids Res.* 13: 7327-7339), glutenin promoters from wheat (Lamacchia et al. (2001) *J. Exp. Bot.* 52: 243-250), the zein promoters in maize (Marzabal et al. (1998) *Plant J.* 16: 41-52), and the granule-bound starch synthase 1 (gbss1) gene in wheat (Kluth et al. (2002) *Plant Mol. Biol.* 49: 669-682).

Tubers/root storage specific promoters include, but are not limited to the potato class I patatin family members, B33 and PAT 21 (Jefferson et al. (1990; Liu et al. (1991), the potato granule-bound starch synthase (GBSS) promoter, sweet potato, sporamin and β-amylase promoters (Maeo et al. (2001) *Plant Mol. Biol.* 46: 627-637), e.g., the gSPO-A1 promoter (Ohta et al. (1991) *Mol. Gen. Genet.* 225: 369-378).

Promoters specific to legume-*rhizobium*-associated root nodules include promoters of genes expressed early in nodule organogenesis (ENOD genes) (see, e.g., Lauridsen et al. (1993) *Plant J.* 3: 484-492; Vijn et al. (1995) *Plant Mol. Biol.* 28: 1103-1110; Fang and Hirsch (1998) *Plant Physiol.* 116: 53-68; Hohnjec et al. (2000) *Mol. Gen. Genet.* 264: 241-250), late nodulin promoters (see, e.g., Sandal et al. (1987) *Nucleic Acids Res.* 15: 1507-1519; Stougaard et al. (1987) *EMBO J.* 6: 3565-3569), leghemoglobin promoters, the *Sesbania rostrata* leghemoglobin glb3 promoter (see, e.g., Szabados et al. (1990) *Plant Cell* 2: 973-986; Szczy-glowski et al. (1996) *Plant Mol. Biol.* 31: 931-935), and the like.

Root specific promoters are described, for example, by Yamamoto et al. (1991) *Plant Cell* 3: 371-382. Non-plant root-specific promoters include the promoters of the rooting loci (rol) genes found in the R1 (root-inducing) plasmid of *A. rhizogenes* (e.g., the rolD promoter), Domain A of the CaMV 35S promoter (Benfey and Chua (1989) *Plant Cell* 2: 849-856), the TobRB7 promoter from tobacco (Yamamoto et al. (1991) *Plant Cell* 3: 371-382), and the like.

Promoters specific to leaves/green tissues include, but are not limited to, promoters from the rbcS multigene family encoding the small subunit of ribulose-1,5-bisphosphate carboxylase such as the pea rbcS-3A promoter the alfalfa rbcS promoter the Rubisco promoter, promoters from the chlorophyll a/b-binding (Cab) protein genes (e.g., CAB2 promoter) (Piechulla et al. (1998) *Plant Mol. Biol.* 38: 655-662), the alfalfa 1532 bp RAc promoter, and the like.

Table 4 shows illustrative, but non-limiting examples of tissue specific promoters.

Illustrative, but non-limiting examples of tissue specific promoters are shown in Table 4.

TABLE 4 shows illustrative, but non-limiting examples of tissue specific promoters.

| Tissue | Illustrative Promoters |
|---|---|
| Fruit specific | Apple ACC oxidase |
| | Tomato polygalactouronidase |
| | Tomato E8 |
| | Tomato PDS |
| Green tissue specific | Pea rbcs-3A |
| | *Arabidopsis* CAB2 |
| | Alfalfa RAc |
| Nodule specific | *Vicia faba* VfEnod12 |
| | Bean NVP30 |
| | *S. rostrata* leghemoglobin |

TABLE 4-continued shows illustrative, but non-limiting examples of tissue specific promoters.

| Tissue | Illustrative Promoters |
|---|---|
| Root specific | *A. rhizogenes* rolD |
| | Domain A, CaMV 35S |
| | Tobacco TobRB7 |
| Tuber/storage organ specific | Potato patatin B33 |
| | Potato patatin PAT21 |
| | Potato GBSS |
| Seed specific | Bean beta-phaseolin |
| | Cotton alpha-globulin |
| | Wheat gbss1 |
| | Zma10 Kz or Zmag12 (maize zein gene) |
| | Zmag12 (maize glutelin gene) |
| Seed coat specific | Pea GsGNS2 |
| Floral specific | *Chrysanthemum* UEP1 |
| | Bean CHS15 |
| | *Petunia* EPSPS |
| Pollen specific | Maize ZMC5 |
| | Tomato lat52 |
| Pistil specific | Pear PsTL1 |
| | Potato SK2 |

In certain embodiments, the peptide(s) described herein are expressed under the control of the CaMV promoter. As used herein, the phrase "CaMV 35S" promoter includes variations of CaMV 35S promoter, e.g. promoters derived by means of ligations with operator regions, random or controlled mutagenesis, etc.). In certain embodiments, the peptide(s) described herein are expressed under the control of the E8 promoter. In certain embodiments, the peptide(s) described herein are expressed under the control of the hybrid tomato E4/E8 plant promoter (see, e.g., U.S. Pat. No. 6,118,049).

Vectors

As indicated above, the nucleic acid encoding the peptide(s) described herein is placed in a vector (e.g., a plasmid vector) under control of the desired promoter. In certain embodiments the vector (e.g., plasmid vector) can further encode one or more selectable markers (e.g., an antibiotic resistance marker such as the npt II gene for kanamycin resistance) and markers that confer selection by hygromycin, streptomycin, spectinomycin, or phosphinotri-cin. Illustrative selectable markers for use in plants include, but are not limited to neomycin phosphotransferase, hygro-mycin phosphotransferase, dihydrofolate reductase, chloramphenicol acetyl transferase, gentamycin acetyl transferase, nopaline synthase, octopine synthase, p-galac-tosidase, p-glucuronidase, streptomycin phosphotransferase, bleomycin resistance, firefly luciferase, bacterial luciferase, threonine dehydratase, metallothionein i1, epsp synthase, phosphinothricin acetyl transferase, acetolactate synthase, bromoxynil nitrilase, and the like.

In certain embodiments the vector can encode a signal peptide (e.g., ALPAH-Al1-*Phaseolus vulgaris*). Sequences that can be provided include, for example, a leader sequence (e.g., to allow secretion or vacuolar targeting), and translation termination signals.

More generally a number of vectors for plant cell transformation and heterologous gene expression are known to those of skill in the art. For example, the structures of a wide array of plasmids that have proven effective in (a) plant transformation and expression of heterologous genes including constructs that confer resistance to kanamycin, hygro-mycin, streptomycin, spectinomycin and phosphinotricin, or that confer β-glucuronidase (GUS) gene expression are described by Jones et al. (1992) *Transgenic Res.*, 1: 285-297. Binary vector constructs that carry polylinkers of the pUC and Bluescript types, plasmids that permit the expression of any heterologous reading frame from either nopaline synthase (nos) or octopine synthase (ocs) promoters, as well as the cauliflower mosaic virus 35S promoter, using either the nopaline synthase or octopine synthase 3' polyadenylation sequences, are also presented in this reference. These constructs permit a choice of orientation of the resulting transgene of interest, relative to the orientation of the selection marker gene. Most of the plasmids described by Jones et al. (supra.) are publicly/commercially available.

Illustrative and non-limiting examples of vectors include the pRL200 vector that has been used to stably transform lettuce (see, e.g., Kanamoto et al. (2006) *Transgenic Res.*, 15: 205-217), the pCAMBI1381-GUS plasmid has been used to target specific tissues in tomatoes (see, e.g., Lim et al. (2012) *Molecules and Cells* 34: 53-59), the pSBS4642 vector, the chloroplast transformation vector pLD, and the like.

Means of constructing the heterologous "gene" and incorporating it into a plasmid are well known to those of skill in the art. For example the heterologous "gene" can be chemically synthesized using a DNA synthesizer. Commercial services can also provide nucleic acid sequences synthesized to order. The construct can then be cloned into the vector using, for example, PCR cloning procedures. Methods of making the nucleic acid constructs described herein are well known to those of skill in the art, and specific methods are illustrated in the examples. Cloning and transformation methods, DNA vectors and the use of regulatory sequences are well known to the skilled artisan and may for instance be found in Current Protocols in Molecular Biology, F. M. Ausubel et al, Wiley Interscience, 2004, incorporated herein by reference.

In certain embodiments the marker genes (e.g., selectable markers) are removed from the transgenic plant. Methods of removing selectable markers are well known to those of skill in the art. In one illustrative, but non-limiting approach the marker genes are eliminated using MAT vector systems. MAT (Multi-Auto-Transformation) vectors are designed to use the oncogenes (ipt, iaaM/H, rol) of *Agrobacterium*, which control the endogenous levels of plant hormones and the cell responses to plant growth regulators, to differentiate transgenic cells, and to select marker-free transgenic plants. The oncogenes are combined with the site-specific recombination system (R/RS). At transformation, the oncogenes regenerate transgenic plants and then are removed by the R/RS system to generate marker-free transgenic plants. Protocols for the choice of a promoter for the oncogenes and the recombinase (R) gene, the state of plant materials and the tissue culture conditions are described, for example, by Ebinuman et al. (2005) *Meth. Mol. Biol.*, 286: 237-254.

Host Plant Selection

A wide variety of plant species have been genetically transformed with foreign DNA, using several different techniques to insert genes (see, e.g., Wu (1989) Pp. 35-15 In: *Plant Biotechnology*, Kung, S, and Arntzen, eds., Butterworth Publishers, Boston, Mass.; Deak et al. (1986) *Plant Cell Rep.* 5, 97-100; McCormick et al. (1986) *Plant Cell Rep.*, 5: 81-84; Shahin and Simpson (1986) *Hort. Sci.* 21: 1199-1201; Umbeck et al. (1987) *Bio/Technology* 5: 263-266; Christon et al. (1990) *Trends Biotechnol.* 8: 145-151; Datta et al. (1990) *Bio/Technology* 8: 736-740; Hinchee et al. (1988) *Bio/Technology* 6: 915-922; Raineri et al. (1990) *Bio/Technology*, 8: 33-38; Fromm et al. (1990) *Bio/Technology* 8: 833-839; and the like). Since many edible plants used by humans for food or as components of animal feed are dicotyledenous plants, in certain embodiments, it is preferred to employ dicotyledons for expression of the peptide(s) described herein, although monocotyledon transformation is also applicable especially in the production of certain grains useful for animal feed.

In certain embodiments the host plant selected for genetic transformation has edible tissue in which the peptide(s) of interest can be expressed. Thus, in various embodiments, the peptide(s) can be expressed in a part of the plant, such as the fruit, leaves, stems, seeds, or roots, which may be consumed by a human or an animal for which the peptide(s) are intended.

Various other considerations can inform selection of the host plant. It is sometimes preferred that the edible tissue of the host plant not require heating prior to consumption since the heating may reduce the effectiveness of apolipoprotein or mimetic for animal or human use. Also, it is sometimes preferred that the host plant express the peptide(s) in the form of a drinkable liquid.

In certain embodiments plants that are suitable for expression of the peptide(s) described herein include any dicotyledon or monocotyledon that is edible in part or in whole by a human or an animal. Illustrative plants include, for example, tomatoes, carrots, potatoes, apples, pears, plums, peaches, oranges, kiwis, papayas, pineapples, guava, lilikoi, starfruit, lychee, mango, grape, pomegranate, mustard greens, kale, chard, lettuce, soybean, rice, corn and other grains (e.g., wheat, rice, barley, bulgur, faro, kamut, kañiwa, millet, oats, quinoa, rice, rye, sorghum, spelt, teff, triticale, and the like), berries such as strawberries, blueberries, blackberries, goji berries, and raspberries, banana, rice, turnip, maize, grape, fig, plum, potato, safflower seeds, nuts (e.g., almond, walnut, pecan, peanut, cashew, macademia, hazelnut, etc.), legumes (e.g., alfalfa, clover, peas, beans (including black beans), lentils, lupins, mesquite, carob, soybeans, and the like), and the like. In certain embodiments expression in plants such as tobacco and the like, is also contemplated.

Methods of Gene Transfer into Plants

Any of a number of transformation protocols can be used to transform the plant cells and plants described herein. While certain preferred embodiments described below utilize particular transformation protocols, it will be understood by those of skill in the art that any transformation method may be utilized within the definitions and scope of the invention.

There are a number of methods for introducing foreign genes into both monocotyledenous and dicotyledenous plants (see, e.g., Potrykus (1991) *Annu. Rev. Plant Physiol, Plant Mol. Biol.* 42: 205-225; Shimamoto et al. (1989) *Nature* 338: 274-27, and the like. Methods for stable integration of exogenous DNA into plant genomic DNA include for example *agrobacterium*-mediated gene transfer, direct DNA uptake including methods for direct uptake DNA into protoplasts, DNA uptake induced by brief electric shock of plant cells, DNA injection into plant cells or tissues by particle bombardment, or by the use of micropipette systems, or by the direct incubation of DNA with germinating pollen; and the use of plant virus as gene vectors.

Plant transformation and regeneration in dicotyledons by *Agrobacterium tumefaciens* (*A. tumefaciens*) is well documented. The application of the *Agrobacterium tumefaciens* system with, for example, the leaf disc transformation method (see, e.g., Horsch et al. (1988) Pp. 1-9 In: *Plant Molecular Biology Manual* AS, Kluwer Academic Publishers, Dordrecht) permits efficient gene transfer, selection and regeneration.

Monocotyledons have also been found to be capable of genetic transformation by *Agrobacterium tumefaciens* as well as by other methods such as direct DNA uptake mediated by PEG (polyethylene glycol), or electroporation. Successful transfer of foreign genes into corn (see, e.g., Rhodes et al. (1989) *Science* 240: 204-207) and rice (see, e.g., Toriyama et al. (1988) *Bio/Technology* 6: 1072-1074; Zhang and Wu (1988) *Theor. Appl. Genet.* 76: 835-840), tomato (see, e.g., Frary and Earl (1996) *Plant Cell Rept.* 15: 235-240), as well as wheat and sorghum protoplasts, and numerous other species has been demonstrated.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. One illustrative approach is the leaf disc procedure which can be performed with any tissue explant that provides a good source for initiation of whole plant differentiation. The *Agrobacterium* system is especially viable in the creation of transgenic dicotyledenous plants.

As indicated above there are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Another method of vector transfer is the transmission of genetic material using modified plant viruses. DNA of interest is integrated into DNA viruses, and these viruses are used to infect plants at wound sites.

One method of transfection utilizing *Agrobacterium tumafaciens* is illustrated herein in the Examples. Using these teachings, numerous other plants can be similarly transformed. Those skilled in the art should recognize that there are multiple choices of *Agrobacterium* strains and plasmid construction strategies that can be used to optimize genetic transformation of plants. They will also recognize that *A. tumefaciens* may not be the only *Agrobacterium* strain used. Other *Agrobacterium* strains such as *A. rhizogenes* might be more suitable in some applications.

Methods of inoculation of the plant tissue vary depending upon the plant species and the *Agrobacterium* delivery system. A very convenient approach is the leaf disc procedure which can be performed with any tissue explant that provides a good source for initiation of whole plant differentiation. The addition of nurse tissue may be desirable under certain conditions. Other procedures such as the in vitro transformation of regenerating protoplasts with *A. tumefaciens* may be followed to obtain transformed plant cells as well.

It is noted that heterologous genes have been expressed in a wide variety of plants, particular edible plants. Thus, for example, a minimal peach chlorophyll a/b-binding protein gene (Lhcb2*Pp/) promoter (Cab19) and an enhanced mas35S CaMV promoter has been used to express heterologous genes in tomatoes (see, e.g., Bassett et al. (2007) *BMC Biotechnology* 7: 47). A 35S::PtFT1 promoter (35S CaMV promoter) has been used successfully in plums (see, e.g., Srinivasan *PLoS ONE* 7(7):e40715) and in apples (see, e.g., Trankener et al. (2010) *Planta* 232: 1309-1324). Suc2 promoter sequence of the *A. Thaliana* SUC2 gene (sucrose-H+ symporter) has also been used (Id.). Another promoter used in apples was the Pgst1 promoter from potato (see, e.g., Malnoy et al. (2006) *Transgenic Res.*, 15: 83-93). The 35S CaMV promoter has been used in apples for many years (see, e.g., Gleave (1992) *Plant Mol Biol.* 20: 1203-1207). Other promoters that are derivatives of the 35S CaMV promoter have been used in apples such as the potato proteinase inhibitor II (Pint) promoter (see, e.g., Ko et al. (2002) *J. Amer. Soc. Hort. Sci.* 127: 515-519). Butelli et al. used a binary vector (pDEL.ROS) containing both Delila and Roseal cDNAs from snapdragon under the control of the E8 promoter from tomato to produce tomatoes enriched in anthocyanins (see e.g., Butelli et al. (2008) *Nature Biotechnology* 26: 1301-1308). Kesanakurti et al. (2012) *Physiologia Plantarum* 146: 136-148) used the E8 promoter to produce tomato plants to transgenically produce tomato anionic peroxidase (tap1). Yang et al. (2012) *Transgenic Res.* 21: 1043-1056) demonstrated that the *Gentiana lutea* zeaxanthin epoxidase (GlZEP) promoter was highly expressed in transgenic tomato plants.

In view of the foregoing, one of skill will recognize that using the teachings and examples provided herein, any of peptides (e.g., apoA-I mimetic peptides) described herein can be expressed in an effective amount in a plant tissue with at most routine experimentation.

Method of Administering Transgenic Plants and Plant Products for Therapeutic and/or Prophylactic Use.

In various embodiments methods for the prophylaxis and/or treatment of various pathologies, especially pathologies characterized by an inflammatory response (see, e.g., Table 5) are provided. In certain embodiments the methods involve administering to a mammal in need thereof (e.g., a human, a non-human mammal) at least a portion of a transgenic plant as described herein, and/or an apolipoprotein or apolipoprotein mimetic peptide derived from such a transgenic plant. In certain embodiments all or a portion of the plant is administered to the mammal. In certain embodiments the mammal is administered the peptide in the form of a food, and/or a protein powder, and/or a nutritional supplement, and/or a "power bar", and/or a "defined diet".

In various embodiments the methods are used in the prophylaxis and/or treatment of pathologies that include, but are not limited to atherosclerosis, arthritis, cancer, diabetes, hepatic fibrosis, macular degeneration, kidney disease, obesity, osteoporosis, scleroderma, systemic lupus erythematosus, transplant vasculopathy, and vascular dementia.

In certain embodiments the pathology is atherosclerosis and the administration is for the treatment of disease or is a prophylactic administration. In certain embodiments, the prophylactic administration is to a subject (e.g., a human or non-human mammal) showing one or more risk factors for atherosclerosis (e.g., obesity, family history, elevated cholesterol, hypertension, diabetes, metabolic syndrome, low levels of HDL-cholesterol, elevated levels of triglycerides, or levels of high sensitivity CRP that are in the upper half of normal or are frankly elevated, and the like).

In certain embodiments the pathology is a cancer and the administration is as a therapeutic method in its own right and/or to augment therapeutic methods and/or to reduce adverse side effects to therapeutic methods (e.g., chemotherapy, radiotherapy, etc.). Various cancers for which the administration is believed to be suitable include, but are not limited to ovarian cancer, colon cancer, myeloma or multiple myeloma, breast cancer, bone cancer, cervical cancer, brain cancer, lung cancer, skin cancer including malignant melanoma, and prostate cancer.

In certain embodiments the administration is to prevent the onset, slow the onset and/or slow the progression of Alzheimer's disease and/or other dementia.

Administration of Transgenic Plant or Plant Part.

In certain embodiments the mammal is administered the transgenic plant expressing a peptide comprising or consisting of one or more apolipoprotein domains (e.g., 6F domains, 4F domains, etc.). In certain embodiments the mammal is fed all of the plant, or certain parts of the plant. Such parts include for example, fruit, leaves, seed, root, stem, flower, and the like. In certain embodiments, the plant or portion thereof is provided in the form of a juice, pulp, or ground portion(s) of the plant.

In certain embodiments the plant, or portion thereof, is provided in a lyophilized form or in a dried form (e.g., as a dried fruit, dried tomato, etc.). In certain embodiments the plant or portion thereof is lyophilized and/or dried and then ground into a powder that can be administered in that form to the subject and/or combined with other dietary components (e.g., as a food ingredient) for administration to the subject.

Protein Powder

In certain embodiments the mammal is administered a protein powder comprising a peptide comprising or consisting of one or more apolipoprotein domains (e.g., 6F domains, 4F domains, etc.) isolated from the transgenic plant(s) described herein, and/or the transgenic plant or at least a portion thereof. In certain embodiments the protein powder further comprise an additional protein. Illustrative proteins include, but are not limited to whey protein (e.g., whey concentrate, whey isolate, and whey hydrolysate), casein protein (or milk protein), soy protein, egg-white protein, hemp seed protein, rice protein, pea protein, and the like.

In certain embodiments a peptide comprising or consisting of one or more apolipoprotein domains (or apolipoprotein mimetics) is isolated from the transgenic plant and simply combined/mixed with the protein powder. In certain embodiments the plant, or a portion thereof, is dried and ground up into a plant powder that can be combined/mixed with the protein powder.

Methods of isolating/producing protein powder are well known to those of skill in the art. Typical methods involve a crude isolation step (e.g., filtering processes to separate lactose from milk in the preparation of whey protein) followed by a concentration step, e.g., an ion exchange purification to purify the protein without denaturing it. In certain embodiments the isolated recombinant protein, or powdered plant/plant component is simply added to a commercially available protein powder.

Food or Food Ingredient Comprising a Plant or Plant Part.

In certain embodiments the mammal is administered a food or a food ingredient that comprises at least a portion of the transgenic plant expressing a peptide comprising or consisting of one or more apolipoproteins or mimetics thereof (e.g., 6F domains, 4F domains, etc.). Typically the portion is at least a portion of the transgenic plant capable of being ingested for its nutritional value and/or taste where the consumed portion comprises the recombinant peptide comprising or consisting of the peptide(s). For these purposes a plant or portion thereof is considered to have nutritional value when it provides a source of metabolizable energy, supplementary or necessary vitamins or co-factors, roughage or otherwise beneficial effect upon ingestion by the subject mammal.

Thus, where the mammal to be treated with the food, or food ingredient, is an herbivore capable of bacterial-aided digestion of cellulose, such a food might be represented by a transgenic monocot grass. Similarly, although transgenic lettuce plants do not substantially contribute energy sources, building block molecules such as proteins, carbohydrates or fats, or other necessary or supplemental vitamins or cofactors, a lettuce plant transgenic for the apolipoprotein(s) described herein used as a food for that mammal would fall under the definition of a food as used herein if the ingestion of the lettuce contributed roughage to the benefit of the mammal, even if the mammal could not digest the cellulosic component of lettuce.

It is noted, that in various embodiments, dried plant parts, in particular dried fruits can readily be used as foods (e.g., dried pears, dried apples, dried tomatoes, dried plums, etc.). Similarly these dried plant parts (e.g., dried fruits) can readily be incorporated into foods and thereby form components of that food. Thus, for example dried tomatoes are widely used in foods such as bruschetta, pizza, tomato sauce, and the like. Where the plant part is provided as a powder it can readily be incorporated as an ingredient in a number of different foods (e.g., energy-, or protein-bars, smoothies, and the like).

Nutritional Supplement.

In certain embodiments a peptide comprising or consisting of one or more apolipoprotein domains (e.g., domains comprising a 6F sequence, a 4F sequence, etc.) isolated from the transgenic plant(s) described herein, and/or the transgenic plant or at least a portion thereof is provided as a component of a nutritional supplement (e.g., a vitamin supplement, a protein supplement, etc.). Illustrative vitamin supplements include, for example, vitamin A supplements, vitamin B supplements, vitamin D supplements, vitamin C supplements, fatty acid supplements (e.g., omega 3 fatty acids), mineral supplements such as calcium, zinc, and iron, and various combinations thereof.

In certain embodiments a peptide comprising or consisting of one or more apolipoprotein domains (e.g., domains comprising a 6F sequence, a 4F sequence, etc.) isolated from the transgenic plant(s) described herein, and/or the transgenic plant or at least a portion thereof is provided as a component of a multivitamin formulation or combined in a multi-component package with other vitamin/FA/mineral supplements. In certain embodiments where the plant or portion thereof is used in such a supplement the plant or portion thereof is dried and ground, e.g., to a fine powder and then incorporated into a multivitamin, or tableted or encapsulated by itself. In certain embodiments the vitamin supplement comprises vitamin A, and/or vitamin B1, and/or B2, and/or B6 and/or B12, and/or vitamin C, and/or vitamin E, and/or a fatty acid.

Defined Diet/Meal Replacement Product.

In certain embodiments a peptide comprising or consisting of one or more apolipoprotein domains (e.g., domains comprising a 6F sequence, a 4F sequence, etc.) isolated from the transgenic plant(s) described herein, and/or the transgenic plant or at least a portion thereof is provided as a component of a "defined diet" and/or meal replacement products (MRPs). A defined diet is a diet, optionally prepackaged, that is intended to meet all the dietary requirements of a particular subject. For example, for humans a defined diet can be a pre-determined diet designed to facilitate a particular dietary goal (e.g., weight reduction, reduction of allergens, lactose, weight gain, protein elevation, etc.). In the case of non-human mammals (e.g., canines, felines, porcines, equines, bovines, etc.) the "defined diet" can be provided in the form an animal food product. The animal food product can be designed to meet particular dietary goals, e.g., as described above for a human.

In certain embodiments, the animal food product can be provided as the component of a treatment regimen (e.g., for a farm animal, pet, etc.) afflicted with, or at risk for, a particular pathology, e.g., cancer, atherosclerosis, kidney disease, etc.

Meal replacement products are a form of defined diet, either pre-packaged powdered drink mixes or edible bars designed to replace prepared meals. MRPs are generally high in protein, low in fat, have a low to moderate amount of carbohydrates, and contain a wide array of vitamins and minerals. The majority of MRPs use whey protein, casein (often listed as calcium caseinate or micellar casein), soy protein, and/or egg albumin as protein sources. Carbohydrates are typically derived from maltodextrin, oat fiber, brown rice, and/or wheat flour. Some MRPs also contain flax oil powder as a source of essential fatty acids. MRPs can also contain other ingredients. These can include, but are not limited to creatine monohydrate, glutamine peptides, L-glutamine, calcium alpha-ketoglutarate, additional amino acids, lactoferrin, conjugated linoleic acid, and medium chain triglycerides.

In certain embodiments the "defined diet" comprises one or more food items. Each food item may be individually prepackaged. In addition, one or more of the food items may be nutritionally enhanced by fortification of vitamins and minerals and/or by incorporation of the peptide or transgenic plant or portion thereof.

The individual food items may be prepared by processing, e.g., mixing, precooking, cooking, freezing, dehydrating or freeze-drying, such that the meal may be maintained in a frozen or dry condition for an extended period. Additionally, an individual food item may be packaged in such a way that, before consumption, the food item must be mixed by hand or blender, cooked by placing the food component on a stove top, in an oven or microwave, or prepared by adding cool, hot or boiling water or by submerging the food item into boiling water. One or more of the food items may be shelf-stable. Preferably, a food item has a sufficiently long storage or shelf-life such that defined diet may be stored in advance of consumption. In certain embodiments a storage or shelf-life under retail conditions in a range of about six to twelve months is desirable.

In certain embodiments individual food items may be in the form of solids, semi-solids or liquids and may include, but are not limited to, soup products, protein supplements, grain foods, starch foods, fruit or vegetables foods, nutritional drinks and beverages.

In various embodiments, the peptide comprising or consisting of one or more apolipoprotein domains (e.g., domains comprising a 6F sequence, a 4F sequence, etc.) isolated from the transgenic plant(s) described herein, and/or the transgenic plant or at least a portion thereof is simply combined with/incorporated into the defined diet and/or meal replacement product (MRP). In certain embodiments the plant is dried and ground to a powder that can be added to one or more of the food components comprising the defined diet or MRP. In certain embodiments, the plant or a portion thereof can itself serve as a food comprising the defined diet/MRP. For example, where the transgenic plant is a transgenic tomato plant, the plant can be provided as a dried tomato (e.g., in a salad or pizza), as a tomato paste, tomato juice, or whole tomato in the meal as provided.

Power Bars.

In certain embodiments a peptide comprising or consisting of one or more apolipoprotein domains (e.g., domains comprising a 6F sequence, a 4F sequence, etc.) isolated from the transgenic plant(s) described herein, and/or the transgenic plant or at least a portion thereof is provided as a component of a "power bar"/energy bar. Energy bars are supplemental bars that typically contain cereals and/or dried fruit(s), and/or other high energy foods and/or fiber targeted at people that require quick energy or that are on certain weight loss regimens, but do not have time for a meal. They are different from energy drinks, which contain caffeine, whereas bars provide food energy.

Numerous power bar formulations are known to those of skill in the art. In certain embodiments the peptide comprising or consisting of one or more apolipoprotein domains is incorporated into the power bar as a protein (amino acid) component. In certain embodiments the transgenic plant or at least a portion thereof is provided as a component of the power bar. In various embodiments the plant can be provided as all or a portion of a fruit and/or fiber component of the power bar formulation.

Use of "Non-Transgenic" Tomato

It was also a surprises discovery that non-transgenic tomatoes, while lacking the activity demonstrated by the transgenic plants described herein can increase PON activity and/or decrease inflammation. Accordingly in certain embodiments the use of a tomato concentrate to increase PON activity and/or to decrease inflammation (e.g. as measured by SAA levels) is contemplated.

Animal Uses.

As indicated above, in various embodiments, a peptide comprising or consisting of one or more apolipoprotein domains (e.g., domains comprising a 6F sequence, a 4F sequence, etc.) isolated from the transgenic plant(s) described herein, and/or the transgenic plant or at least a portion thereof is provided as a component of an animal diet. The diet can be provided to simply maintain a healthy animal or in certain embodiments, the diet is optimized to facilitate a prophylactic or therapeutic effect.

Illustrative animal diets include, but are not limited to diets for juvenile animals, diets for normal adult animals, diets for old animals, weight loss diets, dental health diets, thyroid health diets, gastrointestinal health diets, hypoallergenic diets, kidney health diets, bladder health diets, aging diets, and the like. In certain embodiments the diet is a diet optimized for treatment of an animal with kidney disease and/or with cancer. In certain embodiments the diet is designed for administration to an animal receiving chemotherapy and/or radiotherapy.

In certain embodiments the peptide comprising one or more apolipoprotein domain is simply added to the diet as an additional protein (amino acid) source. In certain embodiments the plant or a portion thereof is incorporated into the diet. In certain embodiments the plant or portion thereof is dried and ground up into a powder for incorporation into the diet. The plan or portion thereof can be incorporated into a wet animal food or a dried (e.g., pellet) animal food. In certain embodiments the plant or portion thereof additional provides a fiber component of the diet.

Other Therapeutic Peptides.

While the constructs, plants, and methods described above are described with respect to apoproteins, it is believed the same delivery methods (e.g., consumption of a plant, plant part, or plant product) can be used to deliver other therapeutic peptides.

A wide variety of other therapeutic peptides are known to those of skill in the art and it is believed they can be expressed in plants in therapeutically effective amounts as described herein. Such peptides include, but are not limited to, growth hormone (e.g., isolated and/or human, porcine, or bovine growth hormones), natural, synthetic, or recombinant growth hormone releasing hormones (GHRH), interferons (e.g., alpha, beta, and gamma interferon), interleukins (e.g., interleukin-1, interleukin, 2, etc.), natural, synthetic or recombinant insulin (e.g., porcine, bovine, human insulins), insulin-like growth factor-1 (IGF-1), insulin-like growth factor-2 (IGF2, somatostatin), heparin, heparinoids, dermatans, chondroitins, calcitonin (e.g., natural, synthetic, or recombinant salmon, porcine, eel, chicken, and human calcitonin), antigens (e.g., influenza antigen, hepatitis A, B, C antigen, HPV antigen, etc.), antibodies (polyclonal and monoclonal) (e.g., HERCEPTIN®, RITUXAN®, AVASTIN®, ERBITUX®, etc.), oxytocin, leutinizing-hormone-releasing hormone (LHRH), follicle stimulating hormone (FSH); glucocerebrosidase, thrombopoietin; filgrastim; prostaglandins; vasopressin; cromolyn sodium (e.g., sodium or disodium chromoglycate), vancomycin, desferrioxamine (DFO); parathyroid hormone (PTH) including its fragments, antimicrobials (e.g., anti-bacterial agents, including anti-fungal agents, etc.), and the like. In addition, the therapeutic peptides include analogs, fragments, mimetics or modified derivatives of these compounds (e.g., polyethylene glycol (PEG)-modified derivatives, glycosylated derivatives, etc.), or any combination thereof.

Therapeutic/Prophylactic Applications of Apoproteins.

It has been demonstrated that the peptides described herein (e.g., the peptides listed in Tables 1, 2, and/or 3) are therapeutically and/or prophylactically effective in a number of indications characterized by an inflammatory response. Such indications include, for example atherosclerosis as described for example, in U.S. Pat. Nos. 6,664,230, 6,933,279, 7,144,862, 7,166,578, 7,199,102 and PCT Publication Nos: PCT/US2001/026497 (WO 2002/015923), and PCT/US2008/085409, which are incorporated herein by reference for the peptides and indications described herein.

Accordingly, it is believed that transgenic plants as described herein expressing the peptides or portions thereof are similarly effective in such indications. Thus, in certain embodiments, methods for the treatment or prophylaxis of a pathology characterized by an inflammatory response are provided where the method comprises administering to a mammal in need thereof an effective amount of: at least a portion of a transgenic plant expressing one or more peptides from Tables 1, 2, and/or 3; and/or an apolipoprotein or apolipoprotein mimetic peptide expressed in a plant as described herein, and/or a food comprising at least a portion of a transgenic plant capable of being ingested for its nutritional value, where the plant expresses a peptide comprising an amino acid sequence that is an apolipoprotein or apolipoprotein mimetic as described herein, and/or a protein powder, wherein at least a portion of the protein powder comprises an apolipoprotein or apolipoprotein mimetic peptide expressed in a plant as described herein, and/or a comprising a transgenic plant (or portion thereof) and/or an apolipoprotein or apolipoprotein mimetic peptide as described herein.

In certain embodiments the apolipoprotein peptide is comprises an amino acid sequence selected from the group consisting of DWLKAFYDKFFEKFKEFF (6F, SEQ ID NO:17), FFEKFKEFFKDYFAKLWD (rev6F, SEQ ID NO: 25), DWFKAFYDKVAEKFKEAF (4F, SEQ ID NO:15), FAEKFKEAVKDYFAKFWD (rev4F, SEQ ID NO: 23), LLEQLNEQFNWVSRLANL (SEQ ID NO:609), and LVGRQLEEFL (SEQ ID NO:612).

An illustrative, but non-limiting list of indications/conditions for which the peptides described herein have been shown to be effective and/or are believed to be effective is shown in Table 5.

TABLE 5

Illustrative conditions in which the peptides described herein (e.g., 4F, 6F, etc.) have been shown to be or are believed to be effective.

atherosclerosis/symptoms/consequences thereof
    plaque formation
    lesion formation
    myocardial infarction
    stroke
congestive heart failure
vascular function:
    arteriole function
    arteriolar disease
        associated with aging
        associated with Alzheimer's disease
        associated with chronic kidney disease
        associated with hypertension
        associated with multi-infarct dementia
        associated with subarachnoid hemorrhage
    peripheral vascular disease
pulmonary disease:
    chronic obstructive pulmonary disease (COPD),
    emphysema
    asthma
    idiopathic pulmonary fibrosis
    pulmonary fibrosis
    adult respiratory distress syndrome
osteoporosis
Paget's disease
coronary calcification
autoimmune:
        rheumatoid arthritis
        polyarteritis nodosa
        polymyalgia rheumatica
        lupus erythematosus
        multiple sclerosis
        Wegener's granulomatosis
        central nervous system vasculitis (CNSV)
        Sjögren's syndrome
        Scleroderma
        polymyositis
AIDS inflammatory response
infections:
    bacterial
    fungal
    viral
    parasitic
    influenza (including avian flu)
    viral pneumonia
    endotoxic shock syndrome
    sepsis
    sepsis syndrome
    (clinical syndrome where it appears that the patient is septic but no organisms are recovered from the blood)
trauma/wound:
    organ transplant
    transplant atherosclerosis
    transplant rejection
    corneal ulcer
    chronic/non-healing wound
    ulcerative colitis
    reperfusion injury (prevent and/or treat)
    ischemic reperfusion injury (prevent and/or treat)
    spinal cord injuries (mitigating effects)
cancers
    myeloma/multiple myeloma
    ovarian cancer
    breast cancer
    colon cancer
    bone cancer
    cervical cancer
    prostate cancer
osteoarthritis
inflammatory bowel disease
allergic rhinitis
cachexia
diabetes
Alzheimer's disease
implanted prosthesis
biofilm formation
Crohns' disease

TABLE 5-continued

Illustrative conditions in which the peptides described herein (e.g., 4F, 6F, etc.) have been shown to be or are believed to be effective.

renal failure (acute renal failure, chronic renal failure)
sickle cell disease, sickle cell crisis
amelioration of adriamycin toxicity
amelioration of anthracylin toxicity
to improve insulin sensitivity
to treat the metabolic syndrome
to increase adiponectin
to reduce abdominal fat
dermatitis, acute and chronic
    eczema
    psoriasis
    contact dermatitis
    scleroderma
diabetes and related conditions
    Type I Diabetes
    Type II Diabetes
    Juvenile Onset Diabetes
    Prevention of the onset of diabetes
    Diabetic Nephropathy
    Diabetic Neuropathy
    Diabetic Retinopathy
erectile dysfunction
macular degeneration
multiple sclerosis
nephropathy
neuropathy
Parkinson's Disease
peripheral vascular disease
meningitis
Specific biological activities:
    increase Heme Oxygenase 1
    increase extracellular superoxide dismutase
    prevent endothelial sloughing
    prevent the association of myeloperoxidase with ApoA-I
    prevent the nitrosylation of tyrosine in ApoA-I
    render HDL anti-inflammatory
    improve vasoreactivity
    increase the formation of pre-beta HDL
    promote reverse cholesterol transport
    promote reverse cholesterol transport from macrophages
    synergize the action of statins It is noted that the conditions listed in Table 5 are intended to be illustrative and not limiting.

Methods of Preventing or Reducing the Uptake of Dietary Pro-Inflammatory Micro-Lipid Components.

Without being bound by a particular theory, it is believed that a major action of the transgenic plants described herein that express/contain an apolipoprotein or mimetic thereof (e.g., a plant expressing the 6F peptide) is the reduction in small intestine levels of lysophosphatidic acid (LPA). This could be mediated by several mechanisms. It was previously postulated that the formation of LPA occurs by two pathways (Aoki et al. (2008) *Biochimica et Biophysica Acta*, 1781: 513-518)). The first involves the action of $PLA_1$ or $PLA_2$ on a phospholipid such as phosphatidylcholine to produce a lysophospholipid (i.e. the removal of a fatty acid from position one or two from the phospholipid). The next step is the action by a Phospholipase D such as autotaxin to remove the choline and yield the lysophosphatidic acid. The second pathway involves phosphatidic acid which is either formed from the action of phospholipase D on a phospholipid such as phosphatidylcholine generating phosphatidic acid or the action of diacyl glycerol kinase (DGK) on diacyglycerol (DAG) which results in the formation of phosphatidic acid. These processes can occur in the enterocyte or in the lumen of the small intestine or prior to ingestion of food.

Another possible mechanism for regulating LPA levels involves three enzymes known as lysophosphatidic acid phosphatase 1, 2 or 3 (LPP1, LPP2, LPP3). These phosphatases rapidly remove the phosphate from LPA and hence contribute to regulation of LPA levels.

To explore the mechanism of action, a microarray experiment to determine gene expression levels in the small intestine from mice fed the Western Diet or a chow diet and given or not given D-4F in their drinking water was performed. It was previously shown that D-4F administration reduces LPA levels similar to transgenic 6F tomatoes. In this experiment, none of the enzymes involved in the formation of LPA changed their expression significantly in the microarray. While this experiment does not completely rule out the effect of the apolipoprotein mimetics on these enzymes, without being bound to a particular theory, it is believed the transgenic plants described herein alter/reduce LPA by another mechanism.

In particular it is believed that the mechanism of action of the transgenic 6F tomatoes described herein is that they block, or at least partially inhibit, the uptake of precursors into the enterocyte such as phosphatidic acid (PA) or they block, or at least partially inhibit, the uptake into the enterocyte of pre-formed LPA which is contained in the diet. Such a mechanism is consistent with the known action of the apoA-I mimetic peptides. In this regard, it is noted that the binding affinity of L-4F for LPA approaches the binding affinity of avidin for biotin, which is the highest binding affinity known.

Figure 33:
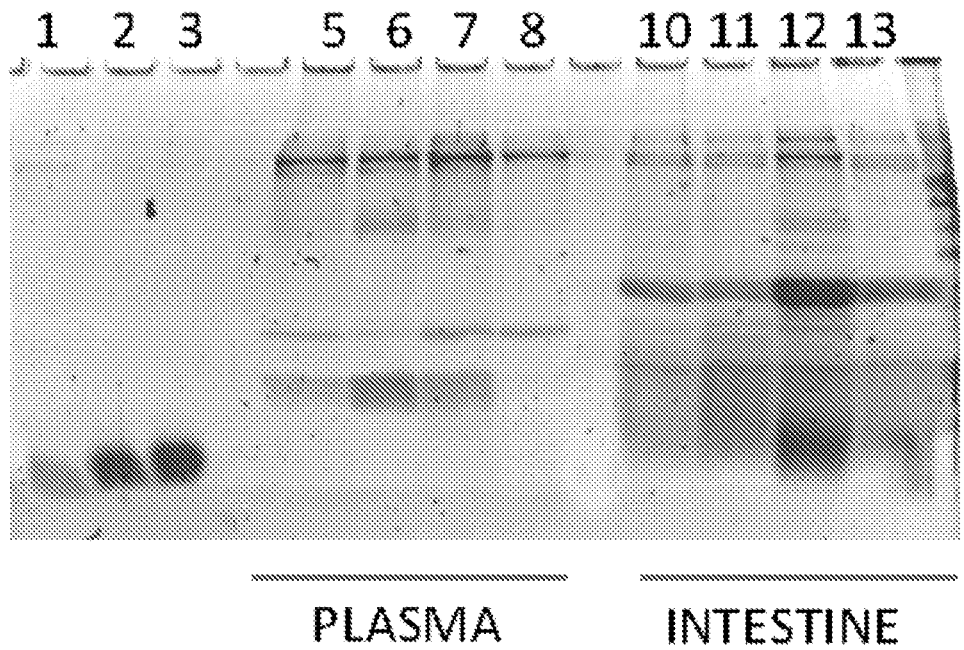
FIG. 33 shows that intact 6F peptide is identified in the small intestine but not in the plasma. Female LDLR−/− mice 8-9 months of age (n=6) were fasted overnight and fed WD with transgenic 6F lyophilized tomato powder added to WD to provide 900 μg of 6F in 2 grams of diet. Over a period of 30-90 minutes, each mouse ate all of the 2 grams of diet. Approximately 2 hours after finishing the food the mice were bled and the small intestine was obtained (including contents), homogenized in acetonitrile:water (1:1), chromatographed by HPLC and subjected to SDS PAGE as described in Materials and Methods of Example 3. Plasma was lyophilized and resuspended in acetonitrile:water (1:1), chromatographed by HPLC and subjected to SDS PAGE as described in Materials and Methods of Example 3. 12.5, 25 and 37.5 μg, of chemically synthesized 6F without end blocking groups were applied to lanes 1, 2 and 3, respectively. Plasma following HPLC from 4 of the 6 mice was applied to lanes 5, 6, 7 and 8. Small intestine following HPLC from the four mice shown in lanes 5, 6, 7 and 8 was applied to lanes 10, 11, 12 and 13, respectively. The far right lane contains molecular weight markers. The lanes were scanned for quantification as described in Materials and Methods of Example 3.

Without being bound to a particular theory, it is believed that lipid components of the diet can be divided into two classes: macro-lipid components of the diet and micro-lipid components of the diet. The former in a Western diet would include phospholipids such as phosphatidylcholine and sterols such as cholesterol. These are present in milligram amounts per gram of diet. Even lysophosphatidylcholine is likely to be present in milligram quantities after phosphatidylcholine is acted upon in the Duodenum by $PLA_2$. The micro-lipid components are present in microgram amounts per gram of diet. As shown in FIG. 33 the amount of intact 6F peptide found in the small intestine about two hours after the mice consumed the Western diet with transgenic 6F tomatoes was 15.6±7.4 µg 6F per 200 mg small intestine. It is believed to be unlikely that this amount of peptide could bind and prevent the uptake of significant amounts of phospholipids or lysophosphatidylcholine or sterol. However, this amount of peptide could bind and prevent the uptake of microgram quantities of phosphatidic acid (PA) such as is present in foods (see, e.g., Tanaka et al. ((2012) *Agric. Food Chem.*, 60: 4156-4161) or preformed LPA which is present in hen egg yolk at 44.23 nmol/g tissue or in hen egg white (8.81 nmol/g tissue) (Nakane et al. (2001) *Lipids*, 36: 413-419).

Accordingly, in view of the foregoing, methods of preventing or reducing the uptake of dietary pro-inflammatory micro-lipid components (e.g., lysophosphatidic acid, phosphatidic acid, and the like) are contemplated. In certain embodiments the method comprises administering to the mammal an effective amount of at least a portion of a transgenic plant as described and/or claimed herein; and/or an apolipoprotein or apolipoprotein mimetic peptide according as described and/or claimed herein; and/or a food or food ingredient as described and/or claimed herein; and/or a protein powder as described and/or claimed herein; and/or a nutritional supplement as described and/or claimed herein. In certain embodiments the mammal is administered at least a portion of a transgenic plant as described and/or claimed herein. In certain embodiments the mammal is administered a fruit or part of a fruit of the transgenic plant. In certain embodiments the fruit is selected from the group consisting of a tomato, an apple, a pear, a plum, a peach, an orange, a kiwi, a payaya, a pineapple, a guava, a lilikoi, a starfruit, a lychee, a mango, a pomegranate, and a plum. In certain embodiments the fruit is a tomato.

The foregoing plants, plant components, methods, formulations and modes of administration described above are intended to be illustrative and not limiting. Using the teaching provided herein numerous other plants, plant components, methods, formulations and/or modes of administration will be available to one of skill in the art.

EXAMPLES

The following examples are offered to illustrate, but not to limit the claimed invention.

Example 1

Activity of the 6F Peptide

Figure 2:
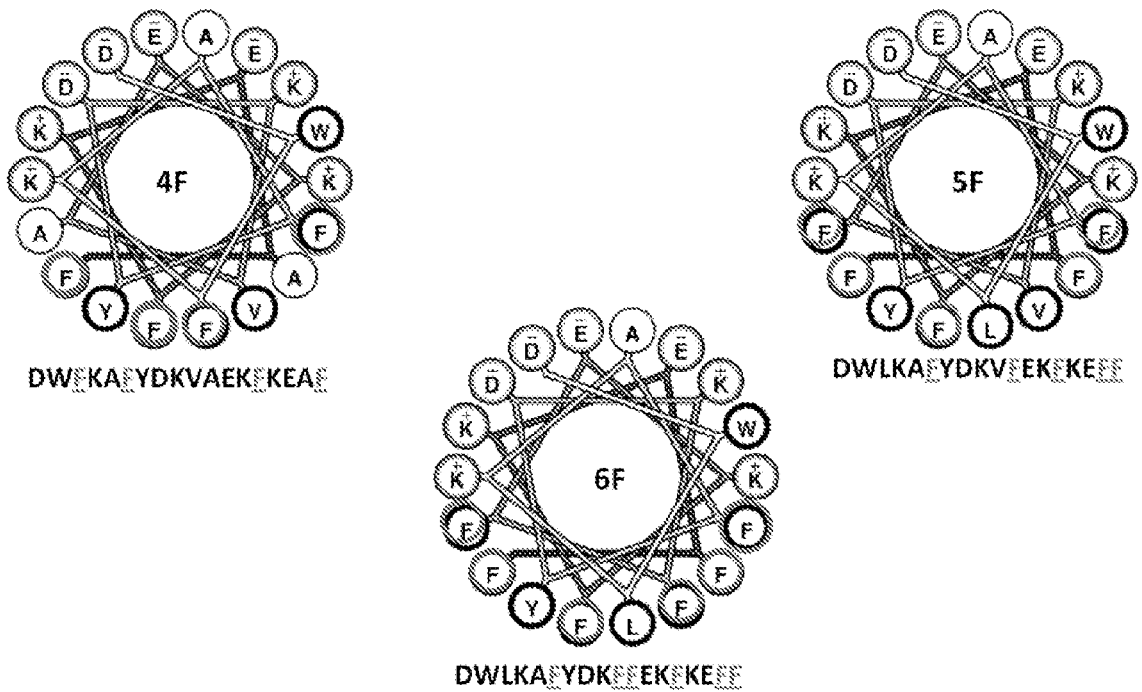
FIG. 2 shows helical wheel diagrams of the α-helical peptides 4F (SEQ ID NO:15), 5F (SEQ ID NO:3), and 6F (SEQ ID NO:17).

FIG. 1 compares the efficacy of a variety of apoA-I mimetic peptides in inhibiting monocyte chemotactic activity production by human artery wall cells exposed to human LDL. Peptides 4F, 5F and 6F were found to be indistinguishable in this assay. FIG. 2 shows that the peptides 4F, 5F and 6F differ by the number of phenylalanine residues on the hydrophobic face of the peptide.

The peptide 6F is described in U.S. Pat. No. 7,199,102 B2. Unlike the 4F peptide, which included blocking groups to maximize activity with oral administration, the 6F peptide was shown to be active orally in vivo even without blocking groups, e.g., as shown by the experiment described in FIG. 3 measuring serum amyloid A (SAA) levels. In mice and rabbits SAA levels are highly correlated with the extent of atherosclerosis.

Figure 3:
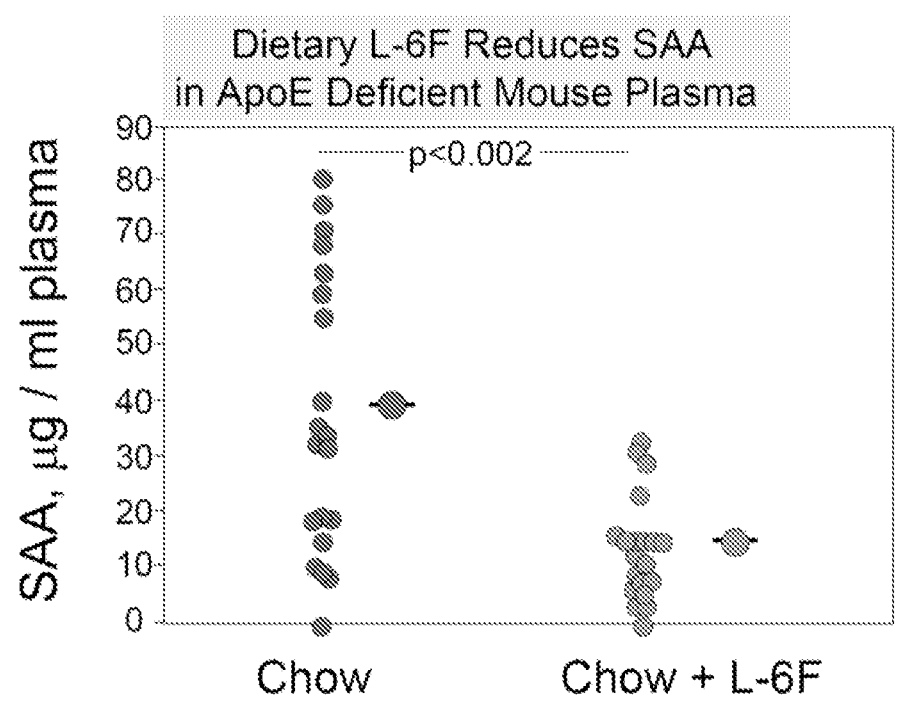
FIG. 3 shows that dietary L-6F (without blocking groups) reduces SAA in ApoE deficient mice. Groups of female apoE null mice (n=20) 16 to 18 months of age, were maintained on rodent chow that did not contain peptide (Chow) or contained 1.2 mg L-6F without blocked end groups per 4 grams of chow (Chow+L-6F) providing a dose ~60 mg/kg/day of L-6F without blocked end groups. The mice in both groups consumed approximately 4 grams of the chow per day. Thus, L-6F only constituted ~0.03% of the diet by weight. On day 10 blood was removed, plasma was separated and serum amyloid A (SAA) was determined by ELISA.

The experiment described in FIG. 3 was performed with all of the mice on a chow diet. The experiment shown in FIG. 16B was performed with all of the mice on a Western Diet. The experiments shown in FIG. 16C demonstrate that adding L-6F peptide without blocking groups to WD resulted in a significant decrease in atherosclerosis.

Having demonstrated that L-6F without blocking groups was efficacious in a mouse model of atherosclerosis, we next asked the following question. If we were successful in expressing L-6F without blocking groups in a lower life form that could be eaten by humans would it still be biologically active? If the answer to the question was no; nothing would have been gained by genetically expressing the peptide. For example, if we expressed L-6F without blocking groups in a tomato it would be entirely possible that during the process of ripening which is a highly oxidative process, the peptide might be destroyed, or the peptide might be saturated with oxidized lipids formed during the ripening process and therefore the peptide might be present but non-functional. To test this question we performed the experiments shown in FIG. 28A. The data in FIG. 28A indicate that L-6F without blocking groups was still biologically active even in the presence of a substantial amount of ripened tomato.

We previously reported that lysophosphatidic acid (LPA) levels were significantly reduced after treatment with L-4F (containing blocking groups) in a mouse model of ovarian cancer. LPA is a known tumor growth factor and is also known to accelerate atherosclerosis in mouse models. The reduction in LPA levels in mice treated with 4F was associated with a significant reduction in tumor volume and a reduction in the number of tumor nodules in the mouse model of ovarian cancer.

Figure 28A:
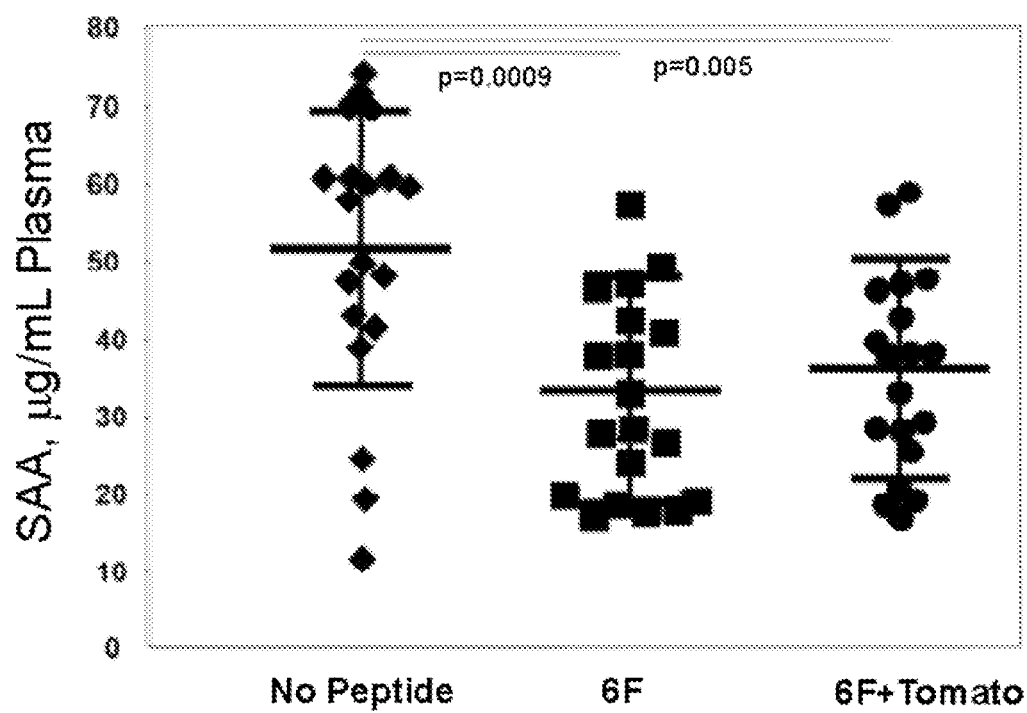
FIG. 28A. Female apoE$^{-/-}$ mice 6-7 months of age (n=19 per group) were placed on WD for one week. Subsequently, they were continued on WD and received no peptide or WD plus L-6F without end blocking groups at a dose of 60 mg/kg/day or they received the same dose of peptide, but which was first added to homogenized ripened tomato and then mixed into WD so that the homogenized tomato constituted 20% by weight of the diet. After one week the mice were bled and plasma SAA levels were determined as described in Materials and Methods in Example 3.
Figure 28B:
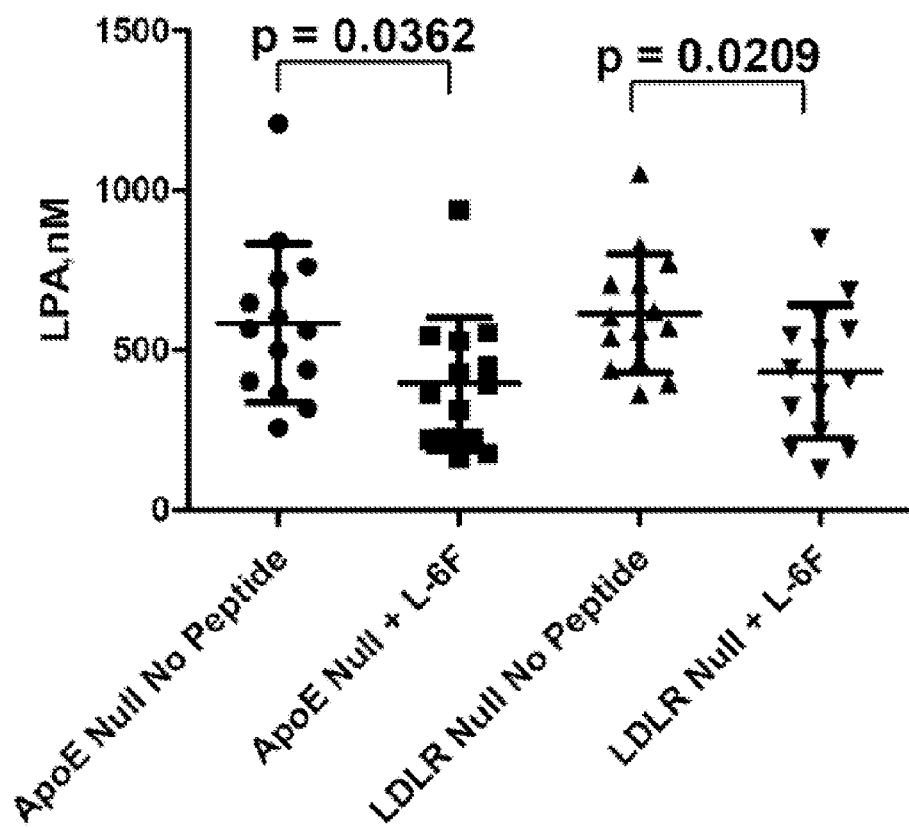
FIG. 28B. Groups of female apoE$^{-/-}$ (ApoE Null) mice 12 months of age were fed WD containing 10% homogenized ripened tomato for 3 weeks without or with L-6F without end blocking groups at a dose of 60 mg/kg/day (n=14 per group). Female LDLR$^{-/-}$ (LDLR Null) mice 7-8 months of age were treated similarly (n=14). After 3 weeks the mice were bled and plasma lysophosphatidic acid levels were determined by ELISA as described in Materials and Methods in Example 3.

As shown below in FIG. 28B, adding L-6F without blocking groups to WD containing 10% ripened tomato homogenate significantly decreased LPA levels in both apoE null and LDLR null mice.

Example 2

Transgenic Plants Expressing the 6F Peptide

This example described the cloning and expression of the 6F peptide in tomato plants. This example further shows that transgenic plants stably expressing the 6F peptide have substantial biological activity.

Cloning of the 6F Gene into the Plant Transformation Vector

The strategy for expressing the 6F peptide in tomato plants is shown in FIG. 4. Basically, a nucleic acid encoding the 6F peptide was constructed in which the codon usage was optimized for expression in tomato plants (see, e.g., www.kazusa.or.jp/codon/cgi-bin/showcodon.cgi?species=4081. The DNA further encoded a signal peptide (M-I-M-A-S-S-K-L-L-S-L-A-L-F-L-A-L-L-S-H-A-N-S, SEQ ID NO:2).

The original gene encoding the apoA-I mimetic peptide 6F is 54-bp long, and encodes a protein of 18 aa (D-L-K-A-F-Y-D-K-F-F-E-K-F-K-E-F-F, SEQ ID NO:17) with a molecular mass of 2435.81 Da. The expression cassette of the 6F protein comprised the plant-derived 23 amino acid M-I-M-A-S-S-K-L-L-S-L-A-L-F-L-A-L-L-S-H-A-N-S (SEQ ID NO:2) signal peptide (SP), 69 bp long (Pogrebnyak et al. (2005) *Proc. Natl. Acad. Sci. USA* 102: 9062-9067). The Codon usage table (www.kazusa.or.jp/codon) specific for *Lycopersicon esculentum* was used to design the DNA sequence (TCT AGA ATG ATT ATG GCT TCT TCT AAA CTT CTT TCT CTT GCT CTT TTT CTT GCT CTT CTT TCT CAT GCT AAT TCT GAT TGG CTT AAA GCT TTT TAT GAT AAA TTT TTT GAA AAA TTT AAA GAA TTT TTT TGA GAG CTC, SEQ ID NO:4) and it was synthesized from DNA 2.0 (www.dna20.com). The cassette was cloned into XbaI/SacI site replacing GUS gene of plant binary vector pBI121 and TGA stop codon was introduced before the SacI site (*Arabidopsis* biological resource centre, ABRC, www.arabidopsis.org) under CaMV S35 promoter. The sequence was verified by DNA sequencing. The vector also contains the npt II gene for kanamycin selection of transgenic plants. A schematic illustration of the vector is shown in FIG. 15.

Figure 15:
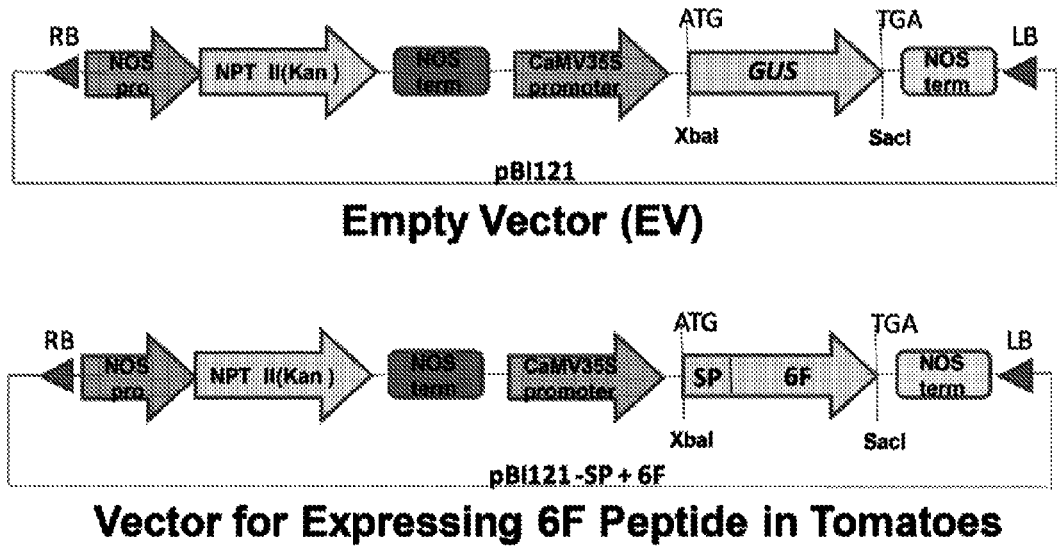
FIG. 15 provides a schematic diagram of the full length pBI121-p6F cassette. The top panel depicts the pBI121 vector, which is referred to in the examples as the empty vector (EV). The bottom panel shows the vector for expressing the 6F peptide in which the GUS gene has been replaced at the XbaI/SacI site by the plant-derived signal peptide (SP) and the gene encoding 6F under the CaMV35S promoter and nopaline synthase terminator (NOS term) as described in the Example 3.

FIG. 5 shows *Agrobacterium tumefaciens* LBA4404 that was transformed with and without the sequence for 6F shown in FIG. 4 and above and using the vector illustrated in FIG. 15.

Generation of Transgenic Plants.

Transgenic plants were generated as a work for hire by the St. Louis Donald Danforth Plant Science Centre, Missouri in collaboration with Dr. Kevin Lutke. A total of 1,200 tomato cotyledons (*Lycopersicon esculentum*) were transformed by 6F (in two experiments) and empty vector (one experiment) containing *Agrobacterium* using the method described by Frary et al. (1996) *Plant Cell Rept.*, 16: 235-240. Initially, sixty kanamycin-resistant founder plants (44 6F vector and 16 empty vector) were generated and further used for molecular analyses.

Figure 6:
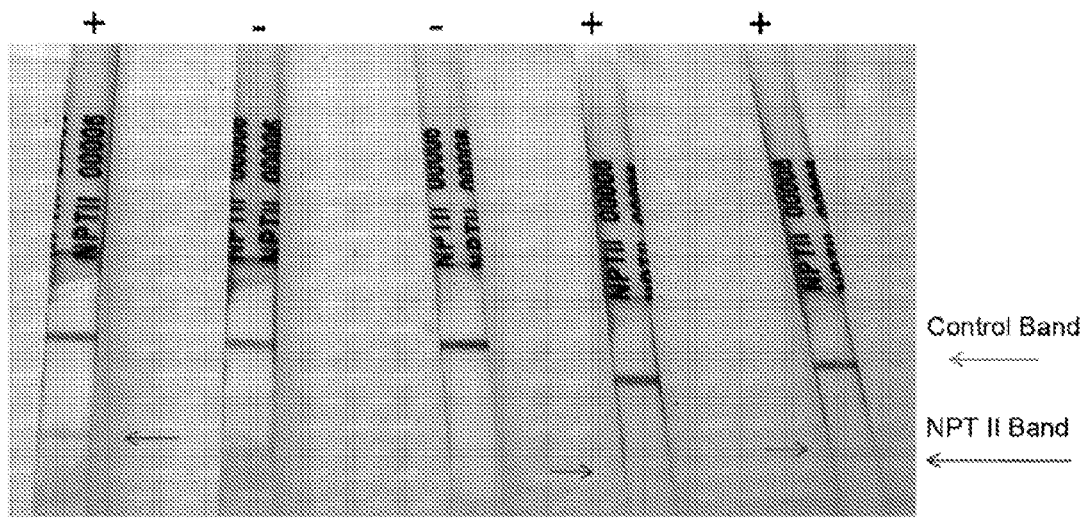
FIG. 6 shows NPT II which confers resistance to kanamycin and which was included in the vector described in FIG. 15 and was expressed in some of the transformed plants (+) but not all (−).
Figure 7:
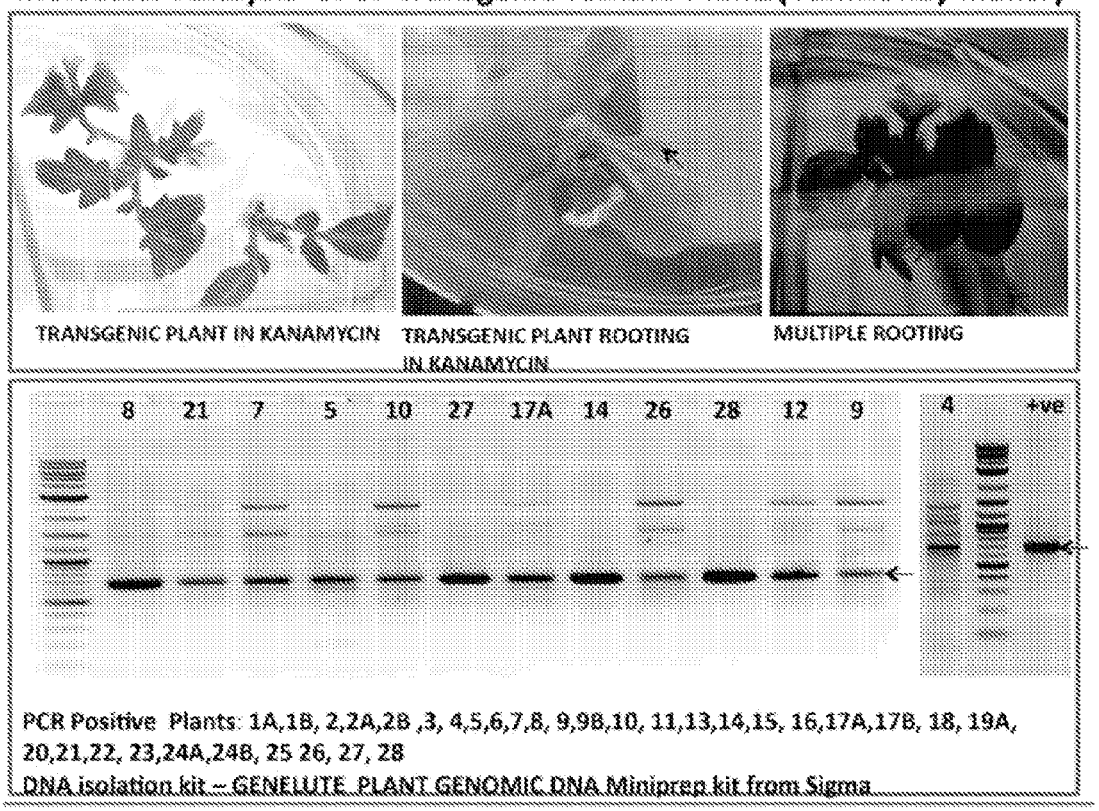
FIG. 7 shows selection and analysis of transgenic plants. The top panel shows pictures of example plants being selected in kanamycin. The bottom panel shows examples of PCR positive plants from the 33 positive plants listed at the bottom of the bottom panel. Approximately 120 plants were ultimately tested.

FIG. 6 shows expression of the NPT II band from plants that were found to be resistant or not resistant to kanamycin, while FIG. 7 shows examples of the plants being selected in Kanamycin and examples of PCR positive plants.

Analysis of Transgenic Plant Material.

Figure 17:
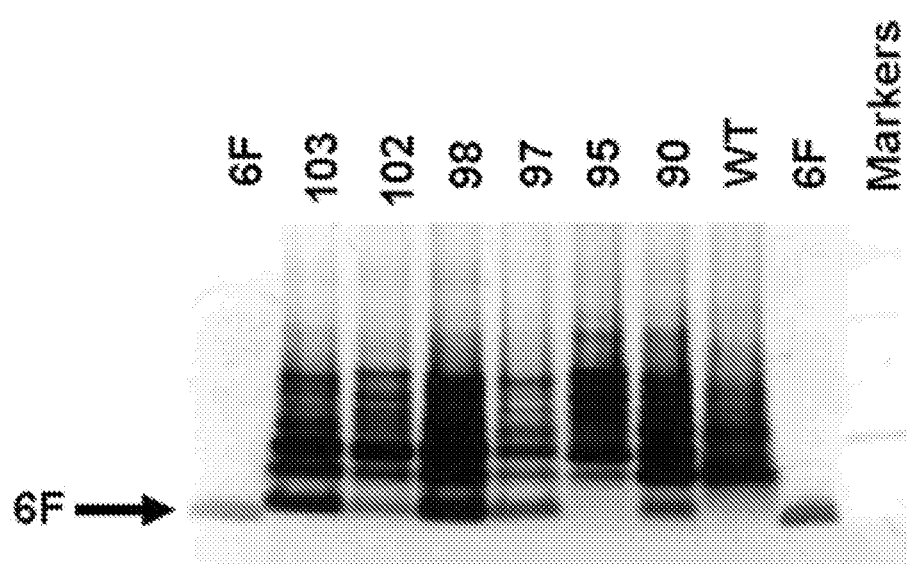
FIG. 17 shows that SDS PAGE gels from most (but not all) tomato lines that were positive for the 6F gene contained a band that migrated with authentic chemically synthesized 6F without end blocking groups. Proteins were extracted from the tomatoes derived from plant lines shown in the Figure. All except wild-type (WT) were PCR positive for the 6F gene. 100 μg of protein from each tomato line was added to each lane and run on SDS PAGE gels using the protocol described in the Materials and Methods in Example 3. Line 95 was positive for the 6F gene but did not express the peptide suggesting that the gene was inserted into the genome in a location that did not allow expression at the protein level.

The presence of the 6F gene in transgenic plants was confirmed by PCR using genomic DNA isolated with the genelute Plant Genomic DNA mini prep kit (Sigma) and 6F specific primers (TGATATCTCCACTGACGT (SEQ ID NO:650) and CGAGAAAGGAAGGGAAGAAAG (SEQ ID NO:651)) yielding a product of 712 bp. Independent kanamycin resistant transgenic plants were PCR-confirmed for the presence of p6F transgene and were further analyzed for peptide by mass spectrometric analysis. FIG. 17 shows SDS gels demonstrating positive expression of the 6F peptide at the amino acid level in most plant lines containing the 6F gene.

Protein Extraction and Analysis

A freeze-dry lyophilizer system (VirTis, Gardner, N.Y.) was used to obtain lyophilized tomato fruit tissues. Proteins from the lyophilized fruit pulp were obtained by homogenization in a mortar pestle with liquid nitrogen and homogenized in extraction buffer (50 mM Tris-Cl, 150 mM NaCl, 2% Nonidet P-40, 1% desoxycholic acid, 0.5% SDS) at pH 8.0 with complete protease inhibitor mixture (Roche Applied Science, Indianapolis). The total soluble proteins 100 μg per lane were resolved on 4-20% gradient. Mini Protean TGX gels (Bio-Rad) were stained with Sypro Ruby (Invitrogen) overnight. For MS analysis, the 6F peptide band was in-gel digested as described previously (8). Briefly, the band of interest was excised and in-gel trypsin digested (5-10 ng/μl of Gold trypsin, V5280, Promega) overnight at 37° C., eluted in 50% acetonitrile containing 0.1% trifluoroacetic acid followed by zip tip C-18, Tip size P10 (Millipore) and subjected to MS/MS analysis. Table 6 shows an example of the semi-quantitative method used to identify the level of peptide expression in these gels.

TABLE 6

Semi-quantification of peptide expression in SDS gels shown in FIG. 17. The intensity of the signal was graded on a scale of zero (−) to 4 (++++).

| Line | Expression |
|---|---|
| 90 | ++ |
| 95 | − |
| 97 | ++ |
| 98 | ++++ |
| 102 | + |
| 106 | ++ |
| 118 | ++ |
| 119 | + |
| 120 | − |
| 128 | +++ |
| 131 | +++ |
| 103 | +++ |

Figure 18A:
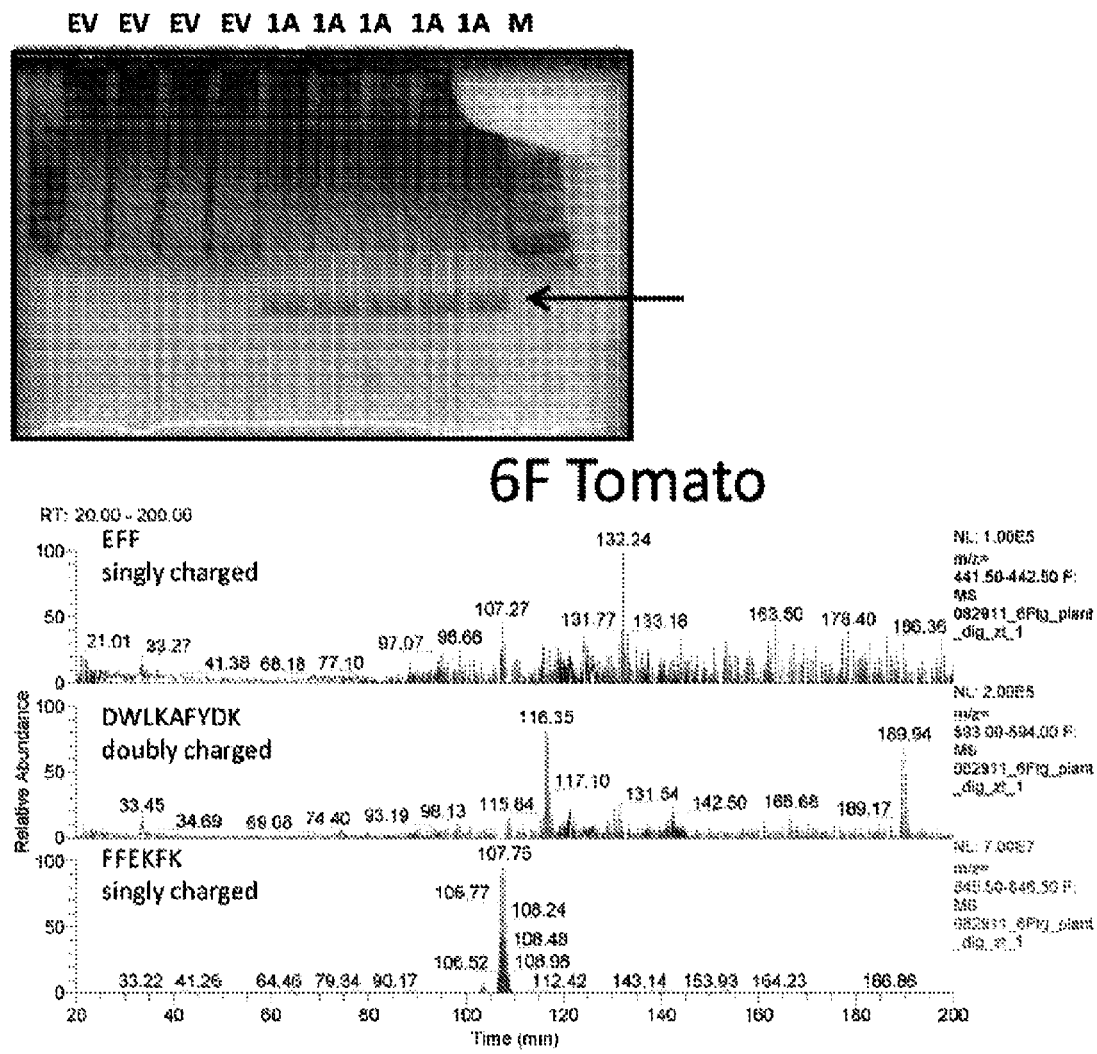
FIGS. 18A and 18B show that regions of SDS PAGE gels containing a band migrating with authentic 6F demonstrated the LC-ESI-MS signature of 6F (FIG. 18A) while the same region on gels without a band did not (FIG. 18B). Following HPLC and SDS PAGE, the region on each lane corresponding to 6F in the inset was excised and in-gel trypsin digested and subjected to LCESI-MS analysis using an LCQAdvantage Max ion trap mass spectrometer (ThermoElectron, Inc.) equipped with electrospray ionization source as described in Materials and Methods in Example 3.
Figure 18B:
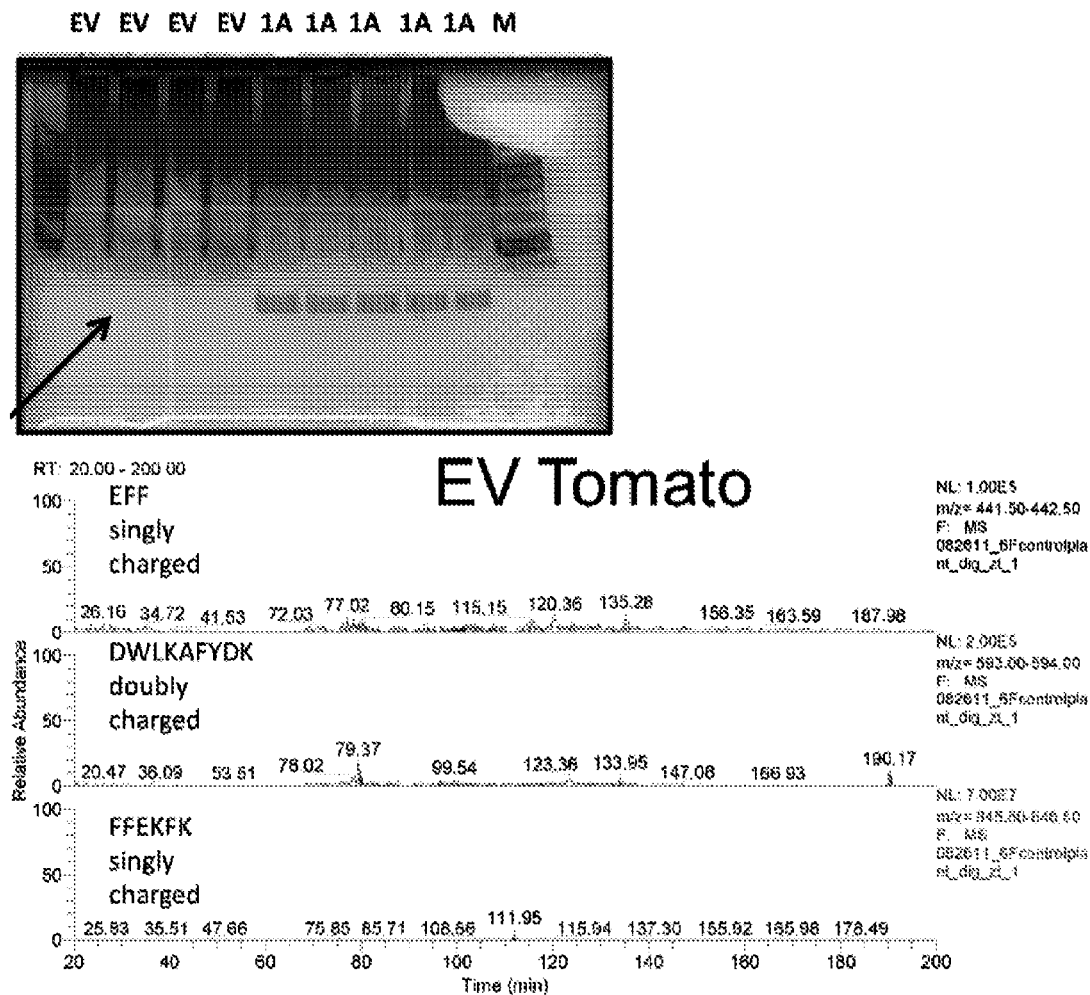

As noted above, the areas of each lane that was presumed positive for 6F peptide expression in gels such as that shown in FIG. 17 and the same areas of some lanes that were presumed not to express 6F peptide were cut out extracted and analyzed by LC-ESI-MS/MS. FIG. 18A below shows LC-ESI-MS data from control tomato (i.e., tomato plant infected with empty vector) and FIG. 18B shows LC-ESI-MS data from transgenic 6F tomato. The inset in the upper figures shows SDS gels of tomato control (TC) and a transgenic 6F tomato line 1A. The arrow indicates the 6F band from the transgenic 6F tomato line 1A.

Using the techniques shown in the examples above, positive founder lines were selected and grown to collect seeds. The seeds were again germinated and homozygous plants were selected using the selection process described above. An example of two homozygous lines producing tomatoes positive for 6F peptide are shown in FIG. 29.

Figure 8:
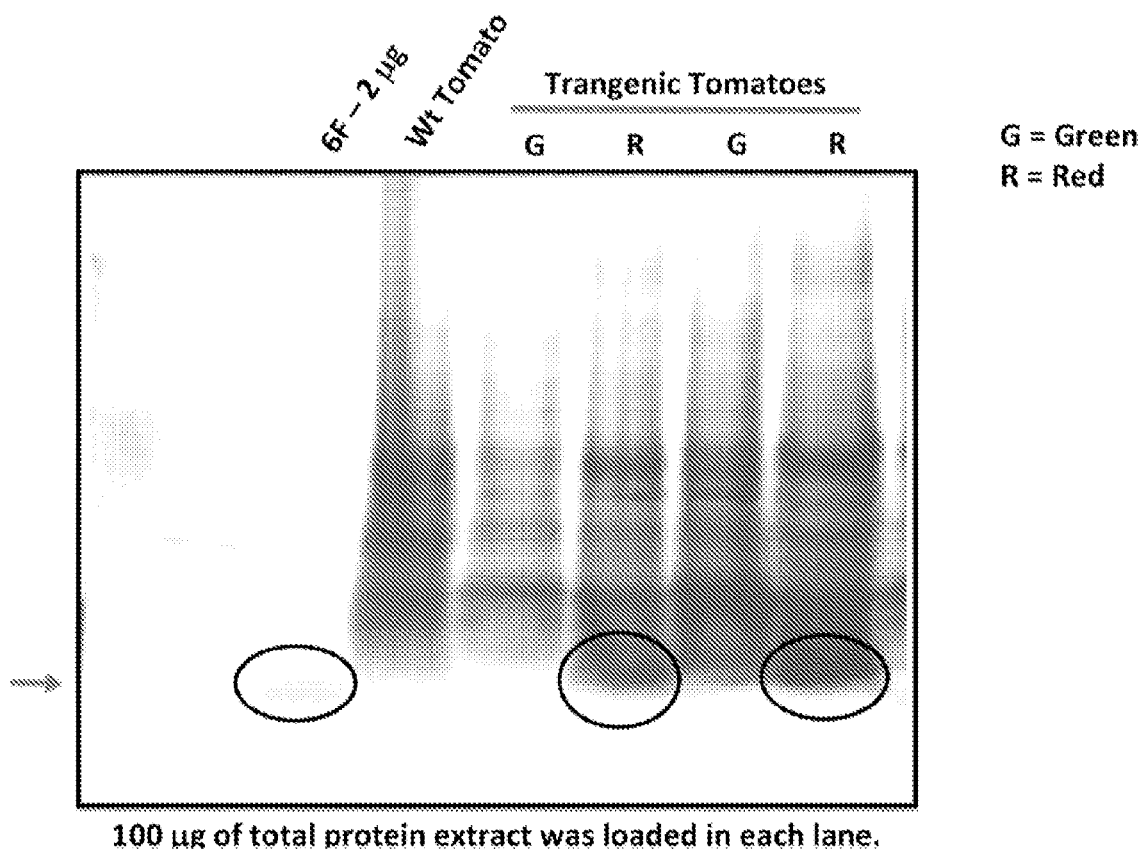
FIG. 8 shows that the transgenic expression of 6F dramatically increases with the oxidation associated with ripening (i.e. as the green tomatoes turn red). SDS gels were run after loading 2 μg of synthetic L-6F without blocking groups, or 100 μg of protein extract from a control wild type tomato (Wt Tomato) or 100 μg of protein extract from transgenic 17A tomatoes that were harvested Green (G) or Red (R). The arrow points to the area of the gel where the L-6F peptide ran. The circles indicate the bands in each lane containing either the authentic synthetic L-6F peptide (first lane on the left at the bottom of the gel) or the putative 6F peptide which was only seen in the protein extracts of the ripened red (R) tomatoes.
Figure 29:
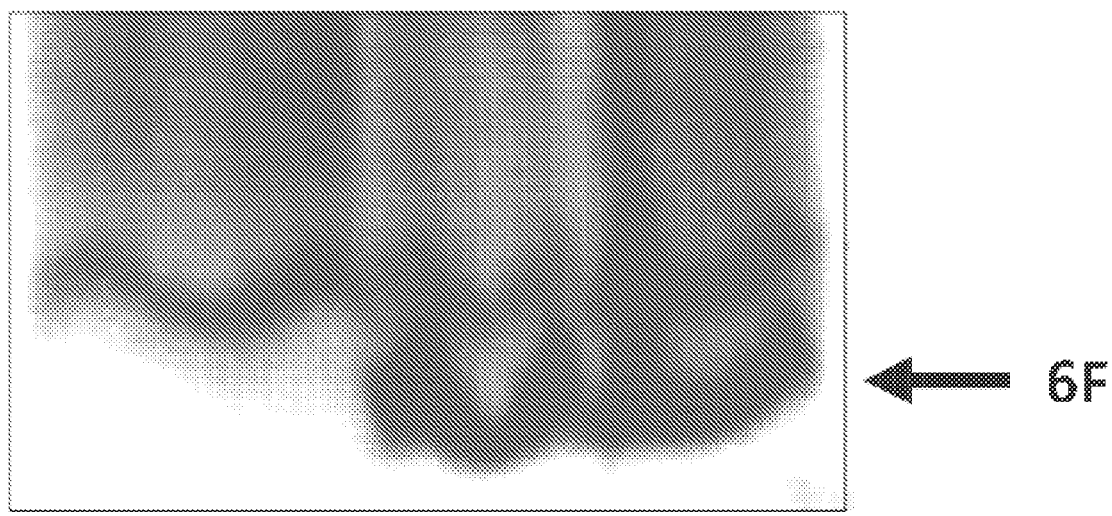
FIG. 29 shows an SDS gels from a control homozygous line and from two homozygous lines (1A and 17A) expressing 6F. Proteins were extracted from a control homozygous tomato line and two homozygous lines identified as expressing the 6F peptide (1A and 17A) and the proteins were subjected to SDS PAGE as described in Materials and Methods of Example 3. The lane containing authentic chemically synthesized 6F is not shown in the figure.

The bands from 1A and 17A shown in FIG. 29 were confirmed to be 6F by LC-ESI-MS/MS. Remarkably as shown in FIG. 8, the expression of the 6F peptide dramatically increased as the tomatoes underwent the oxidative stress of ripening (i.e. converted from green to red tomatoes).

Figure 9:
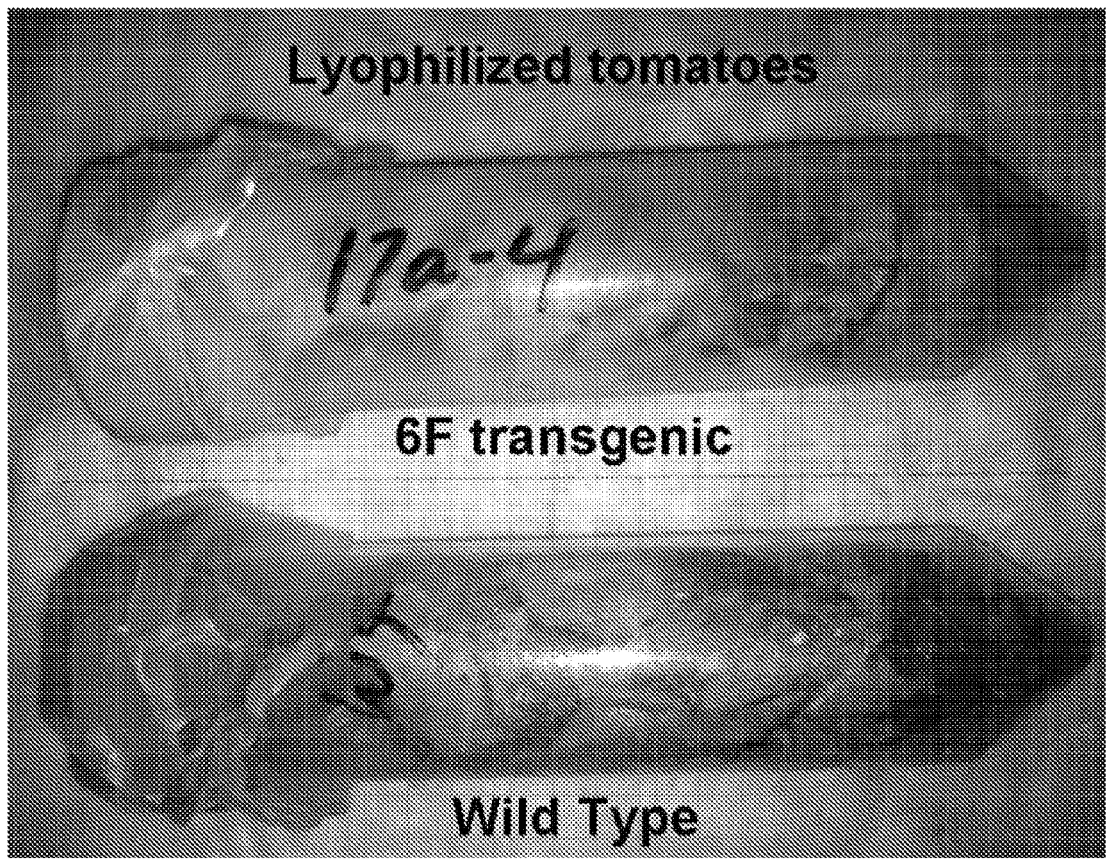
FIG. 9 shows lyophilized tomatoes from the 6F transgenic line 17a-4 and the control wild-type tomatoes.
Figure 10:
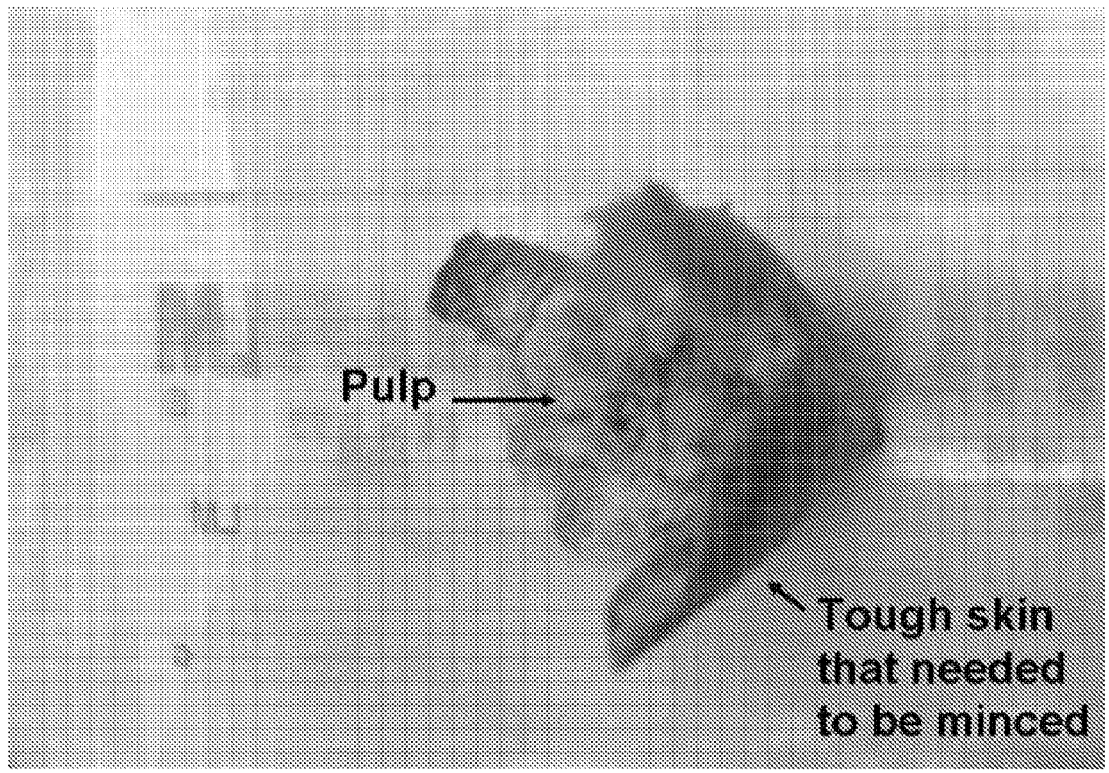
FIG. 10 shows different portions of the lyophilized tomatoes shown in FIG. 9.

Ripened control tomatoes (Wild Type) and tomatoes from the homozygous transgenic tomato line 17A (17a-4) (6F-Transgenic) were lyophilized. FIG. 9 shows the appearance of the lyophilized tomatoes. FIG. 10 shows examples of the different portions of the lyophilized tomato. The pulp was readily powdered in a mortar while the skin was tough and needed to be minced prior to being powdered in the mortar.

Figure 11:
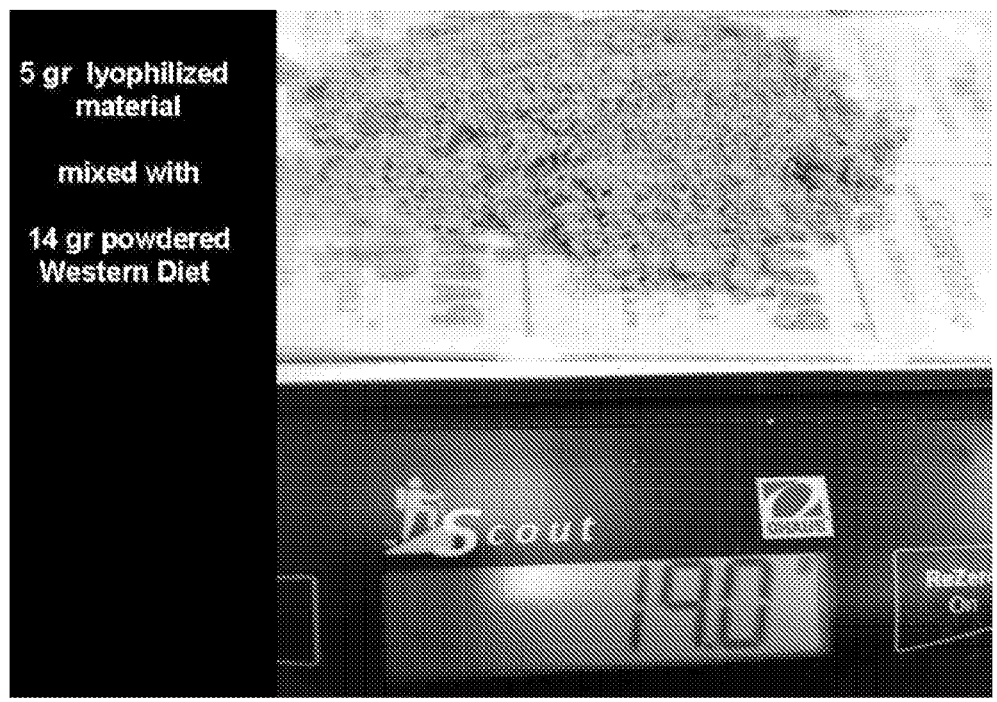
FIG. 11. Five grams (5 gr) of lyophilized material was thoroughly mixed with 14 grams (14 gr) of powdered Western Diet to give the material shown in the top panel. The scale on the bottom indicates the total weight was 19 grams.
Figure 12:
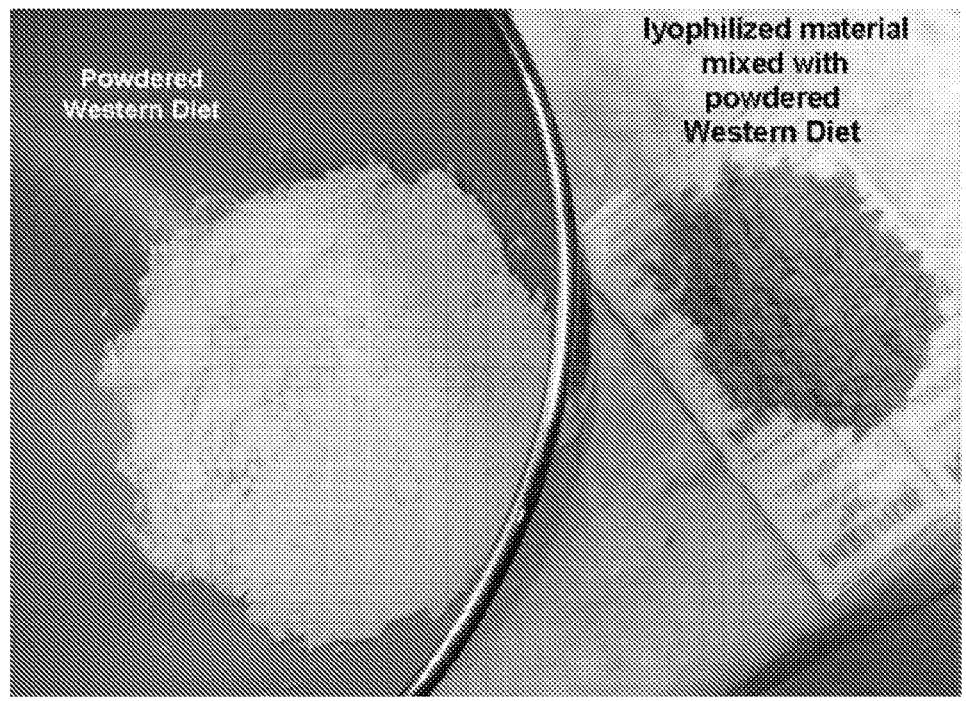
FIG. 12. The lyophilized material shown in FIG. 11 was mixed into a much larger quantity of powdered Western Diet which is shown in the mixing bowl. After mixing, the diet contained 2.2% of lyophilized ripened tomatoes.

The lyophilized material was mixed with powdered Western Diet as shown in FIG. 11. The 19 grams of the material shown in FIG. 11 was then mixed with a much larger quantity of powdered Western Diet which is shown in the large mixing bowl in FIG. 12.

Figure 13:
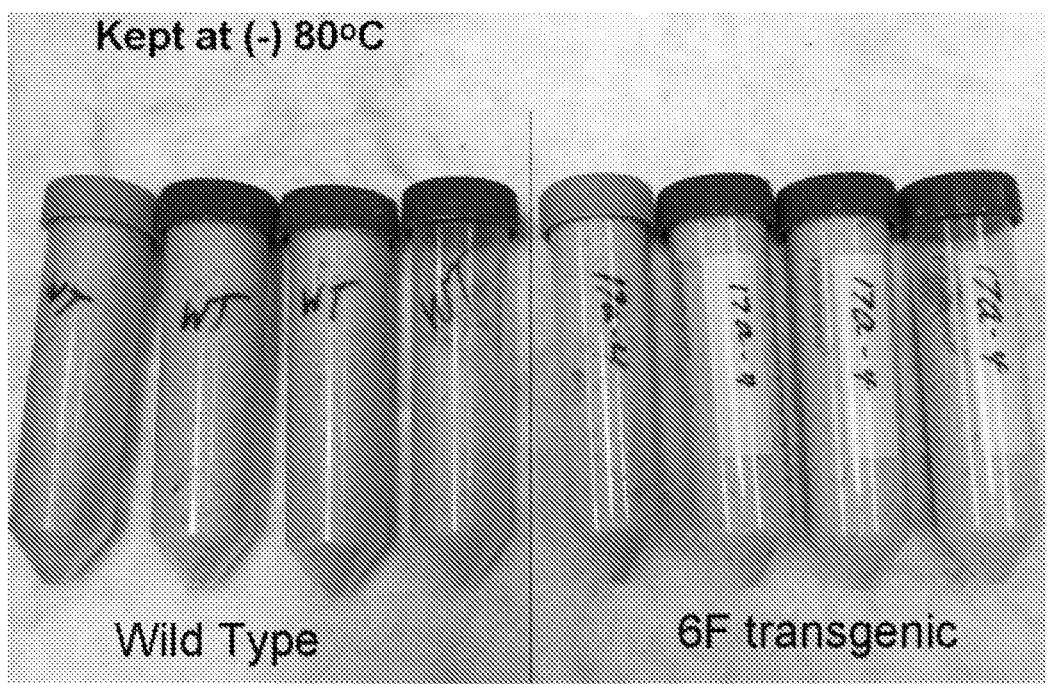
As shown in FIG. 13 below there was no difference in the appearance of the diet prepared from wild-type control (WT) or transgenic 6F tomatoes (17a-4).

The diet stored in tubes as shown in FIG. 13 was kept at −80° C. until use. Tubes containing sufficient diet for each night were removed, thawed and tightly compacted and 16 grams were provided for each cage of four mice (see e.g., FIG. 27) each evening.

After two weeks the mice were fasted and blood was obtained from the retro-orbital sinus and plasma serum amyloid A (SAA) levels were determined by ELISA. The results are shown below in FIG. 14.

Figure 19A:
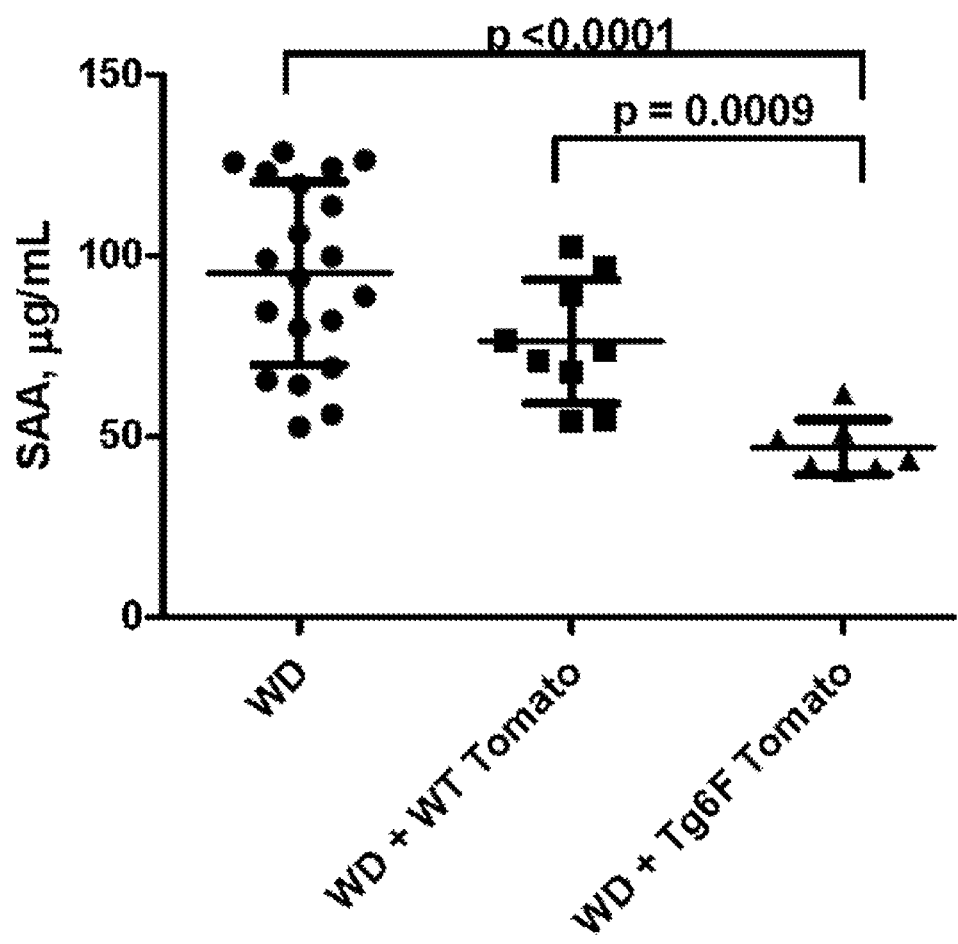
FIGS. 19A-19K show that feeding transgenic 6F tomatoes to LDLR$^{-/-}$ mice for two weeks improved a number of plasma biomarkers. Female LDLR$^{-/-}$ mice 10 weeks of age were housed four in each cage and each cage was given each night compacted WD containing no lyophilized tomatoes (n=20), or compacted WD containing 2.2% by weight of ground lyophilized wild-type (WT) tomato (n=8), or compacted WD containing 2.2% by weight of ground lyophilized transgenic 6F (Tg6F) tomato. The mice in all cages ate all of the diet each night. The mice receiving the Tg6F tomatoes received 800 μg of 6F per mouse per day (40 mg/kg/day). After two weeks the mice were bled and the following plasma biomarkers were measured.
Figure 19B:
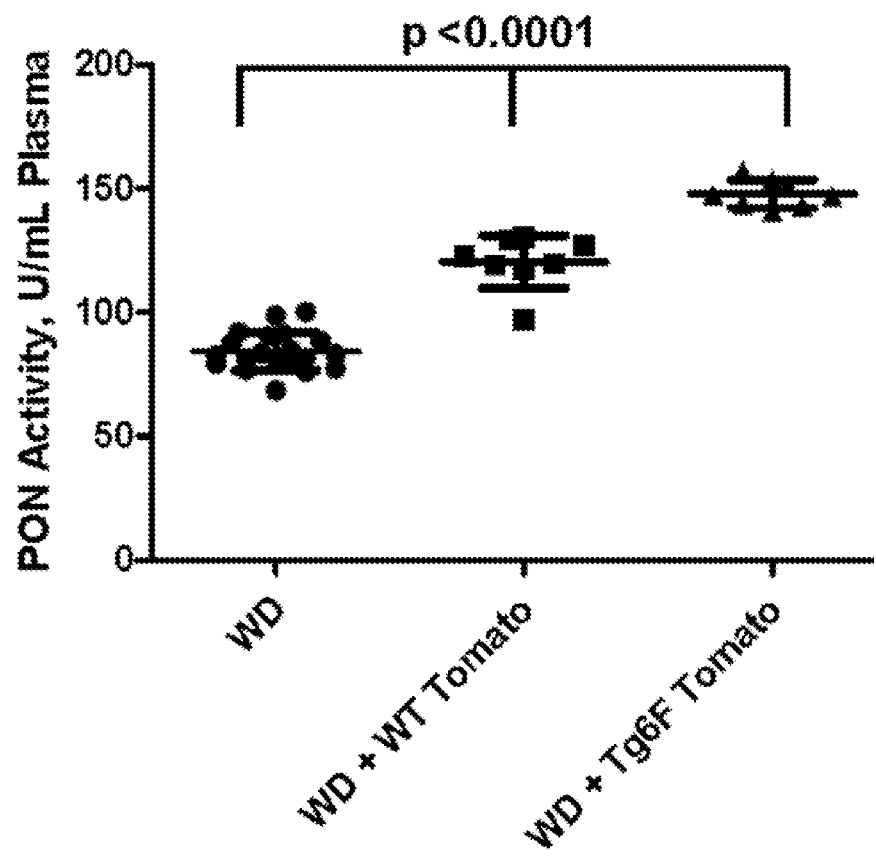
Figure 19C:
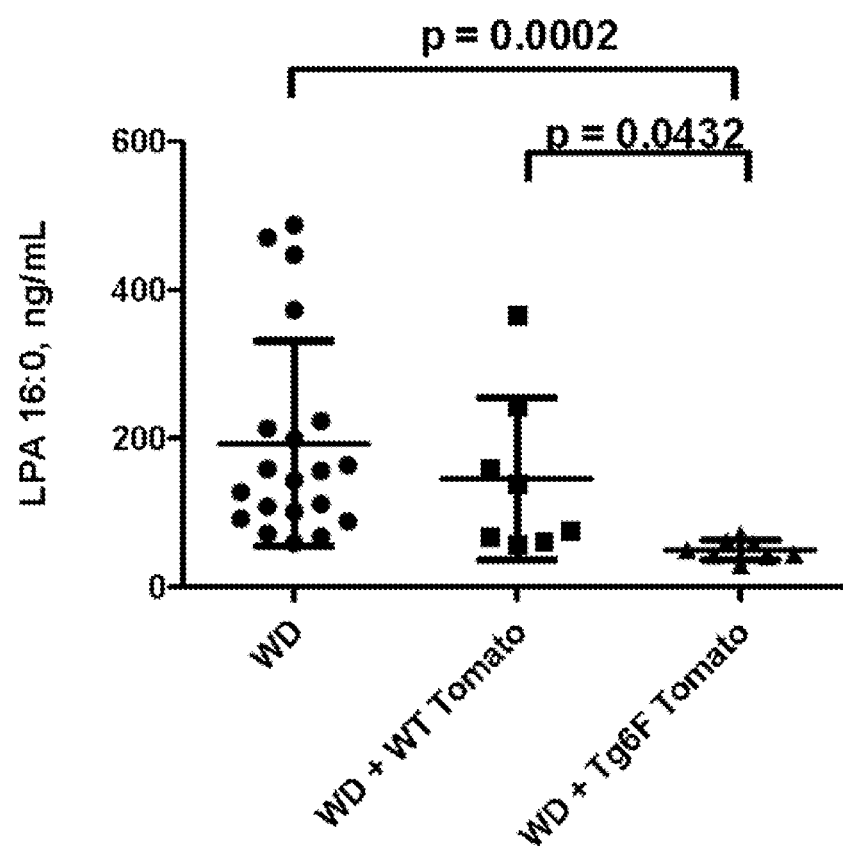
Figure 19D:
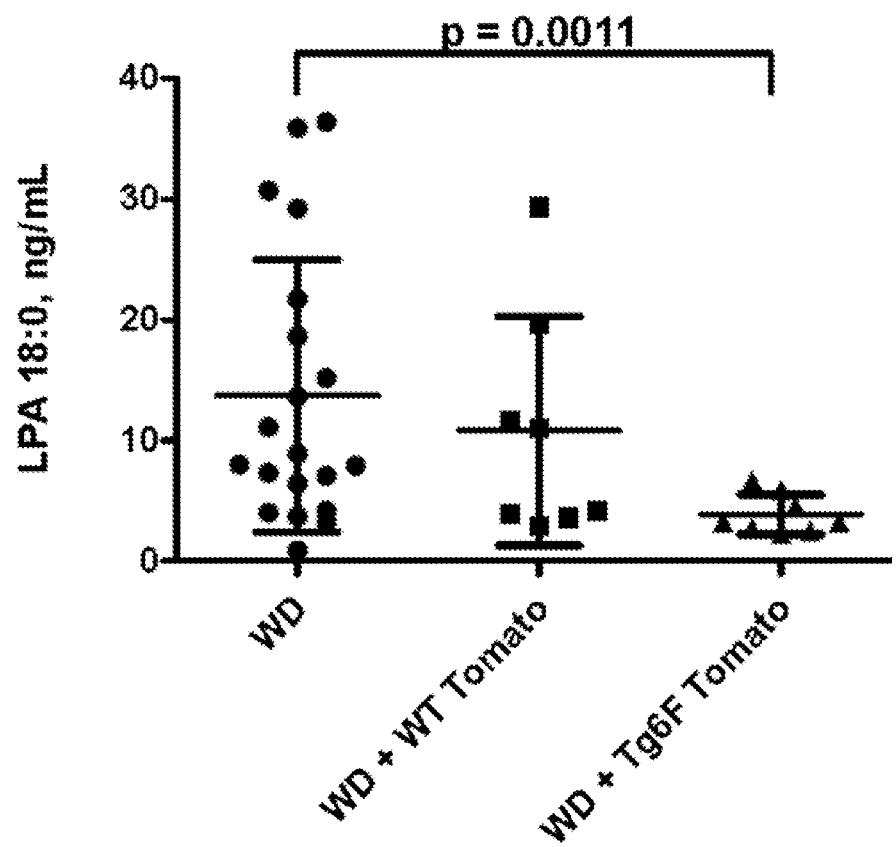
Figure 19E:
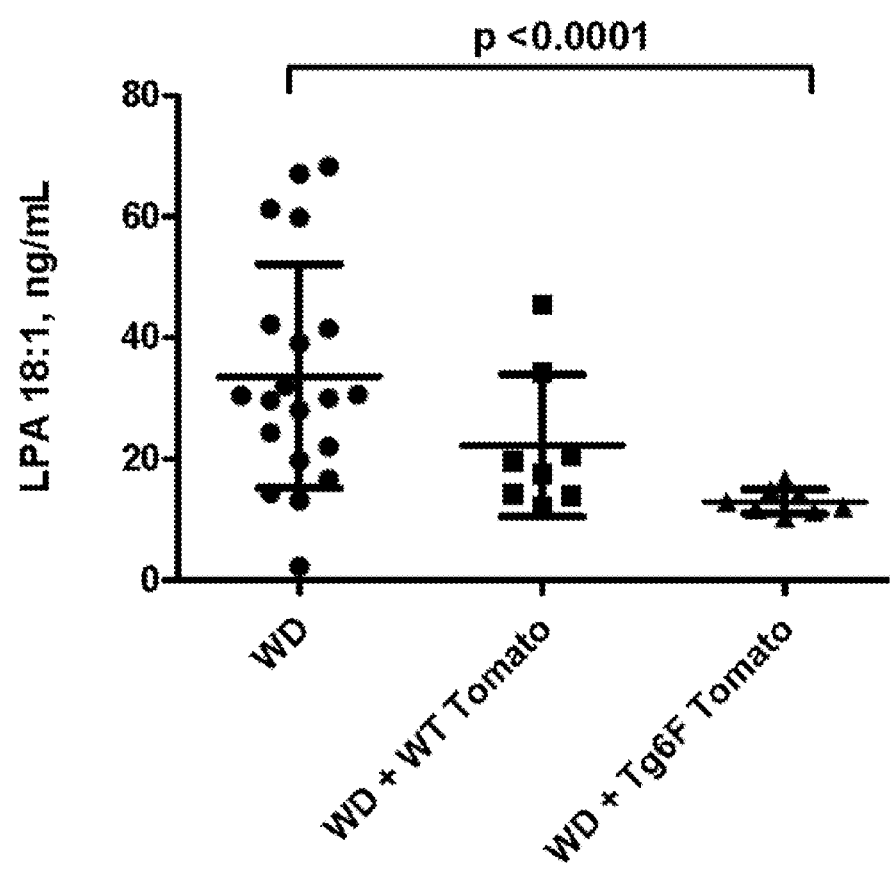
Figure 19F:
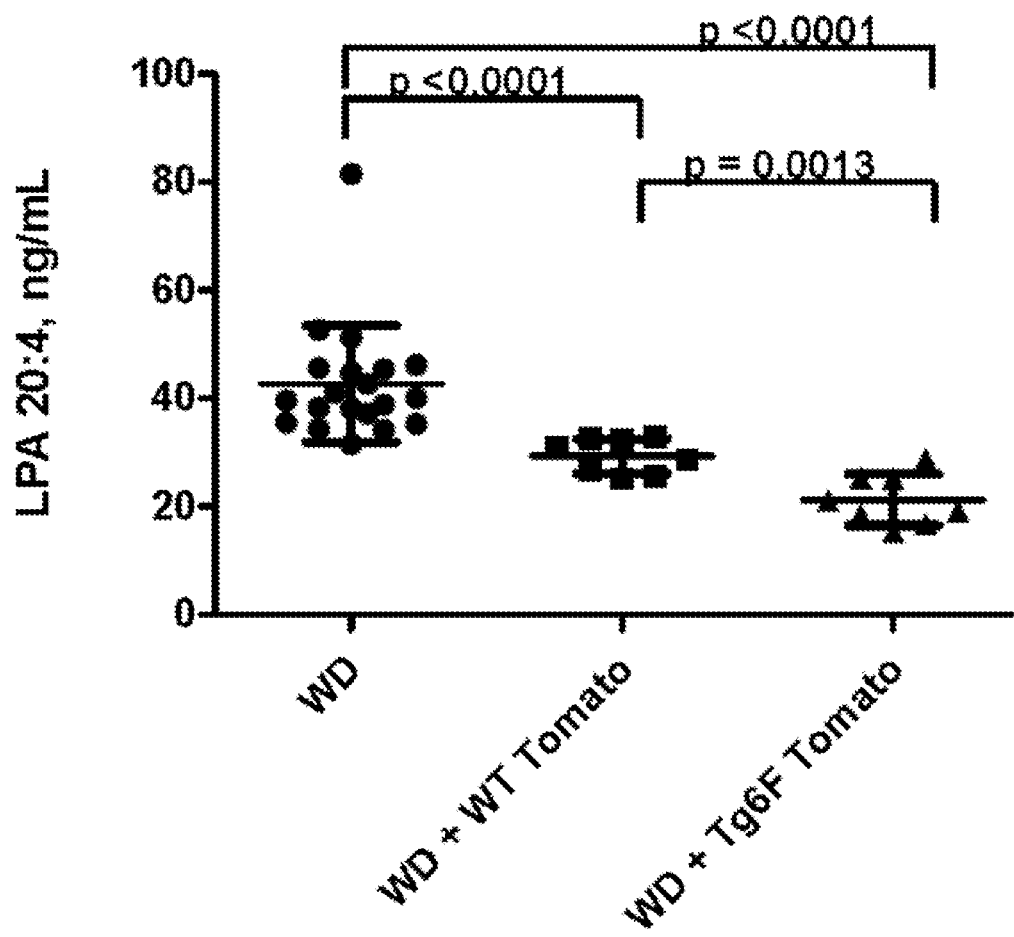
Figure 19G:
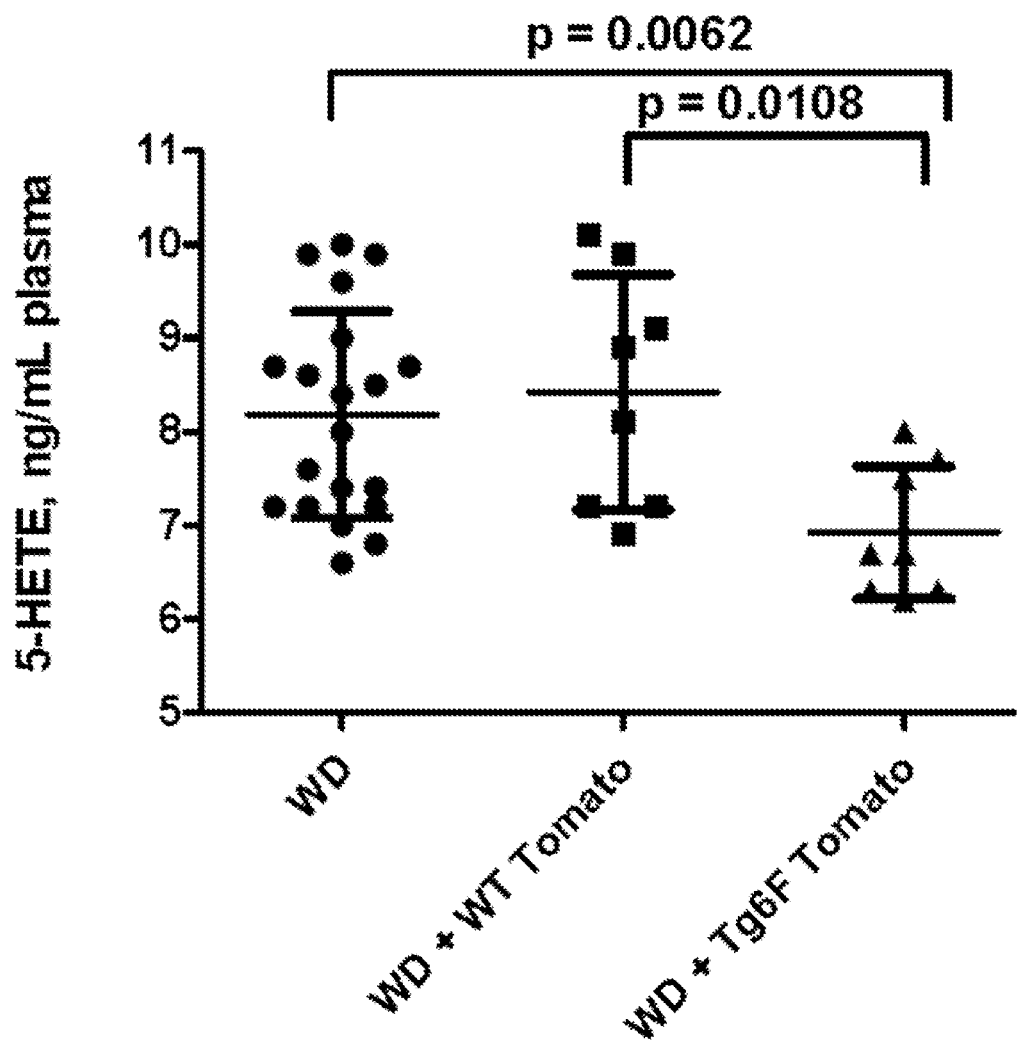
Figure 19H:
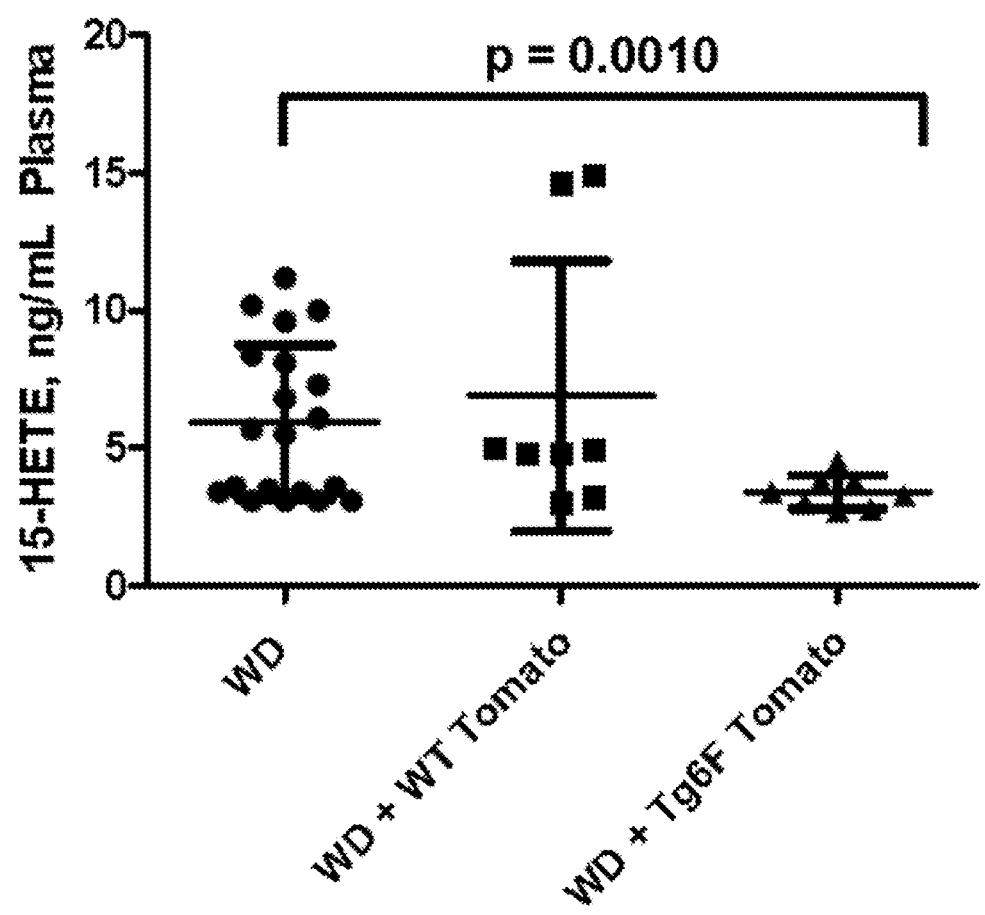
Figure 19I:
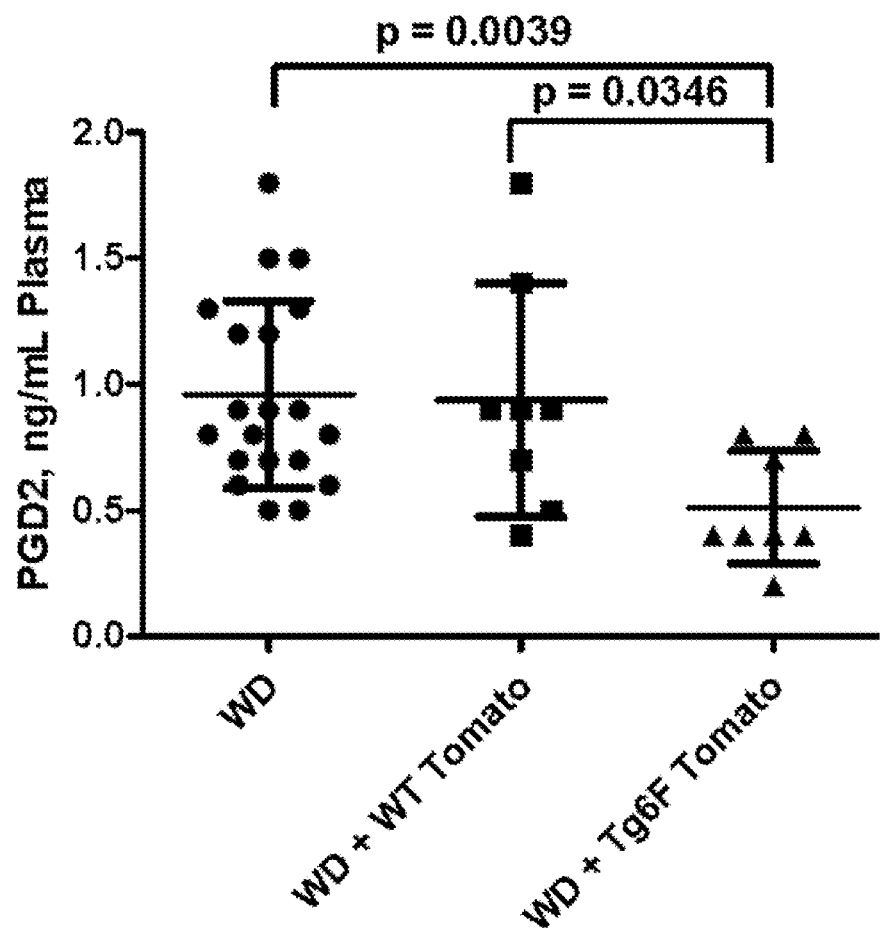
Figure 19J:
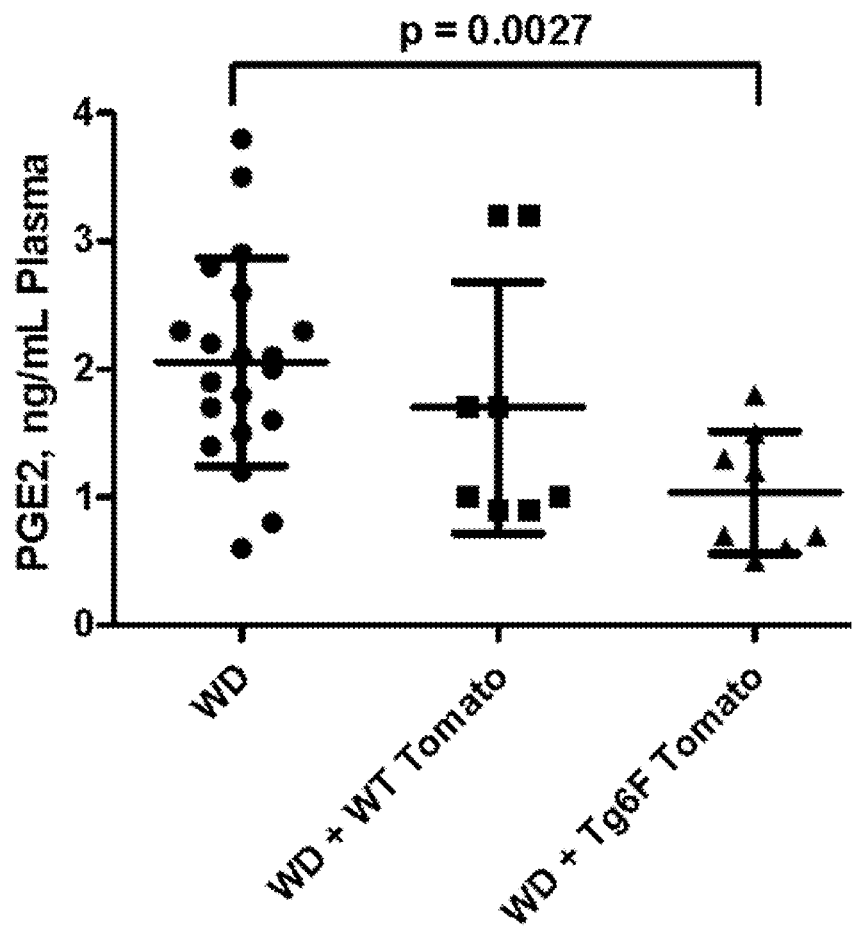
Figure 19K:
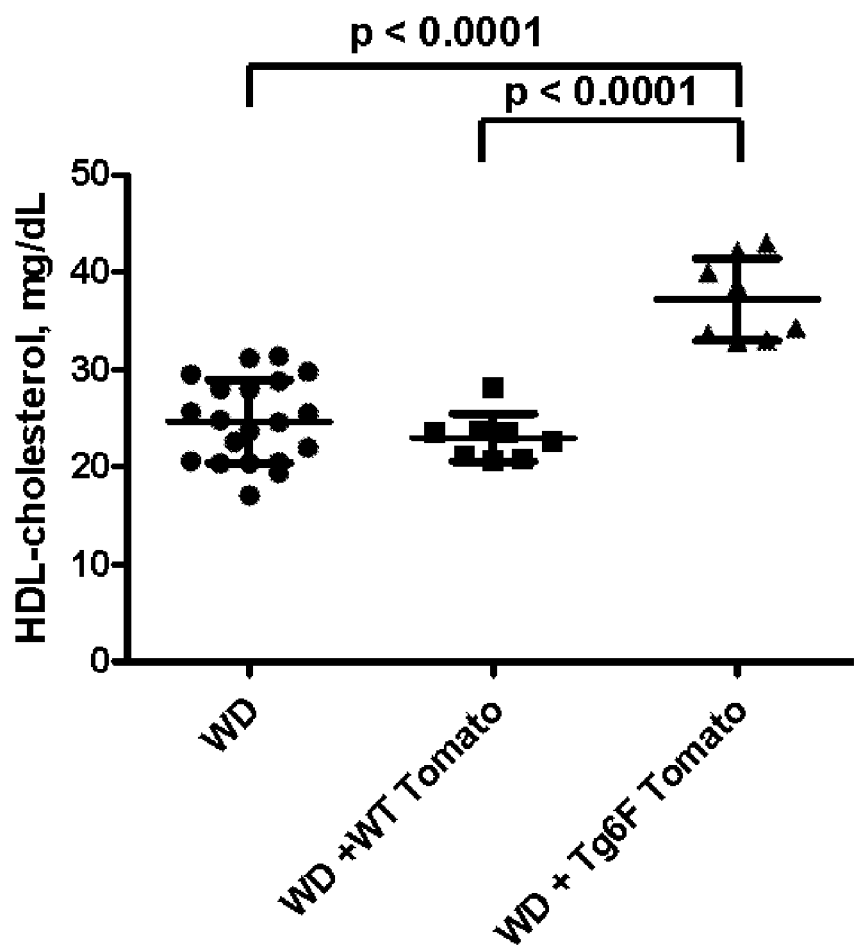

The data in FIG. 19B demonstrate that feeding the ripened lyophilized transgenic 17A tomatoes to LDLR null mice also significantly increased the plasma activity of the potent antioxidant enzyme paroxonase (PON).

The importance of the increase in paraoxonase activity shown in FIG. 19 lies in the very strong inverse relationship between paraoxonase activity, oxidative stress and cardiovascular risk in humans (9) (i.e. the higher the paraoxonase activity, the lower the cardiovascular risk).

The data in FIGS. 19C-19F demonstrate that feeding the ripened lyophilized transgenic 17A tomatoes to LDLR null mice also significantly decreased plasma levels of lysophosphatidic acid (LPA).

Figure 14:
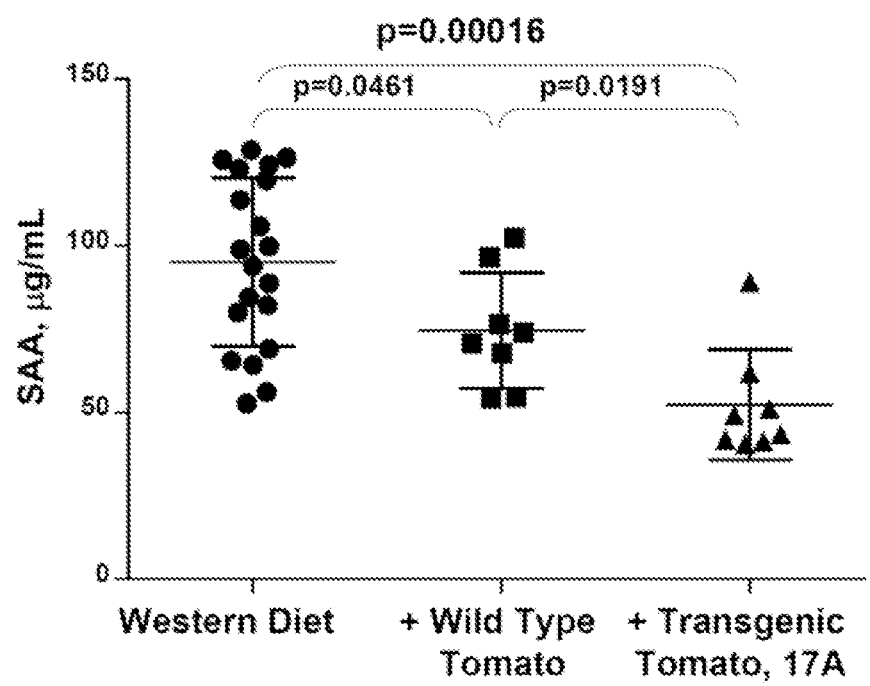
FIG. 14. Ripened lyophilized tomatoes expressing 6F peptide (Transgenic Tomato, 17A) significantly decreased serum amyloid A (SAA) levels in LDLR null mice on a Western Diet. Sixteen grams of compacted Western Diet containing no lyophilized tomatoes (n=20), or containing lyophilized control (Wild Type) tomatoes (n=8), or containing lyophilized transgenic 6F tomatoes from line 17A (n=8) were provided for each cage of 4 female LDLR null mice (10 weeks of age) each night for 2 weeks. The lyophilized tomato added to the Western Diet amounted to 2.2% of the total diet by weight for both the control and transgenic 6F tomatoes. The mice in all cages ate all of the diet each night. The mice receiving the transgenic 6F tomatoes received 800 μg of 6F per mouse per day (40 mg/kg/mouse/day) as determined by LC-ESI-MS/MS analysis. After two weeks the mice were bled and plasma serum amyloid A (SAA) levels were determined by ELISA.

The data in FIGS. 14 and 19B demonstrate that feeding lyophilized ripened tomatoes expressing the 6F peptide can significantly reduce inflammation in a mouse model of atherosclerosis (decrease SAA levels) and increase the potent plasma antioxidant enzyme paraoxonase. The data in FIGS. 19C-19F demonstrate that one mechanism of action may be through the significant reduction in plasma lysophospatidic acid (LPA) levels. LPA has been shown to be a potent promoter of tumor growth (Su et al. (2010 Proc. Natl. Acad. Sci. USA 107:19997-20002) and a potent promoter of inflammation and atherosclerosis (Zhou et al. (2011) Cell Metab. 13:592-600). Thus, the methods described herein make possible the production of peptides that modulate disease in a form that is economical and easy to provide and that may reduce atherosclerosis, cancer and inflammation among other important diseases.

Example 3

A Novel Approach to Oral ApoA-I Mimetic Therapy

Abbreviations

The following abbreviations are used in this example: ApoE null mice, apoE$^{-/-}$; docosahexaenoic acid 22:6 (n-3), DHA; eicosapentoaenoic acid 20:5 (n-3), EPA; eicosatrienoic acid, EET; empty vector, EV; the peptide D-W-L-K-A-F-YD-K-F-F-E-K-F-K-E-F-F (SEQ ID NO:17) synthesized from all L-amino acids, 6F; hydroxyeicosatetraenoic acid, HETE; HDL inflammatory index, HII; low density lipoprotein receptor null mice, LDLR$^{-/-}$; lysophosphatidic acid, LPA; paroxonase-1 activity, PON; prostaglandin, PG; serum amyloid A, SAA; intravenously, IV; subcutaneously, SQ; thromboxane, TX, Western diet, WD.

Summary of the Example

As described herein, transgenic tomato plants were constructed with an empty vector (EV) or a vector expressing an apoA-I mimetic peptide, 6F. EV or 6F tomatoes were harvested, lyophilized, ground into powder, added to Western Diet (WD) at 2.2% by weight, and fed to LDLR$^{-/-}$ mice at 45 mg/kg/day 6F. After 13 weeks, percent aorta with lesions was 4.1±4, 3.3±2.4, and 1.9±1.4 for WD, WD+EV and WD+6F, respectively (WD+6F vs. WD, p=0.0134; WD+6F vs. WD+EV, p=0.0386; WD+EV vs. WD, not significant). While body weight did not differ, plasma serum amyloid A (SAA), total cholesterol, triglycerides, and lysophosphatidic acid (LPA) levels were less in WD+6F mice; p<0.0295. HDL-cholesterol and paroxonase-1 activity (PON) were higher in WD+6F mice (p=0.0055, p=0.0254, respectively), but not in WD+EV mice. Plasma SAA, total cholesterol, triglycerides, LPA and 15-HETE levels positively correlated with lesions (p<0.0001); HDL-cholesterol and PON were inversely correlated (p<0.0001). After feeding WD+6F) intact 6F was detected in small intestine (but not in plasma); ii) small intestine LPA was decreased compared to WD+EV (p<0.0469); iii) small intestine LPA 18:2 positively correlated with percent aorta with lesions (p<0.0179). These data suggest that 6F acts in the small intestine and provide a novel approach to oral apoA-I mimetic therapy.

Details

This report describes the results of a search for a peptide that does not require chemically added end groups for efficacy and which can be produced in genetically engineered plants. The search began by reviewing our previously published data in light of our more recent findings. The peptide 4F was similar in efficacy to 6F based on our in vitro assays (Datta et al. (2001) *J. Lipid Res.* 42: 1096-1104). The 4F peptide was initially chosen due to its increased solubility compared to 6F because we thought that absorption of the peptide was required to achieve some critical plasma peptide level. Since this did not turn out to be the case, we turned our attention to the 6F peptide. Neither the 4F or 6F peptide has any sequence homology to apoA-I. The first apoA-I mimetic peptide with 18 amino acids was known as "18A" (Anantharamaiah (1986) *Meth. Enzymol.* 128: 627-647). The terminal charges of this peptide were modified by adding end blocking groups, which resulted in increased lipid affinity for non-oxidized lipids (Venkatachalapathi et al. (1993) *Proteins Structure Function Genet.* 15: 349-359; Yancey et al. (1995) *Biochemistry.* 34: 7955-7965). The 18A peptide is also known as "2F" because the peptide has two phenylalanine residues on the hydrophobic face at positions 6 and 18. While the 2F peptide bound non-oxidized lipids with affinities similar to apoA-I it was not very effective in preventing LDL-induced MCP-1 production by cultured human artery wall cells and it failed to decrease diet induced atherosclerosis in mice (Datta et al. (2001) *J. Lipid Res.* 42: 1096-1104). Consequently a number of 18 amino acid peptides were synthesized and tested for their ability to inhibit LDL-induced MCP-1 production by cultured human artery wall cells (Id.). As previously reviewed (Navab et al., (2005) *Arterioscler. Thromb. Vasc. Biol.* 25: 1325-1331), based on their physical properties these peptides could be separated into 2 groups. Group I consisted of 2F with phenylalanine residues at positions 6 and 18; 3F$^3$ with an additional phenylalanine residue at position 3; 3F$^{14}$ with an additional phenylalanine residue at position 14; and 4F with two additional phenylalanine residues at positions 3 and 14. Of this first group of peptides, only the 4F peptide was highly effective in preventing LDL-induced MCP-1 production by cultured human artery wall cells (Id.) and was biologically active in mouse models (Navab et al. (2010) *Arterioscler. Thromb. Vasc. Biol.* 30: 164-168; Handattu et al. (2007) *J. Biol. Chem.* 282: 1980-1988). Group II consisted of the 5F peptide with 3 additional phenylalanine residues at positions 11, 14, and 17; the 6F peptide with 4 additional phenylalanine residues at positions 10, 11, 14, and 17; and the 7F peptide with 5 additional residues at positions 3, 10, 11, 14 and 17. Of this second group both 5F and 6F were able to efficiently inhibit LDL-induced MCP-1 production by cultured human artery wall cells; 7F did not (Datta et al., (2001) *J. Lipid Res.* 42: 1096-1104). The 5F peptide was also biologically active in vivo inhibiting atherosclerosis in a mouse model (Garber et al. (2001) *J. Lipid Res.* 42: 545-552), and inhibiting tumor angiogenesis in mice (Gao et al. (2011) *Integr. Biol.* (Camb), 3: 479-489).

Comparing circular dichroism data for the peptides in phosphate-buffered saline in the absence or presence of dimyristoyl phosphatidylcholine (DMPC) showed that the percent helicity of the peptides on interacting with DMPC increased for all of the peptides tested except for 4F and 6F (Datta et al. (2001) *J. Lipid Res.* 42: 1096-1104). Because of this similarity between 4F and 6F in interacting with DMPC, which we previously demonstrated was highly effective in a mouse model of atherosclerosis when it was administered orally (Navab et al. (2003) *Circulation.* 108: 1735-1739); we chose to initially focus our attention on the 6F peptide instead of the 5F peptide. As shown by the experiments reported here, the 6F peptide is efficacious without chemically added end groups, it can be expressed in genetically engineered tomatoes, and perhaps most remarkably, the 6F peptide is effective when the tomatoes are fed, even without isolation and purification of the peptide.

Materials and Methods.

Materials

The peptide 6F (D-W-L-K-A-F-Y-D-K-F-F-E-K-F-K-E-F-F, SEQ ID NO: 17) was chemically synthesized from all L-amino acids by solid phase synthesis as described (Datta et al. (2001) *J. Lipid Res.* 42: 1096-1104) using Wang resin (Advanced Chem Tech, Louisville, Ky.) to obtain C-terminal free acid after the cleavage of the peptide from the resin except that the N-terminal acetylation step was omitted. The vector pBI121 containing a kanamycin resistant gene (NPT II), a cauliflower mosaic virus 35 S promoter (CaMV35S) and a nopaline synthase terminator (NOS) was obtained from "The *Arabidopsis* Information Resource" (TAIR) (www.arabidopsis.org; stock number CD3-388, vector pBI121). *Agrobacterium tumefaciens* LBA 4404 was obtained from Invitrogen, Electromax (Catalogue number 18313-015). ELISA Kits for determination of lysophosphatidic acid (LPA) were purchased from Echelon (Catalogue # k-2800s). All other materials were purchased from previously described sources (Navab et al. (2011) *J. Lipid Res.* 52: 1200-1210; Navab et al. (2012) *J. Lipid Res.* 53: 437-4458).

Mice

Figure 27:
FIG. 27. Compacted Western Diet (WD) containing no lyophilized tomatoes, or containing ground lyophilized control tomatoes or containing ground lyophilized transgenic 6F tomatoes were provided for each cage of 4 female LDLR$_{-/-}$ mice each night. The example shown is from mice receiving transgenic 6F tomato at 2.2% by weight of WD.

Female wild-type C57BL/6J or female LDLR$^{-/-}$ or apoE$^{-/-}$ mice originally purchased from Jackson laboratories on a C57BL/6J background were obtained from the breeding colony of the Department of Laboratory and Animal Medicine at the David Geffen School of Medicine at UCLA. The mice used in these studies were of different ages, which are stated in each legend. The mice were maintained on a chow diet (Ralston Purina) before being switched to WD (Teklad, Harlan, catalog #TD88137). The addition of chemically synthesized 6F peptide to the diet was accomplished as previously described for the addition of the 4F peptide (Navab et al. (2011) *J. Lipid Res.* 52: 1200-1210); preparation and addition of tomato with or without transgenic 6F to WD is described below in the section, "Processing and Analysis of Tomatoes". For experiments in which WD with or without 2.2% by weight of powdered tomato were presented to the mice, the preparations, which were stored at −80° C. until use, were thawed each evening, tightly compacted and presented to each cage of four mice each night. FIG. 27 shows an example of the tightly compacted WD presented to the mice. All experiments involving mice were approved by the UCLA Animal Research Committee.

Determination of Plasma and Intestinal Constituents and Atherosclerotic Lesions

Plasma was collected and analyzed for total cholesterol, triglycerides, serum amyloid A (SAA), HDL-cholesterol, paraoxonase-1 activity (PON) as described previously (Navab et al. (2011) *J. Lipid Res.* 52: 1200-1210; Navab et al. (2012) *J. Lipid Res.* 53: 437-445). Perfusion of the mice to remove all blood from tissues prior to harvesting the small intestine and preparation of small intestine samples were performed as previously described (Navab et al. (2012) *J. Lipid Res.* 53: 437-445). Tissue levels of cholesterol were measured as previously described (Navab et al. (2011) *J. Lipid Res.* 52: 1200-1210). Levels of arachidonic acid and its metabolites were measured by LC-ESI-MS/MS as described previously (Navab et al. (2012) *J. Lipid Res.* 53: 437-445). Lysophosphatidic acid was measured either by ELISA according to the manufacturer's instructions or LC-ESI/MS/MS as described previously (Navab et al. (2011) *J. Lipid Res.* 52: 1200-1210). The percent of the aorta with atherosclerosis was determined by en face analysis as previously described (Navab et al. (2011) *J. Lipid Res.* 52: 1200-1210; Morgantini et al. (2010) *Diabetes* 59: 3223-3228).

Generation of Transgenic Tomato Plants

The strategy that we chose involves the use of the bacterium *Agrobacterium tumefaciens*, which carries a Ti plasmid that can be manipulated to insert a gene of interest into plant cells (Frary and Earle (1996) *Plant Cell Reports,* 16: 235-240). To accomplish this we used the plant binary vector pBI121 that contains a kanamycin resistance gene (NPTII), a cauliflower mosaic virus 35 S promoter (CaMV35S), the GUS gene that encodes for the marker protein β-glucuronidase and a nopaline synthase terminator (NOS term) (FIG. 15). The gene encoding 6F is 54-bp long and encodes the 18 amino acids D-W-L-K-A-F-Y-D-K-F-F-E-K-F-K-E-F-F (SEQ ID NO:17) with a molecular mass of 2435.81 Da. The expression cassette for 6F also contained the plant-derived signal peptide (SP) with 23-amino acids (M-I-M-A-S-S-K-L-L-S-L-A-L-F-L-A-L-S-H-A-N-S, SEQ ID NO:2), 69-bp long (Pogrebnyak et al. (2005) *Proc. Natl. Acad. Sci. USA,* 102: 9062-9067). The codon usage table (www.kazusa.or.jp/codon) specific for *Lycopersicon esculentum* was used to design the DNA sequence: TCT AGA ATG ATT ATG GCT TCT TCT AAA CTT CTT TCT CTT GCT CTT TTT CTT GCT CTT CTT TCT CAT GCT AAT TCT GAT TGG CTT AAA GCT TTT TAT GAT AAA TTT TTT GAA AAA TTT AAA GAA TTT TTT TGA GAG CTC (SEQ ID NO:4). The DNA was synthesized from DNA 2.0 (www.dna20.com). The cassette was cloned into the XbaI/SacI site replacing the GUS gene of the plant binary vector pBI121 and a TGA stop codon was introduced before the SacI site (*Arabidopsis* biological resource center, ABRC, www.arabidopsis.org) under a CaMVS35 promoter (FIG. 15). The sequence was verified by DNA sequencing. The vector also contained the npt II gene for kanamycin selection of transgenic plants (FIG. 15). *Agrobacterium tumefaciens* strain LBA4404 was transformed with and without the cassette containing the sequences for the plant-derived signal peptide and for 6F. Transformations without the cassette containing the sequences for the plant-derived signal peptide and 6F are referred to as empty vector (EV), which still contains the GUS gene in the pBI121 vector that encodes for the marker protein beta-glucuronidase. Copies harboring the binary vector were sequence verified in the UCLA GeneSeq Core and then used for plant transformation using the strategy of Frary and Earle (Frary and Earle (1996) *Plant Cell Reports,* 16: 235-240).

Transgenic plants were generated through a core service contract with the Saint Louis Donald Danforth Plant Science Centre, Missouri (Dr. Kevin Lutke). Initially, a total of 1,200 tomato cotyledons (*Lycopersicon esculentum*) were transformed for 6F in two separate experiments and empty vector in one experiment using the procedure described by Frary and Earle (Id.). The presence of the 6F gene in transgenic plants was confirmed by PCR using genomic DNA isolated with the Genelute Plant Genomic DNA Mini Prep kit (Sigma) and primers (TGA TAT CTC CAC TGA CGT (SEQ ID NO:652) and CGA GAA AGG AAG GGA AGA AAG (SEQ ID NO:653)) yielding a product of 712-bp. Thirty-three plants positive for the 6F gene were initially identified from approximately 120 plants that had been selected in kanamycin. Positive founder lines were selected and grown to collect seeds. Subsequently, the seeds were again germinated; homozygous plants were selected, grown and allowed to produce ripened tomatoes from which the seeds were again collected. The process was repeated a minimum of 3 times to ensure that the lines were homozygous.

Identification and Quantification of 6F in Tomatoes

The seeds from homozygous ripened tomatoes were removed and the remaining seedless tomato pulp and skin were rapidly frozen and shipped by overnight courier to UCLA where they were processed in a freeze-dry lyophilizer system (VirTis, Gardner, N.Y.) to obtain lyophilized tomato fruit tissue (pulp plus skin). For SDS-PAGE gel analysis, proteins from the lyophilized fruit were obtained by homogenization with a mortar and pestle in liquid nitrogen and homogenized in extraction buffer (50 mM Tris-Cl, 150 mM NaCl, 2% Nonidet P-40, 1% desoxycholic acid, 0.5% SDS) at pH 8.0 with complete protease inhibitor mixture (Roche Applied Science, Indianapolis). The total soluble proteins, 100 μg per lane were resolved on 4-20% gradient gels; samples of 500 μg per lane were resolved on 20% SDS-PAGE gels. Mini Protean TGX gels (Bio-Rad) were stained with Sypro Ruby (Invitrogen) or silver stain (Invitrogen). For LC-ESI-MS/MS or LC-ESI-MS analyses the 6F peptide band was in-gel digested as previously described (Hellman et al. (1995) *Anal Biochem.* 224: 451-455). Briefly, the band of interest was excised and in-gel trypsin digested (5-10 ng/mL of Gold trypsin, V5280, Promega) overnight at 37° C., eluted in 50% acetonitrile containing 0.1% trifluoroacetic acid followed by Zip-Tip C-18, Tip size P10 (Millipore), and subjected to LC-ESI-MS/MS analysis using a 4000 QTRAP quadruple mass spectrometer (Applied Biosystems) equipped with electrospray ionization source or analysis was performed by LC-ESI-MS on an LCQAdvantage Max ion trap mass spectrometer (ThermoElectron, Inc.) equipped with electrospray ionization source as previously described (Watson et al. (2011) *J. Lipid Res.* 52: 361-373; Navab et al. (2011) *J. Lipid Res.* 52: 1200-1210). Quantification of 6F peptide in the lyophilized tomato by LC-ESI-MS/MS or LC-ESI-MS was accomplished by using a $^{15}$N-labeled chemically synthesized 6F peptide without end blocking groups. When the 6F fractions from the HPLC prior to injection into the mass spectrometer were subjected to SDS PAGE analysis and the bands migrating with authentic 6F peptide were in-gel trypsin digested, on subsequent examination in the mass spectrometer, only the signature for 6F was seen (i.e. no other protein or peptide could be detected in these bands). Consequently, SDS PAGE analysis of protein extracts of lyophilized tomatoes following LC (but without MS analysis) was used for routine quantification of 6F. For routine quantification, the gels were scanned by densitometry and the results calculated from a standard curve generated by the lanes containing chemically synthesized 6F peptide without end blocking groups.

Identification and Quantification of 6F in Small Intestine and Plasma

For analysis of the small intestine, 200 mg of small intestine (including contents) were homogenized in 10 mL of acetonitrile:water (1:1) and the homogenates were lyophilized and re-suspended in 400 µL of acetonitrile:water (1:1). For analysis of plasma, 100 µl of plasma were lyophilized and brought up in 400 µl of acetonitrile:water (1:1). Samples were run on HPLC using a C-18 Reverse Phase analytical column and a gradient solvent system of acetonitrile: water (30% to 80% in 20 min) in the presence of 0.1% TFA and monitored at 280 nm. Chemically synthesized 6F samples (5 µg in the same solvent as samples) were injected and retention times were obtained. Unknown samples (200 µl out of original 400 µl) were injected and 0.5 mL fractions were collected. Samples corresponding to the retention time of the chemically synthesized 6F were dried and analyzed by SDS gel electrophoresis as described above and the bands migrating with chemically synthesized 6F were quantified by scanning and comparison to known quantities of chemically synthesized 6F (without blocking groups) run on the same gels.

Addition of Tomatoes to WD

For in vivo experiments, the lyophilized tomato fruit tissue was thoroughly ground to a fine powder in liquid nitrogen without the extraction buffer and was then thoroughly mixed with increasing quantities of powdered WD to yield WD containing 2.2% lyophilized tomato powder, which was frozen and stored at −80° C. until use. In some experiments, wild-type tomatoes were used instead of the EV tomatoes as controls. This is explicitly indicated in the figure legends. In these instances, the wild-type tomatoes were grown in Saint Louis and processed identically to the EV and 6F tomatoes.

Determination of Lycopene Content of Tomatoes

Lycopene content in the tomatoes was determined by previously described methods (Lucini et al. (2012) *J. Sci. Food Agric.* 92: 1297-1303). Briefly, the ground lyophilized tomato powder was suspended in NaCl (3.42 M) and extracted using ethyl acetate and cyclohexane (1:1; v/v) by centrifuging for 5 min at 600×g. The organic layer was carefully removed and the OD was measured at a wavelength 503 nm in triplicates in a spectrophotometer (FLUOstar omega, BMG Labtech) as described (Lavecchia and Zuorro (2008) *Eur. Food Res. Technol.*, 228: 153-158). Lycopene standards from Sigma (Catalog Number L9879) were used for generating the standard curves.

Statistical Analysis

Statistical analyses were performed by ANOVA, unpaired two-tail t test or by linear regression using GraphPad Prism version 5.03 (GraphPad Software, San Diego, Calif.).

Results

Is the 6F Peptide without End Blocking Groups Effective In Vivo?

Figure 16A:
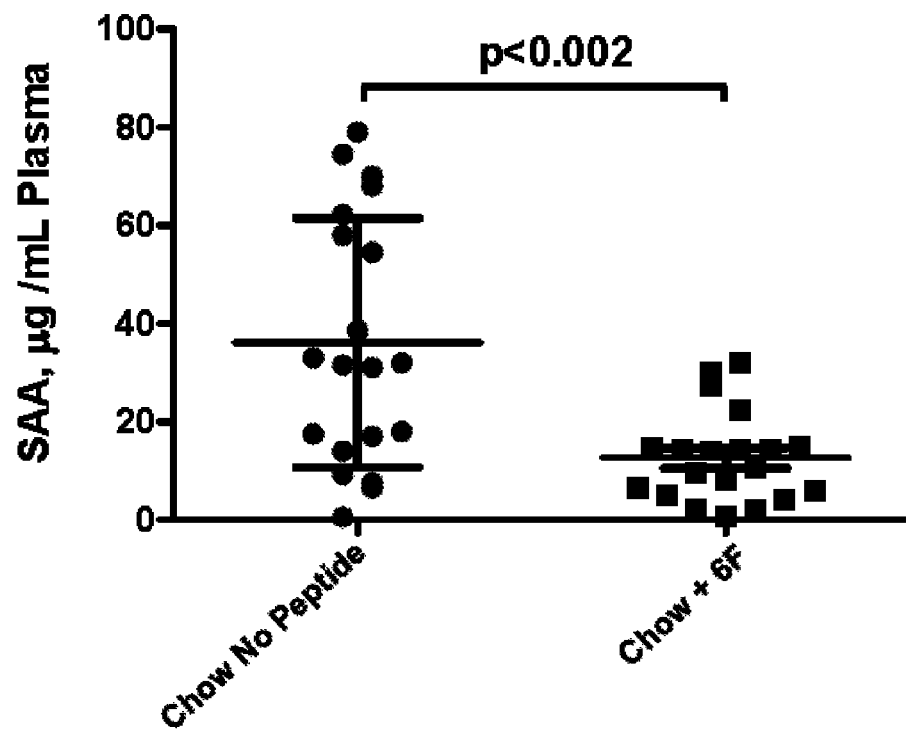
FIGS. 16A-16C show that the 6F peptide synthesized from all L-amino acids without end blocking groups when fed to apoE$^{-/-}$ mice significantly reduced plasma serum amyloid A (SAA) levels and decreased the percent of the aorta with atherosclerotic lesions.
Figure 16B:
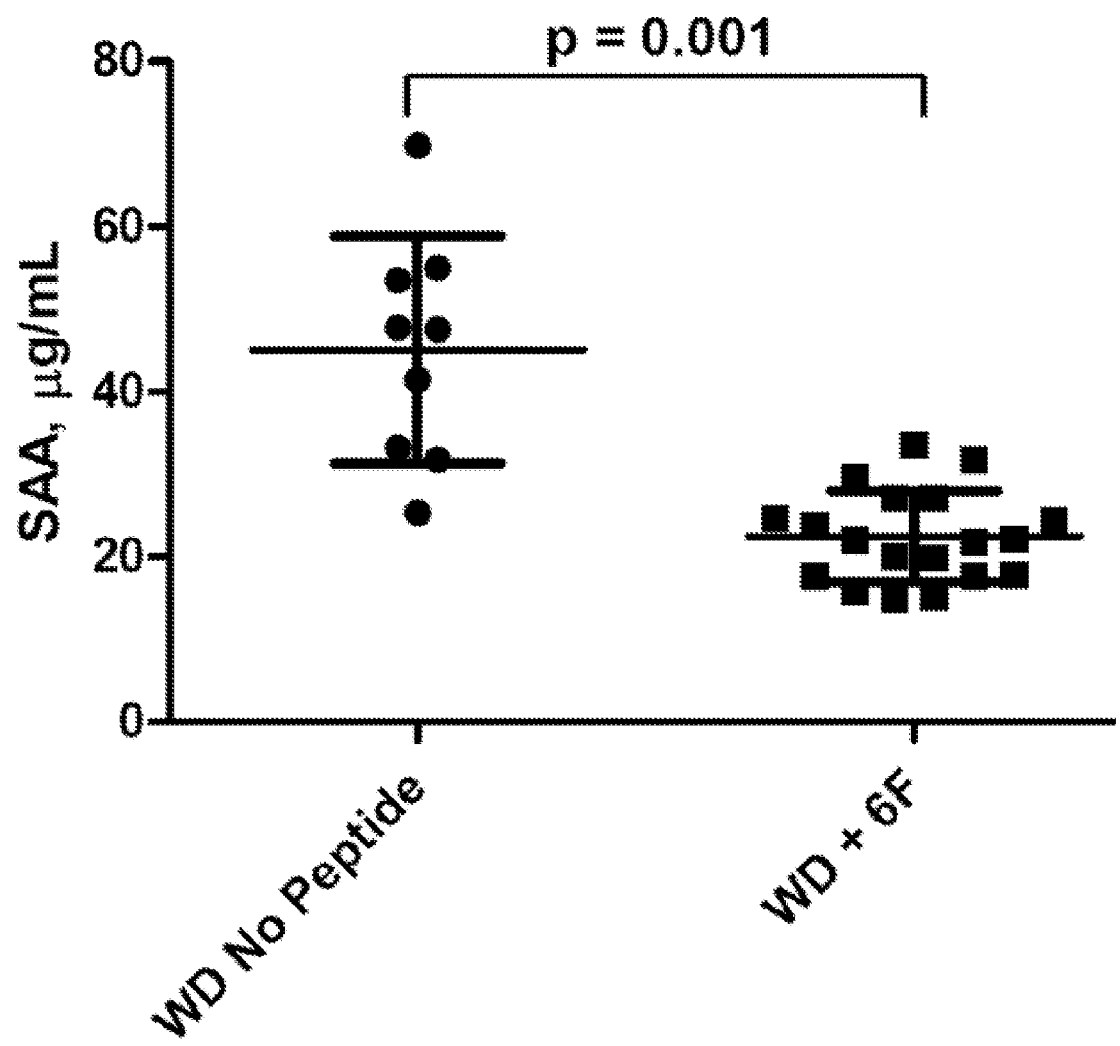
Figure 16C:
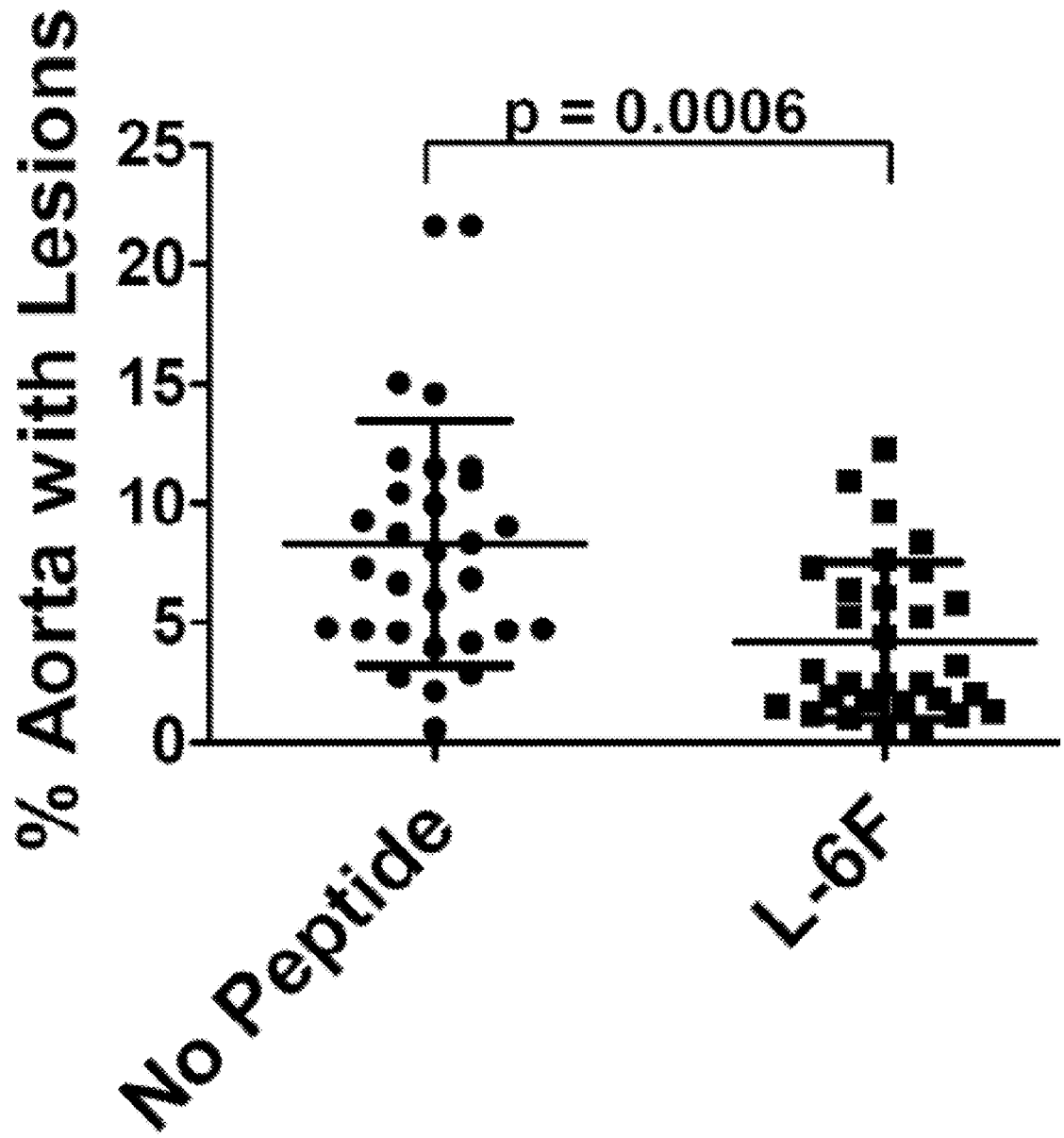

As shown in FIG. 16A, feeding apoE$^{-/-}$ mice the 6F peptide without end blocking groups by incorporating the peptide into mouse chow significantly decreased plasma SAA levels. Feeding apoE$^{-/-}$ mice the 6F peptide without end blocking groups by incorporating the peptide into WD also decreased plasma SAA levels (FIG. 16B) and decreased the percent of the aorta with atherosclerotic lesions (FIG. 16C).

Would the 6F Peptide without End Blocking Groups be Efficacious in More than One Mouse Model of Atherosclerosis if it was Mixed with Homogenized Tomato Before Incorporation into the Diet?

The efficacy of apoA-I mimetic peptides is thought to be due to their ability to bind oxidized lipids (Van Lenten et al. (2008) *J. Lipid Res.* 49: 2302-2311). Before proceeding with an attempt to produce the peptide in a genetically engineered plant such as a tomato, we thought it was important to determine if homogenized tomato might saturate the peptide with plant lipids rendering it ineffective. As shown in FIG. 28A this was not the case for plasma SAA levels. As shown in FIG. 28B, incorporating the 6F peptide without end blocking groups into WD containing 10% ripened tomato homogenate resulted in a significant decrease in plasma levels of the potent growth factor lysophosphatidic acid (LPA) in both apoE$^{-/-}$ and LDR$^{-/-}$ mice. Having assured ourselves that the presence of tomato fruit would not alter the efficacy of the 6F peptide we then set out to determine if we could genetically engineer tomatoes to express the 6F peptide.

Can the 6F Peptide be Expressed in the Fruit of Tomato Plants?

As shown in FIG. 17, most of the tomato lines that were PCR positive for 6F expressed a band on SDS PAGE gels that migrated similarly to authentic chemically synthesized 6F without end blocking groups. Other tomato lines in FIG. 17 did not (e.g., line 95 and the wild-type [WT] control). Tomato line 95 did show PCR evidence of gene insertion, but presumably the gene was not expressed at the protein level. Following HPLC and SDS PAGE, the region on each lane corresponding to 6F was excised and in-gel trypsin digested and subjected to LC-ESI-MS/MS or LC-ESI-MS analysis as described in Materials and Methods. FIG. 18A demonstrates that the bands migrating similarly to authentic 6F exhibited the LC-ESI-MS signature for 6F while the same region from those lanes without bands did not (FIG. 18B). The 6F peptide was found to account for between 0.6 and 1.0% of the weight of the lyophilized tomatoes. Founder lines were selected and grown to collect seeds. Homozygous lines were generated as described in Materials and Methods. SDS PAGE gels from a control homozygous line and from two homozygous lines (1A and 17A) expressing 6F are shown in FIG. 29. Having been successful in producing the 6F peptide in homozygous transgenic tomatoes we next set out to determine if feeding these tomatoes compared to control tomatoes would show a beneficial effect on plasma biomarkers in short-term feeding studies.

Would Feeding WD for Two Weeks with Tomatoes Transgenic for 6F Improve Plasma Biomarkers Compared to No Added Tomato or Compared to Feeding Wild-Type Tomatoes?

At the start of these experiments we had a limited supply of homozygous transgenic tomatoes and an even more limited supply of homozygous EV tomatoes. Thus, we designed experiments with relatively few mice measuring biomarkers after short-term feeding. In the first short-term experiment we used wild-type (WT) tomato as the control tomato. These were grown identically to the EV and transgenic 6F tomatoes in the Saint Louis Core facility and were processed identically as stated in Materials and Methods. Feeding ground lyophilized transgenic 6F tomato at 2.2% of the WD to female LDLR$^{-/-}$ mice 10 weeks of age (40 mg/kg/mouse/day of 6F) for two weeks significantly improved many (but not all) of the biomarkers measured (FIGS. 19A-19K). Not shown in FIG. 19 are data indicating no significant improvement in plasma total cholesterol, triglycerides, free arachidonic acid or thromboxane B$_2$ levels after feeding either the WT or transgenic 6F tomatoes.

Would Feeding WD for Two Weeks with Tomatoes Transgenic for 6F Improve Plasma Biomarkers Compared to No Added Tomato or Compared to Feeding Empty Vector Tomatoes?

Figure 30A:
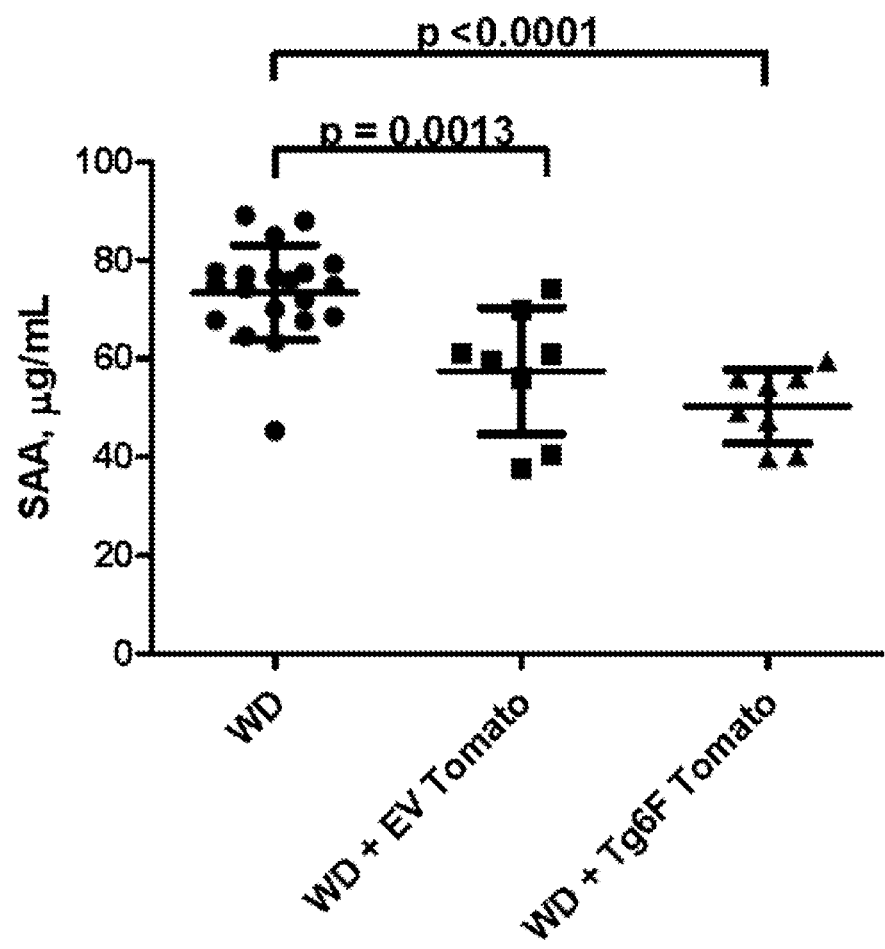
FIG. 30A: Female LDLR−/− mice 4-5 months of age were housed four in each cage and each cage was given each night compacted WD containing no lyophilized tomatoes (n=20), or compacted WD containing 2.2% by weight of ground lyophilized empty vector (EV) tomato (n=8), or compacted WD containing 2.2% by weight of ground lyophilized transgenic 6F (Tg6F) tomato. The mice in all cages ate all of the diet each night. The mice receiving the Tg6F tomatoes received 800 μg of 6F per mouse per day (40 mg/kg/day). After two weeks the mice were bled and plasma Serum Amyloid A (SAA) was determined by ELISA as described in Materials and Methods of Example 3.
Figure 30B:
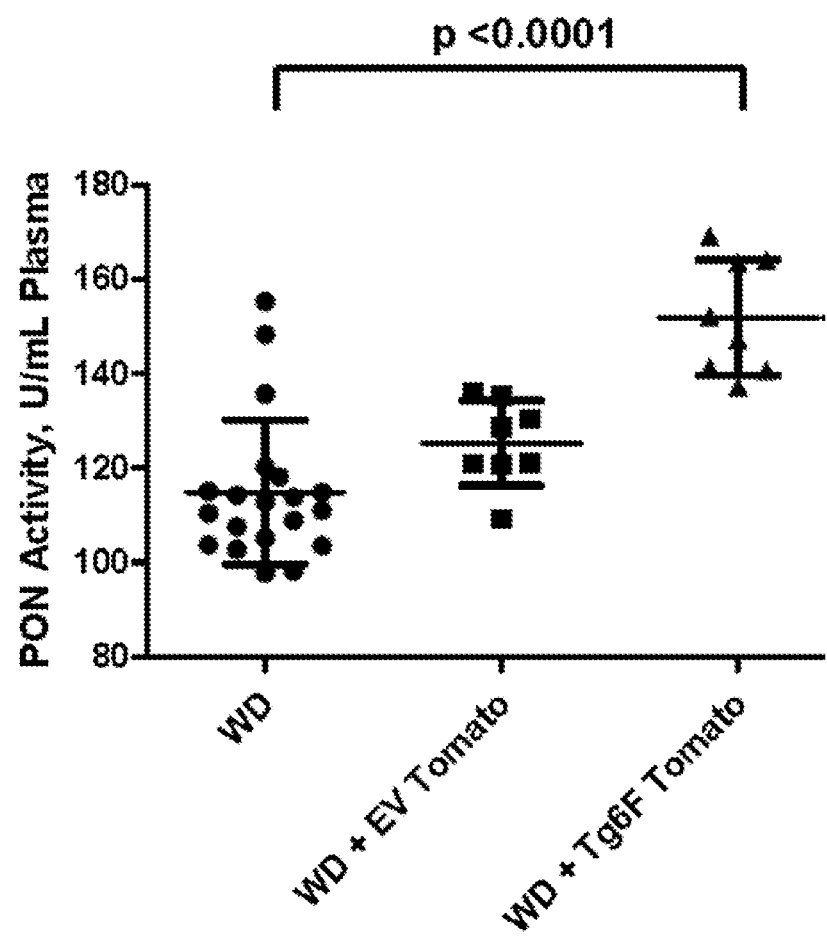
FIG. 30B: Paraoxonase-1 (PON) activity was determined in the plasma of the mice described in FIG. 30A as described in Materials and Methods of Example 3.
Figure 30C:
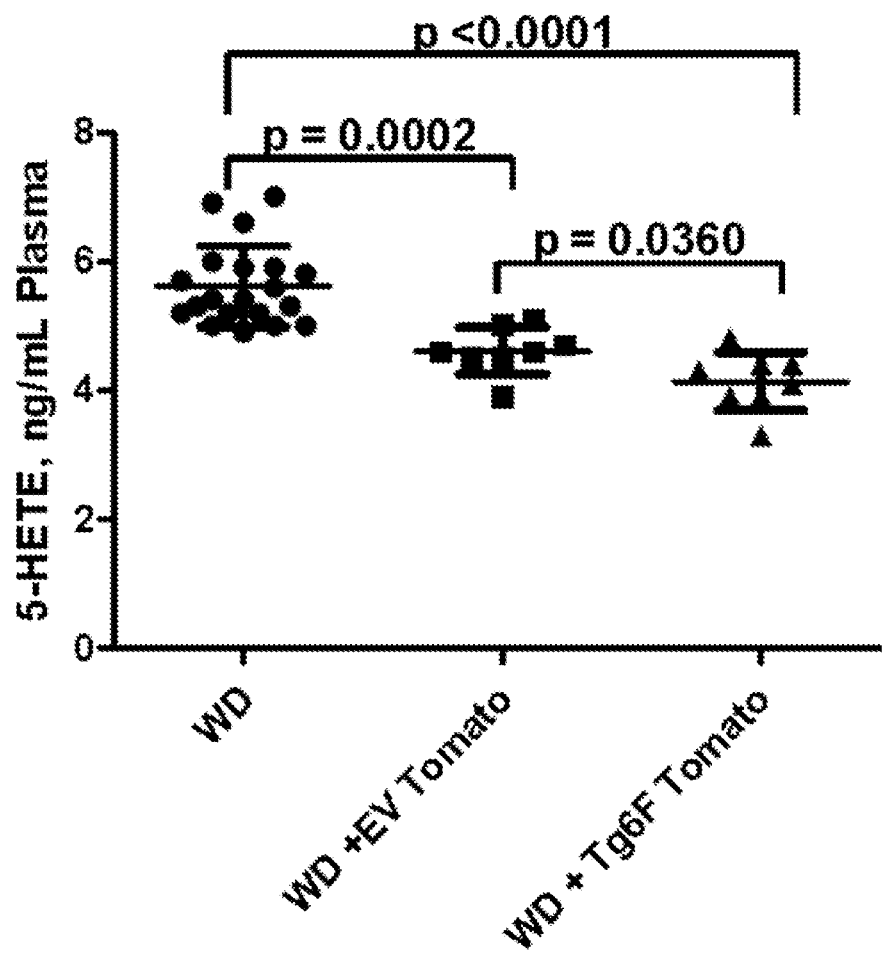
FIG. 30C: 5-HETE levels were determined in the plasma of the mice described in FIG. 30A as described in Materials and Methods of Example 3.
Figure 30D:
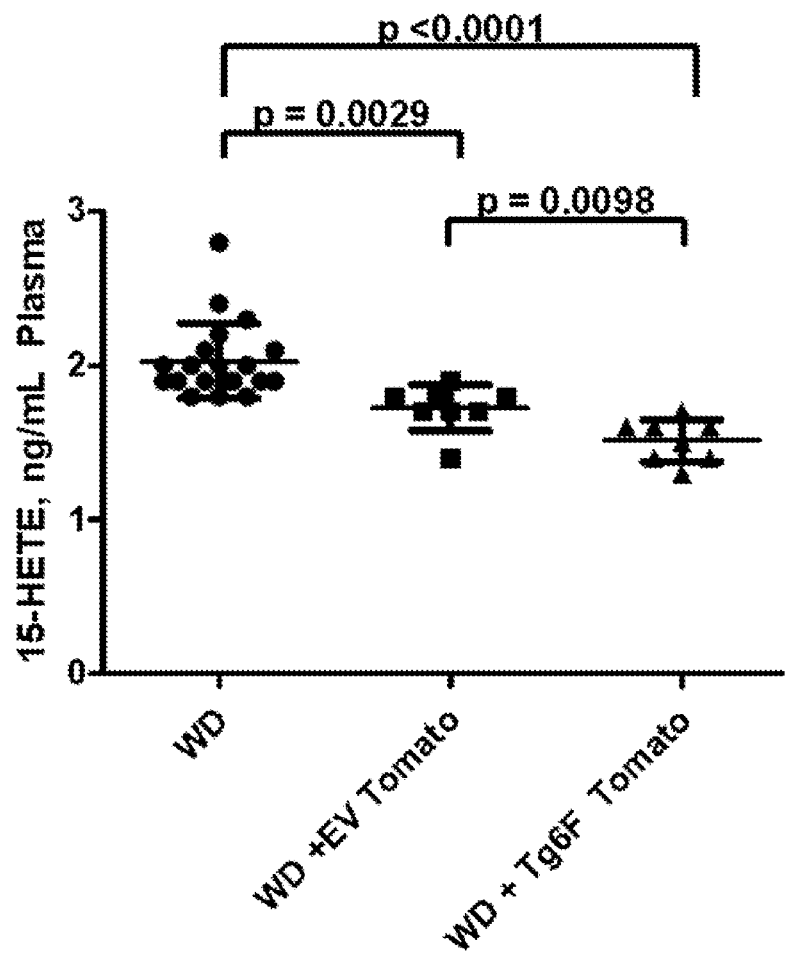
FIG. 30D: 15-HETE levels were determined in the plasma of the mice described in FIG. 30A as described in Materials and Methods of Example 3.
Figure 30E:
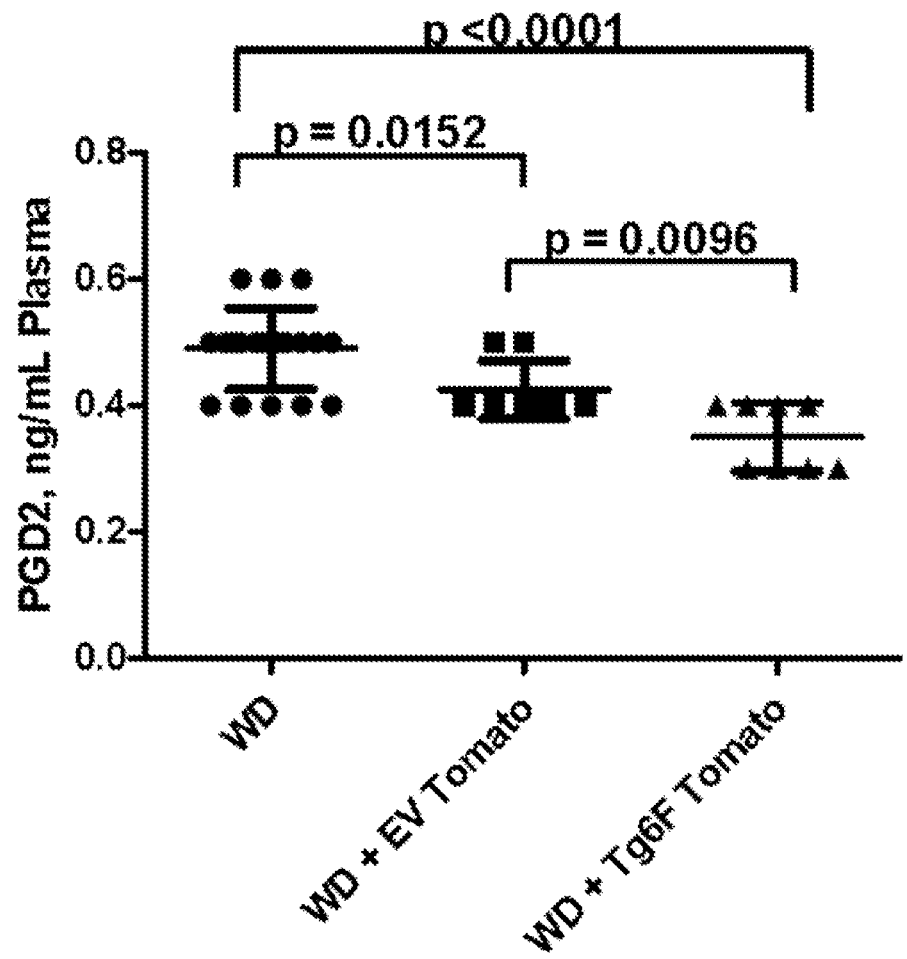
FIG. 30E: PGD2 levels were determined in the plasma of the mice described in FIG. 30A as described in Materials and Methods of Example 3.
Figure 30F:
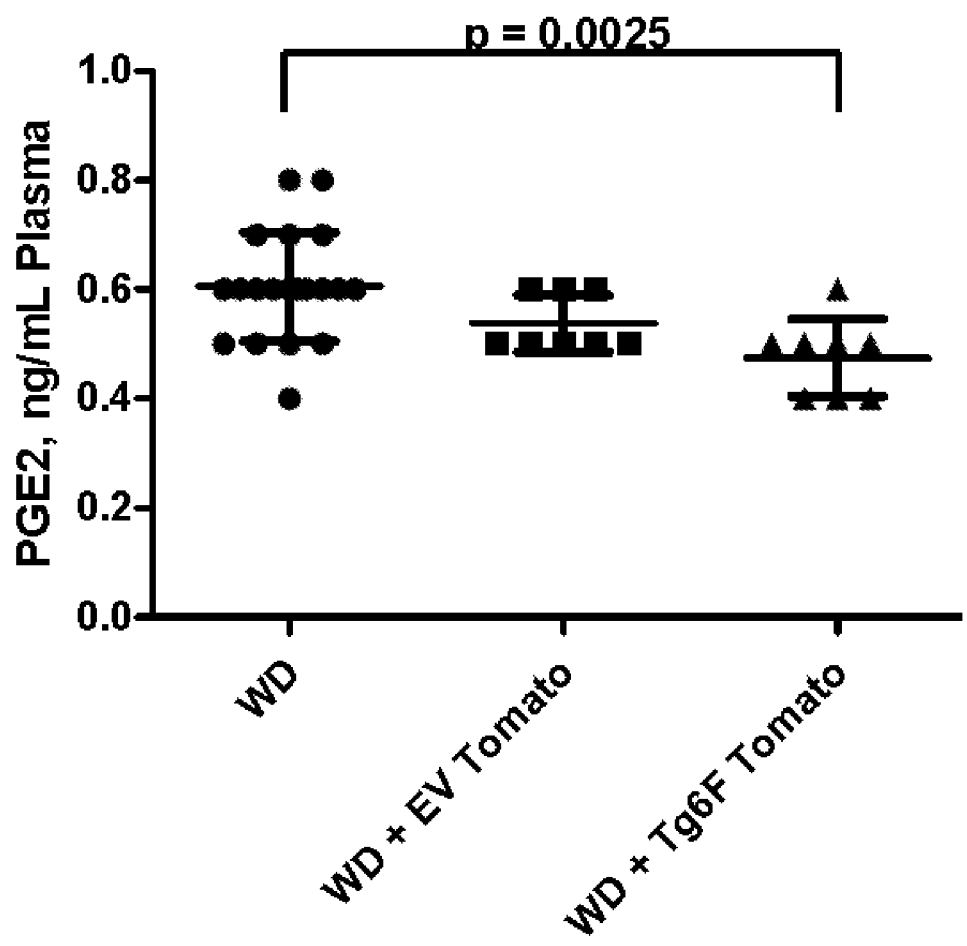
FIG. 30F.
Figure 30G:
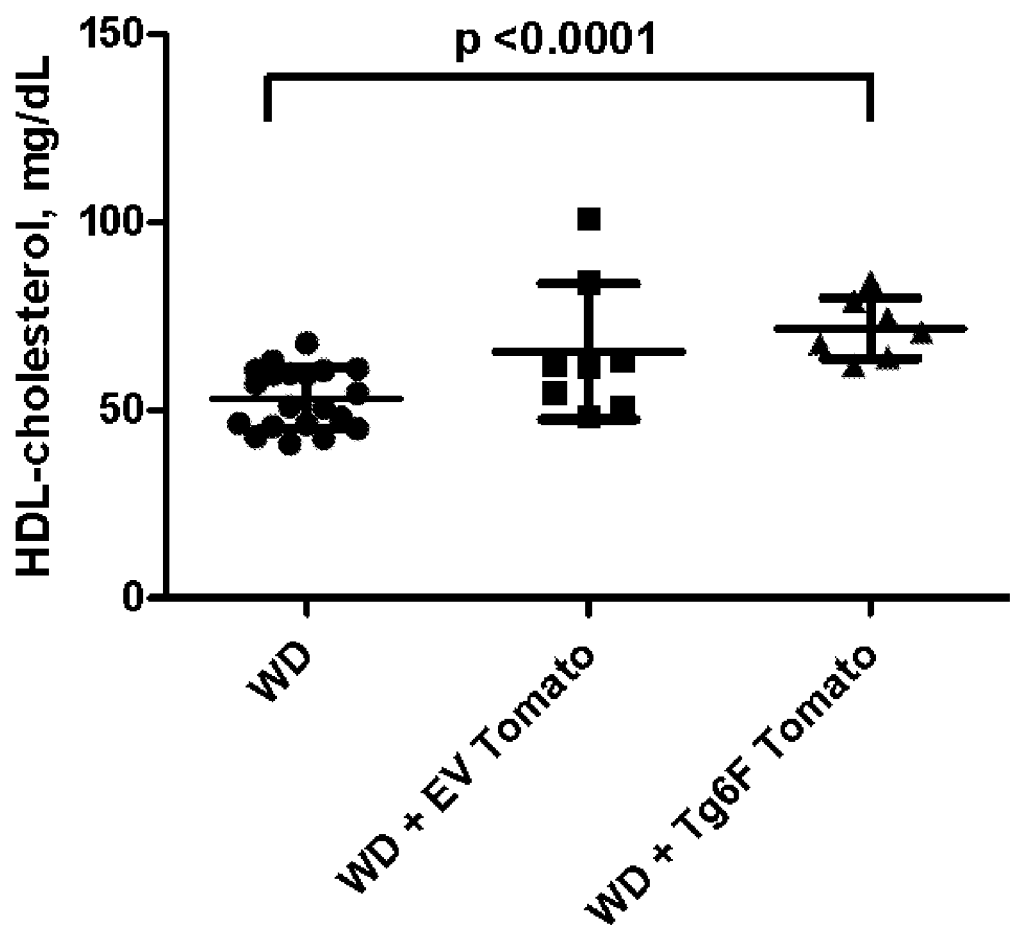
FIG. 30G: HDL-cholesterol levels were determined in the plasma of the mice described in FIG. 30A as described in Materials and Methods of Example 3.

The second experiment differed from the first experiment in the following details: i) the mice were older (4-5 months of age); ii) the control tomatoes were empty vector (EV) tomatoes instead of wild-type tomatoes; iii) not all of the biomarkers measured in the first experiment were repeated in the second. The results were similar between the two experiments as shown in FIG. 30. Feeding EV tomatoes with WD for two weeks significantly decreased SAA levels; feeding transgenic 6F tomatoes slightly decreased SAA levels beyond that of the EV tomatoes but this difference did not reach statistical significance (FIG. 30A). Feeding WD with transgenic 6F tomatoes significantly increased paraoxonase-1 activity (PON); feeding EV tomatoes did not (FIG. 30B). Feeding WD with EV tomatoes significantly decreased plasma free 5-HETE, 15-HETE, and PGD2, levels; feeding transgenic 6F tomatoes significantly reduced these levels more than feeding WD with EV tomatoes (FIGS. 30C-30E). Feeding WD with transgenic 6F tomatoes significantly reduced plasma PGE2 levels, while feeding EV tomatoes did not (FIG. 30F). Feeding WD with transgenic 6F tomatoes significantly increased plasma HDL-cholesterol levels; feeding EV tomatoes did not (FIG. 30G). Not shown in FIG. 30 are data indicating no significant improvement in plasma total cholesterol, triglycerides, free arachidonic acid or thromboxane B$_2$ levels after feeding either the EV or transgenic 6F tomatoes.

To summarize and contrast these two experiments, in both short-term feeding experiments transgenic 6F tomatoes significantly decreased plasma SAA, free 5-HETE, 15-HETE, PGD2, and PGE2 levels and increased both plasma PON activity and HDL-cholesterol levels. Additionally, in the first experiment in which LPA levels were measured feeding the transgenic 6F tomatoes significantly decreased plasma LPA 16:0, 18:0, 18:1, and 20:4 levels but feeding the WT tomatoes only significantly decreased plasma LPA 20:4 levels, which were significantly decreased even further by the transgenic 6F tomatoes. In the second short-term experiment but not in the first, feeding the control (EV) tomatoes significantly reduced plasma SAA levels. In the first short-term experiment feeding the control (WT) tomatoes significantly increased PON activity, but in the second experiment feeding the control (EV) tomatoes did not. In the first short-term experiment feeding the control (WT) tomatoes did not significantly decrease plasma free 5-HETE, 15-HETE, PGD2, or PGE2 levels, but in the second experiment feeding the control (EV) tomatoes significantly decreased plasma free 5-HETE, 15-HETE, and PGD2 levels and these levels were significantly decreased even further by feeding the transgenic 6F tomatoes. In both short-term experiments feeding the control tomatoes failed to alter HDL-cholesterol levels. In both short-term experiments plasma free arachidonic acid levels, total cholesterol levels, and triglyceride levels were not changed by feeding any of the tomatoes.

Since Control Tomatoes Improved Some of the Biomarkers in these Short-Term Feeding Experiments, could the Superior Performance of the Transgenic 6F Tomatoes be Due to an Induction of Higher Levels of Antioxidants in the Transgenic 6F Tomatoes?

Figure 20:
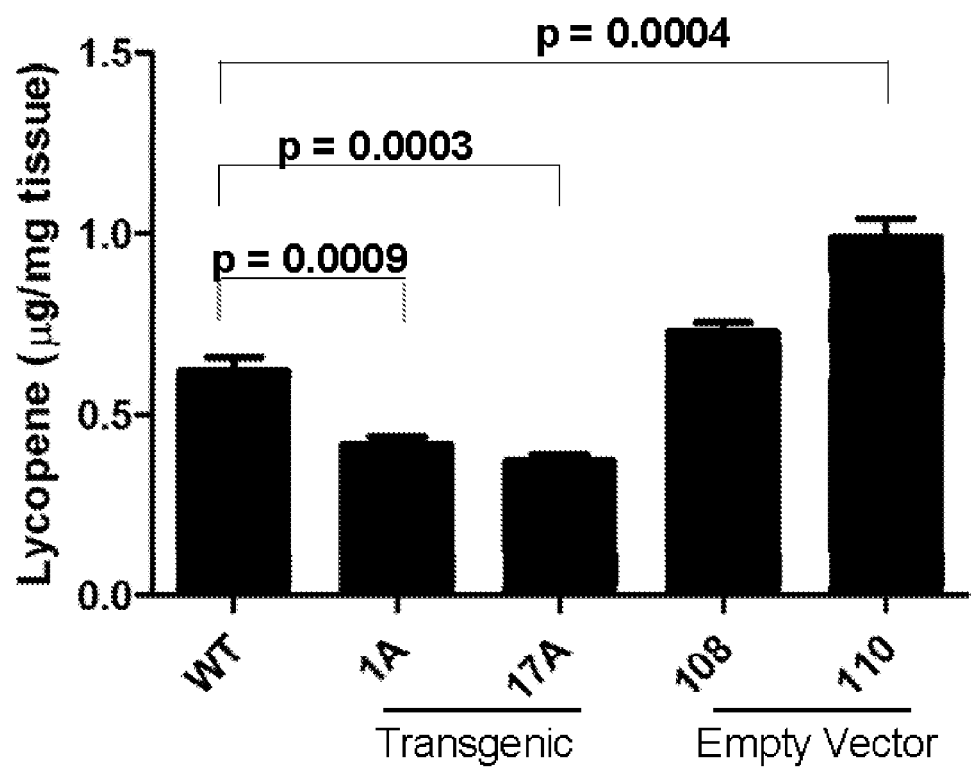
FIG. 20 shows that lycopene content of transgenic 6F tomatoes is slightly but significantly less than that of wild-type or empty vector tomatoes. The lycopene content of ripened tomatoes that were wild-type (WT), transgenic for 6F (1A; 17A), or empty vector (108; 110) was determined as described in Materials and Methods in Example 3.

To test this question we measured the content of the major tomato antioxidant, lycopene. As shown in FIG. 20 surprisingly, the homozygous transgenic 6F tomato lines 1A and 17A (the latter was used in the two short-term feeding experiments described above) had slightly but significantly less lycopene content compared to WT tomatoes or compared to EV tomato lines 108 and 110 (the latter was used in the second short-term feeding experiment).

Would Feeding WD for 13 Weeks with Tomatoes Transgenic for 6F Improve Plasma Biomarkers and Aortic Atherosclerosis Compared to No Added Tomato or Compared to Feeding Empty Vector Tomatoes?

Figure 21A:
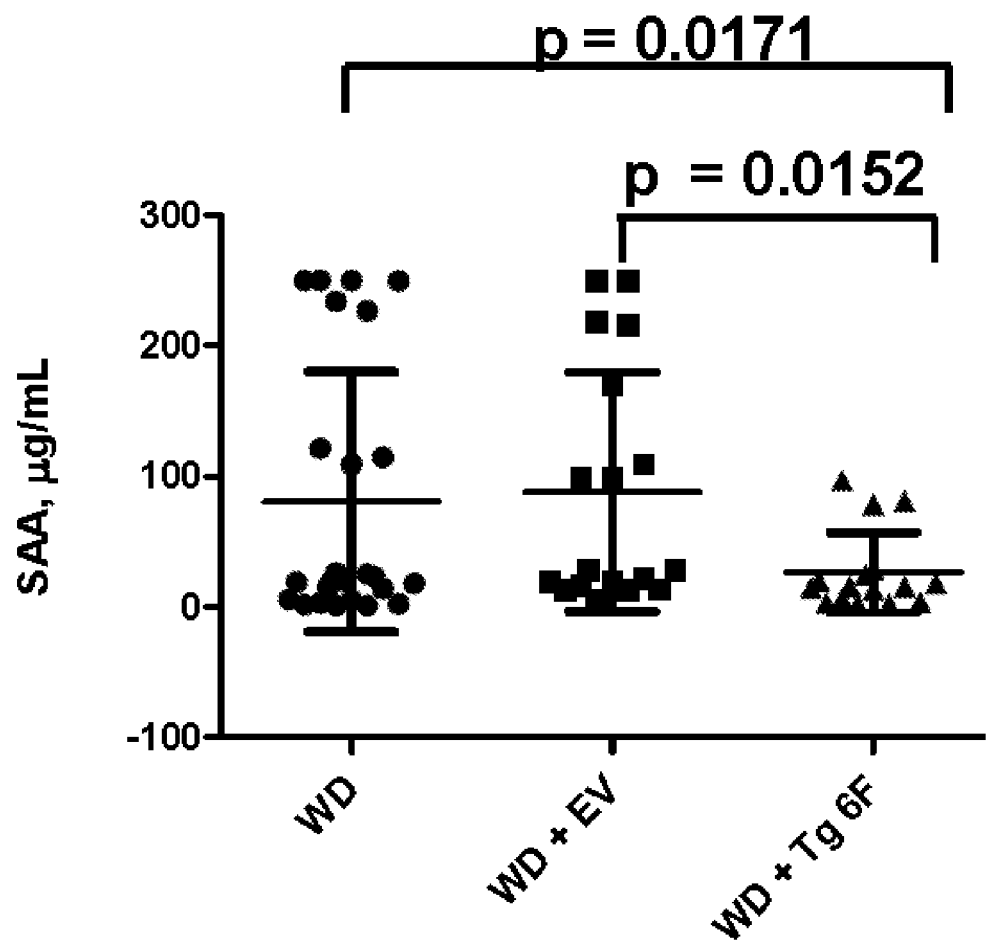
FIGS. 21A-21I show that feeding transgenic 6F tomatoes to LDLR$^{-/-}$ mice for 13 weeks improved a number of plasma biomarkers. Female LDLR$^{-/-}$ mice age 7-9 months of age were housed four in each cage and each cage was given each night compacted WD containing no lyophilized tomatoes (n=28), or compacted WD containing 2.2% by weight of ground lyophilized empty vector (EV) tomato (from line 110) (n=20), or compacted WD containing 2.2% by weight of ground lyophilized transgenic 6F (Tg6F) tomato (from line 17A) to provide 900 μg of 6F per mouse per day (45 mg/kg/day). The mice in all cages ate all of the diet each night. After 13 weeks the mice were bled and the following measurements were made as described in Materials and Methods in Example 3.
Figure 21B:
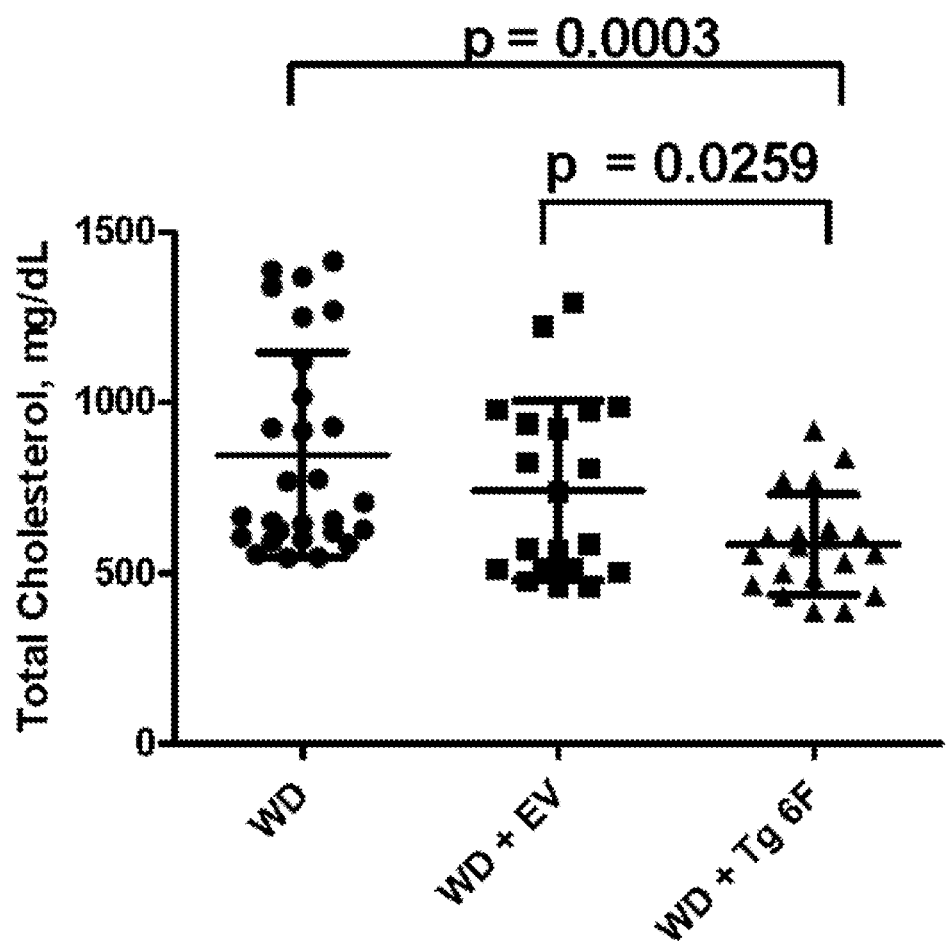
Figure 21C:
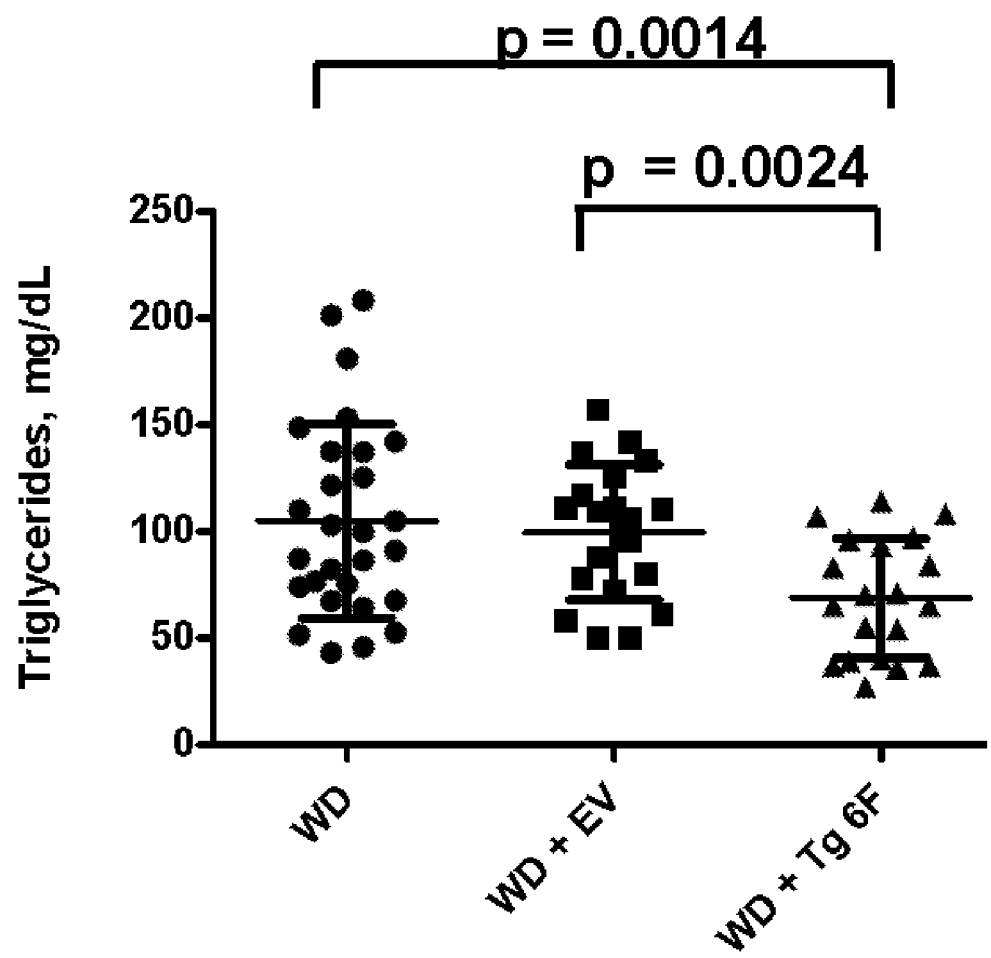
Figure 21D:
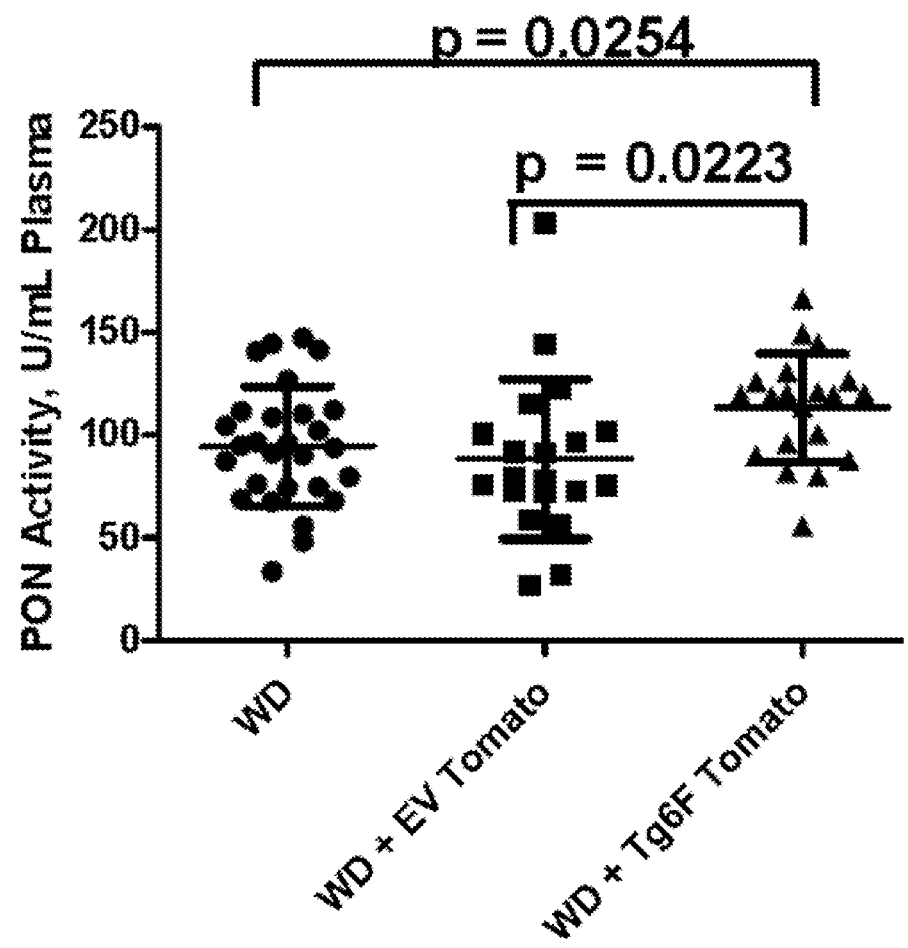
Figure 21E:
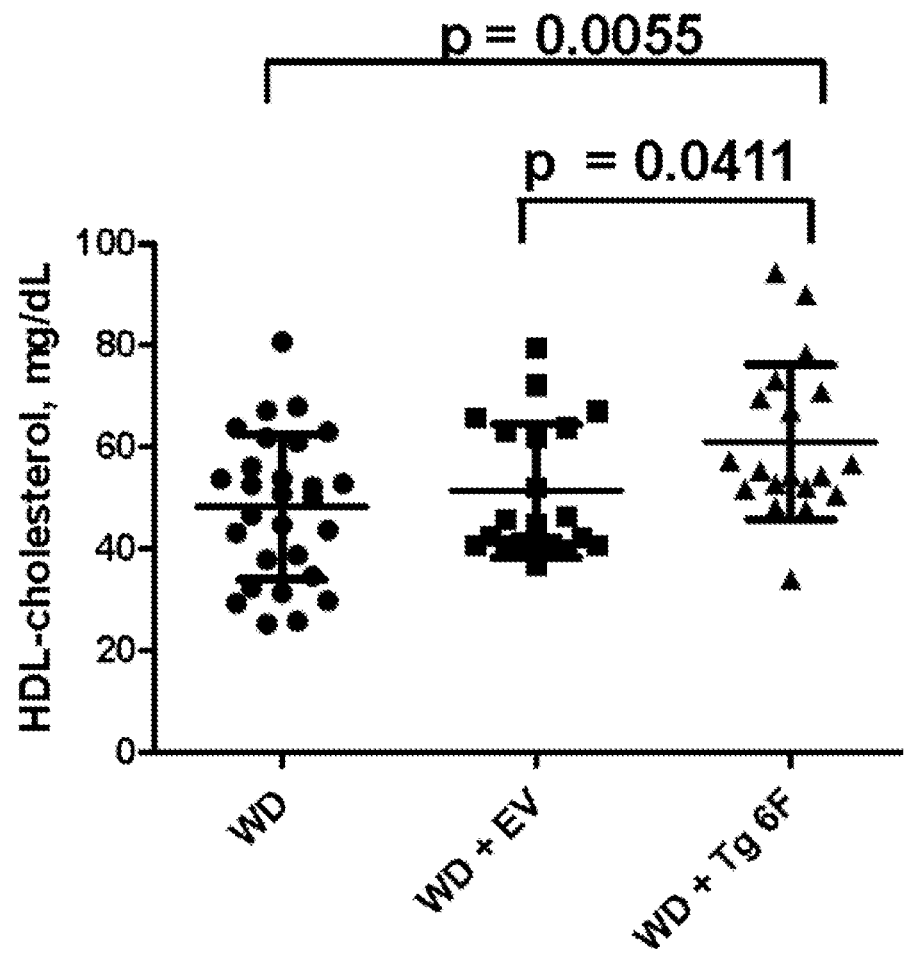
Figure 21F:
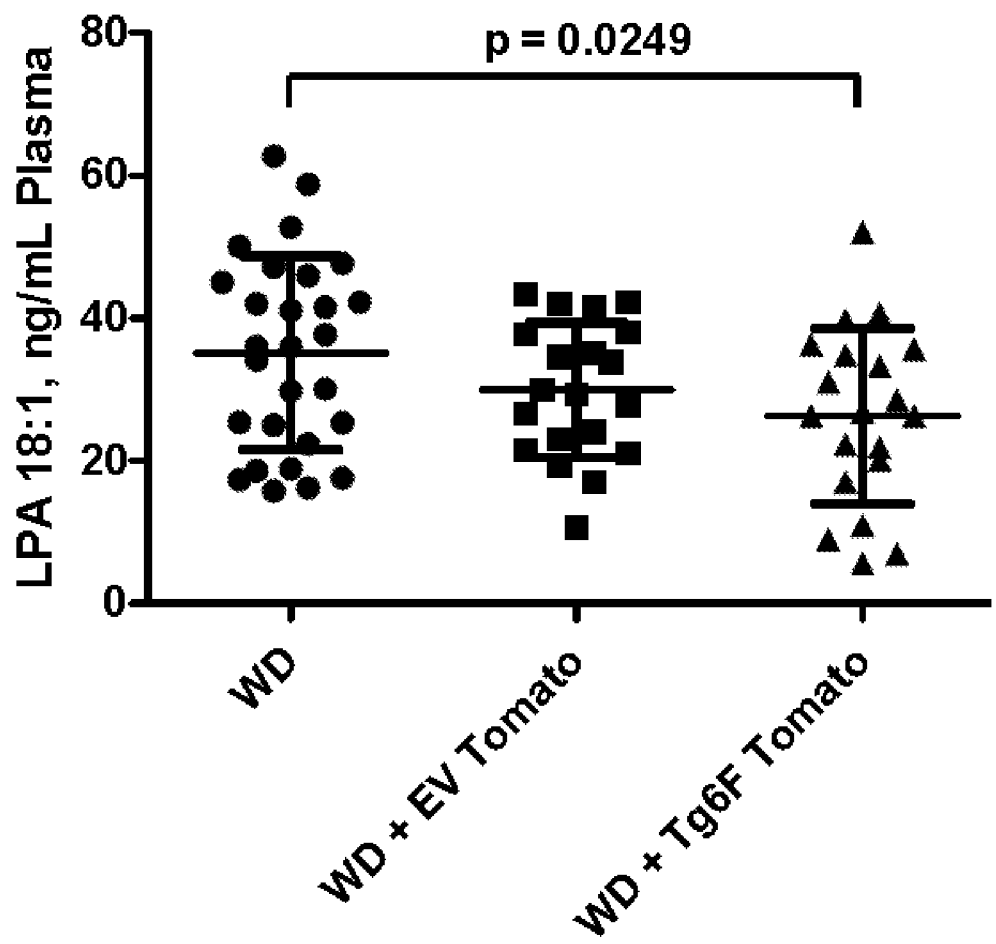
Figure 21G:
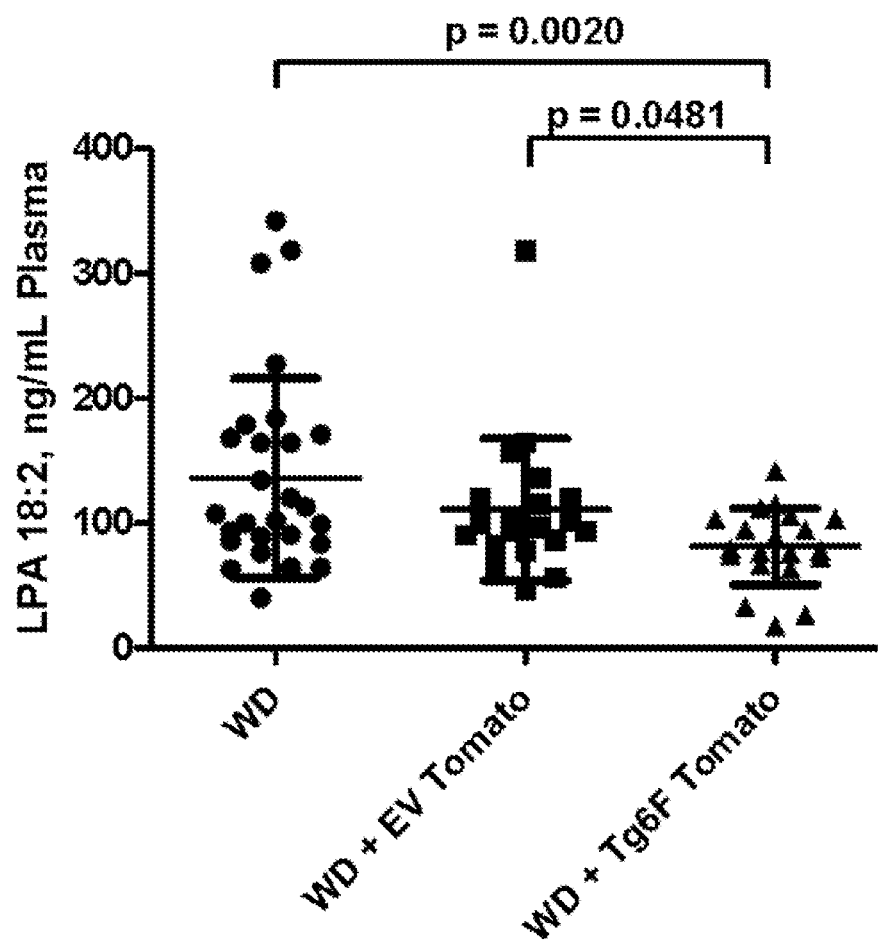
Figure 21H:
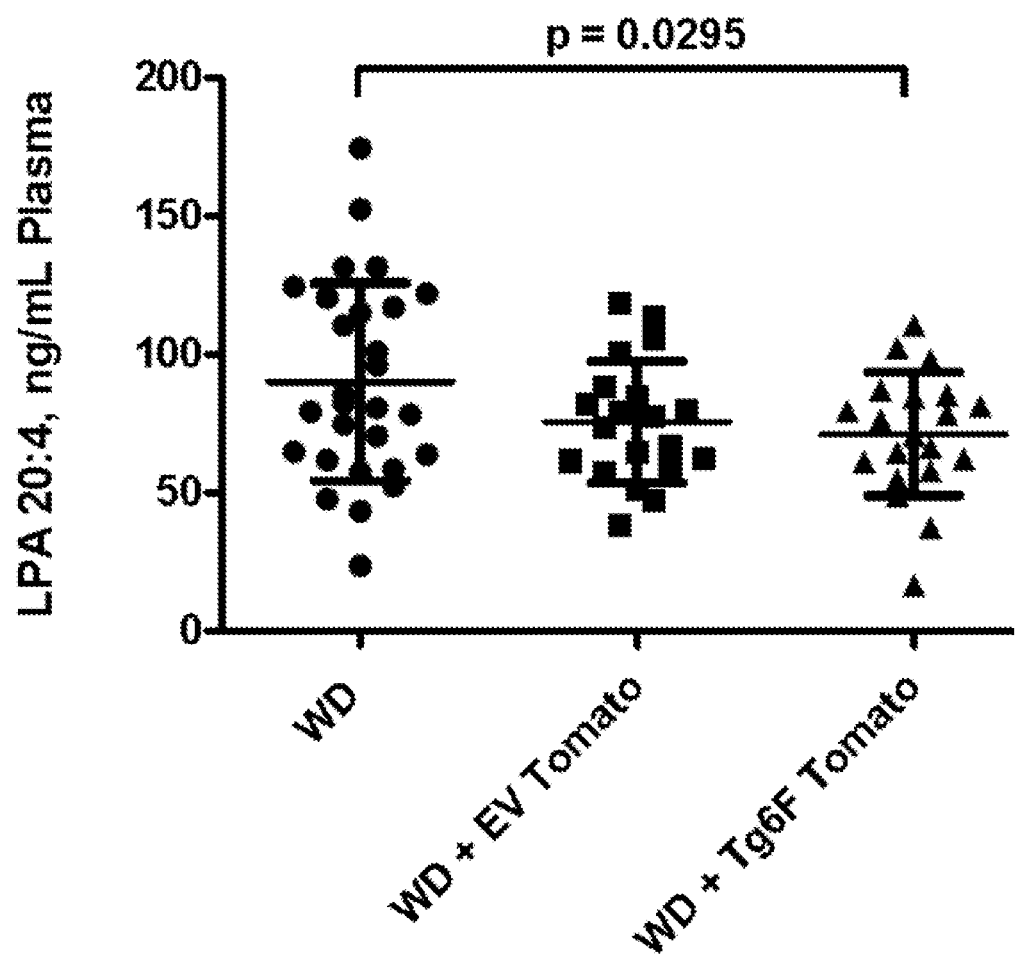
Figure 21I:
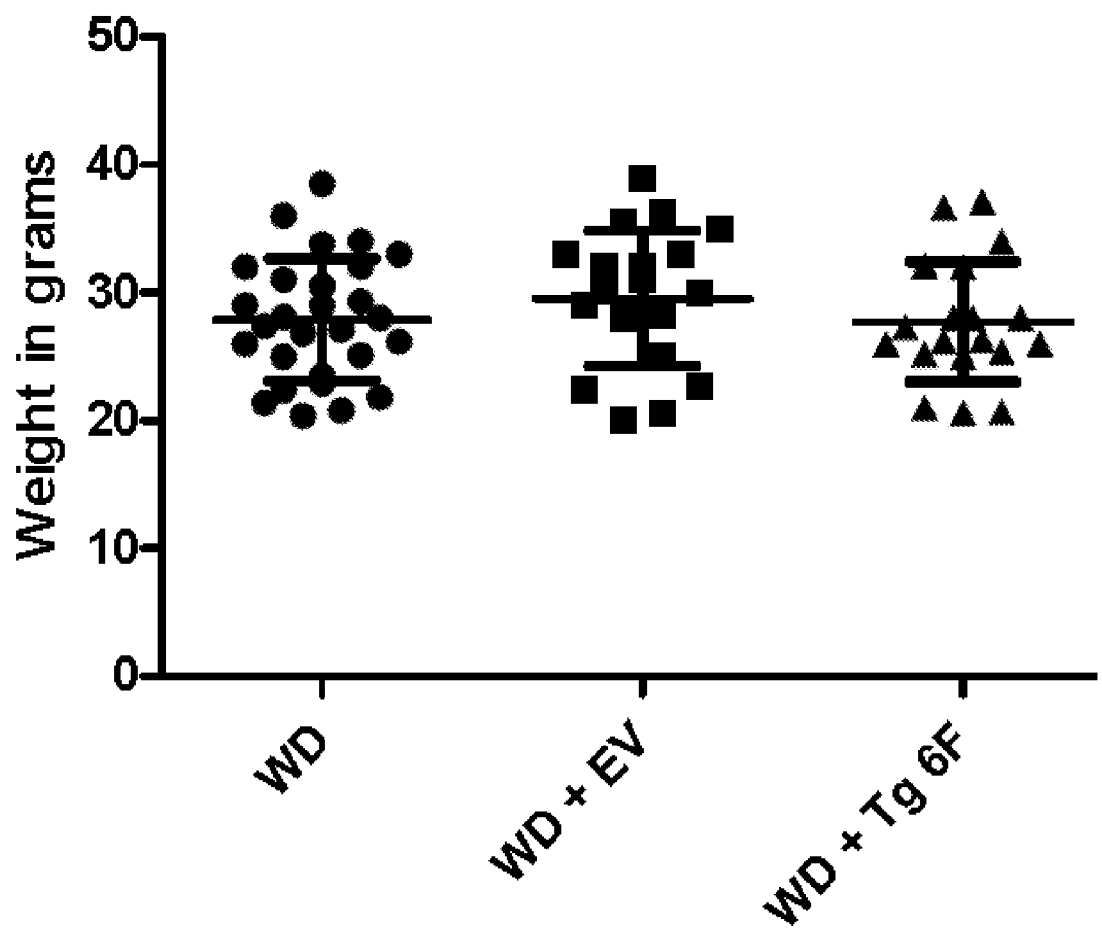
Figure 22A:
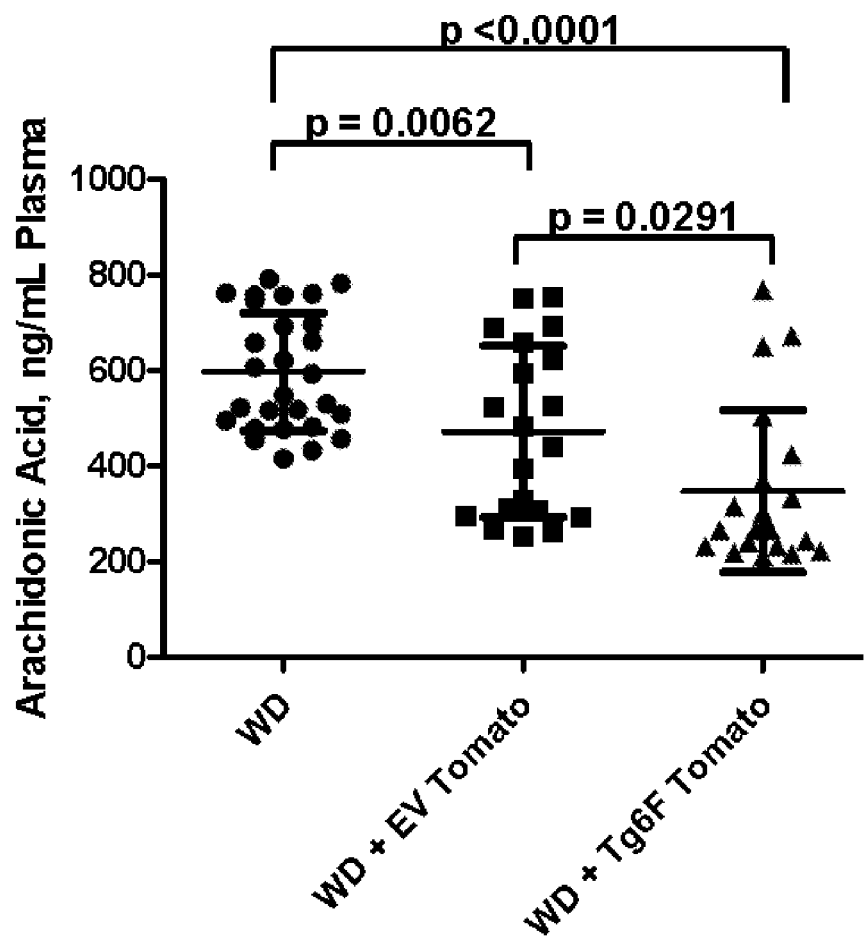
FIGS. 22A-22E show that feeding empty vector (EV) and transgenic 6F tomatoes decreased some biomarkers and increased others. The plasma from the mice described in FIG. 21 was analyzed as described in Materials and Methods for FIG. 22A: Free arachidonic acid.
Figure 22B:
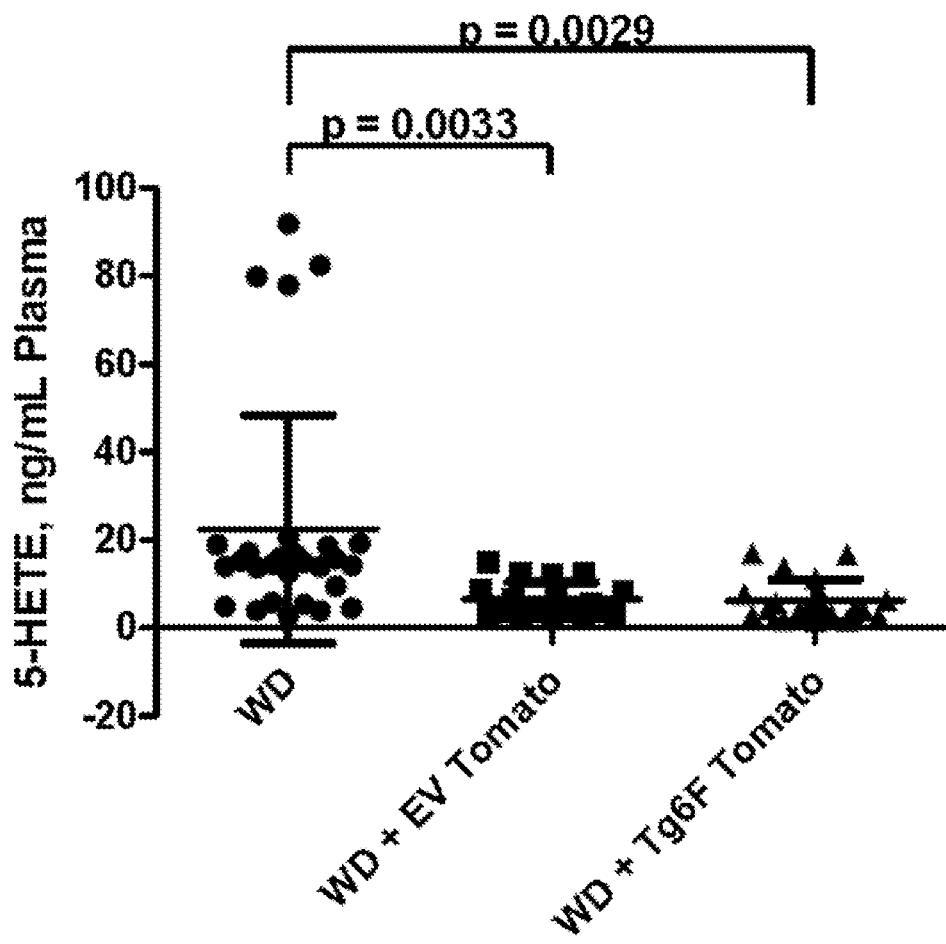
Figure 22C:
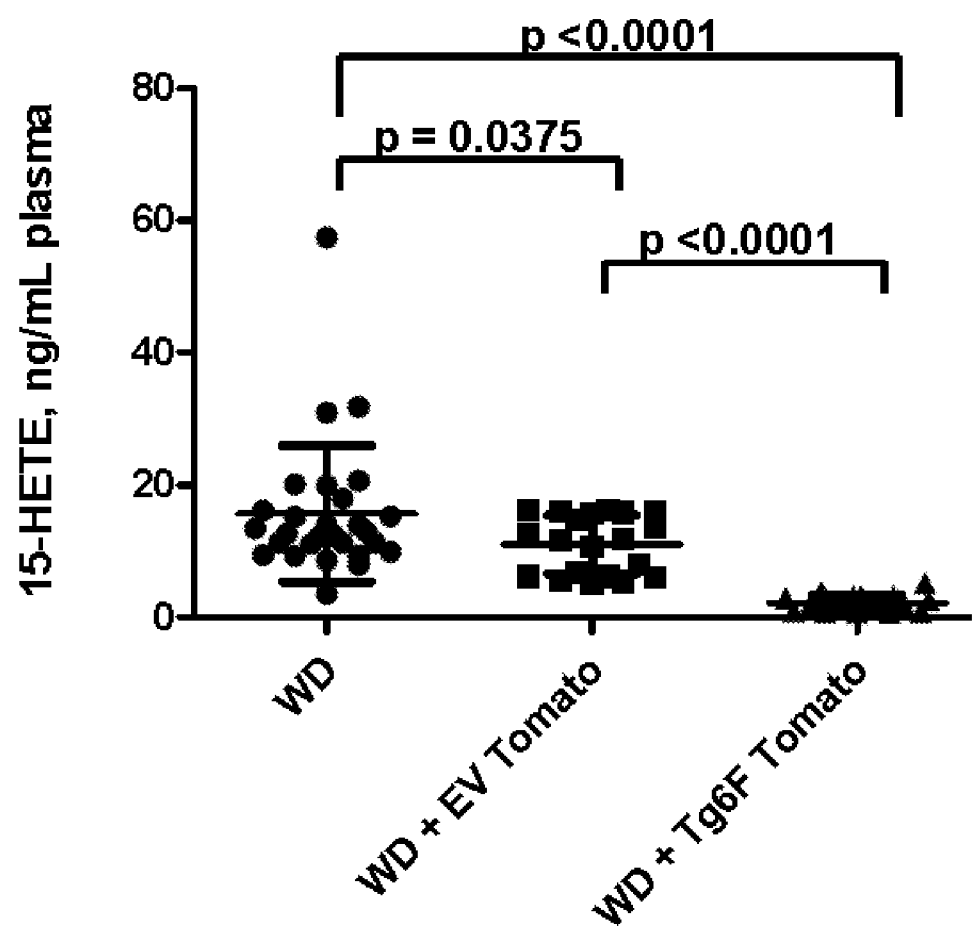
Figure 22D:
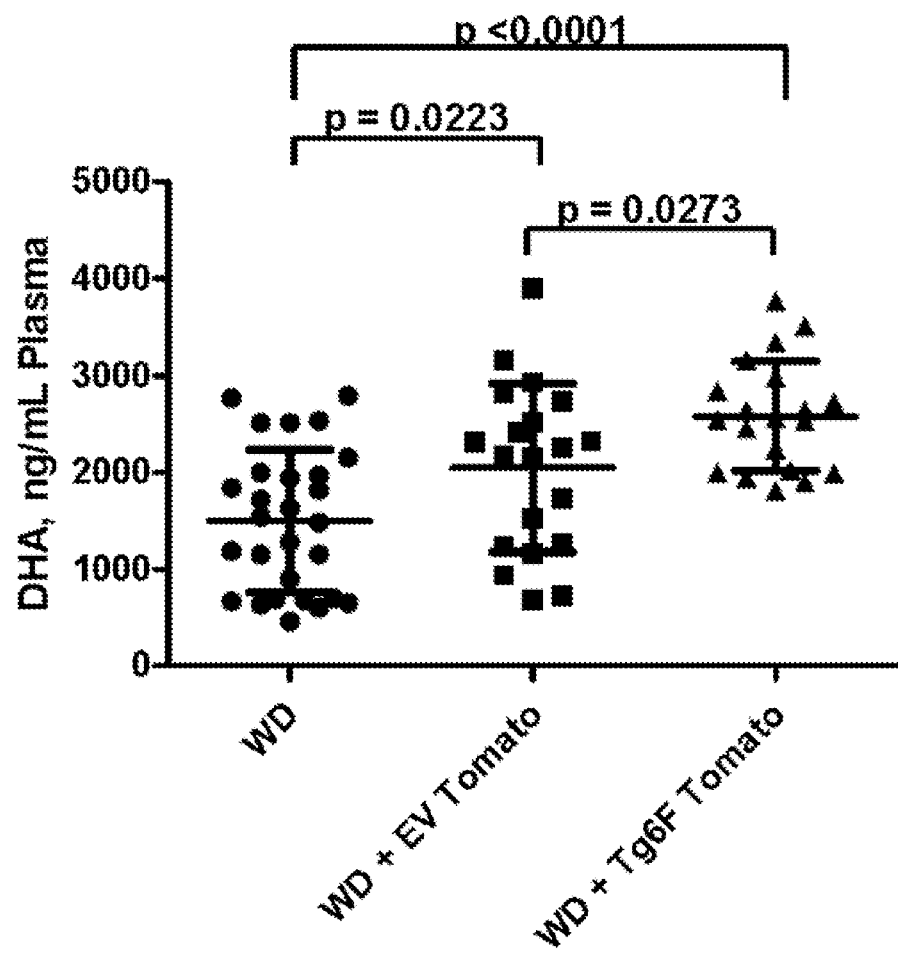
Figure 22E:
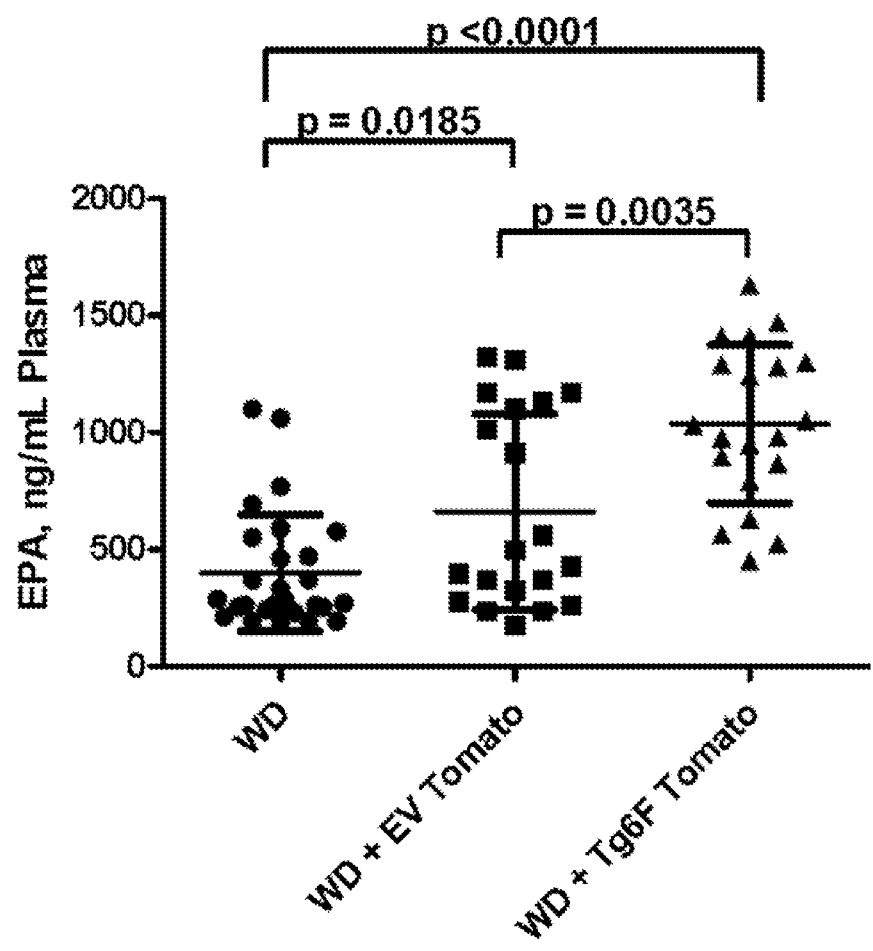
Figure 23:
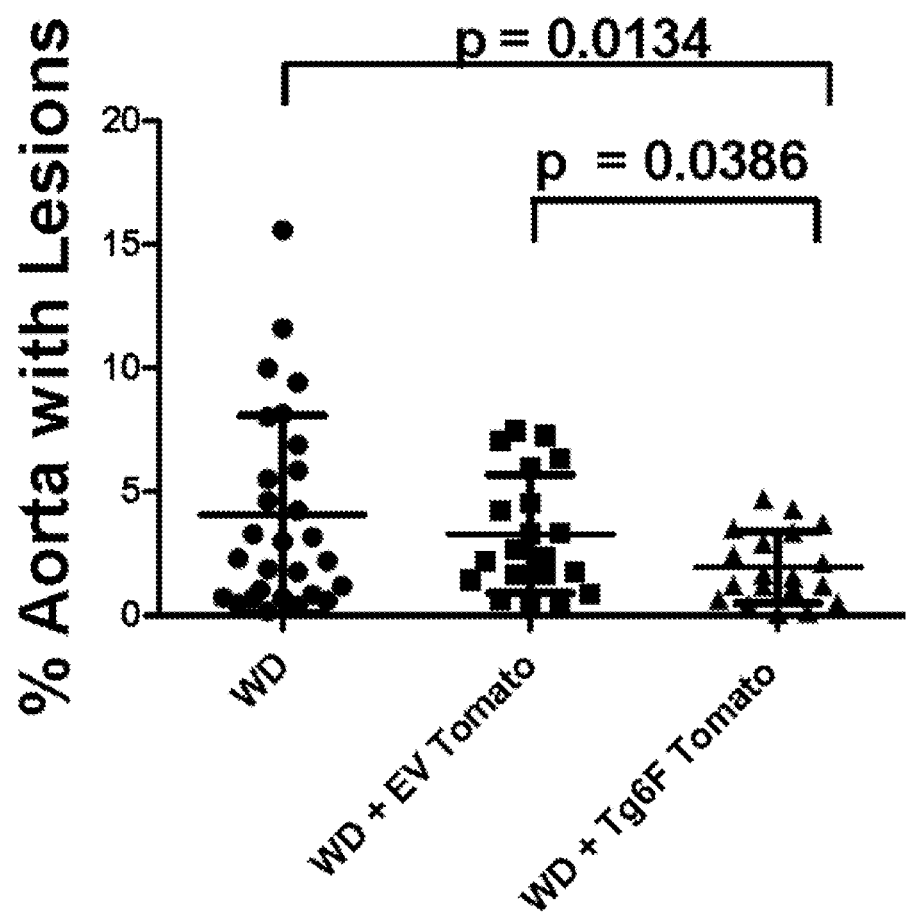
FIG. 23 shows that feeding transgenic 6F tomatoes but not EV tomatoes significantly decreased the percent of aorta with atherosclerotic lesions. The aorta from the mice described in FIG. 21 were harvested and analyzed to determine the percent of the aorta with atherosclerotic lesions as described in Materials and Methods in Example 3. The aorta from one of the mice fed transgenic 6F was severely damaged during the harvest and was not processed. The aortas from all other mice were successfully harvested, processed and analyzed.
Figure 24A:
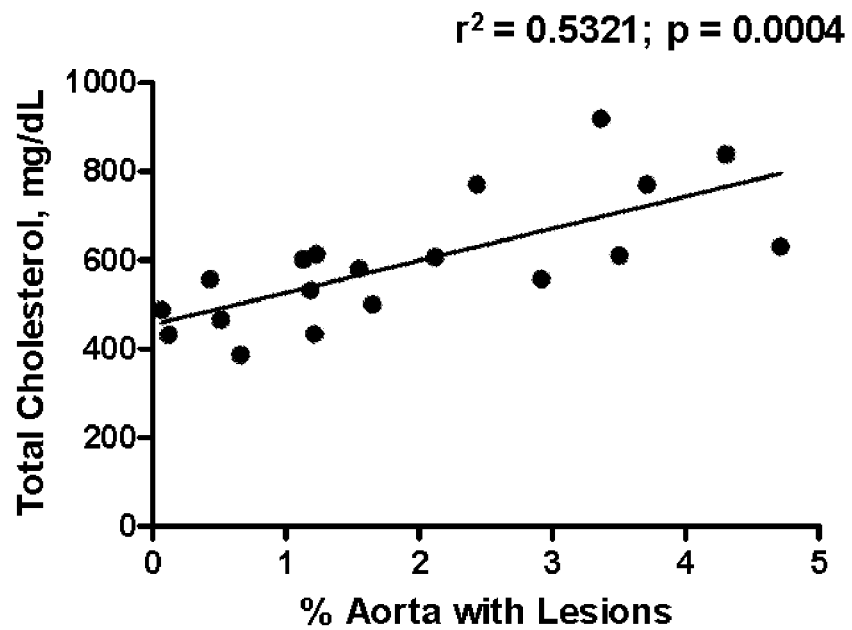
FIGS. 24A-24E show that the percent of aorta with atherosclerotic lesions in mice receiving WD and transgenic 6F tomatoes was positively and significantly correlated with plasma total cholesterol, and triglycerides and was significantly and inversely correlated with PON activity and HDL-cholesterol. There was no correlation with body weight. Linear regression of data from individual mice described in FIGS. 21-23 that received WD and transgenic 6F tomatoes is shown for the percent aorta with atherosclerotic lesions
Figure 24B:
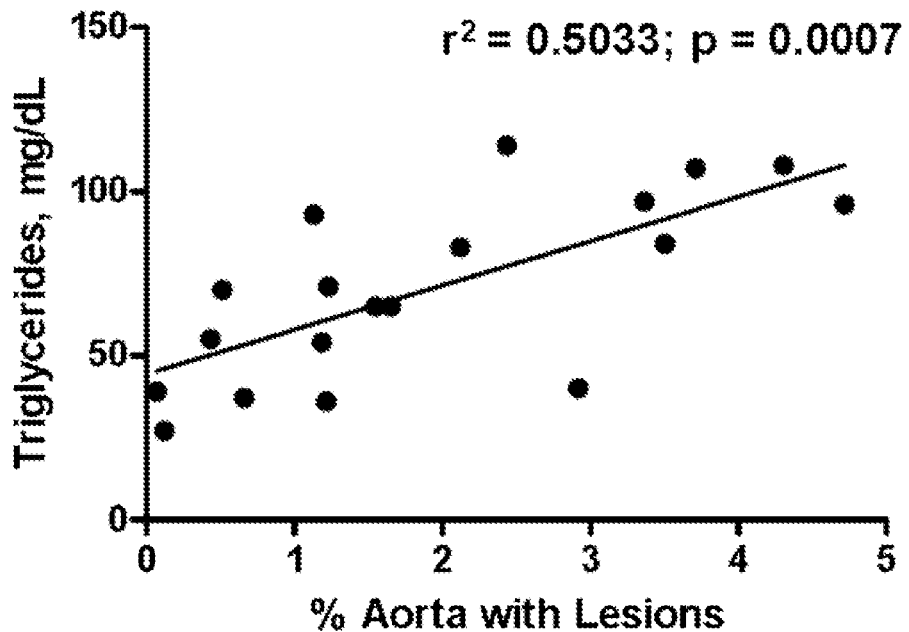
Figure 24C:
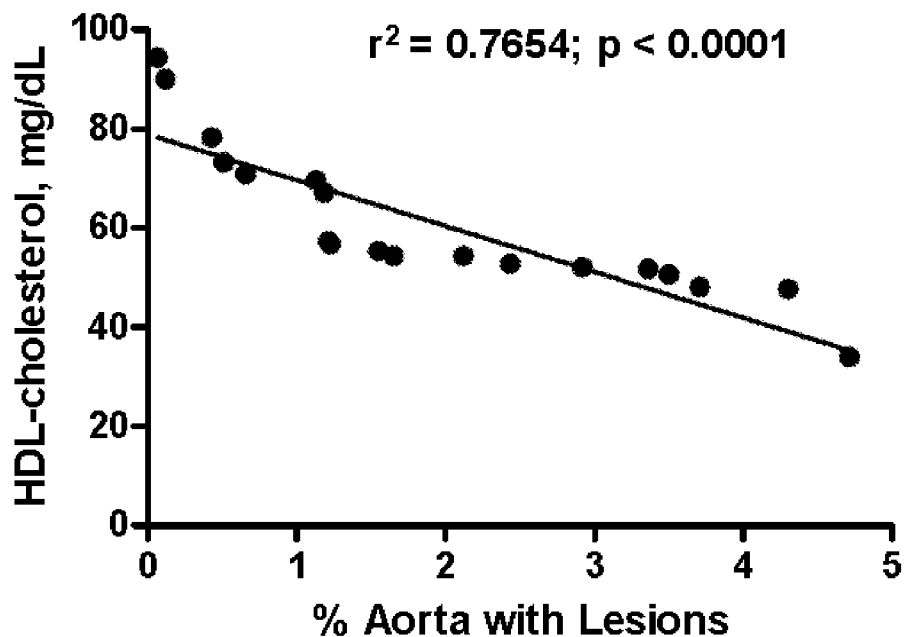
Figure 24D:
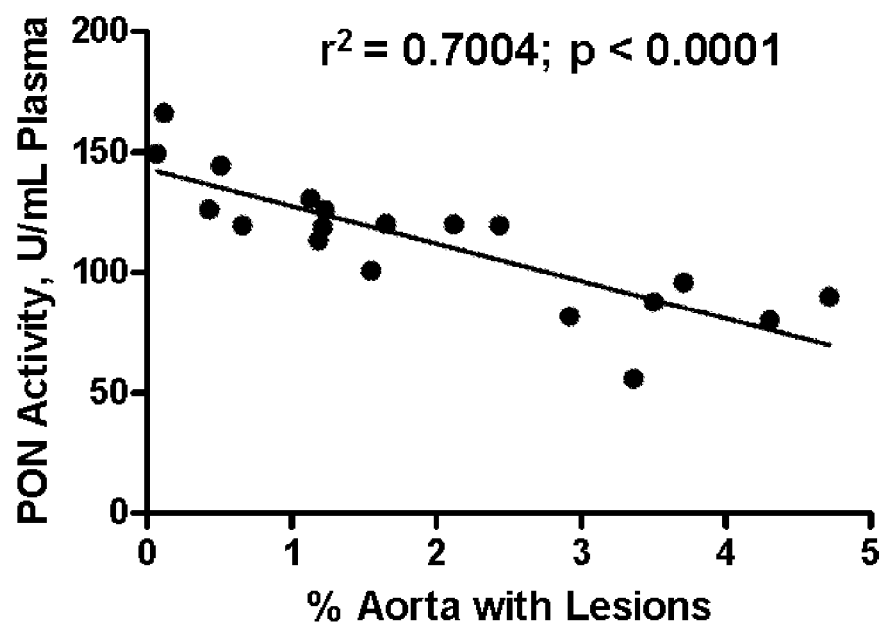
Figure 24E:
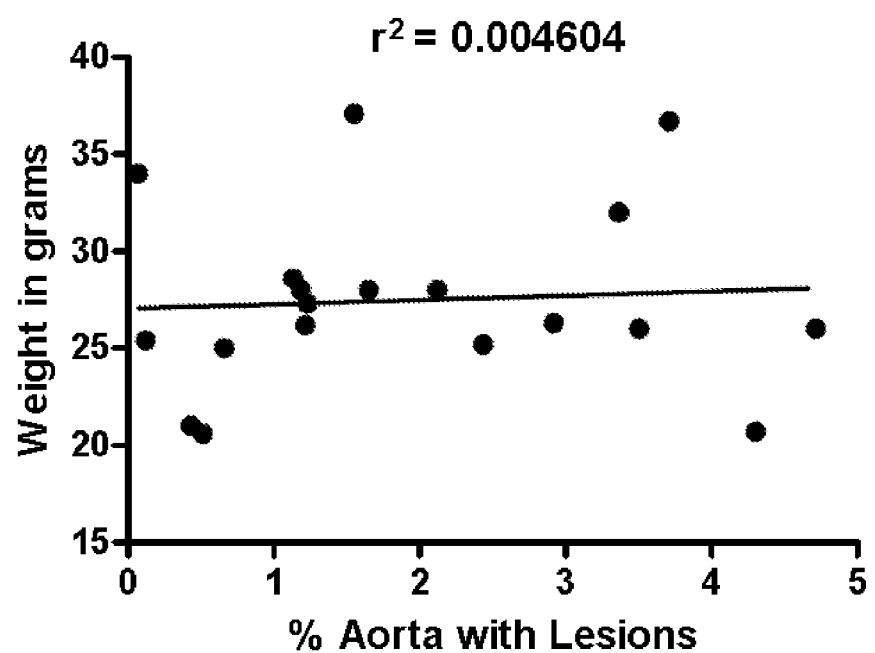
Figure 25A:
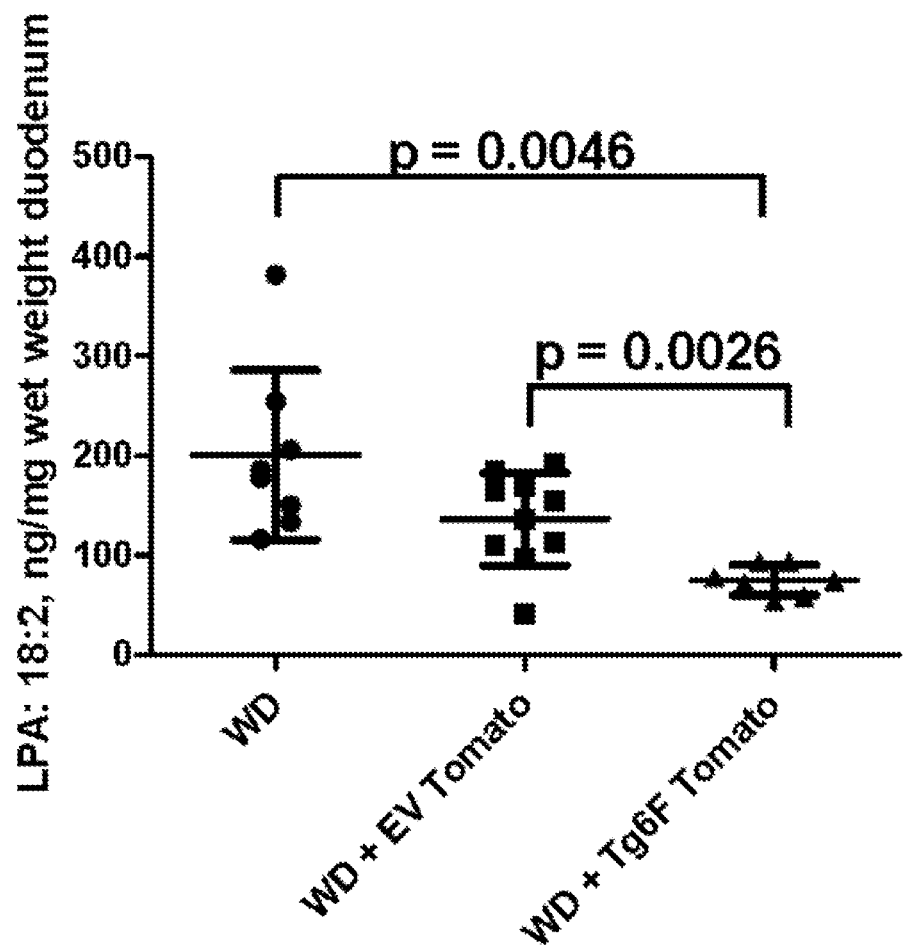
FIGS. 25A-25F show that addition of transgenic 6F tomatoes (Tg6F) to the Western Diet (WD) significantly reduced the levels of lysophosphatidic acid (LPA) in the small intestine, while addition of the empty vector (EV) tomatoes did not. The levels of LPA 18:2 and LPA 20:4 were determined by LC-ESI-MS/MS in a random subset of the mice described in FIGS. 21-23 as described in Materials and Methods in Example 3.
Figure 25B:
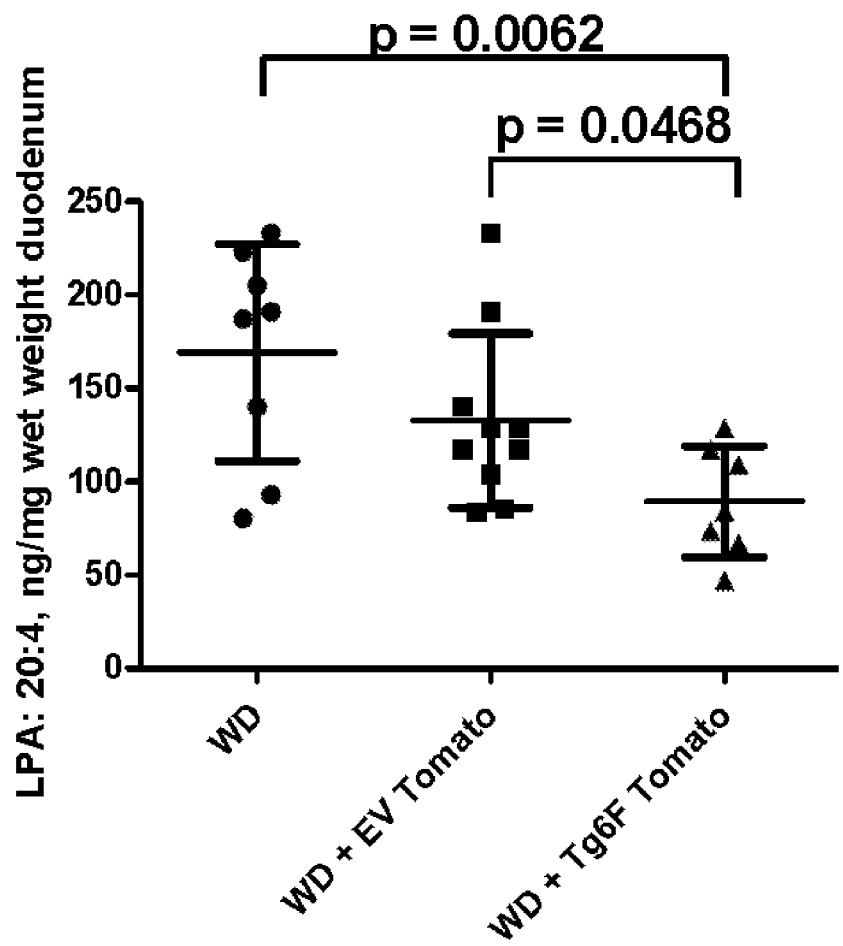
Figure 25C:
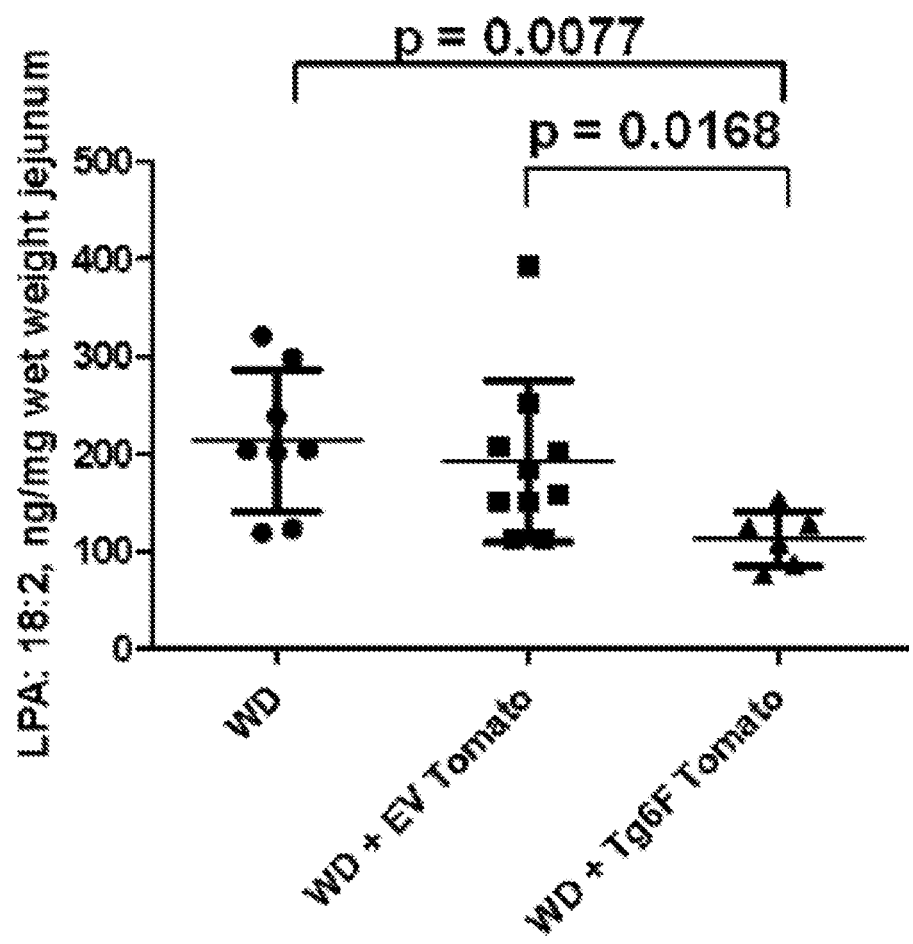
Figure 25D:
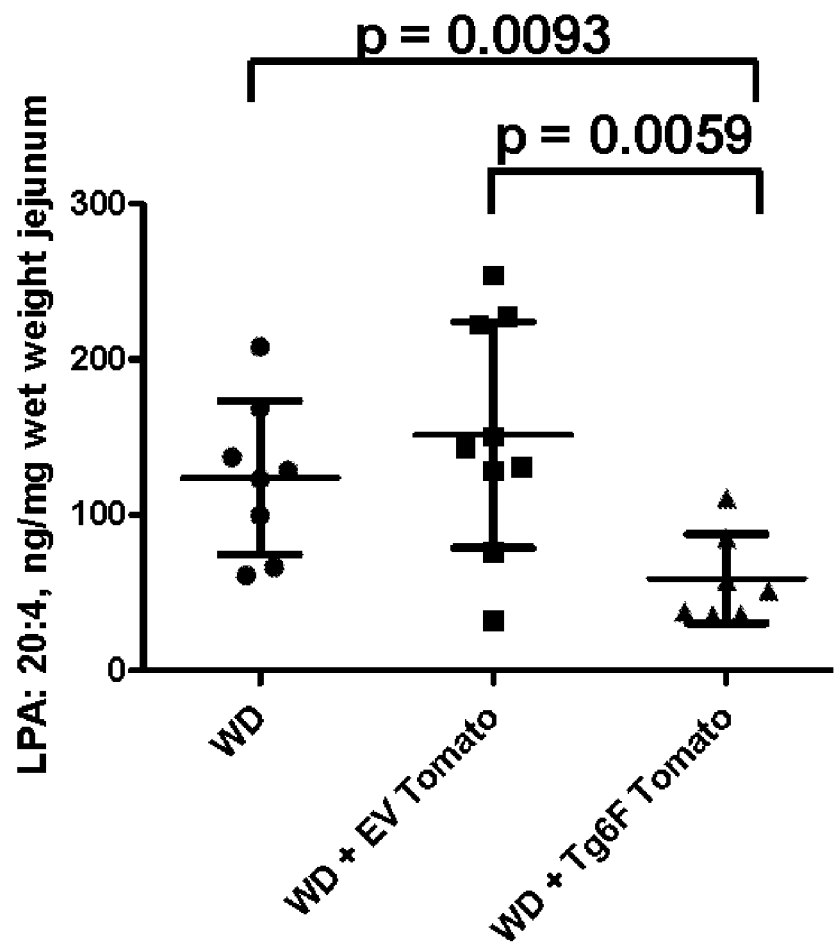
Figure 25E:
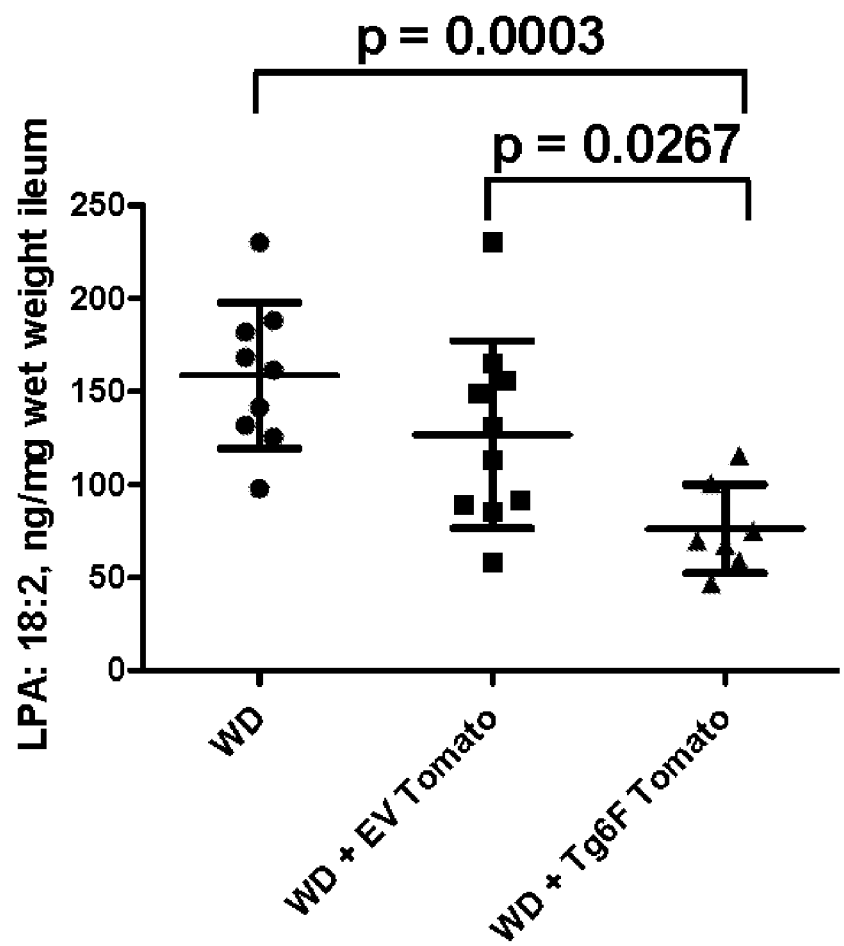
Figure 25F:
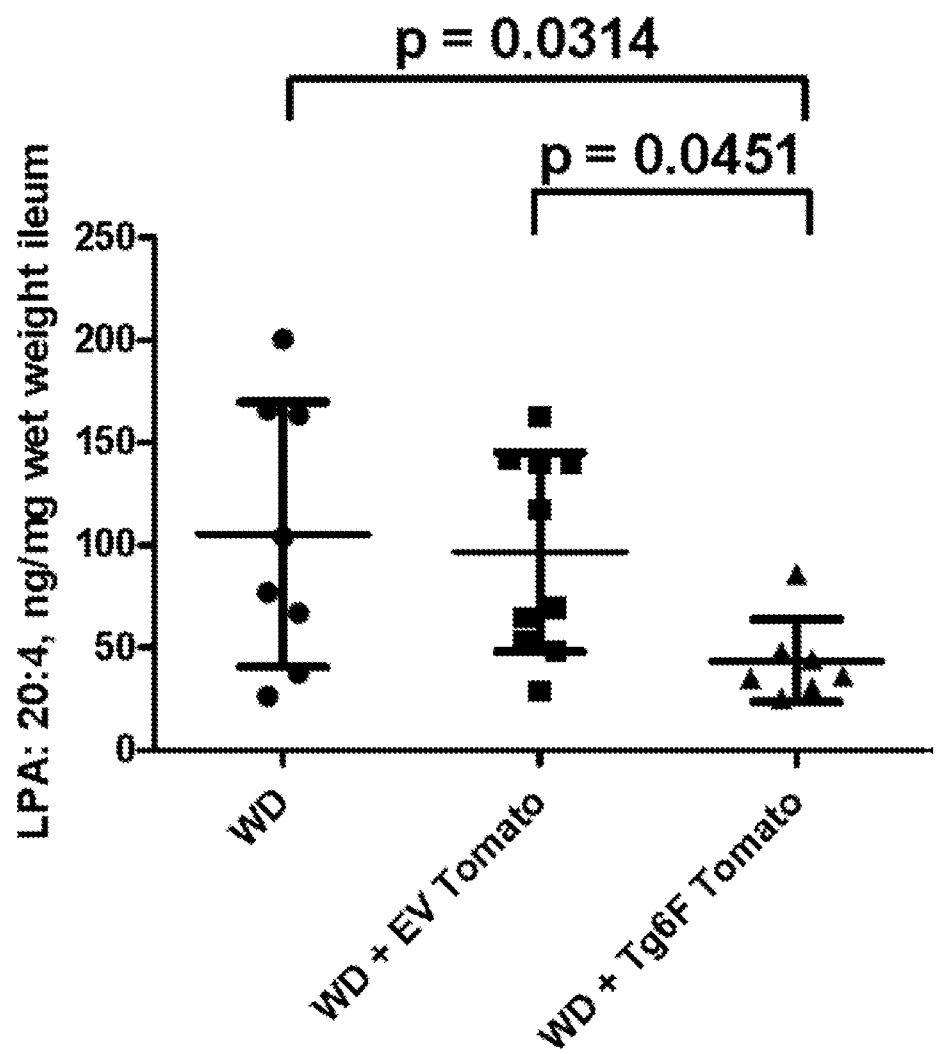
Figure 26A:
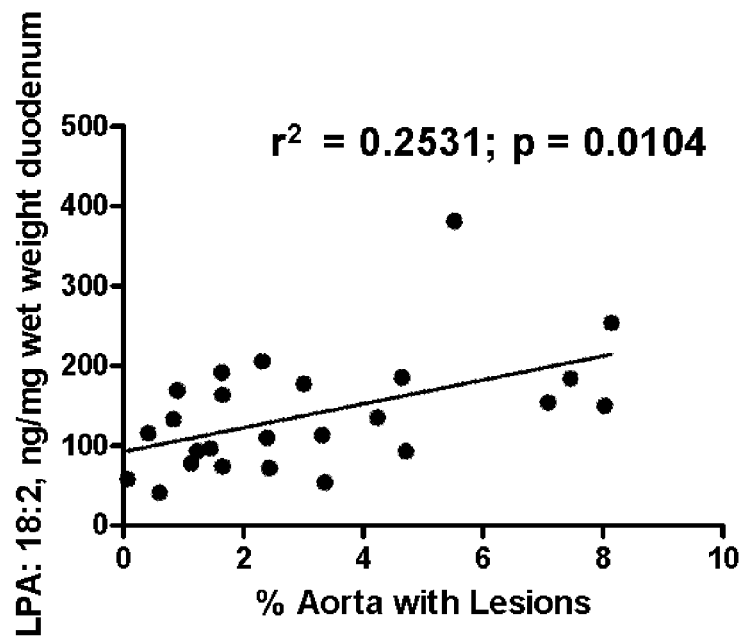
FIGS. 26A-26F show that the levels of LPA in the small intestine significantly correlated with the percent aorta with atherosclerotic lesions. The levels of LPA in the small intestine of the mice described in FIGS. 25A-25F were plotted against the percent aorta with lesions for each mouse, and linear regression was performed as described in Materials and Methods in Example 3.
Figure 26B:
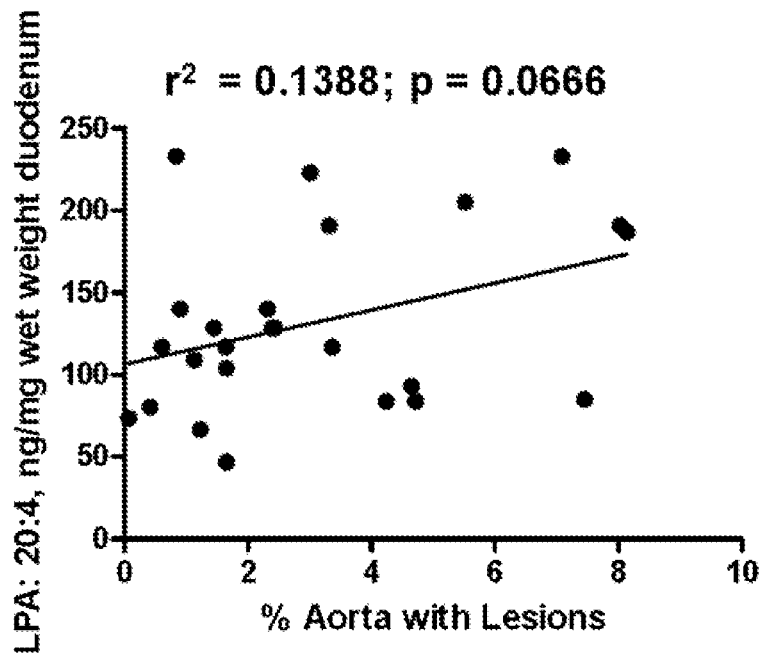
Figure 26C:
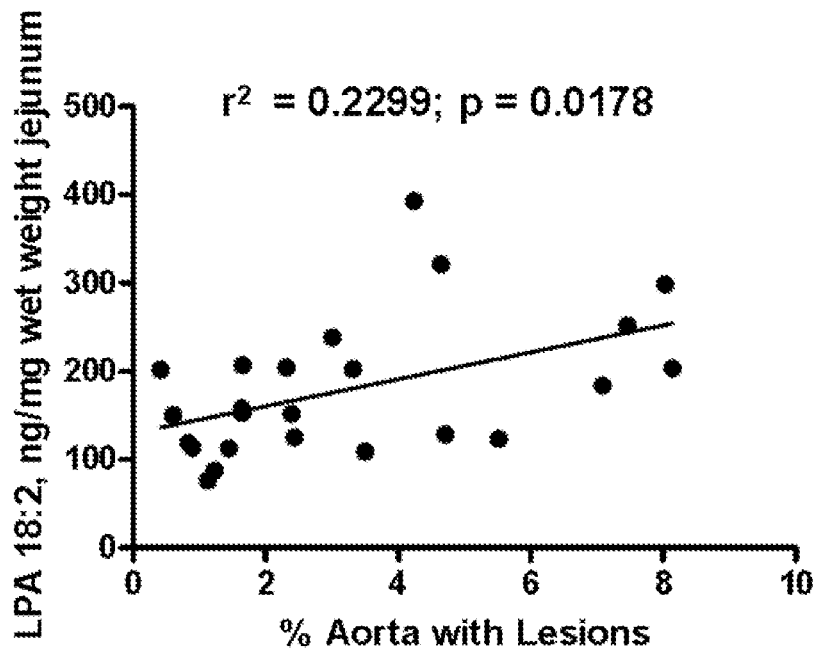
Figure 26D:
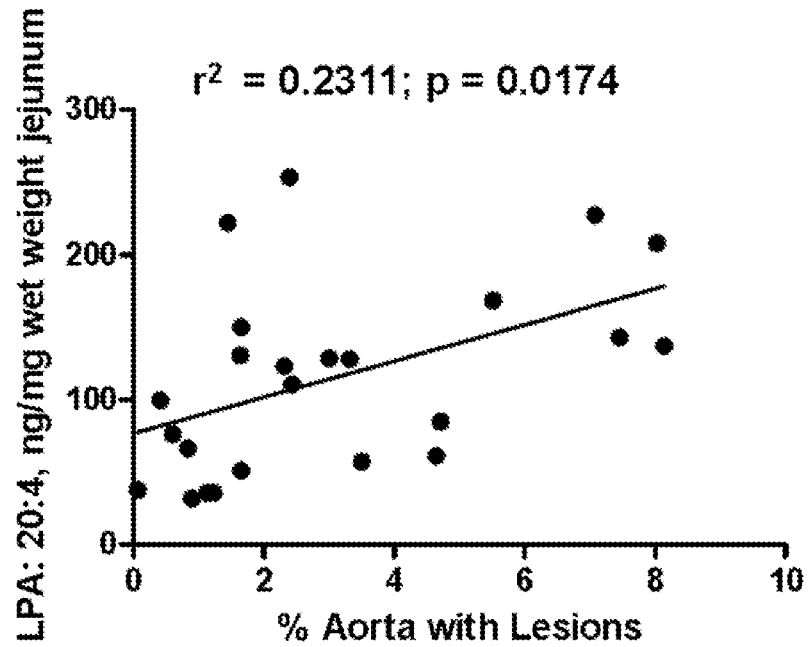
Figure 26E:
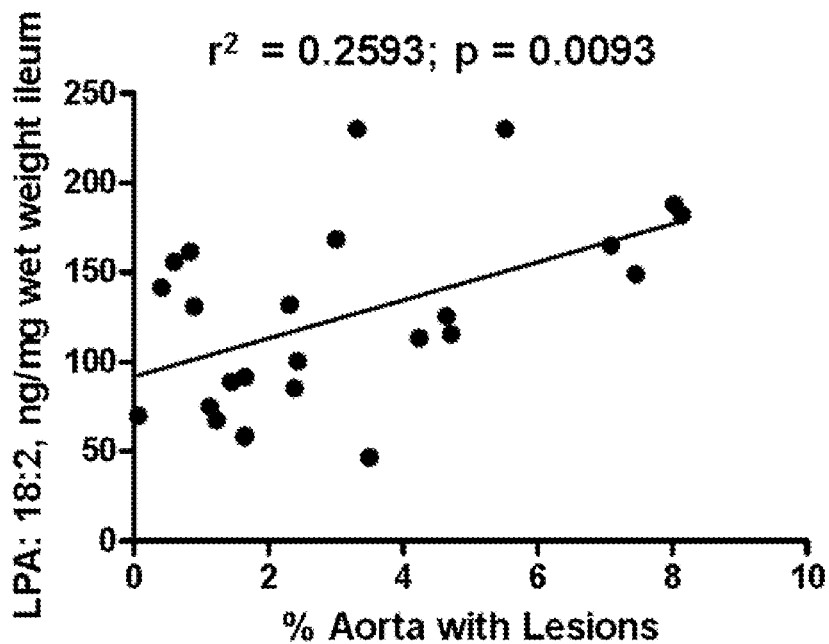
Figure 26F:
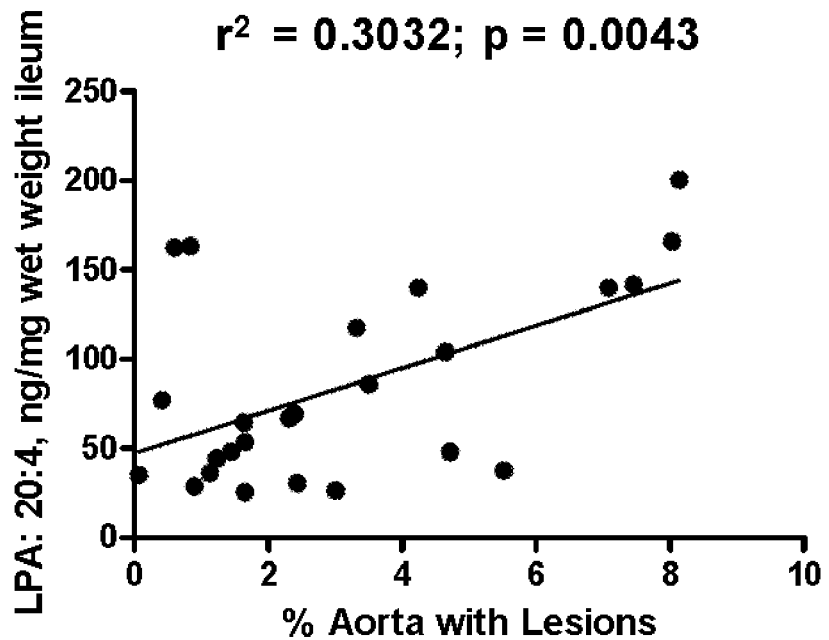

As shown in FIGS. 21A-21E after 13 weeks of feeding WD with transgenic 6F tomatoes (but not EV tomatoes) there was a significant reduction in plasma SAA, total cholesterol, and triglycerides and a significant increase in plasma PON activity and HDL-cholesterol levels. There also was a significant decrease in plasma lysophosphatidic acid (LPA) levels for LPA 18:1 (FIG. 21F), LPA 18:2 (FIG. 21G), and LPA 20:4 (FIG. 21H) in the mice fed transgenic 6F tomatoes (but not EV tomatoes). However, there was no significant difference in levels of LPA 16:0 or LPA 18:0 (data not shown). As shown in FIG. 21I there was also no difference in body weight between the three groups. While the EV tomatoes did not affect parameters mentioned above, feeding both the EV and the transgenic 6F tomatoes significantly reduced plasma levels of free arachidonic acid, 5-HETE, 15-HETE and increased plasma levels of free DHA and EPA (FIGS. 22A-22E). Plasma levels of free 12-HETE, 20-HETE, PGD2, PGE2, TXB2, 14,15-EET, and 8-iso PGF2α were not significantly improved by feeding either EV or transgenic 6F tomatoes (data not shown). As shown in FIG. 23, feeding WD with transgenic 6F tomato significantly reduced the percent of aorta with atherosclerosis as determined by en face analysis compared to WD alone or WD+EV tomato; the latter was not significantly different from WD alone.

Which Biomarkers Correlated with the Percent of Aorta with Atherosclerotic Lesions?

Figure 31A:
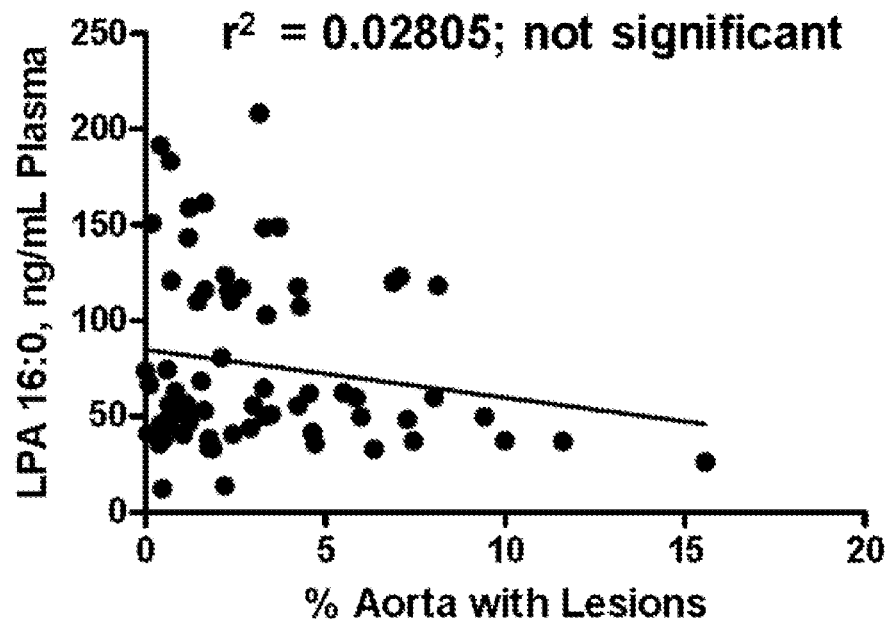
FIG. 31A: Linear regression of data from individual mice described in FIGS. 21-23 is shown for the percent aorta with atherosclerotic lesions and plasma levels of lysophosphatidic acid (LPA) 16:0.
Figure 31B:
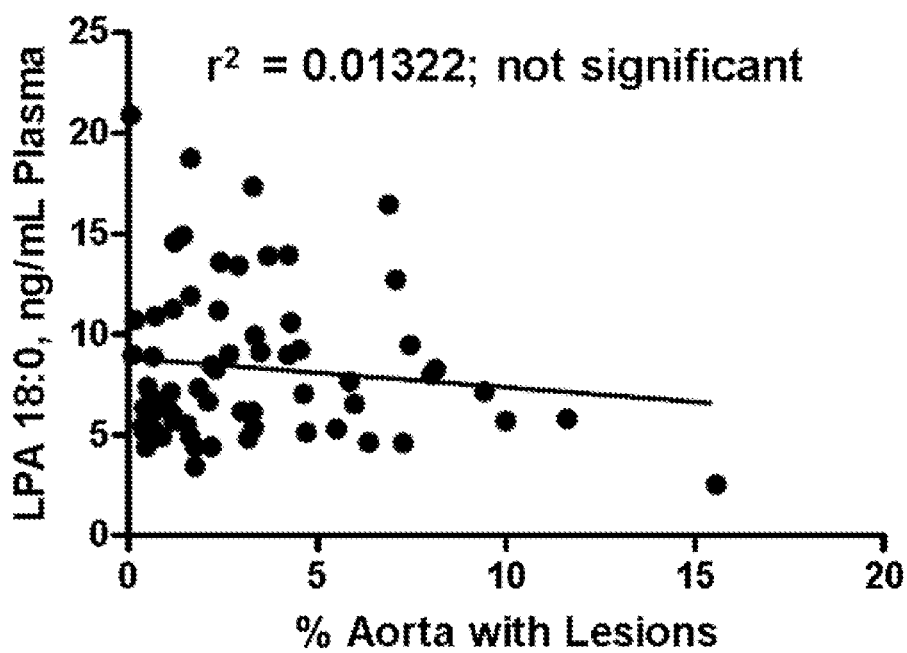
FIG. 31B: Linear regression of data from individual mice described in FIGS. 21-23 is shown for the percent aorta with atherosclerotic lesions and plasma levels of LPA 18:0.
Figure 31C:
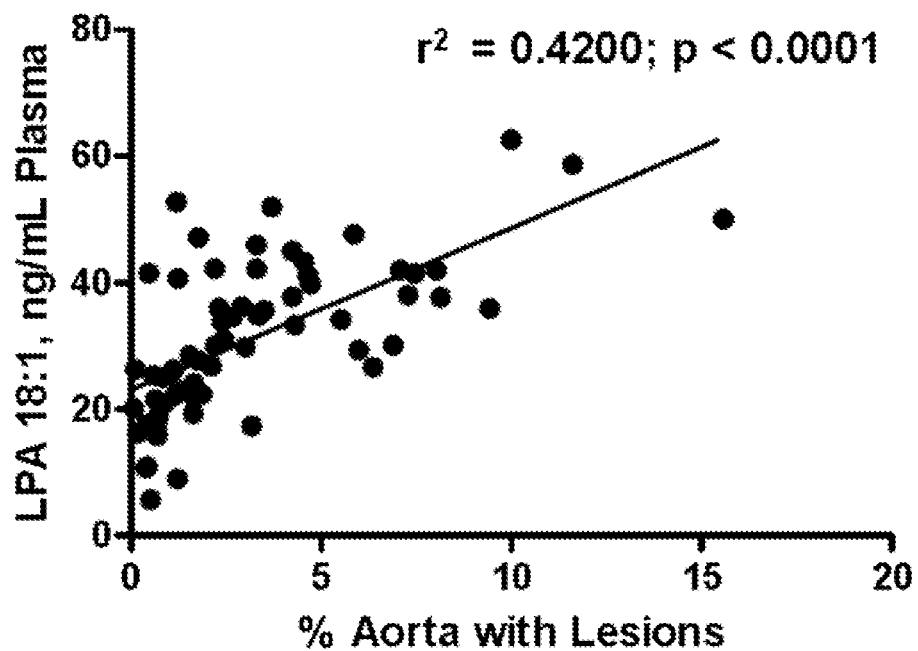
FIG. 31C: Linear regression of data from individual mice described in FIGS. 21-23 is shown for the percent aorta with atherosclerotic lesions and plasma levels of LPA 18:1.
Figure 31D:
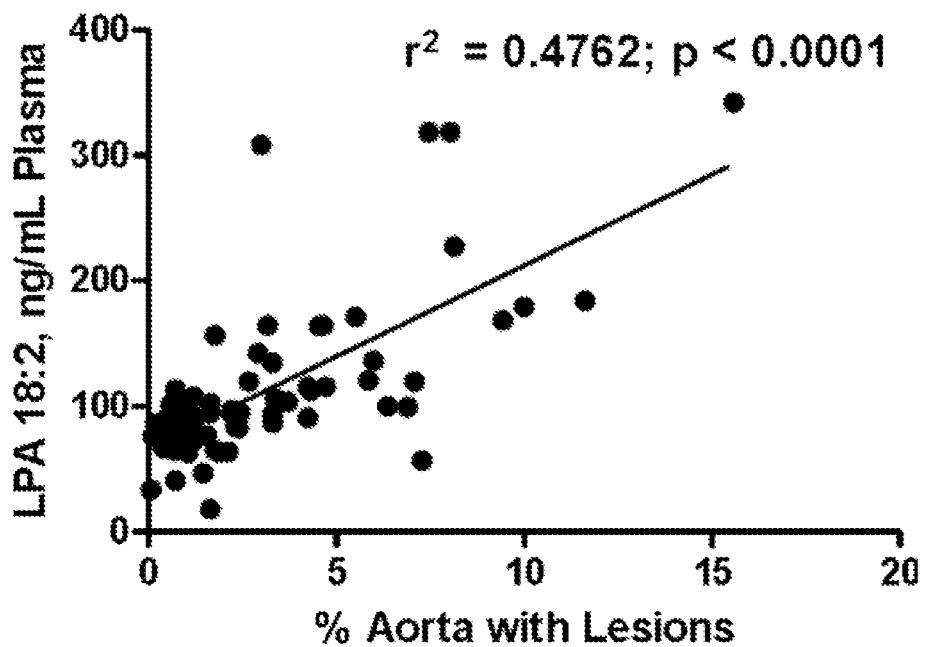
FIG. 31D: Linear regression of data from individual mice described in FIGS. 21-23 is shown for the percent aorta with atherosclerotic lesions and plasma levels of LPA 18:2.
Figure 31E:
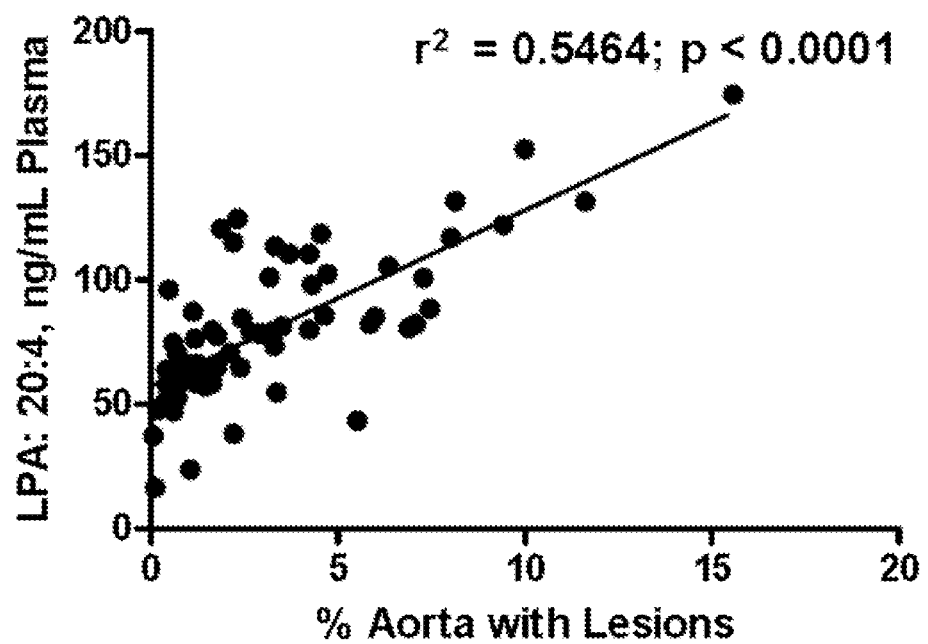
FIG. 31E: Linear regression of data from individual mice described in FIGS. 21-23 is shown for the percent aorta with atherosclerotic lesions and plasma levels of LPA 20:4.

Using linear regression of individual data for all mice regardless of treatment revealed a significant positive correlation between the percent of aorta with atherosclerotic lesions and plasma SAA ($r^2$=0.5358, $p<0.0001$); Total cholesterol ($r^2$=0.5937, $p<0.0001$); Triglycerides ($r^2$=0.3425, $p<0.0001$); and free 15-HETE ($r^2$=0.2666, $p<0.0001$). There was also a very weak but significant positive correlation between lesions and plasma free PGD2 levels ($r^2=0.06078$, $p=0.046$). There was a significant inverse correlation between the percent of aorta with atherosclerosis and PON activity ($r^2=0.2585$, $p<0.0001$) and HDL-cholesterol levels ($r^2=0.5948$, $p<0.0001$). There was a very weak but significant inverse correlation between the percent aorta with atherosclerotic lesions and plasma levels of free EPA ($r^2=0.09596$, $p=0.0107$). There was no significant correlation between the percent aorta with atherosclerotic lesions and body weight, plasma free arachidonic acid, 5-HETE, 12-HETE, 20-HETE, PGE2, TXB2, 14,15-EET, DHA, or 8-isoPGF2α (data not shown). As shown in FIGS. 31A and 31B there was no correlation between the plasma levels of LPA 16:0 or LPA 18:0 and the percent of aorta with lesions. In contrast as shown in FIGS. 31C-31E there was a significant correlation between the levels of LPA 18:1, LPA 18:2 and LPA 20:4 levels with the percent of the aorta with lesions. These correlations were for all mice with all treatments. The correlation between some of these plasma biomarkers and the percent of aorta with lesions for mice that received WD with transgenic 6F tomatoes is shown in FIGS. 24A-24E.

Were Small Intestine Lipid Levels Altered by the Treatments?

Figure 32A:
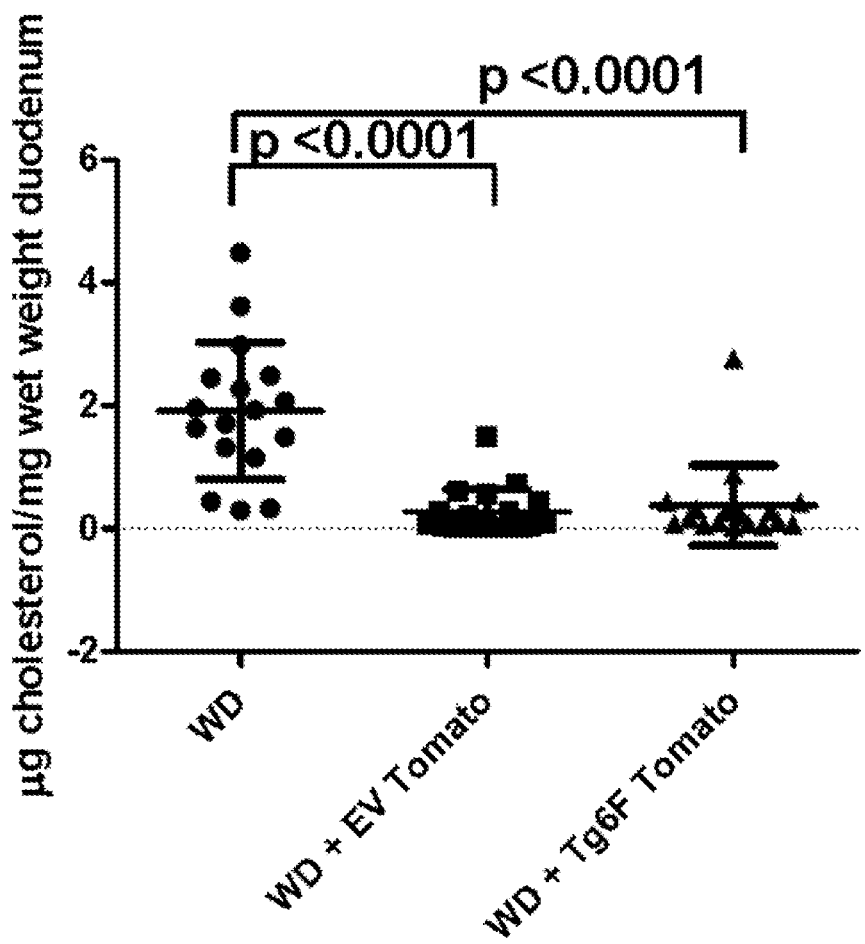
FIG. 32A: The cholesterol content of the duodenum was measured in a random subset of the mice in FIGS. 21-23 as described in Materials and Methods of Example 3.
Figure 32B:
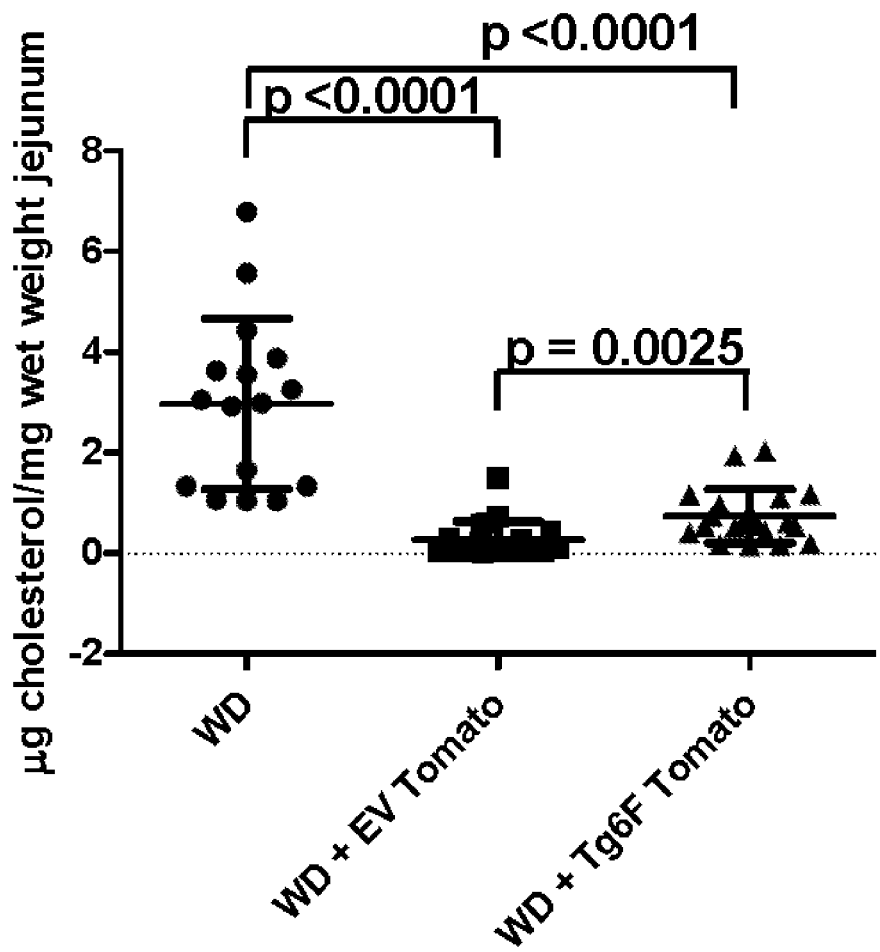
FIG. 32B: The cholesterol content of the jejunum was measured in the mice described in FIG. 32A as described in Materials and Methods of Example 3.
Figure 32C:
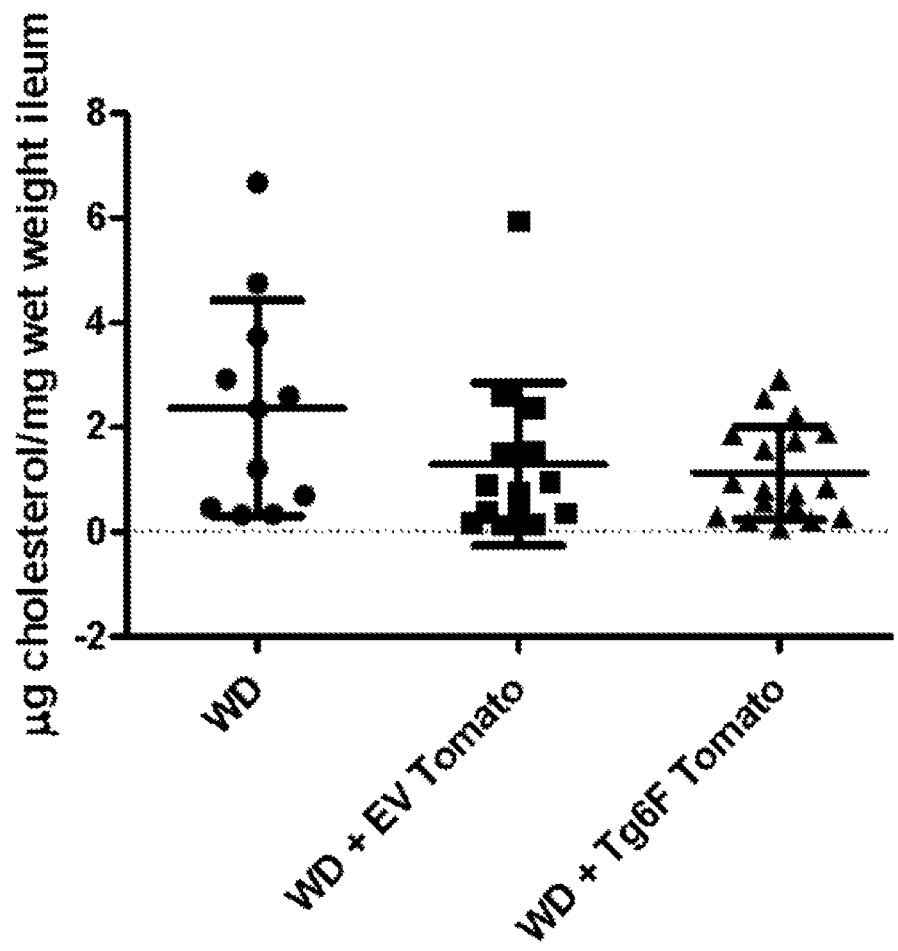
FIG. 32C: The cholesterol content of the Ileum was measured in the mice shown in FIG. 32A as described in Materials and Methods of Example 3.
Figure 32D:
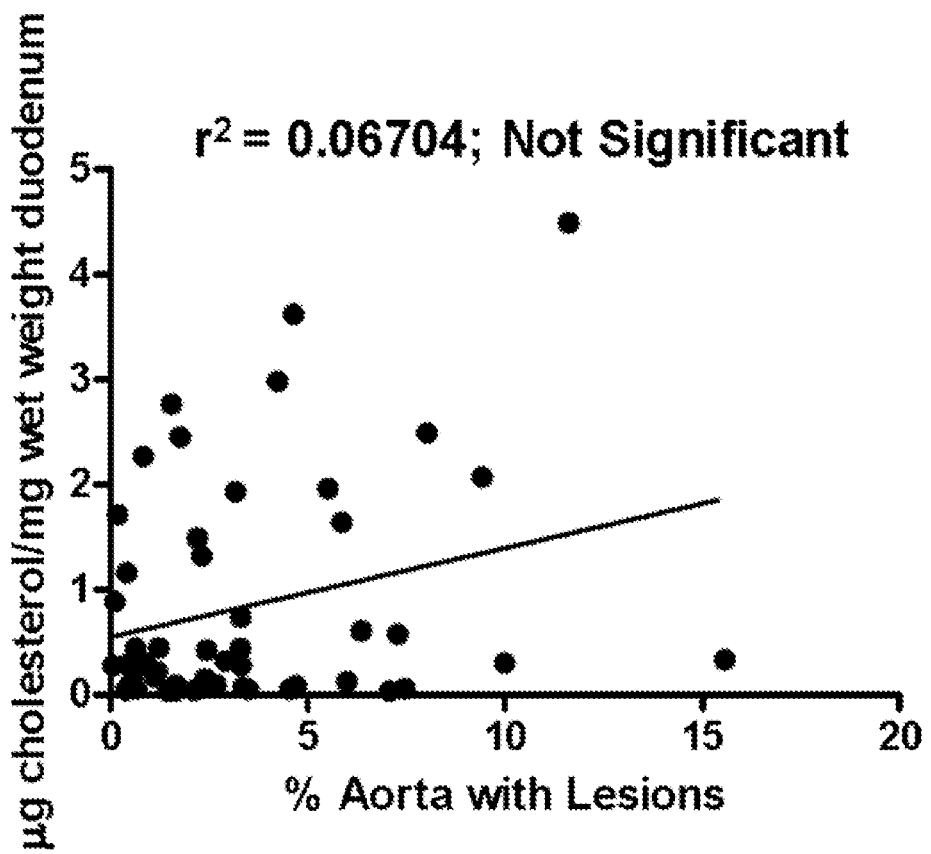
FIG. 32D: The duodenum cholesterol content of the mice described in FIG. 32A was plotted against the percent aorta with lesions for each mouse and linear regression was performed as described in Materials and Methods of Example 3.
Figure 32E:
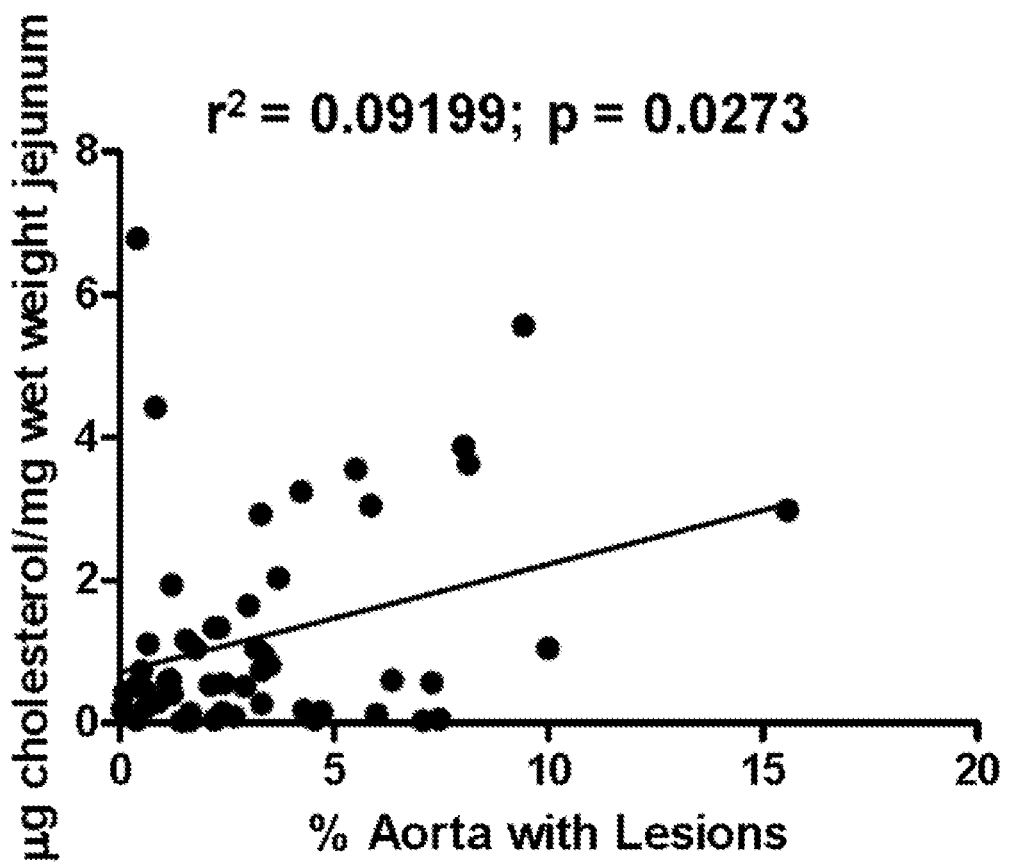
FIG. 32E: The jejunum cholesterol content of the mice described in FIG. 32B was plotted against the percent aorta with lesions for each mouse and linear regression was performed as described in Materials and Methods of Example 3.
Figure 32F:
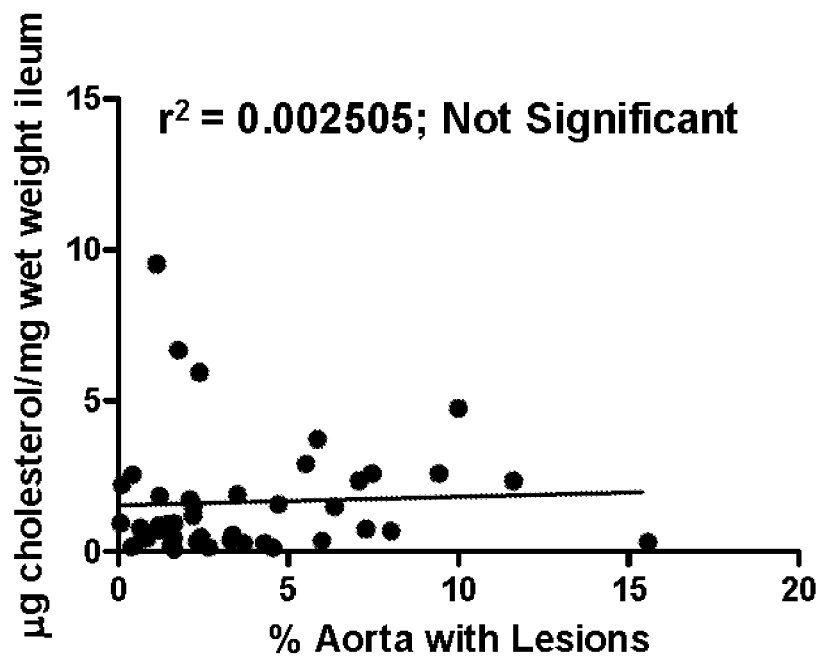
FIG. 32F: The ileum cholesterol content of the mice described in FIG. 32C was plotted against the percent aorta with lesions for each mouse and linear regression was performed as described in Materials and Methods of Example 3.

We were able to measure tissue cholesterol and LPA levels in the duodenum, jejunum and ileum in a random subset of the mice described in FIGS. 21-23. As shown in FIGS. 32A-32C, addition of both the empty vector (EV) and the transgenic 6F tomatoes to the WD significantly reduced tissue cholesterol levels in the duodenum and jejunum, but not in the ileum. Addition of EV tomatoes to WD modestly but significantly reduced jejunum cholesterol levels more than did the addition of transgenic 6F tomatoes (FIG. 32B); cholesterol levels in the duodenum were not different between mice fed EV tomatoes or transgenic 6F tomatoes (FIG. 32A). As shown in FIG. 32E, jejunum cholesterol levels were very weakly but significantly correlated with the percent aorta with lesions in these mice, but there was no significant correlation of lesions with tissue cholesterol levels in either the duodenum (FIG. 32D) or ileum (FIG. 32F). In contrast to these results for small intestine cholesterol levels, as shown in FIGS. 25A-25F, adding transgenic 6F tomatoes to WD compared to adding EV tomatoes to WD significantly reduced levels of LPA 18:2 and LPA 20:4 in the duodenum, jejunum and ileum. As shown in FIGS. 26A-26F, except for LPA 20:4 in the duodenum, which approached significance (but did not reach it), the levels of LPA 18:2 and LPA 20:4 in the duodenum, jejunum and ileum significantly correlated with the percent aorta with atherosclerotic lesions in these mice.

Where does the Peptide Act?

The data presented above indicate that the peptide in the transgenic 6F tomatoes is acting in the small intestine. If this were the case, we might expect to find intact peptide in the small intestine of mice eating WD with transgenic 6F tomatoes, but little to no intact peptide in the plasma. The mice described in FIG. 33 were fasted overnight for 20 hours and then fed WD with lyophilized transgenic 6F tomato powder containing 900 μg of 6F in 2 grams of diet. Over a period of 30-90 minutes each of six mice ate all of the 2 grams of diet. Approximately 2 hours after the mice finished eating they were bled and their small intestines were harvested and analyzed as described in Materials and Methods. Intact 6F peptide was found in the small intestine of each of these six mice in microgram quantities (Mean±SD was 15.6±7.4 μg 6F per 200 mg small intestine). In these studies the lower limit of detection for 6F peptide in the plasma was 100 ng/mL. No 6F peptide was detected in the plasma of any of the six mice. Thus ~2 hours after eating the transgenic 6F tomatoes, intact 6F peptide was found in the small intestine, but not in the plasma. These data are consistent with the peptide acting in the small intestine.

Discussion

In our original work on apoA-I mimetic therapy, we concluded that D-4F but not L-4F would be effective orally (Navab et al. (2002) *Circ.* 105: 290-292). This conclusion was based on experiments in which LDLR$^{-/-}$ mice were administered either L-4F or D-4F by stomach tube in a single dose of 5 mg/kg/mouse. Four hours after this single dose, the inflammatory properties of HDL and LDL as determined in a cell-based assay were dramatically and significantly improved in the case of D-4F but not L-4F. Using $^{125}$I-peptides, we also found that after oral administration of L-4F there was virtually no intact peptide in plasma, but after administration of D-4F there was intact peptide identified in the plasma. Since L-4F was ineffective and D-4F was effective in this study it was assumed that it was necessary for intact peptide to gain access to the plasma to be effective (Id.). Supporting this assumption was the finding that when given by injection at a dose of 10 mg/kg/day to cholesterol-fed rabbits, the efficacy of L-4F and D-4F was identical (Van Lenten et al. (2007) *J. Lipid Res.* 48: 2344-2353). A phase I/II study in humans was undertaken in which D-4F was administered orally in doses ranging from 0.43-7.14 mg/kg. Maximum plasma peptide levels were low (Cmax 15.9±6.5 ng/mL) but doses of 4.3 and 7.14 mg/kg significantly improved the HDL inflammatory index (HII), while doses of 0.43 and 1.43 mg/kg were not effective (Bloedon et al. (2008) *J. Lipid Res.* 49: 1344-1352). Subsequently, in preclinical studies it was found that D-4F had delayed clearance from tissues, particularly liver and kidney making its use in humans problematic; this was not the case for L-4F (Watson et al. (2011) *J. Lipid Res.* 52: 361-373). Since it was known that L-4F and D-4F were equally efficacious when given by injection (Van Lenten et al. (2007) *J. Lipid Res.* 48: 2344-2353), and it was thought that plasma levels of the peptide would be the critical success factor for its efficacy, studies in humans were designed to achieve high plasma levels with low doses of L-4F administered IV or SQ (Watson et al. (2011) *J. Lipid Res.* 52: 361-373). Doses of 0.042-1.43 mg/kg of L-4F produced high plasma levels of peptide (e.g., Cmax 3,255±630 ng/mL in the IV study), but surprisingly there was no improvement in HII (Id.). After this disappointing result, we returned to mouse models to understand this paradox and unexpectedly found that i) plasma levels did not predict efficacy—the dose administered predicted efficacy and ii) while the concentration of peptide differed by orders of magnitude in plasma and liver depending on the route of administration, the concentration of peptide in the feces (Navab et al. (2011) *J. Lipid Res.* 52: 1200-1210) and small intestine (Navab et al. (2012) *J. Lipid Res.* 53: 437-445) was similar at similar doses regardless of whether the peptide was administered orally or SQ. To explain equal efficacy at each dose administered regardless of the route of administration there should be equal concentrations of peptide in at least one compartment containing a major site of action. In two separate studies (Navab et al. (2011) *J. Lipid Res.* 52: 1200-1210; Navab et al. (2012) *J. Lipid Res.* 53: 437-445) the intestine was found to be that compartment.

Administering L-4F orally (incorporated into mouse chow) at a dose of 10 mg/kg/day to female apoE$^{-/-}$ mice starting at 9.5 months of age and continuing for six months together with adding a low dose of statin in the drinking water did not significantly change aortic atherosclerosis (Navab et al. (2009) *J. Lipid Res.* 50: 1538-1547). In contrast, if the L-4F were administered with niclosamide which binds to L-4F and protects it against trypsin degradation in the intestine, the peptide not only inhibited lesion progression, it actually induced lesion regression in these old mice (Id.). In a subsequent study, we reasoned that if instead of administering the peptide with niclosamide, we simply increased the dose by 10-fold, enough L-4F might survive degradation after oral administration to be effective. Indeed this was the case. Administering L-4F in mouse chow at a dose of 100 mg/kg/day significantly decreased plasma LPA levels and significantly decreased tumor burden in a mouse model of ovarian cancer (Su et al. (2010) *Proc. Natl. Acad. Sci. USA*, 107: 19997-20002).

These studies suggested that oral apoA-I mimetic therapy using peptides synthesized from all L-amino acids might be feasible if we used high doses of the peptide. Unfortunately, producing sufficient peptide to make therapy in humans practical was not likely because the 4F peptide requires end blocking groups that can only be added through chemical synthesis. Using mouse models, we explored the possibility of using 4F peptide without end blocking groups but found the activity of the peptide to be dramatically reduced (data not shown). This led us to seek alternative peptides synthesized from all L-amino acids that might be effective without end blocking groups. As described here, 6F was found to be such a peptide.

Based on our previous work (Navab et al. (2011) *J. Lipid Res.* 52: 1200-1210; Navab et al. (2012) *J. Lipid Res.* 53: 437-445; Su et al. (2010) *Proc. Natl. Acad. Sci. USA*, 107: 19997-20002) we chose to test peptide doses of 40-100 mg/kg/day. Adding the 6F peptide synthesized from all L-amino acids without end blocking groups to diets of apoE$^{-/-}$ or LDLR$^{-/-}$ mice (chow or WD) at a dose of 60 mg/kg/day resulted in significantly decreased plasma SAA (FIGS. 16A and 16B). In addition, the percent of aorta with atherosclerosis also significantly decreased (FIG. 16C). We chose to first test transgenic expression of the 6F peptide in tomatoes because we reasoned that the peptide should be expressed in a plant that could be eaten without cooking to avoid denaturing the peptide. Adding the 6F peptide to homogenized tomato did not lead to a loss of efficacy (FIG. 28). The 6F peptide was successfully expressed in tomato plants and was found in ripened tomato fruit (FIGS. 17, 18, and FIG. 29). Feeding ground lyophilized tomatoes containing 6F to LDLR$^{-/-}$ mice on WD for two weeks favorably altered some plasma biomarkers (FIG. 19, and FIG. 30), but did not alter plasma total cholesterol or triglyceride levels. In some of these experiments feeding the ground lyophilized control tomatoes decreased some of the biomarkers raising the possibility that the superior effects of the 6F transgenic tomatoes might be due to increased antioxidant content. This did not turn out to be the case for the major antioxidant in tomatoes, lycopene (FIG. 20). Since the addition to the diet of chemically synthesized L-6F without blocking groups produced biologic results similar to those achieved with the addition of lyophilized transgenic 6F tomatoes, it is likely that at least some of these effects were due to the presence of the peptide in the tomatoes. Based on the data in FIG. 20, it is also likely that the beneficial effects of the transgenic 6F tomatoes were not due to their lycopene content. However, we certainly cannot exclude that a portion (if not all) of the beneficial effects of expressing the 6F peptide in tomatoes is due to an increase in an as yet unidentified non-lycopene, non-6F component of these tomatoes.

Extending the feeding experiments to 13 weeks and using EV tomatoes as the control revealed that only the 6F transgenic tomatoes significantly decreased plasma SAA, total cholesterol, triglycerides, and LPA levels, and increased plasma HDL-cholesterol and PON activity (FIG. 21), and decreased the percent of aorta with lesions (FIG. 23); all without changing body weight (FIG. 21I). However, the EV tomatoes did decrease plasma levels of free arachidonic acid and some of its metabolites and increased DHA and EPA (FIG. 22) suggesting that there was likely a benefit from the antioxidant content of the control tomatoes. The increase in DHA and EPA plasma levels may have been due to decreased oxidation of these highly unsaturated fatty acids on feeding the control tomatoes. The further increase in plasma DHA and EPA levels on feeding the transgenic 6F tomatoes likely represents a further reduction in the WD-induced oxidative stress beyond that achieved by the antioxidants contained in the control tomatoes.

Based on correlations between the percent of atherosclerosis and the various biomarkers measured it seems likely that the mechanism of action of the transgenic 6F tomatoes involves alteration in lipid metabolism in the intestine that favorably alters plasma total cholesterol, triglycerides, LPA levels, HDL-cholesterol, and PON activity, which result in decreased systemic inflammation (SAA levels) and atherosclerosis without changing body weight. It has been reported that LPA can alter the secretion of apoB containing lipoproteins from hepatocytes (Shen et al. (2012) *Atherosclerosis*, 222: 154-157) and LPA 20:4 promotes atherosclerosis in mouse models (Zhou et al. (2011) *Cell Metabolism*, 13: 592-600). As shown in FIG. 25, feeding transgenic 6F tomatoes significantly reduced LPA 18:2 and LPA 20:4 levels in the duodenum, jejunum and ileum. The levels of these LPA species were significantly correlated with the percent of the aorta with atherosclerotic lesions as shown in FIG. 26. Thus, one possibility is that the reduction in intestinal and plasma LPA levels accounts in part for the observed decrease in plasma total cholesterol, triglycerides and the percent aorta with atherosclerotic lesions. It is interesting to note that the plasma levels of unsaturated LPA species significantly correlated with the percent of aorta with atherosclerosis while the levels of saturated LPA species did not.

As shown in FIG. 32, feeding both EV and transgenic 6F tomatoes significantly decreased the levels of cholesterol in the duodenum and jejunum, but neither reduced cholesterol levels in the ileum. As shown in FIG. 21B only the transgenic 6F tomatoes significantly decreased plasma cholesterol levels. Additionally and in contrast to the case for plasma cholesterol levels (FIG. 24A), the levels of cholesterol in the small intestine were either very weakly correlated with the percent of aorta with lesions (FIG. 32E) or were not correlated with the percent of aorta with lesions (FIGS. 32D and 32F).

It is possible that the transgenic 6F tomatoes decreased the absorption of cholesterol or triglycerides in the 13 week feeding studies. However if this were the case, it is not clear why plasma total cholesterol and triglycerides were not significantly decreased in the two week feeding studies.

In preliminary unpublished studies in a mouse model of ovarian cancer we found that adding the lyophilized transgenic 6F tomatoes to chow gave results similar to those previously reported for L-4F (Su et al. (2010) *Proc. Natl. Acad. Sci. USA*, 107: 19997-20002). These studies, taken with the data provided herein, suggest that the efficacy of the transgenic 6F tomatoes does not require either hyperlipidemia or a WD.

This is the first report of transgenically expressing a peptide in a fruit that when fed to mice results in the anti-inflammatory properties described here. The particular mechanisms of action and/or modes of interaction with the intestine are under investigation. In this regard, it is noted that the data in FIG. 33 indicate that ~2 hours after the mice finished eating 900 μg of 6F contained in transgenic tomatoes, intact 6F peptide was identified in the small intestine in microgram quantities (15.6±7.4 μg 6F per 200 mg small intestine), but no peptide was detected in the plasma with methods that would have detected 100 ng/mL. Without being bound to a particular theory, it is possible that the 6F peptide is protected from trypsin degradation by being expressed in a fruit (e.g., the tomato fruit) similar to the case with niclosamide.

Example 4

Use of the E8 Tomato Promoter to Express Apo-AI Mimetic Peptides in Plants

In various embodiments, use of alternative promoters such as the E8 promoter or the E4/E8 hybrid promoter to express any one or more of the various peptides described herein is contemplated. The E8 promoter is described in detail in Kurokawa et al. (2013) *An E8 promoter-HSP terminator cassette promotes the high-level accumulation of recombinant protein predominantly in transgenic tomato fruits: a case study of miraculin, Plant Cell. Rep.*, January 11 (Epub ahead of print) PMID: 23306632.

Figure 34:
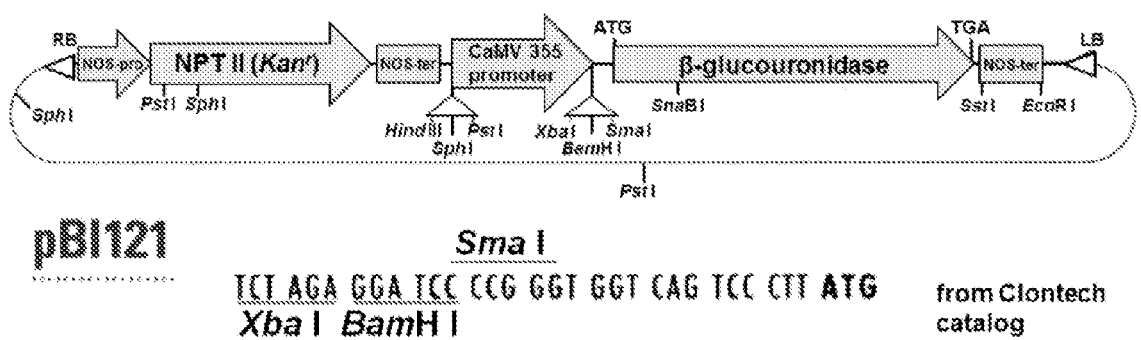
FIG. 34 illustrates the structure of the plasmid pBI121 vector. Illustrated nucleotide sequence tct aga gga tcc ccg ggt ggt cag tcc ctt atg (SEQ ID NO:654).
Figure 36:
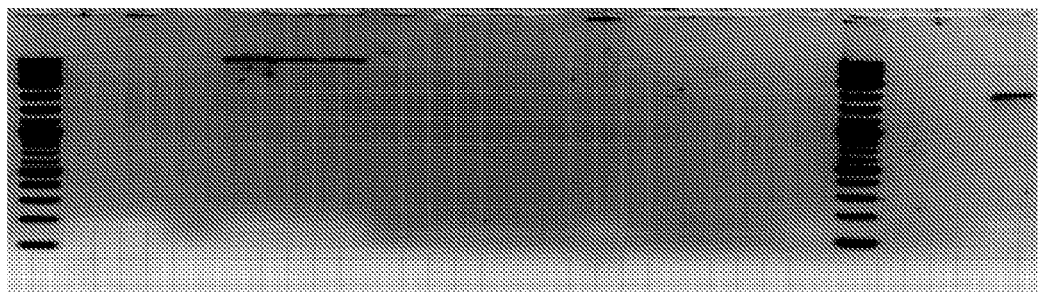
FIG. 36 shows a SDS PAGE gel illustrating isolation of the pBI121 vector back bone after digestion at HindIII/BamHI.

Plasmid pBI121 (see, e.g., FIGS. 34 and 35) was grown in bacterial cultures. The plasmid was isolated and digested at Hind III and BamH I sites to remove the CaMV 35S promoter. The pBI121 vector back bone after digestion at HindIII/BamHI was isolated on an SDS PAGE gel (FIG. 36).

Figure 37:
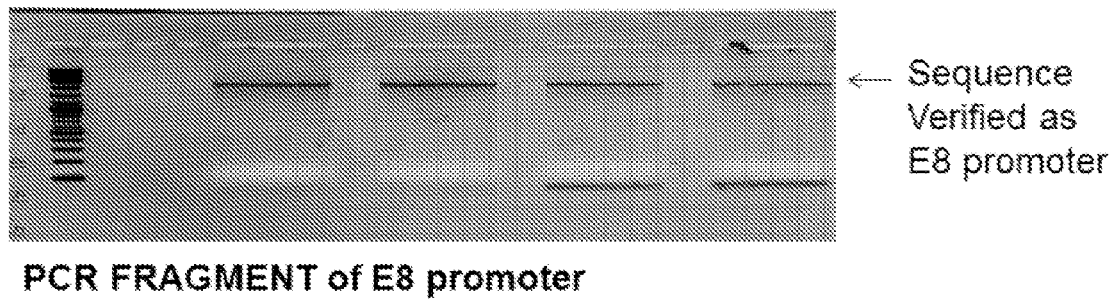
FIG. 37 illustrates PCR amplification of the E8 promoter fragment.

Tomato genomic DNA was isolated and primers for the E8 promoter carrying the Hind III and BamH I restriction sites were prepared. The E8 prompter was PCR amplified and the sequence was verified (see FIG. 37).

Figure 38:
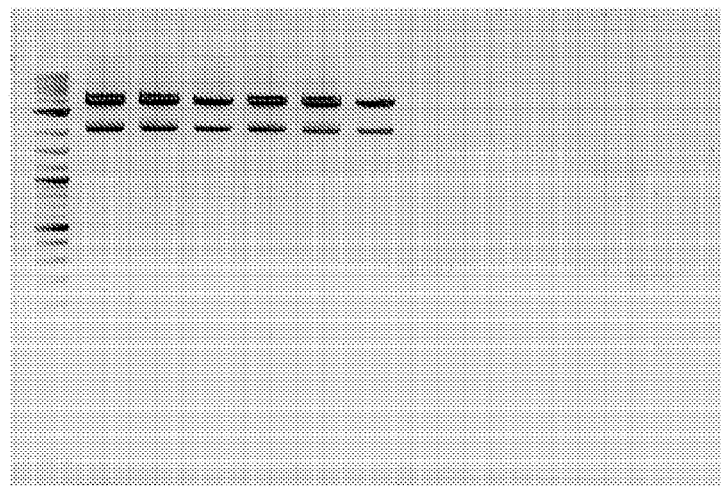
FIG. 38 illustrates PCR confirmation of +ve colonies.
Figure 39:
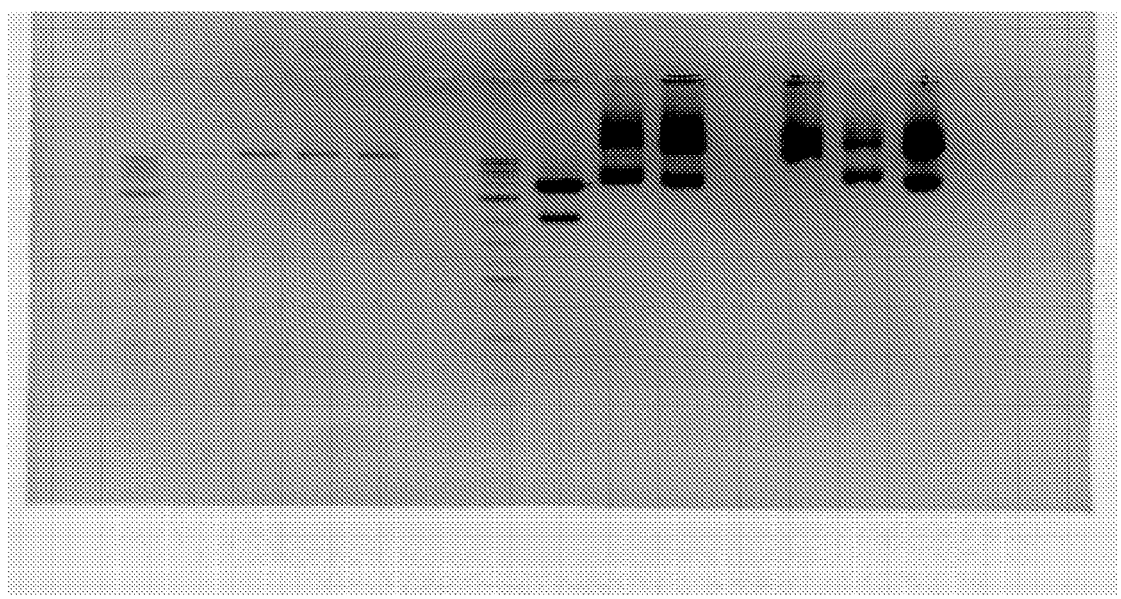
FIG. 39 shows the results of a HinD III/BamH I digestion.

The pBI121 vector back bone (FIG. 36) and E8 PCR fragment (FIG. 37) carrying the HindIII and BamHI restriction sites were ligated. Bacteria were transformed with the ligated product. Positive Colonies were grown further and PCR was used to confirm +ve colonies (FIG. 38). The presence of the construct was confirmed by HinDIII/BamHI Digestion and an SDS PAGE analysis of the product (FIG. 39).

The protocol resulted in bacteria carrying the modified pBI121 plasmid, which contains the E8-driven GUS gene. The GUS gene can be substituted (e.g., as described above) with a nucleic acid encoding any of the peptides (e.g., 6F) described herein to provide a construct for transfecting a plant to express the peptide under control of the E8 promoter.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A transgenic tomato plant comprising cells that express a peptide one or more domains of which comprise the amino acid sequence DWLKAFYDKFFEKFKEFF (SEQ ID NO: 17) wherein said peptide in a fruit of said plant is effective to decrease plasma levels of lysophosphatidic acid (LPA) in a mammal, and/or to decrease serum amyloid A (SAA) levels in said mammal, and/or to increase plasma paraoxonase activity in said mammal when said fruit is fed to said mammal as a lyophilized powder.

2. The transgenic plant of claim 1, wherein said peptide comprises one domain that comprises the amino acid sequence of said apolipoprotein or apolipoprotein mimetic peptide.

3. The transgenic plant of claim 1, wherein said peptide comprises at least two domains that comprise the amino acid sequence of said apolipoprotein or apolipoprotein mimetic peptide.

4. The transgenic plant of claim 1, wherein the amino acid sequence of said peptide consists of the sequence DWLKAFYDKFFEKFKEFF (SEQ ID NO:17).

5. The transgenic plant of claim 1, wherein said peptide in the fruit of said plant is effective to decrease plasma levels of lysophosphatidic acid (LPA) in a mammal, and/or to decrease serum amyloid A (SAA) levels in said mammal, and/or to increase plasma paraoxonase activity in said mammal when said fruit is fed to said mammal as a component of a food or diet.

6. The transgenic plant of claim 1, wherein said peptide in the fruit of said plant is effective to decrease plasma levels of lysophosphatidic acid (LPA) in a mammal when at least a portion of the fruit of said plant is fed to said mammal.

7. The transgenic plant of claim 1, wherein said peptide in the fruit of said plant is effective to significantly decrease serum amyloid A (SAM levels in a mouse model of atherosclerosis when at least a portion of the fruit of said plant is fed to said mouse.

8. The transgenic plant of claim 1, wherein said peptide in the fruit of said plant is effective to increase plasma paraoxonase activity in a mammal, when at least a portion of the fruit of said plant is fed to the mammal.

9. The transgenic plant of claim 1, wherein said peptide is expressed by a nucleic acid construct stably integrated into the plant genome.

10. The transgenic plant of claim 1, wherein said peptide is expressed under the control of a CaMV promoter.

11. The transgenic plant of claim 1, wherein said peptide is expressed under the control of an E8 promoter.

12. The transgenic plant of claim 1, wherein said peptide is expressed under the control of an E4/E8 hybrid promoter.

13. A transgenic seed of a transgenic plant according to claim 1.

14. A transgenic fruit of a transgenic plant according to claim 1.

15. A transgenic leaf of a transgenic plant according to claim 1.

16. A transgenic root or tuber of a transgenic plant according to claim 1.

17. A cutting of a transgenic plant according to claim 1.

18. A clone of a transgenic plant according to claim 1.

19. A food comprising at least a portion of a transgenic plant capable of being ingested for its nutritional value, said plant expressing a peptide comprising an amino acid sequence that is an apolipoprotein or apolipoprotein mimetic, wherein said food comprises a fruit of a transgenic plant according to claim 1.

20. A protein powder, wherein at least a portion of said protein powder comprises a powdered fruit of a plant according to claim 1.

21. A nutritional supplement comprising:
a fruit of a transgenic plant according to claim 1.

22. A powdered fruit of a plant comprising a powdered freeze dried transgenic fruit of a plant according to claim 1.

* * * * *

SEQUENCE LISTING

```
<160> NUMBER OF SEQ ID NOS: 654

<210> SEQ ID NO 1
<211> LENGTH: 18
<212> TYPE: PRT
<213> ORGANISM: Artificial
<220> FEATURE:
<223> OTHER INFORMATION: Recombinant peptide

<400> SEQUENCE: 1

Asp Trp Phe Lys Ala Phe Tyr Asp Lys Val Ala Glu Lys Phe Lys Glu
1               5                   10                  15

Ala Phe

<210> SEQ ID NO 2
<211> LENGTH: 23
<212> TYPE: PRT
<213> ORGANISM: Artificial
<220> FEATURE:
<223> OTHER INFORMATION: Recombinant peptide

<400> SEQUENCE: 2

Met Ile Met Ala Ser Ser Lys Leu Leu Ser Leu Ala Leu Phe Leu Ala
1               5                   10                  15

Leu Leu Ser His Ala Asn Ser
            20

<210> SEQ ID NO 3
<211> LENGTH: 18
<212> TYPE: PRT
<213> ORGANISM: Artificial
```

<220> FEATURE:
<223> OTHER INFORMATION: Recombinant peptide

<400> SEQUENCE: 3

Asp Trp Leu Lys Ala Phe Tyr Asp Lys Val Phe Glu Lys Phe Lys Glu
1               5                   10                  15

Phe Phe

<210> SEQ ID NO 4
<211> LENGTH: 138
<212> TYPE: DNA
<213> ORGANISM: Artificial
<220> FEATURE:
<223> OTHER INFORMATION: Recombinant nucleic acid

<400> SEQUENCE: 4

```
tctagaatga ttatggcttc ttctaaactt ctttctcttg ctcttttct tgctcttctt    60 tctcatgcta attctgattg gcttaaagct ttttatgata aatttttga aaaatttaaa   120 gaattttttt gagagctc                                                138
```

<210> SEQ ID NO 5
<211> LENGTH: 2190
<212> TYPE: DNA
<213> ORGANISM: Lycopersicon esculentum

<400> SEQUENCE: 5

```
tccctaatga tattgttcat gtaattaagt tttgtggaag tgagagagtc caattttgaa    60
agaaaagagt cagaaaacgt aatattttaa aagtctaaat ctttctacaa ataagagcaa   120
atttatttat tttttaatcc aataaatatt aatggaggac aaattcaatt cactttggtt   180
gtaaaataaa cttaaaccaa taaccaaaga actaataaat cctgaagtgg aattattaag   240
gataaatgta catagacgat gaagaaataa taggttcgat gaattaataa taattaagga   300
tgttacaatc atcatgtgcc aagtatatac acaatattct atgggattta aatttcgtt    360 acttcactta acttttgcgt aaataaaacg aattatctga tattttataa taaaacagtt   420
aattaagaac catcattttt aacaacatag atatatattt tctaatagtt taatgatact   480
tttaaatctt ttaaattttta tgtttctttt agaaaataaaa aattcaaaaa attaaatata   540
tttacaaaaa ctacaatcaa acacaacttc atatattaaa agcaaaatat attttgaaaa   600
tttcaagtgt cctaacaaat aagacaagag gaaaatgtac gatgagagac ataagagaa    660 ctaataattg aggagtccta atatataaa taaagtttat tagtaaactt aattattaag    720
gactcctaaa atatatgata ggagaaaatg aatggtgaga gatattggaa aacttaataa   780
ttaaggattt taaaatatat ggtaaaagat aggcaaagta tccattatcc cctttaact    840 tgaagtctac taggcgcatg tgaaagttga ttttttgtca cgtcatatag ctataacgta   900 aaaaagaaa gtaaaatttt taattttttt taatatatga catattttaa acgaaatata    960
ggacaaaatg taaatgaata gtaaaggaaa caaagattaa tacttacttt gtaagaattt  1020
aagataaatt taaaatttaa tagatcaact ttacgtctag aaagaccccat atctagaagg  1080 aatttcacga aatcggccct tattcgaaaa taacttttaa ataatgaatt ttaaatttta  1140
agaaataata tccaatgaat aaatgacatg tagcattta cctaaatatt tcaactattt   1200
taatccaata ttaatttgtt ttattcccaa caatagaaag tcttgtgcag acatttaatc  1260
tgacttttcc agtactaaat attaattttc tgaagatttt cgggtttagt ccacaagttt  1320
tagtgagaag ttttgctcaa atttttaggtg agaaggtttg atatttatct tttgttaaat  1380
```

```
taatttatct aggtgactat tatttattta agtagaaatt catatcatta cttttgccaa    1440
cttgtagtca taataggagt aggtgtatat gatgaaggaa taaacaagtt cagtgaagtg    1500
attaaaataa aatataattt aggtgtacat caaataaaaa ccttaaagtt tagaaaggca    1560
ccgaataatt ttgcatagaa gatattagta aatttataaa aataaaagaa atgtagttgt    1620
caagttgtct tctttttttt ggataaaaat agcagttggc ttatgtcatt cttttacaac    1680
ctccatgcca cttgtccaat tattgacact taactaatta gtttgattca tgtatgaata    1740
ctaaataatt ttttaggact gactcaaata ttttatatt atcatagtaa tatttatcta     1800 attttagga ccacttatta cttaataata aattaactac aactatatta ttgttgtgaa     1860
acaacaacgt tttggttgtt atgatgaaac gtacactata tcagtatgaa aaattcaaaa    1920
cgattagtat aaattatatt gaaaatttga tatttttcta ttcttaatca gacgtattgg    1980
gtttcatatt ttaaaaaggg actaaactta gaagagaagt ttgtttgaaa ctacttttgt    2040
ctctttcttg ttcccatttc tctcttagat ttcaaaaagt gaactacttt atctctttct    2100
ttgttcacat tttattttat tctattataa atatggcatc ctcatattga gatttttaga    2160
aattattcta atcattcaca gtgcaaaaga                                     2190
```

<210> SEQ ID NO 6
<211> LENGTH: 7
<212> TYPE: PRT
<213> ORGANISM: Artificial
<220> FEATURE:
<223> OTHER INFORMATION: Peptide linker

<400> SEQUENCE: 6

Lys Val Glu Pro Leu Arg Ala
1               5

<210> SEQ ID NO 7
<211> LENGTH: 4
<212> TYPE: PRT
<213> ORGANISM: Artificial
<220> FEATURE:
<223> OTHER INFORMATION: Peptide linker

<400> SEQUENCE: 7

Gly Gly Gly Gly
1

<210> SEQ ID NO 8
<211> LENGTH: 5
<212> TYPE: PRT
<213> ORGANISM: Artificial
<220> FEATURE:
<223> OTHER INFORMATION: Peptide linker

<400> SEQUENCE: 8

Gly Gly Gly Gly Ser
1               5

<210> SEQ ID NO 9
<211> LENGTH: 10
<212> TYPE: PRT
<213> ORGANISM: Artificial
<220> FEATURE:
<223> OTHER INFORMATION: Peptide linker

<400> SEQUENCE: 9

Gly Gly Gly Gly Ser Gly Gly Gly Gly Ser

-continued

```
<210> SEQ ID NO 10
<211> LENGTH: 15
<212> TYPE: PRT
<213> ORGANISM: Artificial
<220> FEATURE:
<223> OTHER INFORMATION: Peptide linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 18
<212> TYPE: PRT
<213> ORGANISM: Artificial
<220> FEATURE:
<223> OTHER INFORMATION: Recombinant peptide

<400> SEQUENCE: 11

Asp Trp Leu Lys Ala Phe Tyr Asp Lys Val Ala Glu Lys Leu Lys Glu
1               5                   10                  15

Ala Phe

<210> SEQ ID NO 12
<211> LENGTH: 18
<212> TYPE: PRT
<213> ORGANISM: Artificial
<220> FEATURE:
<223> OTHER INFORMATION: Recombinant peptide

<400> SEQUENCE: 12

Asp Trp Leu Lys Ala Phe Tyr Asp Lys Val Ala Glu Lys Leu Lys Glu
1               5                   10                  15

Ala Phe

<210> SEQ ID NO 13
<211> LENGTH: 18
<212> TYPE: PRT
<213> ORGANISM: Artificial
<220> FEATURE:
<223> OTHER INFORMATION: Recombinant peptide

<400> SEQUENCE: 13

Asp Trp Phe Lys Ala Phe Tyr Asp Lys Val Ala Glu Lys Leu Lys Glu
1               5                   10                  15

Ala Phe

<210> SEQ ID NO 14
<211> LENGTH: 18
<212> TYPE: PRT
<213> ORGANISM: Artificial
<220> FEATURE:
<223> OTHER INFORMATION: Recombinant peptide

<400> SEQUENCE: 14

Asp Trp Leu Lys Ala Phe Tyr Asp Lys Val Ala Glu Lys Phe Lys Glu
1               5                   10                  15

Ala Phe

<210> SEQ ID NO 15
<211> LENGTH: 18
<212> TYPE: PRT
```

<213> ORGANISM: Artificial
<220> FEATURE:
<223> OTHER INFORMATION: Recombinant peptide

<400> SEQUENCE: 15

Asp Trp Phe Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial
<220> FEATURE:
<223> OTHER INFORMATION: Recombinant peptide

<400> SEQUENCE: 16

Asp Trp Leu Lys Ala Phe Tyr Asp Lys Val Phe Glu Lys Phe Lys Glu
1               5                   10                  15

Phe Phe

<210> SEQ ID NO 17
<211> LENGTH: 18
<212> TYPE: PRT
<213> ORGANISM: Artificial
<220> FEATURE:
<223> OTHER INFORMATION: Recombinant peptide

<400> SEQUENCE: 17

Asp Trp Leu Lys Ala Phe Tyr Asp Lys Phe Phe Glu Lys Phe Lys Glu
1               5                   10                  15

Phe Phe

<210> SEQ ID NO 18
<211> LENGTH: 18
<212> TYPE: PRT
<213> ORGANISM: Artificial
<220> FEATURE:
<223> OTHER INFORMATION: Recombinant peptide

<400> SEQUENCE: 18

Asp Trp Phe Lys Ala Phe Tyr Asp Lys Phe Phe Glu Lys Phe Lys Glu
1               5                   10                  15

Phe Phe

<210> SEQ ID NO 19
<211> LENGTH: 18
<212> TYPE: PRT
<213> ORGANISM: Artificial
<220> FEATURE:
<223> OTHER INFORMATION: Recombinant peptide

<400> SEQUENCE: 19

Asp Trp Leu Lys Ala Phe Tyr Asp Lys Val Ala Glu Lys Leu Lys Glu
1               5                   10                  15

Phe Phe

<210> SEQ ID NO 20
<211> LENGTH: 18
<212> TYPE: PRT
<213> ORGANISM: Artificial
<220> FEATURE:
<223> OTHER INFORMATION: Recombinant peptide

```
<400> SEQUENCE: 20

Phe Ala Glu Lys Leu Lys Glu Ala Val Lys Asp Tyr Phe Ala Lys Leu
1               5                   10                  15

Trp Asp

<210> SEQ ID NO 21
<211> LENGTH: 18
<212> TYPE: PRT
<213> ORGANISM: Artificial
<220> FEATURE:
<223> OTHER INFORMATION: Recombinant peptide

<400> SEQUENCE: 21

Phe Ala Glu Lys Leu Lys Glu Ala Val Lys Asp Tyr Phe Ala Lys Leu
1               5                   10                  15

Trp Asp

<210> SEQ ID NO 22
<211> LENGTH: 18
<212> TYPE: PRT
<213> ORGANISM: Artificial
<220> FEATURE:
<223> OTHER INFORMATION: Recombinant peptide

<400> SEQUENCE: 22

Phe Ala Glu Lys Leu Lys Glu Ala Val Lys Asp Tyr Phe Ala Lys Phe
1               5                   10                  15

Trp Asp

<210> SEQ ID NO 23
<211> LENGTH: 18
<212> TYPE: PRT
<213> ORGANISM: Artificial
<220> FEATURE:
<223> OTHER INFORMATION: Recombinant peptide

<400> SEQUENCE: 23

Phe Ala Glu Lys Phe Lys Glu Ala Val Lys Asp Tyr Phe Ala Lys Phe
1               5                   10                  15

Trp Asp

<210> SEQ ID NO 24
<211> LENGTH: 18
<212> TYPE: PRT
<213> ORGANISM: Artificial
<220> FEATURE:
<223> OTHER INFORMATION: Recombinant peptide

<400> SEQUENCE: 24

Phe Phe Glu Lys Phe Lys Glu Phe Val Lys Asp Tyr Phe Ala Lys Leu
1               5                   10                  15

Trp Asp

<210> SEQ ID NO 25
<211> LENGTH: 18
<212> TYPE: PRT
<213> ORGANISM: Artificial
<220> FEATURE:
<223> OTHER INFORMATION: Recombinant peptide

<400> SEQUENCE: 25

Phe Phe Glu Lys Phe Lys Glu Phe Phe Lys Asp Tyr Phe Ala Lys Leu
1               5                   10                  15
```

Trp Asp

<210> SEQ ID NO 26
<211> LENGTH: 18
<212> TYPE: PRT
<213> ORGANISM: Artificial
<220> FEATURE:
<223> OTHER INFORMATION: Recombinant peptide

<400> SEQUENCE: 26

Phe Phe Glu Lys Phe Lys Glu Phe Phe Lys Asp Tyr Phe Ala Lys Phe
1               5                   10                  15

Trp Asp

<210> SEQ ID NO 27
<211> LENGTH: 18
<212> TYPE: PRT
<213> ORGANISM: Artificial
<220> FEATURE:
<223> OTHER INFORMATION: Recombinant peptide

<400> SEQUENCE: 27

Asp Trp Leu Lys Ala Phe Tyr Asp Lys Val Phe Glu Lys Phe Lys Glu
1               5                   10                  15

Ala Phe

<210> SEQ ID NO 28
<211> LENGTH: 18
<212> TYPE: PRT
<213> ORGANISM: Artificial
<220> FEATURE:
<223> OTHER INFORMATION: Recombinant peptide

<400> SEQUENCE: 28

Asp Trp Leu Lys Ala Phe Tyr Asp Lys Val Phe Glu Lys Leu Lys Glu
1               5                   10                  15

Phe Phe

<210> SEQ ID NO 29
<211> LENGTH: 18
<212> TYPE: PRT
<213> ORGANISM: Artificial
<220> FEATURE:
<223> OTHER INFORMATION: Recombinant peptide

<400> SEQUENCE: 29

Asp Trp Leu Lys Ala Phe Tyr Asp Lys Val Ala Glu Lys Phe Lys Glu
1               5                   10                  15

Phe Phe

<210> SEQ ID NO 30
<211> LENGTH: 18
<212> TYPE: PRT
<213> ORGANISM: Artificial
<220> FEATURE:
<223> OTHER INFORMATION: Recombinant peptide

<400> SEQUENCE: 30

Asp Trp Leu Lys Ala Phe Tyr Asp Lys Val Phe Glu Lys Phe Lys Glu
1               5                   10                  15

Phe Phe

```
<210> SEQ ID NO 31
<211> LENGTH: 18
<212> TYPE: PRT
<213> ORGANISM: Artificial
<220> FEATURE:
<223> OTHER INFORMATION: Recombinant peptide

<400> SEQUENCE: 31

Glu Trp Leu Lys Leu Phe Tyr Glu Lys Val Leu Glu Lys Phe Lys Glu
1               5                   10                  15

Ala Phe

<210> SEQ ID NO 32
<211> LENGTH: 18
<212> TYPE: PRT
<213> ORGANISM: Artificial
<220> FEATURE:
<223> OTHER INFORMATION: Recombinant peptide

<400> SEQUENCE: 32

Glu Trp Leu Lys Ala Phe Tyr Asp Lys Val Ala Glu Lys Phe Lys Glu
1               5                   10                  15

Ala Phe

<210> SEQ ID NO 33
<211> LENGTH: 18
<212> TYPE: PRT
<213> ORGANISM: Artificial
<220> FEATURE:
<223> OTHER INFORMATION: Recombinant peptide

<400> SEQUENCE: 33

Glu Trp Leu Lys Ala Phe Tyr Asp Lys Val Ala Glu Lys Leu Lys Glu
1               5                   10                  15

Phe Phe

<210> SEQ ID NO 34
<211> LENGTH: 18
<212> TYPE: PRT
<213> ORGANISM: Artificial
<220> FEATURE:
<223> OTHER INFORMATION: Recombinant peptide

<400> SEQUENCE: 34

Glu Trp Leu Lys Ala Phe Tyr Asp Lys Val Phe Glu Lys Phe Lys Glu
1               5                   10                  15

Ala Phe

<210> SEQ ID NO 35
<211> LENGTH: 18
<212> TYPE: PRT
<213> ORGANISM: Artificial
<220> FEATURE:
<223> OTHER INFORMATION: Recombinant peptide

<400> SEQUENCE: 35

Glu Trp Leu Lys Ala Phe Tyr Asp Lys Val Phe Glu Lys Leu Lys Glu
1               5                   10                  15

Phe Phe

<210> SEQ ID NO 36
<211> LENGTH: 18
<212> TYPE: PRT
<213> ORGANISM: Artificial
```

```
<220> FEATURE:
<223> OTHER INFORMATION: Recombinant peptide

<400> SEQUENCE: 36

Glu Trp Leu Lys Ala Phe Tyr Asp Lys Val Ala Glu Lys Phe Lys Glu
1               5                   10                  15

Phe Phe

<210> SEQ ID NO 37
<211> LENGTH: 18
<212> TYPE: PRT
<213> ORGANISM: Artificial
<220> FEATURE:
<223> OTHER INFORMATION: Recombinant peptide

<400> SEQUENCE: 37

Glu Trp Leu Lys Ala Phe Tyr Asp Lys Val Phe Glu Lys Phe Lys Glu
1               5                   10                  15

Phe Phe

<210> SEQ ID NO 38
<211> LENGTH: 14
<212> TYPE: PRT
<213> ORGANISM: Artificial
<220> FEATURE:
<223> OTHER INFORMATION: Recombinant peptide

<400> SEQUENCE: 38

Ala Phe Tyr Asp Lys Val Ala Glu Lys Leu Lys Glu Ala Phe
1               5                   10

<210> SEQ ID NO 39
<211> LENGTH: 14
<212> TYPE: PRT
<213> ORGANISM: Artificial
<220> FEATURE:
<223> OTHER INFORMATION: Recombinant peptide

<400> SEQUENCE: 39

Ala Phe Tyr Asp Lys Val Ala Glu Lys Phe Lys Glu Ala Phe
1               5                   10

<210> SEQ ID NO 40
<211> LENGTH: 14
<212> TYPE: PRT
<213> ORGANISM: Artificial
<220> FEATURE:
<223> OTHER INFORMATION: Recombinant peptide

<400> SEQUENCE: 40

Ala Phe Tyr Asp Lys Val Ala Glu Lys Phe Lys Glu Ala Phe
1               5                   10

<210> SEQ ID NO 41
<211> LENGTH: 14
<212> TYPE: PRT
<213> ORGANISM: Artificial
<220> FEATURE:
<223> OTHER INFORMATION: Recombinant peptide

<400> SEQUENCE: 41

Ala Phe Tyr Asp Lys Phe Phe Glu Lys Phe Lys Glu Phe Phe
1               5                   10

<210> SEQ ID NO 42
```

<211> LENGTH: 14
<212> TYPE: PRT
<213> ORGANISM: Artificial
<220> FEATURE:
<223> OTHER INFORMATION: Recombinant peptide

<400> SEQUENCE: 42

Ala Phe Tyr Asp Lys Phe Phe Glu Lys Phe Lys Glu Phe Phe
1               5                   10

<210> SEQ ID NO 43
<211> LENGTH: 14
<212> TYPE: PRT
<213> ORGANISM: Artificial
<220> FEATURE:
<223> OTHER INFORMATION: Recombinant peptide

<400> SEQUENCE: 43

Ala Phe Tyr Asp Lys Val Ala Glu Lys Phe Lys Glu Ala Phe
1               5                   10

<210> SEQ ID NO 44
<211> LENGTH: 14
<212> TYPE: PRT
<213> ORGANISM: Artificial
<220> FEATURE:
<223> OTHER INFORMATION: Recombinant peptide

<400> SEQUENCE: 44

Ala Phe Tyr Asp Lys Val Ala Glu Lys Leu Lys Glu Phe Phe
1               5                   10

<210> SEQ ID NO 45
<211> LENGTH: 14
<212> TYPE: PRT
<213> ORGANISM: Artificial
<220> FEATURE:
<223> OTHER INFORMATION: Recombinant peptide

<400> SEQUENCE: 45

Ala Phe Tyr Asp Lys Val Phe Glu Lys Phe Lys Glu Ala Phe
1               5                   10

<210> SEQ ID NO 46
<211> LENGTH: 14
<212> TYPE: PRT
<213> ORGANISM: Artificial
<220> FEATURE:
<223> OTHER INFORMATION: Recombinant peptide

<400> SEQUENCE: 46

Ala Phe Tyr Asp Lys Val Phe Glu Lys Leu Lys Glu Phe Phe
1               5                   10

<210> SEQ ID NO 47
<211> LENGTH: 14
<212> TYPE: PRT
<213> ORGANISM: Artificial
<220> FEATURE:
<223> OTHER INFORMATION: Recombinant peptide

<400> SEQUENCE: 47

Ala Phe Tyr Asp Lys Val Ala Glu Lys Phe Lys Glu Phe Phe
1               5                   10

<210> SEQ ID NO 48
<211> LENGTH: 14

```
<212> TYPE: PRT
<213> ORGANISM: Artificial
<220> FEATURE:
<223> OTHER INFORMATION: Recombinant peptide

<400> SEQUENCE: 48

Lys Ala Phe Tyr Asp Lys Val Phe Glu Lys Phe Lys Glu Phe
1               5                   10

<210> SEQ ID NO 49
<211> LENGTH: 14
<212> TYPE: PRT
<213> ORGANISM: Artificial
<220> FEATURE:
<223> OTHER INFORMATION: Recombinant peptide

<400> SEQUENCE: 49

Leu Phe Tyr Glu Lys Val Leu Glu Lys Phe Lys Glu Ala Phe
1               5                   10

<210> SEQ ID NO 50
<211> LENGTH: 14
<212> TYPE: PRT
<213> ORGANISM: Artificial
<220> FEATURE:
<223> OTHER INFORMATION: Recombinant peptide

<400> SEQUENCE: 50

Ala Phe Tyr Asp Lys Val Ala Glu Lys Phe Lys Glu Ala Phe
1               5                   10

<210> SEQ ID NO 51
<211> LENGTH: 14
<212> TYPE: PRT
<213> ORGANISM: Artificial
<220> FEATURE:
<223> OTHER INFORMATION: Recombinant peptide

<400> SEQUENCE: 51

Ala Phe Tyr Asp Lys Val Ala Glu Lys Leu Lys Glu Phe Phe
1               5                   10

<210> SEQ ID NO 52
<211> LENGTH: 14
<212> TYPE: PRT
<213> ORGANISM: Artificial
<220> FEATURE:
<223> OTHER INFORMATION: Recombinant peptide

<400> SEQUENCE: 52

Ala Phe Tyr Asp Lys Val Phe Glu Lys Phe Lys Glu Ala Phe
1               5                   10

<210> SEQ ID NO 53
<211> LENGTH: 14
<212> TYPE: PRT
<213> ORGANISM: Artificial
<220> FEATURE:
<223> OTHER INFORMATION: Recombinant peptide

<400> SEQUENCE: 53

Ala Phe Tyr Asp Lys Val Phe Glu Lys Leu Lys Glu Phe Phe
1               5                   10

<210> SEQ ID NO 54
<211> LENGTH: 14
<212> TYPE: PRT
```

```
<213> ORGANISM: Artificial
<220> FEATURE:
<223> OTHER INFORMATION: Recombinant peptide

<400> SEQUENCE: 54

Ala Phe Tyr Asp Lys Val Ala Glu Lys Phe Lys Glu Phe Phe
1               5                   10

<210> SEQ ID NO 55
<211> LENGTH: 14
<212> TYPE: PRT
<213> ORGANISM: Artificial
<220> FEATURE:
<223> OTHER INFORMATION: Recombinant peptide

<400> SEQUENCE: 55

Ala Phe Tyr Asp Lys Val Phe Glu Lys Phe Lys Glu Phe Phe
1               5                   10

<210> SEQ ID NO 56
<211> LENGTH: 18
<212> TYPE: PRT
<213> ORGANISM: Artificial
<220> FEATURE:
<223> OTHER INFORMATION: Recombinant peptide

<400> SEQUENCE: 56

Asp Trp Leu Lys Ala Leu Tyr Asp Lys Val Ala Glu Lys Leu Lys Glu
1               5                   10                  15

Ala Leu

<210> SEQ ID NO 57
<211> LENGTH: 18
<212> TYPE: PRT
<213> ORGANISM: Artificial
<220> FEATURE:
<223> OTHER INFORMATION: Recombinant peptide

<400> SEQUENCE: 57

Asp Trp Phe Lys Ala Phe Tyr Glu Lys Val Ala Glu Lys Leu Lys Glu
1               5                   10                  15

Phe Phe

<210> SEQ ID NO 58
<211> LENGTH: 18
<212> TYPE: PRT
<213> ORGANISM: Artificial
<220> FEATURE:
<223> OTHER INFORMATION: Recombinant peptide

<400> SEQUENCE: 58

Asp Trp Phe Lys Ala Phe Tyr Glu Lys Phe Phe Glu Lys Phe Lys Glu
1               5                   10                  15

Phe Phe

<210> SEQ ID NO 59
<211> LENGTH: 18
<212> TYPE: PRT
<213> ORGANISM: Artificial
<220> FEATURE:
<223> OTHER INFORMATION: Recombinant peptide

<400> SEQUENCE: 59

Glu Trp Leu Lys Ala Leu Tyr Glu Lys Val Ala Glu Lys Leu Lys Glu
1               5                   10                  15
```

Ala Leu

<210> SEQ ID NO 60
<211> LENGTH: 18
<212> TYPE: PRT
<213> ORGANISM: Artificial
<220> FEATURE:
<223> OTHER INFORMATION: Recombinant peptide

<400> SEQUENCE: 60

Glu Trp Leu Lys Ala Phe Tyr Glu Lys Val Ala Glu Lys Leu Lys Glu
1               5                   10                  15

Ala Phe

<210> SEQ ID NO 61
<211> LENGTH: 18
<212> TYPE: PRT
<213> ORGANISM: Artificial
<220> FEATURE:
<223> OTHER INFORMATION: Recombinant peptide

<400> SEQUENCE: 61

Glu Trp Phe Lys Ala Phe Tyr Glu Lys Val Ala Glu Lys Leu Lys Glu
1               5                   10                  15

Phe Phe

<210> SEQ ID NO 62
<211> LENGTH: 18
<212> TYPE: PRT
<213> ORGANISM: Artificial
<220> FEATURE:
<223> OTHER INFORMATION: Recombinant peptide

<400> SEQUENCE: 62

Glu Trp Leu Lys Ala Phe Tyr Glu Lys Val Phe Glu Lys Phe Lys Glu
1               5                   10                  15

Phe Phe

<210> SEQ ID NO 63
<211> LENGTH: 18
<212> TYPE: PRT
<213> ORGANISM: Artificial
<220> FEATURE:
<223> OTHER INFORMATION: Recombinant peptide

<400> SEQUENCE: 63

Glu Trp Leu Lys Ala Phe Tyr Glu Lys Phe Phe Glu Lys Phe Lys Glu
1               5                   10                  15

Phe Phe

<210> SEQ ID NO 64
<211> LENGTH: 18
<212> TYPE: PRT
<213> ORGANISM: Artificial
<220> FEATURE:
<223> OTHER INFORMATION: Recombinant peptide

<400> SEQUENCE: 64

Glu Trp Phe Lys Ala Phe Tyr Glu Lys Phe Phe Glu Lys Phe Lys Glu
1               5                   10                  15

Phe Phe

<210> SEQ ID NO 65
<211> LENGTH: 18
<212> TYPE: PRT
<213> ORGANISM: Artificial
<220> FEATURE:
<223> OTHER INFORMATION: Recombinant peptide

<400> SEQUENCE: 65

Asp Phe Leu Lys Ala Trp Tyr Asp Lys Val Ala Glu Lys Leu Lys Glu
1               5                   10                  15

Ala Trp

<210> SEQ ID NO 66
<211> LENGTH: 18
<212> TYPE: PRT
<213> ORGANISM: Artificial
<220> FEATURE:
<223> OTHER INFORMATION: Recombinant peptide

<400> SEQUENCE: 66

Glu Phe Leu Lys Ala Trp Tyr Glu Lys Val Ala Glu Lys Leu Lys Glu
1               5                   10                  15

Ala Trp

<210> SEQ ID NO 67
<211> LENGTH: 18
<212> TYPE: PRT
<213> ORGANISM: Artificial
<220> FEATURE:
<223> OTHER INFORMATION: Recombinant peptide

<400> SEQUENCE: 67

Asp Phe Trp Lys Ala Trp Tyr Asp Lys Val Ala Glu Lys Leu Lys Glu
1               5                   10                  15

Trp Trp

<210> SEQ ID NO 68
<211> LENGTH: 18
<212> TYPE: PRT
<213> ORGANISM: Artificial
<220> FEATURE:
<223> OTHER INFORMATION: Recombinant peptide

<400> SEQUENCE: 68

Glu Phe Trp Lys Ala Trp Tyr Glu Lys Val Ala Glu Lys Leu Lys Glu
1               5                   10                  15

Trp Trp

<210> SEQ ID NO 69
<211> LENGTH: 18
<212> TYPE: PRT
<213> ORGANISM: Artificial
<220> FEATURE:
<223> OTHER INFORMATION: Recombinant peptide

<400> SEQUENCE: 69

Asp Lys Leu Lys Ala Phe Tyr Asp Lys Val Phe Glu Trp Ala Lys Glu
1               5                   10                  15

Ala Phe

<210> SEQ ID NO 70
<211> LENGTH: 18
<212> TYPE: PRT
<213> ORGANISM: Artificial

-continued

<220> FEATURE:
<223> OTHER INFORMATION: Recombinant peptide

<400> SEQUENCE: 70

Asp Lys Trp Lys Ala Val Tyr Asp Lys Phe Ala Glu Ala Phe Lys Glu
1               5                   10                  15

Phe Leu

<210> SEQ ID NO 71
<211> LENGTH: 18
<212> TYPE: PRT
<213> ORGANISM: Artificial
<220> FEATURE:
<223> OTHER INFORMATION: Recombinant peptide

<400> SEQUENCE: 71

Glu Lys Leu Lys Ala Phe Tyr Glu Lys Val Phe Glu Trp Ala Lys Glu
1               5                   10                  15

Ala Phe

<210> SEQ ID NO 72
<211> LENGTH: 18
<212> TYPE: PRT
<213> ORGANISM: Artificial
<220> FEATURE:
<223> OTHER INFORMATION: Recombinant peptide

<400> SEQUENCE: 72

Glu Lys Trp Lys Ala Val Tyr Glu Lys Phe Ala Glu Ala Phe Lys Glu
1               5                   10                  15

Phe Leu

<210> SEQ ID NO 73
<211> LENGTH: 18
<212> TYPE: PRT
<213> ORGANISM: Artificial
<220> FEATURE:
<223> OTHER INFORMATION: Recombinant peptide

<400> SEQUENCE: 73

Asp Trp Leu Lys Ala Phe Val Asp Lys Phe Ala Glu Lys Phe Lys Glu
1               5                   10                  15

Ala Tyr

<210> SEQ ID NO 74
<211> LENGTH: 18
<212> TYPE: PRT
<213> ORGANISM: Artificial
<220> FEATURE:
<223> OTHER INFORMATION: Recombinant peptide

<400> SEQUENCE: 74

Glu Lys Trp Lys Ala Val Tyr Glu Lys Phe Ala Glu Ala Phe Lys Glu
1               5                   10                  15

Phe Leu

<210> SEQ ID NO 75
<211> LENGTH: 18
<212> TYPE: PRT
<213> ORGANISM: Artificial
<220> FEATURE:
<223> OTHER INFORMATION: Recombinant peptide

<400> SEQUENCE: 75

-continued

```
Asp Trp Leu Lys Ala Phe Val Tyr Asp Lys Val Phe Lys Leu Lys Glu
1               5                   10                  15

Phe Phe

<210> SEQ ID NO 76
<211> LENGTH: 18
<212> TYPE: PRT
<213> ORGANISM: Artificial
<220> FEATURE:
<223> OTHER INFORMATION: Recombinant peptide

<400> SEQUENCE: 76

Glu Trp Leu Lys Ala Phe Val Tyr Glu Lys Val Phe Lys Leu Lys Glu
1               5                   10                  15

Phe Phe

<210> SEQ ID NO 77
<211> LENGTH: 18
<212> TYPE: PRT
<213> ORGANISM: Artificial
<220> FEATURE:
<223> OTHER INFORMATION: Recombinant peptide

<400> SEQUENCE: 77

Asp Trp Leu Arg Ala Phe Tyr Asp Lys Val Ala Glu Lys Leu Lys Glu
1               5                   10                  15

Ala Phe

<210> SEQ ID NO 78
<211> LENGTH: 18
<212> TYPE: PRT
<213> ORGANISM: Artificial
<220> FEATURE:
<223> OTHER INFORMATION: Recombinant peptide

<400> SEQUENCE: 78

Glu Trp Leu Arg Ala Phe Tyr Glu Lys Val Ala Glu Lys Leu Lys Glu
1               5                   10                  15

Ala Phe

<210> SEQ ID NO 79
<211> LENGTH: 18
<212> TYPE: PRT
<213> ORGANISM: Artificial
<220> FEATURE:
<223> OTHER INFORMATION: Recombinant peptide

<400> SEQUENCE: 79

Asp Trp Leu Lys Ala Phe Tyr Asp Arg Val Ala Glu Lys Leu Lys Glu
1               5                   10                  15

Ala Phe

<210> SEQ ID NO 80
<211> LENGTH: 18
<212> TYPE: PRT
<213> ORGANISM: Artificial
<220> FEATURE:
<223> OTHER INFORMATION: Recombinant peptide

<400> SEQUENCE: 80

Glu Trp Leu Lys Ala Phe Tyr Glu Arg Val Ala Glu Lys Leu Lys Glu
1               5                   10                  15
```

Ala Phe

<210> SEQ ID NO 81
<211> LENGTH: 18
<212> TYPE: PRT
<213> ORGANISM: Artificial
<220> FEATURE:
<223> OTHER INFORMATION: Recombinant peptide

<400> SEQUENCE: 81

Asp Trp Leu Lys Ala Phe Tyr Asp Lys Val Ala Glu Arg Leu Lys Glu
1               5                   10                  15

Ala Phe

<210> SEQ ID NO 82
<211> LENGTH: 18
<212> TYPE: PRT
<213> ORGANISM: Artificial
<220> FEATURE:
<223> OTHER INFORMATION: Recombinant peptide

<400> SEQUENCE: 82

Glu Trp Leu Lys Ala Phe Tyr Glu Lys Val Ala Glu Arg Leu Lys Glu
1               5                   10                  15

Ala Phe

<210> SEQ ID NO 83
<211> LENGTH: 18
<212> TYPE: PRT
<213> ORGANISM: Artificial
<220> FEATURE:
<223> OTHER INFORMATION: Recombinant peptide

<400> SEQUENCE: 83

Asp Trp Leu Lys Ala Phe Tyr Asp Lys Val Ala Glu Lys Leu Arg Glu
1               5                   10                  15

Ala Phe

<210> SEQ ID NO 84
<211> LENGTH: 18
<212> TYPE: PRT
<213> ORGANISM: Artificial
<220> FEATURE:
<223> OTHER INFORMATION: Recombinant peptide

<400> SEQUENCE: 84

Glu Trp Leu Lys Ala Phe Tyr Glu Lys Val Ala Glu Lys Leu Arg Glu
1               5                   10                  15

Ala Phe

<210> SEQ ID NO 85
<211> LENGTH: 18
<212> TYPE: PRT
<213> ORGANISM: Artificial
<220> FEATURE:
<223> OTHER INFORMATION: Recombinant peptide

<400> SEQUENCE: 85

Asp Trp Leu Lys Ala Phe Tyr Asp Arg Val Ala Glu Arg Leu Lys Glu
1               5                   10                  15

Ala Phe

<210> SEQ ID NO 86

```
<211> LENGTH: 18
<212> TYPE: PRT
<213> ORGANISM: Artificial
<220> FEATURE:
<223> OTHER INFORMATION: Recombinant peptide

<400> SEQUENCE: 86

Glu Trp Leu Lys Ala Phe Tyr Glu Arg Val Ala Glu Arg Leu Lys Glu
1               5                   10                  15

Ala Phe

<210> SEQ ID NO 87
<211> LENGTH: 18
<212> TYPE: PRT
<213> ORGANISM: Artificial
<220> FEATURE:
<223> OTHER INFORMATION: Recombinant peptide

<400> SEQUENCE: 87

Asp Trp Leu Arg Ala Phe Tyr Asp Lys Val Ala Glu Lys Leu Arg Glu
1               5                   10                  15

Ala Phe

<210> SEQ ID NO 88
<211> LENGTH: 18
<212> TYPE: PRT
<213> ORGANISM: Artificial
<220> FEATURE:
<223> OTHER INFORMATION: Recombinant peptide

<400> SEQUENCE: 88

Glu Trp Leu Arg Ala Phe Tyr Glu Lys Val Ala Glu Lys Leu Arg Glu
1               5                   10                  15

Ala Phe

<210> SEQ ID NO 89
<211> LENGTH: 18
<212> TYPE: PRT
<213> ORGANISM: Artificial
<220> FEATURE:
<223> OTHER INFORMATION: Recombinant peptide

<400> SEQUENCE: 89

Asp Trp Leu Arg Ala Phe Tyr Asp Arg Val Ala Glu Lys Leu Lys Glu
1               5                   10                  15

Ala Phe

<210> SEQ ID NO 90
<211> LENGTH: 18
<212> TYPE: PRT
<213> ORGANISM: Artificial
<220> FEATURE:
<223> OTHER INFORMATION: Recombinant peptide

<400> SEQUENCE: 90

Glu Trp Leu Arg Ala Phe Tyr Glu Arg Val Ala Glu Lys Leu Lys Glu
1               5                   10                  15

Ala Phe

<210> SEQ ID NO 91
<211> LENGTH: 18
<212> TYPE: PRT
<213> ORGANISM: Artificial
<220> FEATURE:
```

<223> OTHER INFORMATION: Recombinant peptide

<400> SEQUENCE: 91

Asp Trp Leu Lys Ala Phe Tyr Asp Lys Val Ala Glu Arg Leu Arg Glu
1               5                   10                  15

Ala Phe

<210> SEQ ID NO 92
<211> LENGTH: 18
<212> TYPE: PRT
<213> ORGANISM: Artificial
<220> FEATURE:
<223> OTHER INFORMATION: Recombinant peptide

<400> SEQUENCE: 92

Glu Trp Leu Lys Ala Phe Tyr Glu Lys Val Ala Glu Arg Leu Arg Glu
1               5                   10                  15

Ala Phe

<210> SEQ ID NO 93
<211> LENGTH: 18
<212> TYPE: PRT
<213> ORGANISM: Artificial
<220> FEATURE:
<223> OTHER INFORMATION: Recombinant peptide

<400> SEQUENCE: 93

Asp Trp Leu Arg Ala Phe Tyr Asp Lys Val Ala Glu Arg Leu Lys Glu
1               5                   10                  15

Ala Phe

<210> SEQ ID NO 94
<211> LENGTH: 18
<212> TYPE: PRT
<213> ORGANISM: Artificial
<220> FEATURE:
<223> OTHER INFORMATION: Recombinant peptide

<400> SEQUENCE: 94

Glu Trp Leu Arg Ala Phe Tyr Glu Lys Val Ala Glu Arg Leu Lys Glu
1               5                   10                  15

Ala Phe

<210> SEQ ID NO 95
<211> LENGTH: 37
<212> TYPE: PRT
<213> ORGANISM: Artificial
<220> FEATURE:
<223> OTHER INFORMATION: Recombinant peptide

<400> SEQUENCE: 95

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
        35

<210> SEQ ID NO 96
<211> LENGTH: 37
<212> TYPE: PRT
<213> ORGANISM: Artificial
<220> FEATURE:

<223> OTHER INFORMATION: Recombinant peptide

<400> SEQUENCE: 96

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
            20                  25                  30

Leu Lys Glu Phe Phe
        35

<210> SEQ ID NO 97
<211> LENGTH: 37
<212> TYPE: PRT
<213> ORGANISM: Artificial
<220> FEATURE:
<223> OTHER INFORMATION: Recombinant peptide

<400> SEQUENCE: 97

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
            20                  25                  30

Leu Lys Glu Ala Phe
        35

<210> SEQ ID NO 98
<211> LENGTH: 37
<212> TYPE: PRT
<213> ORGANISM: Artificial
<220> FEATURE:
<223> OTHER INFORMATION: Recombinant peptide

<400> SEQUENCE: 98

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
            20                  25                  30

Leu Lys Glu Ala Phe
        35

<210> SEQ ID NO 99
<211> LENGTH: 37
<212> TYPE: PRT
<213> ORGANISM: Artificial
<220> FEATURE:
<223> OTHER INFORMATION: Recombinant peptide

<400> SEQUENCE: 99

Asp Lys Trp Lys Ala Val Tyr Asp Lys Phe Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
        35

<210> SEQ ID NO 100
<211> LENGTH: 37
<212> TYPE: PRT
<213> ORGANISM: Artificial
<220> FEATURE:
<223> OTHER INFORMATION: Recombinant peptide

<400> SEQUENCE: 100

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
        35

<210> SEQ ID NO 101
<211> LENGTH: 37
<212> TYPE: PRT
<213> ORGANISM: Artificial
<220> FEATURE:
<223> OTHER INFORMATION: Recombinant peptide

<400> SEQUENCE: 101

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
            20                  25                  30

Leu Lys Glu Phe Phe
        35

<210> SEQ ID NO 102
<211> LENGTH: 37
<212> TYPE: PRT
<213> ORGANISM: Artificial
<220> FEATURE:
<223> OTHER INFORMATION: Recombinant peptide

<400> SEQUENCE: 102

Asp Trp Leu Lys Ala Phe Tyr Asp Lys Phe Ala Glu Lys Phe Lys Glu
1               5                   10                  15

Phe Phe Pro Asp Trp Leu Lys Ala Phe Tyr Asp Lys Phe Ala Glu Lys
            20                  25                  30

Phe Lys Glu Phe Phe
        35

<210> SEQ ID NO 103
<211> LENGTH: 18
<212> TYPE: PRT
<213> ORGANISM: Artificial
<220> FEATURE:
<223> OTHER INFORMATION: Recombinant peptide

<400> SEQUENCE: 103

Glu Trp Phe Lys Ala Phe Tyr Glu Lys Val Ala Glu Lys Phe Lys Glu
1               5                   10                  15

Ala Phe

<210> SEQ ID NO 104
<211> LENGTH: 14
<212> TYPE: PRT
<213> ORGANISM: Artificial
<220> FEATURE:
<223> OTHER INFORMATION: Recombinant peptide

<400> SEQUENCE: 104

Asp Trp Phe Lys Ala Phe Tyr Asp Lys Val Ala Glu Lys Phe
1               5                   10

<210> SEQ ID NO 105
<211> LENGTH: 14

```
<212> TYPE: PRT
<213> ORGANISM: Artificial
<220> FEATURE:
<223> OTHER INFORMATION: Recombinant peptide

<400> SEQUENCE: 105

Phe Lys Ala Phe Tyr Asp Lys Val Ala Glu Lys Phe Lys Glu
1               5                   10

<210> SEQ ID NO 106
<211> LENGTH: 14
<212> TYPE: PRT
<213> ORGANISM: Artificial
<220> FEATURE:
<223> OTHER INFORMATION: Recombinant peptide

<400> SEQUENCE: 106

Phe Lys Ala Phe Tyr Glu Lys Val Ala Glu Lys Phe Lys Glu
1               5                   10

<210> SEQ ID NO 107
<211> LENGTH: 14
<212> TYPE: PRT
<213> ORGANISM: Artificial
<220> FEATURE:
<223> OTHER INFORMATION: Recombinant peptide

<400> SEQUENCE: 107

Phe Lys Ala Phe Tyr Asp Lys Val Ala Glu Lys Phe Lys Glu
1               5                   10

<210> SEQ ID NO 108
<211> LENGTH: 14
<212> TYPE: PRT
<213> ORGANISM: Artificial
<220> FEATURE:
<223> OTHER INFORMATION: Recombinant peptide

<400> SEQUENCE: 108

Phe Lys Ala Phe Tyr Glu Lys Val Ala Glu Lys Phe Lys Glu
1               5                   10

<210> SEQ ID NO 109
<211> LENGTH: 18
<212> TYPE: PRT
<213> ORGANISM: Artificial
<220> FEATURE:
<223> OTHER INFORMATION: Recombinant peptide

<400> SEQUENCE: 109

Asp Trp Phe Lys Ala Phe Tyr Asp Lys Val Ala Glu Lys Phe Lys Glu
1               5                   10                  15

Ala Phe

<210> SEQ ID NO 110
<211> LENGTH: 18
<212> TYPE: PRT
<213> ORGANISM: Artificial
<220> FEATURE:
<223> OTHER INFORMATION: Recombinant peptide

<400> SEQUENCE: 110

Glu Trp Phe Lys Ala Phe Tyr Glu Lys Val Ala Glu Lys Phe Lys Glu
1               5                   10                  15

Ala Phe
```

```
<210> SEQ ID NO 111
<211> LENGTH: 14
<212> TYPE: PRT
<213> ORGANISM: Artificial
<220> FEATURE:
<223> OTHER INFORMATION: Recombinant peptide

<400> SEQUENCE: 111

Ala Phe Tyr Asp Lys Val Ala Glu Lys Phe Lys Glu Ala Phe
1               5                   10

<210> SEQ ID NO 112
<211> LENGTH: 14
<212> TYPE: PRT
<213> ORGANISM: Artificial
<220> FEATURE:
<223> OTHER INFORMATION: Recombinant peptide

<400> SEQUENCE: 112

Asp Trp Phe Lys Ala Phe Tyr Asp Lys Val Ala Glu Lys Phe
1               5                   10

<210> SEQ ID NO 113
<211> LENGTH: 18
<212> TYPE: PRT
<213> ORGANISM: Artificial
<220> FEATURE:
<223> OTHER INFORMATION: Recombinant peptide

<400> SEQUENCE: 113

Asp Trp Leu Lys Ala Phe Tyr Asp Lys Val Phe Glu Lys Phe Lys Glu
1               5                   10                  15

Phe Phe

<210> SEQ ID NO 114
<211> LENGTH: 18
<212> TYPE: PRT
<213> ORGANISM: Artificial
<220> FEATURE:
<223> OTHER INFORMATION: Recombinant peptide

<400> SEQUENCE: 114

Glu Trp Leu Lys Ala Phe Tyr Glu Lys Val Phe Glu Lys Phe Lys Glu
1               5                   10                  15

Phe Phe

<210> SEQ ID NO 115
<211> LENGTH: 14
<212> TYPE: PRT
<213> ORGANISM: Artificial
<220> FEATURE:
<223> OTHER INFORMATION: Recombinant peptide

<400> SEQUENCE: 115

Ala Phe Tyr Asp Lys Val Phe Glu Lys Phe Lys Glu Phe Phe
1               5                   10

<210> SEQ ID NO 116
<211> LENGTH: 14
<212> TYPE: PRT
<213> ORGANISM: Artificial
<220> FEATURE:
<223> OTHER INFORMATION: Recombinant peptide

<400> SEQUENCE: 116
```

```
Ala Phe Tyr Glu Lys Val Phe Glu Lys Phe Lys Glu Phe Phe
1               5                   10
```

<210> SEQ ID NO 117
<211> LENGTH: 14
<212> TYPE: PRT
<213> ORGANISM: Artificial
<220> FEATURE:
<223> OTHER INFORMATION: Recombinant peptide

<400> SEQUENCE: 117

```
Asp Trp Leu Lys Ala Phe Tyr Asp Lys Val Phe Glu Lys Phe
1               5                   10
```

<210> SEQ ID NO 118
<211> LENGTH: 14
<212> TYPE: PRT
<213> ORGANISM: Artificial
<220> FEATURE:
<223> OTHER INFORMATION: Recombinant peptide

<400> SEQUENCE: 118

```
Glu Trp Leu Lys Ala Phe Tyr Glu Lys Val Phe Glu Lys Phe
1               5                   10
```

<210> SEQ ID NO 119
<211> LENGTH: 14
<212> TYPE: PRT
<213> ORGANISM: Artificial
<220> FEATURE:
<223> OTHER INFORMATION: Recombinant peptide

<400> SEQUENCE: 119

```
Leu Lys Ala Phe Tyr Asp Lys Val Phe Glu Lys Phe Lys Glu
1               5                   10
```

<210> SEQ ID NO 120
<211> LENGTH: 14
<212> TYPE: PRT
<213> ORGANISM: Artificial
<220> FEATURE:
<223> OTHER INFORMATION: Recombinant peptide

<400> SEQUENCE: 120

```
Leu Lys Ala Phe Tyr Glu Lys Val Phe Glu Lys Phe Lys Glu
1               5                   10
```

<210> SEQ ID NO 121
<211> LENGTH: 18
<212> TYPE: PRT
<213> ORGANISM: Artificial
<220> FEATURE:
<223> OTHER INFORMATION: Recombinant peptide

<400> SEQUENCE: 121

```
Glu Trp Phe Lys Ala Phe Tyr Glu Lys Val Ala Asp Lys Phe Lys Asp
1               5                   10                  15

Ala Phe
```

<210> SEQ ID NO 122
<211> LENGTH: 18
<212> TYPE: PRT
<213> ORGANISM: Artificial
<220> FEATURE:
<223> OTHER INFORMATION: Recombinant peptide

<400> SEQUENCE: 122

```
Glu Trp Phe Lys Ala Phe Tyr Asp Lys Val Ala Asp Lys Phe Lys Glu
1               5                   10                  15

Ala Phe

<210> SEQ ID NO 123
<211> LENGTH: 18
<212> TYPE: PRT
<213> ORGANISM: Artificial
<220> FEATURE:
<223> OTHER INFORMATION: Recombinant peptide

<400> SEQUENCE: 123

Asp Trp Phe Lys Ala Phe Tyr Glu Lys Val Ala Asp Lys Phe Lys Glu
1               5                   10                  15

Ala Phe

<210> SEQ ID NO 124
<211> LENGTH: 18
<212> TYPE: PRT
<213> ORGANISM: Artificial
<220> FEATURE:
<223> OTHER INFORMATION: Recombinant peptide

<400> SEQUENCE: 124

Asp Trp Phe Lys Ala Phe Tyr Glu Lys Val Ala Glu Lys Phe Lys Asp
1               5                   10                  15

Ala Phe

<210> SEQ ID NO 125
<211> LENGTH: 18
<212> TYPE: PRT
<213> ORGANISM: Artificial
<220> FEATURE:
<223> OTHER INFORMATION: Recombinant peptide

<400> SEQUENCE: 125

Asp Phe Trp Lys Ala Phe Tyr Asp Lys Val Ala Glu Lys Phe Lys Glu
1               5                   10                  15

Ala Phe

<210> SEQ ID NO 126
<211> LENGTH: 18
<212> TYPE: PRT
<213> ORGANISM: Artificial
<220> FEATURE:
<223> OTHER INFORMATION: Recombinant peptide

<400> SEQUENCE: 126

Glu Phe Trp Lys Ala Phe Tyr Glu Lys Val Ala Asp Lys Phe Lys Asp
1               5                   10                  15

Ala Phe

<210> SEQ ID NO 127
<211> LENGTH: 18
<212> TYPE: PRT
<213> ORGANISM: Artificial
<220> FEATURE:
<223> OTHER INFORMATION: Recombinant peptide

<400> SEQUENCE: 127

Glu Phe Trp Lys Ala Phe Tyr Asp Lys Val Ala Asp Lys Phe Lys Glu
1               5                   10                  15
```

Ala Phe

<210> SEQ ID NO 128
<211> LENGTH: 18
<212> TYPE: PRT
<213> ORGANISM: Artificial
<220> FEATURE:
<223> OTHER INFORMATION: Recombinant peptide

<400> SEQUENCE: 128

Asp Phe Trp Lys Ala Phe Tyr Glu Lys Val Ala Asp Lys Phe Lys Glu
1               5                   10                  15

Ala Phe

<210> SEQ ID NO 129
<211> LENGTH: 18
<212> TYPE: PRT
<213> ORGANISM: Artificial
<220> FEATURE:
<223> OTHER INFORMATION: Recombinant peptide

<400> SEQUENCE: 129

Asp Phe Trp Lys Ala Phe Tyr Glu Lys Val Ala Glu Lys Phe Lys Asp
1               5                   10                  15

Ala Phe

<210> SEQ ID NO 130
<211> LENGTH: 18
<212> TYPE: PRT
<213> ORGANISM: Artificial
<220> FEATURE:
<223> OTHER INFORMATION: Recombinant peptide

<400> SEQUENCE: 130

Asp Trp Phe Lys Ala Tyr Phe Asp Lys Val Ala Glu Lys Phe Lys Glu
1               5                   10                  15

Ala Phe

<210> SEQ ID NO 131
<211> LENGTH: 18
<212> TYPE: PRT
<213> ORGANISM: Artificial
<220> FEATURE:
<223> OTHER INFORMATION: Recombinant peptide

<400> SEQUENCE: 131

Glu Trp Phe Lys Ala Tyr Phe Glu Lys Val Ala Asp Lys Phe Lys Asp
1               5                   10                  15

Ala Phe

<210> SEQ ID NO 132
<211> LENGTH: 18
<212> TYPE: PRT
<213> ORGANISM: Artificial
<220> FEATURE:
<223> OTHER INFORMATION: Recombinant peptide

<400> SEQUENCE: 132

Glu Trp Phe Lys Ala Tyr Phe Asp Lys Val Ala Asp Lys Phe Lys Glu
1               5                   10                  15

Ala Phe

<210> SEQ ID NO 133

```
<211> LENGTH: 18
<212> TYPE: PRT
<213> ORGANISM: Artificial
<220> FEATURE:
<223> OTHER INFORMATION: Recombinant peptide

<400> SEQUENCE: 133

Asp Trp Phe Lys Ala Tyr Phe Glu Lys Val Ala Asp Lys Phe Lys Glu
1               5                   10                  15

Ala Phe

<210> SEQ ID NO 134
<211> LENGTH: 18
<212> TYPE: PRT
<213> ORGANISM: Artificial
<220> FEATURE:
<223> OTHER INFORMATION: Recombinant peptide

<400> SEQUENCE: 134

Asp Trp Phe Lys Ala Tyr Phe Glu Lys Val Ala Glu Lys Phe Lys Asp
1               5                   10                  15

Ala Phe

<210> SEQ ID NO 135
<211> LENGTH: 18
<212> TYPE: PRT
<213> ORGANISM: Artificial
<220> FEATURE:
<223> OTHER INFORMATION: Recombinant peptide

<400> SEQUENCE: 135

Asp Trp Phe Lys Ala Phe Val Asp Lys Tyr Ala Glu Lys Phe Lys Glu
1               5                   10                  15

Ala Phe

<210> SEQ ID NO 136
<211> LENGTH: 18
<212> TYPE: PRT
<213> ORGANISM: Artificial
<220> FEATURE:
<223> OTHER INFORMATION: Recombinant peptide

<400> SEQUENCE: 136

Glu Trp Phe Lys Ala Phe Val Glu Lys Tyr Ala Asp Lys Phe Lys Asp
1               5                   10                  15

Ala Phe

<210> SEQ ID NO 137
<211> LENGTH: 18
<212> TYPE: PRT
<213> ORGANISM: Artificial
<220> FEATURE:
<223> OTHER INFORMATION: Recombinant peptide

<400> SEQUENCE: 137

Glu Trp Phe Lys Ala Phe Val Asp Lys Tyr Ala Asp Lys Phe Lys Glu
1               5                   10                  15

Ala Phe

<210> SEQ ID NO 138
<211> LENGTH: 18
<212> TYPE: PRT
<213> ORGANISM: Artificial
<220> FEATURE:
```

<223> OTHER INFORMATION: Recombinant peptide

<400> SEQUENCE: 138

Asp Trp Phe Lys Ala Phe Val Glu Lys Tyr Ala Asp Lys Phe Lys Glu
1               5                   10                  15

Ala Phe

<210> SEQ ID NO 139
<211> LENGTH: 18
<212> TYPE: PRT
<213> ORGANISM: Artificial
<220> FEATURE:
<223> OTHER INFORMATION: Recombinant peptide

<400> SEQUENCE: 139

Asp Trp Phe Lys Ala Phe Val Glu Lys Tyr Ala Glu Lys Phe Lys Asp
1               5                   10                  15

Ala Phe

<210> SEQ ID NO 140
<211> LENGTH: 18
<212> TYPE: PRT
<213> ORGANISM: Artificial
<220> FEATURE:
<223> OTHER INFORMATION: Recombinant peptide

<400> SEQUENCE: 140

Asp Trp Phe Lys Ala Phe Tyr Asp Lys Ala Val Glu Lys Phe Lys Glu
1               5                   10                  15

Ala Phe

<210> SEQ ID NO 141
<211> LENGTH: 18
<212> TYPE: PRT
<213> ORGANISM: Artificial
<220> FEATURE:
<223> OTHER INFORMATION: Recombinant peptide

<400> SEQUENCE: 141

Glu Trp Phe Lys Ala Phe Tyr Glu Lys Ala Val Asp Lys Phe Lys Asp
1               5                   10                  15

Ala Phe

<210> SEQ ID NO 142
<211> LENGTH: 18
<212> TYPE: PRT
<213> ORGANISM: Artificial
<220> FEATURE:
<223> OTHER INFORMATION: Recombinant peptide

<400> SEQUENCE: 142

Glu Trp Phe Lys Ala Phe Tyr Asp Lys Ala Val Asp Lys Phe Lys Glu
1               5                   10                  15

Ala Phe

<210> SEQ ID NO 143
<211> LENGTH: 18
<212> TYPE: PRT
<213> ORGANISM: Artificial
<220> FEATURE:
<223> OTHER INFORMATION: Recombinant peptide

<400> SEQUENCE: 143

Asp Trp Phe Lys Ala Phe Tyr Glu Lys Ala Val Asp Lys Phe Lys Glu
1               5                   10                  15

Ala Phe

<210> SEQ ID NO 144
<211> LENGTH: 18
<212> TYPE: PRT
<213> ORGANISM: Artificial
<220> FEATURE:
<223> OTHER INFORMATION: Recombinant peptide

<400> SEQUENCE: 144

Asp Trp Phe Lys Ala Phe Tyr Glu Lys Ala Val Glu Lys Phe Lys Asp
1               5                   10                  15

Ala Phe

<210> SEQ ID NO 145
<211> LENGTH: 18
<212> TYPE: PRT
<213> ORGANISM: Artificial
<220> FEATURE:
<223> OTHER INFORMATION: Recombinant peptide

<400> SEQUENCE: 145

Asp Trp Phe Lys Ala Phe Tyr Asp Lys Val Phe Glu Lys Ala Lys Glu
1               5                   10                  15

Ala Phe

<210> SEQ ID NO 146
<211> LENGTH: 18
<212> TYPE: PRT
<213> ORGANISM: Artificial
<220> FEATURE:
<223> OTHER INFORMATION: Recombinant peptide

<400> SEQUENCE: 146

Glu Trp Phe Lys Ala Phe Tyr Glu Lys Val Phe Asp Lys Ala Lys Asp
1               5                   10                  15

Ala Phe

<210> SEQ ID NO 147
<211> LENGTH: 18
<212> TYPE: PRT
<213> ORGANISM: Artificial
<220> FEATURE:
<223> OTHER INFORMATION: Recombinant peptide

<400> SEQUENCE: 147

Glu Trp Phe Lys Ala Phe Tyr Asp Lys Val Phe Asp Lys Ala Lys Glu
1               5                   10                  15

Ala Phe

<210> SEQ ID NO 148
<211> LENGTH: 18
<212> TYPE: PRT
<213> ORGANISM: Artificial
<220> FEATURE:
<223> OTHER INFORMATION: Recombinant peptide

<400> SEQUENCE: 148

Asp Trp Phe Lys Ala Phe Tyr Glu Lys Val Phe Asp Lys Ala Lys Glu
1               5                   10                  15

Ala Phe

<210> SEQ ID NO 149
<211> LENGTH: 18
<212> TYPE: PRT
<213> ORGANISM: Artificial
<220> FEATURE:
<223> OTHER INFORMATION: Recombinant peptide

<400> SEQUENCE: 149

Asp Trp Phe Lys Ala Phe Tyr Glu Lys Val Phe Glu Lys Ala Lys Asp
1               5                   10                  15

Ala Phe

<210> SEQ ID NO 150
<211> LENGTH: 18
<212> TYPE: PRT
<213> ORGANISM: Artificial
<220> FEATURE:
<223> OTHER INFORMATION: Recombinant peptide

<400> SEQUENCE: 150

Asp Trp Phe Lys Ala Phe Tyr Asp Lys Val Ala Glu Lys Ala Lys Glu
1               5                   10                  15

Phe Phe

<210> SEQ ID NO 151
<211> LENGTH: 18
<212> TYPE: PRT
<213> ORGANISM: Artificial
<220> FEATURE:
<223> OTHER INFORMATION: Recombinant peptide

<400> SEQUENCE: 151

Glu Trp Phe Lys Ala Phe Tyr Glu Lys Val Ala Asp Lys Ala Lys Asp
1               5                   10                  15

Phe Phe

<210> SEQ ID NO 152
<211> LENGTH: 18
<212> TYPE: PRT
<213> ORGANISM: Artificial
<220> FEATURE:
<223> OTHER INFORMATION: Recombinant peptide

<400> SEQUENCE: 152

Glu Trp Phe Lys Ala Phe Tyr Asp Lys Val Ala Asp Lys Ala Lys Glu
1               5                   10                  15

Phe Phe

<210> SEQ ID NO 153
<211> LENGTH: 18
<212> TYPE: PRT
<213> ORGANISM: Artificial
<220> FEATURE:
<223> OTHER INFORMATION: Recombinant peptide

<400> SEQUENCE: 153

Asp Trp Phe Lys Ala Phe Tyr Glu Lys Val Ala Asp Lys Ala Lys Glu
1               5                   10                  15

Phe Phe

<210> SEQ ID NO 154
<211> LENGTH: 18

```
<212> TYPE: PRT
<213> ORGANISM: Artificial
<220> FEATURE:
<223> OTHER INFORMATION: Recombinant peptide

<400> SEQUENCE: 154

Asp Trp Phe Lys Ala Phe Tyr Glu Lys Val Ala Glu Lys Ala Lys Asp
1               5                   10                  15

Phe Phe

<210> SEQ ID NO 155
<211> LENGTH: 18
<212> TYPE: PRT
<213> ORGANISM: Artificial
<220> FEATURE:
<223> OTHER INFORMATION: Recombinant peptide

<400> SEQUENCE: 155

Asp Trp Phe Lys Ala Phe Tyr Asp Lys Val Ala Glu Lys Phe Lys Glu
1               5                   10                  15

Phe Ala

<210> SEQ ID NO 156
<211> LENGTH: 18
<212> TYPE: PRT
<213> ORGANISM: Artificial
<220> FEATURE:
<223> OTHER INFORMATION: Recombinant peptide

<400> SEQUENCE: 156

Glu Trp Phe Lys Ala Phe Tyr Glu Lys Val Ala Asp Lys Phe Lys Asp
1               5                   10                  15

Phe Ala

<210> SEQ ID NO 157
<211> LENGTH: 18
<212> TYPE: PRT
<213> ORGANISM: Artificial
<220> FEATURE:
<223> OTHER INFORMATION: Recombinant peptide

<400> SEQUENCE: 157

Glu Trp Phe Lys Ala Phe Tyr Asp Lys Val Ala Asp Lys Phe Lys Glu
1               5                   10                  15

Phe Ala

<210> SEQ ID NO 158
<211> LENGTH: 18
<212> TYPE: PRT
<213> ORGANISM: Artificial
<220> FEATURE:
<223> OTHER INFORMATION: Recombinant peptide

<400> SEQUENCE: 158

Asp Trp Phe Lys Ala Phe Tyr Glu Lys Val Ala Asp Lys Phe Lys Glu
1               5                   10                  15

Phe Ala

<210> SEQ ID NO 159
<211> LENGTH: 18
<212> TYPE: PRT
<213> ORGANISM: Artificial
<220> FEATURE:
<223> OTHER INFORMATION: Recombinant peptide
```

-continued

<400> SEQUENCE: 159

Asp Trp Phe Lys Ala Phe Tyr Glu Lys Val Ala Glu Lys Phe Lys Asp
1               5                   10                  15

Phe Ala

<210> SEQ ID NO 160
<211> LENGTH: 18
<212> TYPE: PRT
<213> ORGANISM: Artificial
<220> FEATURE:
<223> OTHER INFORMATION: Recombinant peptide

<400> SEQUENCE: 160

Asp Ala Phe Lys Ala Phe Tyr Asp Lys Val Ala Glu Lys Phe Lys Glu
1               5                   10                  15

Trp Phe

<210> SEQ ID NO 161
<211> LENGTH: 18
<212> TYPE: PRT
<213> ORGANISM: Artificial
<220> FEATURE:
<223> OTHER INFORMATION: Recombinant peptide

<400> SEQUENCE: 161

Glu Ala Phe Lys Ala Phe Tyr Glu Lys Val Ala Asp Lys Phe Lys Asp
1               5                   10                  15

Trp Phe

<210> SEQ ID NO 162
<211> LENGTH: 18
<212> TYPE: PRT
<213> ORGANISM: Artificial
<220> FEATURE:
<223> OTHER INFORMATION: Recombinant peptide

<400> SEQUENCE: 162

Glu Ala Phe Lys Ala Phe Tyr Asp Lys Val Ala Asp Lys Phe Lys Glu
1               5                   10                  15

Trp Phe

<210> SEQ ID NO 163
<211> LENGTH: 18
<212> TYPE: PRT
<213> ORGANISM: Artificial
<220> FEATURE:
<223> OTHER INFORMATION: Recombinant peptide

<400> SEQUENCE: 163

Asp Ala Phe Lys Ala Phe Tyr Glu Lys Val Ala Asp Lys Phe Lys Glu
1               5                   10                  15

Trp Phe

<210> SEQ ID NO 164
<211> LENGTH: 18
<212> TYPE: PRT
<213> ORGANISM: Artificial
<220> FEATURE:
<223> OTHER INFORMATION: Recombinant peptide

<400> SEQUENCE: 164

Asp Ala Phe Lys Ala Phe Tyr Glu Lys Val Ala Glu Lys Phe Lys Asp

```
1               5                   10                  15
Trp Phe

<210> SEQ ID NO 165
<211> LENGTH: 18
<212> TYPE: PRT
<213> ORGANISM: Artificial
<220> FEATURE:
<223> OTHER INFORMATION: Recombinant peptide

<400> SEQUENCE: 165

Asp Ala Phe Lys Ala Phe Tyr Asp Lys Val Trp Glu Lys Phe Lys Glu
1               5                   10                  15

Ala Phe

<210> SEQ ID NO 166
<211> LENGTH: 18
<212> TYPE: PRT
<213> ORGANISM: Artificial
<220> FEATURE:
<223> OTHER INFORMATION: Recombinant peptide

<400> SEQUENCE: 166

Glu Ala Phe Lys Ala Phe Tyr Glu Lys Val Trp Asp Lys Phe Lys Asp
1               5                   10                  15

Ala Phe

<210> SEQ ID NO 167
<211> LENGTH: 18
<212> TYPE: PRT
<213> ORGANISM: Artificial
<220> FEATURE:
<223> OTHER INFORMATION: Recombinant peptide

<400> SEQUENCE: 167

Glu Ala Phe Lys Ala Phe Tyr Asp Lys Val Trp Asp Lys Phe Lys Glu
1               5                   10                  15

Ala Phe

<210> SEQ ID NO 168
<211> LENGTH: 18
<212> TYPE: PRT
<213> ORGANISM: Artificial
<220> FEATURE:
<223> OTHER INFORMATION: Recombinant peptide

<400> SEQUENCE: 168

Asp Ala Phe Lys Ala Phe Tyr Glu Lys Val Trp Asp Lys Phe Lys Glu
1               5                   10                  15

Ala Phe

<210> SEQ ID NO 169
<211> LENGTH: 18
<212> TYPE: PRT
<213> ORGANISM: Artificial
<220> FEATURE:
<223> OTHER INFORMATION: Recombinant peptide

<400> SEQUENCE: 169

Asp Ala Phe Lys Ala Phe Tyr Glu Lys Val Trp Glu Lys Phe Lys Asp
1               5                   10                  15

Ala Phe
```

```
<210> SEQ ID NO 170
<211> LENGTH: 18
<212> TYPE: PRT
<213> ORGANISM: Artificial
<220> FEATURE:
<223> OTHER INFORMATION: Recombinant peptide

<400> SEQUENCE: 170

Asp Tyr Phe Lys Ala Phe Trp Asp Lys Val Ala Glu Lys Phe Lys Glu
1               5                   10                  15

Ala Phe

<210> SEQ ID NO 171
<211> LENGTH: 18
<212> TYPE: PRT
<213> ORGANISM: Artificial
<220> FEATURE:
<223> OTHER INFORMATION: Recombinant peptide

<400> SEQUENCE: 171

Glu Tyr Phe Lys Ala Phe Trp Glu Lys Val Ala Asp Lys Phe Lys Asp
1               5                   10                  15

Ala Phe

<210> SEQ ID NO 172
<211> LENGTH: 18
<212> TYPE: PRT
<213> ORGANISM: Artificial
<220> FEATURE:
<223> OTHER INFORMATION: Recombinant peptide

<400> SEQUENCE: 172

Glu Tyr Phe Lys Ala Phe Trp Asp Lys Val Ala Asp Lys Phe Lys Glu
1               5                   10                  15

Ala Phe

<210> SEQ ID NO 173
<211> LENGTH: 18
<212> TYPE: PRT
<213> ORGANISM: Artificial
<220> FEATURE:
<223> OTHER INFORMATION: Recombinant peptide

<400> SEQUENCE: 173

Asp Tyr Phe Lys Ala Phe Trp Glu Lys Val Ala Asp Lys Phe Lys Glu
1               5                   10                  15

Ala Phe

<210> SEQ ID NO 174
<211> LENGTH: 18
<212> TYPE: PRT
<213> ORGANISM: Artificial
<220> FEATURE:
<223> OTHER INFORMATION: Recombinant peptide

<400> SEQUENCE: 174

Asp Tyr Phe Lys Ala Phe Trp Glu Lys Val Ala Glu Lys Phe Lys Asp
1               5                   10                  15

Ala Phe

<210> SEQ ID NO 175
<211> LENGTH: 18
<212> TYPE: PRT
```

```
<213> ORGANISM: Artificial
<220> FEATURE:
<223> OTHER INFORMATION: Recombinant peptide

<400> SEQUENCE: 175

Asp Trp Ala Lys Ala Phe Tyr Asp Lys Val Ala Glu Lys Phe Lys Glu
1               5                   10                  15

Phe Phe

<210> SEQ ID NO 176
<211> LENGTH: 18
<212> TYPE: PRT
<213> ORGANISM: Artificial
<220> FEATURE:
<223> OTHER INFORMATION: Recombinant peptide

<400> SEQUENCE: 176

Glu Trp Ala Lys Ala Phe Tyr Glu Lys Val Ala Asp Lys Phe Lys Asp
1               5                   10                  15

Phe Phe

<210> SEQ ID NO 177
<211> LENGTH: 18
<212> TYPE: PRT
<213> ORGANISM: Artificial
<220> FEATURE:
<223> OTHER INFORMATION: Recombinant peptide

<400> SEQUENCE: 177

Glu Trp Ala Lys Ala Phe Tyr Asp Lys Val Ala Asp Lys Phe Lys Glu
1               5                   10                  15

Phe Phe

<210> SEQ ID NO 178
<211> LENGTH: 18
<212> TYPE: PRT
<213> ORGANISM: Artificial
<220> FEATURE:
<223> OTHER INFORMATION: Recombinant peptide

<400> SEQUENCE: 178

Asp Trp Ala Lys Ala Phe Tyr Glu Lys Val Ala Asp Lys Phe Lys Glu
1               5                   10                  15

Phe Phe

<210> SEQ ID NO 179
<211> LENGTH: 18
<212> TYPE: PRT
<213> ORGANISM: Artificial
<220> FEATURE:
<223> OTHER INFORMATION: Recombinant peptide

<400> SEQUENCE: 179

Asp Trp Ala Lys Ala Phe Tyr Glu Lys Val Ala Glu Lys Phe Lys Asp
1               5                   10                  15

Phe Phe

<210> SEQ ID NO 180
<211> LENGTH: 18
<212> TYPE: PRT
<213> ORGANISM: Artificial
<220> FEATURE:
<223> OTHER INFORMATION: Recombinant peptide
```

```
<400> SEQUENCE: 180

Asp Trp Phe Lys Ala Ala Tyr Asp Lys Val Ala Glu Lys Phe Lys Glu
 1               5                  10                  15

Phe Phe

<210> SEQ ID NO 181
<211> LENGTH: 18
<212> TYPE: PRT
<213> ORGANISM: Artificial
<220> FEATURE:
<223> OTHER INFORMATION: Recombinant peptide

<400> SEQUENCE: 181

Glu Trp Phe Lys Ala Ala Tyr Glu Lys Val Ala Asp Lys Phe Lys Asp
 1               5                  10                  15

Phe Phe

<210> SEQ ID NO 182
<211> LENGTH: 18
<212> TYPE: PRT
<213> ORGANISM: Artificial
<220> FEATURE:
<223> OTHER INFORMATION: Recombinant peptide

<400> SEQUENCE: 182

Glu Trp Phe Lys Ala Ala Tyr Asp Lys Val Ala Asp Lys Phe Lys Glu
 1               5                  10                  15

Phe Phe

<210> SEQ ID NO 183
<211> LENGTH: 18
<212> TYPE: PRT
<213> ORGANISM: Artificial
<220> FEATURE:
<223> OTHER INFORMATION: Recombinant peptide

<400> SEQUENCE: 183

Asp Trp Phe Lys Ala Ala Tyr Glu Lys Val Ala Asp Lys Phe Lys Glu
 1               5                  10                  15

Phe Phe

<210> SEQ ID NO 184
<211> LENGTH: 18
<212> TYPE: PRT
<213> ORGANISM: Artificial
<220> FEATURE:
<223> OTHER INFORMATION: Recombinant peptide

<400> SEQUENCE: 184

Asp Trp Phe Lys Ala Ala Tyr Glu Lys Val Ala Glu Lys Phe Lys Asp
 1               5                  10                  15

Phe Phe

<210> SEQ ID NO 185
<211> LENGTH: 18
<212> TYPE: PRT
<213> ORGANISM: Artificial
<220> FEATURE:
<223> OTHER INFORMATION: Recombinant peptide

<400> SEQUENCE: 185

Asp Trp Phe Lys Ala Phe Ala Asp Lys Val Ala Glu Lys Phe Lys Glu
 1               5                  10                  15
```

Tyr Phe

<210> SEQ ID NO 186
<211> LENGTH: 18
<212> TYPE: PRT
<213> ORGANISM: Artificial
<220> FEATURE:
<223> OTHER INFORMATION: Recombinant peptide

<400> SEQUENCE: 186

Glu Trp Phe Lys Ala Phe Ala Glu Lys Val Ala Asp Lys Phe Lys Asp
1               5                   10                  15

Tyr Phe

<210> SEQ ID NO 187
<211> LENGTH: 18
<212> TYPE: PRT
<213> ORGANISM: Artificial
<220> FEATURE:
<223> OTHER INFORMATION: Recombinant peptide

<400> SEQUENCE: 187

Glu Trp Phe Lys Ala Phe Ala Asp Lys Val Ala Asp Lys Phe Lys Glu
1               5                   10                  15

Tyr Phe

<210> SEQ ID NO 188
<211> LENGTH: 18
<212> TYPE: PRT
<213> ORGANISM: Artificial
<220> FEATURE:
<223> OTHER INFORMATION: Recombinant peptide

<400> SEQUENCE: 188

Asp Trp Phe Lys Ala Phe Ala Glu Lys Val Ala Asp Lys Phe Lys Glu
1               5                   10                  15

Tyr Phe

<210> SEQ ID NO 189
<211> LENGTH: 18
<212> TYPE: PRT
<213> ORGANISM: Artificial
<220> FEATURE:
<223> OTHER INFORMATION: Recombinant peptide

<400> SEQUENCE: 189

Asp Trp Phe Lys Ala Phe Ala Glu Lys Val Ala Glu Lys Phe Lys Asp
1               5                   10                  15

Tyr Phe

<210> SEQ ID NO 190
<211> LENGTH: 18
<212> TYPE: PRT
<213> ORGANISM: Artificial
<220> FEATURE:
<223> OTHER INFORMATION: Recombinant peptide

<400> SEQUENCE: 190

Asp Trp Phe Lys Ala Phe Tyr Asp Lys Ala Ala Glu Lys Phe Lys Glu
1               5                   10                  15

Val Phe

```
<210> SEQ ID NO 191
<211> LENGTH: 18
<212> TYPE: PRT
<213> ORGANISM: Artificial
<220> FEATURE:
<223> OTHER INFORMATION: Recombinant peptide

<400> SEQUENCE: 191

Glu Trp Phe Lys Ala Phe Tyr Glu Lys Ala Ala Asp Lys Phe Lys Asp
1               5                   10                  15

Val Phe

<210> SEQ ID NO 192
<211> LENGTH: 18
<212> TYPE: PRT
<213> ORGANISM: Artificial
<220> FEATURE:
<223> OTHER INFORMATION: Recombinant peptide

<400> SEQUENCE: 192

Glu Trp Phe Lys Ala Phe Tyr Asp Lys Ala Ala Asp Lys Phe Lys Glu
1               5                   10                  15

Val Phe

<210> SEQ ID NO 193
<211> LENGTH: 18
<212> TYPE: PRT
<213> ORGANISM: Artificial
<220> FEATURE:
<223> OTHER INFORMATION: Recombinant peptide

<400> SEQUENCE: 193

Asp Trp Phe Lys Ala Phe Tyr Glu Lys Ala Ala Asp Lys Phe Lys Glu
1               5                   10                  15

Val Phe

<210> SEQ ID NO 194
<211> LENGTH: 18
<212> TYPE: PRT
<213> ORGANISM: Artificial
<220> FEATURE:
<223> OTHER INFORMATION: Recombinant peptide

<400> SEQUENCE: 194

Asp Trp Phe Lys Ala Phe Tyr Glu Lys Ala Ala Glu Lys Phe Lys Asp
1               5                   10                  15

Val Phe

<210> SEQ ID NO 195
<211> LENGTH: 18
<212> TYPE: PRT
<213> ORGANISM: Artificial
<220> FEATURE:
<223> OTHER INFORMATION: Recombinant peptide

<400> SEQUENCE: 195

Asp Trp Tyr Lys Ala Phe Phe Asp Lys Val Ala Glu Lys Phe Lys Glu
1               5                   10                  15

Ala Phe

<210> SEQ ID NO 196
<211> LENGTH: 18
<212> TYPE: PRT
<213> ORGANISM: Artificial
```

<220> FEATURE:
<223> OTHER INFORMATION: Recombinant peptide

<400> SEQUENCE: 196

Glu Trp Tyr Lys Ala Phe Phe Glu Lys Val Ala Asp Lys Phe Lys Asp
1               5                   10                  15

Ala Phe

<210> SEQ ID NO 197
<211> LENGTH: 18
<212> TYPE: PRT
<213> ORGANISM: Artificial
<220> FEATURE:
<223> OTHER INFORMATION: Recombinant peptide

<400> SEQUENCE: 197

Glu Trp Tyr Lys Ala Phe Phe Asp Lys Val Ala Asp Lys Phe Lys Glu
1               5                   10                  15

Ala Phe

<210> SEQ ID NO 198
<211> LENGTH: 18
<212> TYPE: PRT
<213> ORGANISM: Artificial
<220> FEATURE:
<223> OTHER INFORMATION: Recombinant peptide

<400> SEQUENCE: 198

Asp Trp Tyr Lys Ala Phe Phe Glu Lys Val Ala Asp Lys Phe Lys Glu
1               5                   10                  15

Ala Phe

<210> SEQ ID NO 199
<211> LENGTH: 18
<212> TYPE: PRT
<213> ORGANISM: Artificial
<220> FEATURE:
<223> OTHER INFORMATION: Recombinant peptide

<400> SEQUENCE: 199

Asp Trp Tyr Lys Ala Phe Phe Glu Lys Val Ala Glu Lys Phe Lys Asp
1               5                   10                  15

Ala Phe

<210> SEQ ID NO 200
<211> LENGTH: 18
<212> TYPE: PRT
<213> ORGANISM: Artificial
<220> FEATURE:
<223> OTHER INFORMATION: Recombinant peptide

<400> SEQUENCE: 200

Asp Trp Val Lys Ala Phe Tyr Asp Lys Phe Ala Glu Lys Phe Lys Glu
1               5                   10                  15

Ala Phe

<210> SEQ ID NO 201
<211> LENGTH: 18
<212> TYPE: PRT
<213> ORGANISM: Artificial
<220> FEATURE:
<223> OTHER INFORMATION: Recombinant peptide

<400> SEQUENCE: 201

```
Glu Trp Val Lys Ala Phe Tyr Glu Lys Phe Ala Asp Lys Phe Lys Asp
1               5                   10                  15

Ala Phe

<210> SEQ ID NO 202
<211> LENGTH: 18
<212> TYPE: PRT
<213> ORGANISM: Artificial
<220> FEATURE:
<223> OTHER INFORMATION: Recombinant peptide

<400> SEQUENCE: 202

Glu Trp Val Lys Ala Phe Tyr Asp Lys Phe Ala Asp Lys Phe Lys Glu
1               5                   10                  15

Ala Phe

<210> SEQ ID NO 203
<211> LENGTH: 18
<212> TYPE: PRT
<213> ORGANISM: Artificial
<220> FEATURE:
<223> OTHER INFORMATION: Recombinant peptide

<400> SEQUENCE: 203

Asp Trp Val Lys Ala Phe Tyr Glu Lys Phe Ala Asp Lys Phe Lys Glu
1               5                   10                  15

Ala Phe

<210> SEQ ID NO 204
<211> LENGTH: 18
<212> TYPE: PRT
<213> ORGANISM: Artificial
<220> FEATURE:
<223> OTHER INFORMATION: Recombinant peptide

<400> SEQUENCE: 204

Asp Trp Val Lys Ala Phe Tyr Glu Lys Phe Ala Glu Lys Phe Lys Asp
1               5                   10                  15

Ala Phe

<210> SEQ ID NO 205
<211> LENGTH: 18
<212> TYPE: PRT
<213> ORGANISM: Artificial
<220> FEATURE:
<223> OTHER INFORMATION: Recombinant peptide

<400> SEQUENCE: 205

Asp Trp Phe Lys Ala Phe Phe Asp Lys Val Ala Glu Lys Tyr Lys Glu
1               5                   10                  15

Ala Phe

<210> SEQ ID NO 206
<211> LENGTH: 18
<212> TYPE: PRT
<213> ORGANISM: Artificial
<220> FEATURE:
<223> OTHER INFORMATION: Recombinant peptide

<400> SEQUENCE: 206

Glu Trp Phe Lys Ala Phe Phe Glu Lys Val Ala Asp Lys Tyr Lys Asp
1               5                   10                  15
```

Ala Phe

<210> SEQ ID NO 207
<211> LENGTH: 18
<212> TYPE: PRT
<213> ORGANISM: Artificial
<220> FEATURE:
<223> OTHER INFORMATION: Recombinant peptide

<400> SEQUENCE: 207

Glu Trp Phe Lys Ala Phe Phe Asp Lys Val Ala Asp Lys Tyr Lys Glu
1               5                   10                  15

Ala Phe

<210> SEQ ID NO 208
<211> LENGTH: 18
<212> TYPE: PRT
<213> ORGANISM: Artificial
<220> FEATURE:
<223> OTHER INFORMATION: Recombinant peptide

<400> SEQUENCE: 208

Asp Trp Phe Lys Ala Phe Phe Glu Lys Val Ala Asp Lys Tyr Lys Glu
1               5                   10                  15

Ala Phe

<210> SEQ ID NO 209
<211> LENGTH: 18
<212> TYPE: PRT
<213> ORGANISM: Artificial
<220> FEATURE:
<223> OTHER INFORMATION: Recombinant peptide

<400> SEQUENCE: 209

Asp Trp Phe Lys Ala Phe Phe Glu Lys Val Ala Asp Lys Tyr Lys Glu
1               5                   10                  15

Ala Phe

<210> SEQ ID NO 210
<211> LENGTH: 18
<212> TYPE: PRT
<213> ORGANISM: Artificial
<220> FEATURE:
<223> OTHER INFORMATION: Recombinant peptide

<400> SEQUENCE: 210

Asp Trp Phe Lys Ala Phe Phe Asp Lys Val Ala Glu Lys Phe Lys Glu
1               5                   10                  15

Ala Tyr

<210> SEQ ID NO 211
<211> LENGTH: 18
<212> TYPE: PRT
<213> ORGANISM: Artificial
<220> FEATURE:
<223> OTHER INFORMATION: Recombinant peptide

<400> SEQUENCE: 211

Glu Trp Phe Lys Ala Phe Phe Glu Lys Val Ala Asp Lys Phe Lys Asp
1               5                   10                  15

Ala Tyr

<210> SEQ ID NO 212

<211> LENGTH: 18
<212> TYPE: PRT
<213> ORGANISM: Artificial
<220> FEATURE:
<223> OTHER INFORMATION: Recombinant peptide

<400> SEQUENCE: 212

Glu Trp Phe Lys Ala Phe Phe Asp Lys Val Ala Asp Lys Phe Lys Glu
1               5                   10                  15

Ala Tyr

<210> SEQ ID NO 213
<211> LENGTH: 18
<212> TYPE: PRT
<213> ORGANISM: Artificial
<220> FEATURE:
<223> OTHER INFORMATION: Recombinant peptide

<400> SEQUENCE: 213

Asp Trp Phe Lys Ala Phe Phe Glu Lys Val Ala Asp Lys Phe Lys Glu
1               5                   10                  15

Ala Tyr

<210> SEQ ID NO 214
<211> LENGTH: 18
<212> TYPE: PRT
<213> ORGANISM: Artificial
<220> FEATURE:
<223> OTHER INFORMATION: Recombinant peptide

<400> SEQUENCE: 214

Asp Trp Phe Lys Ala Phe Phe Glu Lys Val Ala Glu Lys Phe Lys Asp
1               5                   10                  15

Ala Tyr

<210> SEQ ID NO 215
<211> LENGTH: 18
<212> TYPE: PRT
<213> ORGANISM: Artificial
<220> FEATURE:
<223> OTHER INFORMATION: Recombinant peptide

<400> SEQUENCE: 215

Asp Trp Phe Lys Ala Phe Tyr Asp Lys Phe Ala Glu Lys Phe Lys Glu
1               5                   10                  15

Ala Val

<210> SEQ ID NO 216
<211> LENGTH: 18
<212> TYPE: PRT
<213> ORGANISM: Artificial
<220> FEATURE:
<223> OTHER INFORMATION: Recombinant peptide

<400> SEQUENCE: 216

Glu Trp Phe Lys Ala Phe Tyr Glu Lys Phe Ala Asp Lys Phe Lys Asp
1               5                   10                  15

Ala Val

<210> SEQ ID NO 217
<211> LENGTH: 18
<212> TYPE: PRT
<213> ORGANISM: Artificial
<220> FEATURE:

<223> OTHER INFORMATION: Recombinant peptide

<400> SEQUENCE: 217

Glu Trp Phe Lys Ala Phe Tyr Asp Lys Phe Ala Asp Lys Phe Lys Glu
1               5                   10                  15

Ala Val

<210> SEQ ID NO 218
<211> LENGTH: 18
<212> TYPE: PRT
<213> ORGANISM: Artificial
<220> FEATURE:
<223> OTHER INFORMATION: Recombinant peptide

<400> SEQUENCE: 218

Asp Trp Phe Lys Ala Phe Tyr Glu Lys Phe Ala Asp Lys Phe Lys Glu
1               5                   10                  15

Ala Val

<210> SEQ ID NO 219
<211> LENGTH: 18
<212> TYPE: PRT
<213> ORGANISM: Artificial
<220> FEATURE:
<223> OTHER INFORMATION: Recombinant peptide

<400> SEQUENCE: 219

Asp Trp Phe Lys Ala Phe Tyr Glu Lys Phe Ala Glu Lys Phe Lys Asp
1               5                   10                  15

Ala Val

<210> SEQ ID NO 220
<211> LENGTH: 18
<212> TYPE: PRT
<213> ORGANISM: Artificial
<220> FEATURE:
<223> OTHER INFORMATION: Recombinant peptide

<400> SEQUENCE: 220

Asp Lys Phe Lys Ala Phe Tyr Asp Lys Val Ala Glu Lys Phe Trp Glu
1               5                   10                  15

Ala Phe

<210> SEQ ID NO 221
<211> LENGTH: 18
<212> TYPE: PRT
<213> ORGANISM: Artificial
<220> FEATURE:
<223> OTHER INFORMATION: Recombinant peptide

<400> SEQUENCE: 221

Glu Lys Phe Lys Ala Phe Tyr Glu Lys Val Ala Asp Lys Phe Trp Asp
1               5                   10                  15

Ala Phe

<210> SEQ ID NO 222
<211> LENGTH: 18
<212> TYPE: PRT
<213> ORGANISM: Artificial
<220> FEATURE:
<223> OTHER INFORMATION: Recombinant peptide

<400> SEQUENCE: 222

```
Glu Lys Phe Lys Ala Phe Tyr Asp Lys Val Ala Asp Lys Phe Trp Glu
1               5                   10                  15

Ala Phe

<210> SEQ ID NO 223
<211> LENGTH: 18
<212> TYPE: PRT
<213> ORGANISM: Artificial
<220> FEATURE:
<223> OTHER INFORMATION: Recombinant peptide

<400> SEQUENCE: 223

Asp Lys Phe Lys Ala Phe Tyr Glu Lys Val Ala Asp Lys Phe Trp Glu
1               5                   10                  15

Ala Phe

<210> SEQ ID NO 224
<211> LENGTH: 18
<212> TYPE: PRT
<213> ORGANISM: Artificial
<220> FEATURE:
<223> OTHER INFORMATION: Recombinant peptide

<400> SEQUENCE: 224

Asp Lys Phe Lys Ala Phe Tyr Glu Lys Val Ala Glu Lys Phe Trp Asp
1               5                   10                  15

Ala Phe

<210> SEQ ID NO 225
<211> LENGTH: 18
<212> TYPE: PRT
<213> ORGANISM: Artificial
<220> FEATURE:
<223> OTHER INFORMATION: Recombinant peptide

<400> SEQUENCE: 225

Asp Lys Trp Lys Ala Phe Tyr Asp Lys Val Ala Glu Lys Phe Phe Glu
1               5                   10                  15

Ala Phe

<210> SEQ ID NO 226
<211> LENGTH: 18
<212> TYPE: PRT
<213> ORGANISM: Artificial
<220> FEATURE:
<223> OTHER INFORMATION: Recombinant peptide

<400> SEQUENCE: 226

Glu Lys Trp Lys Ala Phe Tyr Glu Lys Val Ala Asp Lys Phe Phe Asp
1               5                   10                  15

Ala Phe

<210> SEQ ID NO 227
<211> LENGTH: 18
<212> TYPE: PRT
<213> ORGANISM: Artificial
<220> FEATURE:
<223> OTHER INFORMATION: Recombinant peptide

<400> SEQUENCE: 227

Glu Lys Trp Lys Ala Phe Tyr Asp Lys Val Ala Asp Lys Phe Phe Glu
1               5                   10                  15

Ala Phe
```

```
<210> SEQ ID NO 228
<211> LENGTH: 18
<212> TYPE: PRT
<213> ORGANISM: Artificial
<220> FEATURE:
<223> OTHER INFORMATION: Recombinant peptide

<400> SEQUENCE: 228

Asp Lys Trp Lys Ala Phe Tyr Glu Lys Val Ala Asp Lys Phe Phe Glu
1               5                   10                  15

Ala Phe

<210> SEQ ID NO 229
<211> LENGTH: 18
<212> TYPE: PRT
<213> ORGANISM: Artificial
<220> FEATURE:
<223> OTHER INFORMATION: Recombinant peptide

<400> SEQUENCE: 229

Asp Lys Trp Lys Ala Phe Tyr Glu Lys Val Ala Glu Lys Phe Phe Asp
1               5                   10                  15

Ala Phe

<210> SEQ ID NO 230
<211> LENGTH: 18
<212> TYPE: PRT
<213> ORGANISM: Artificial
<220> FEATURE:
<223> OTHER INFORMATION: Recombinant peptide

<400> SEQUENCE: 230

Asp Lys Phe Lys Ala Phe Tyr Asp Lys Trp Ala Glu Val Phe Lys Glu
1               5                   10                  15

Ala Phe

<210> SEQ ID NO 231
<211> LENGTH: 18
<212> TYPE: PRT
<213> ORGANISM: Artificial
<220> FEATURE:
<223> OTHER INFORMATION: Recombinant peptide

<400> SEQUENCE: 231

Glu Lys Phe Lys Ala Phe Tyr Glu Lys Trp Ala Asp Val Phe Lys Asp
1               5                   10                  15

Ala Phe

<210> SEQ ID NO 232
<211> LENGTH: 18
<212> TYPE: PRT
<213> ORGANISM: Artificial
<220> FEATURE:
<223> OTHER INFORMATION: Recombinant peptide

<400> SEQUENCE: 232

Glu Lys Phe Lys Ala Phe Tyr Asp Lys Trp Ala Asp Val Phe Lys Glu
1               5                   10                  15

Ala Phe

<210> SEQ ID NO 233
<211> LENGTH: 18
```

<212> TYPE: PRT
<213> ORGANISM: Artificial
<220> FEATURE:
<223> OTHER INFORMATION: Recombinant peptide

<400> SEQUENCE: 233

Asp Lys Phe Lys Ala Phe Tyr Glu Lys Trp Ala Asp Val Phe Lys Glu
1               5                   10                  15

Ala Phe

<210> SEQ ID NO 234
<211> LENGTH: 18
<212> TYPE: PRT
<213> ORGANISM: Artificial
<220> FEATURE:
<223> OTHER INFORMATION: Recombinant peptide

<400> SEQUENCE: 234

Asp Lys Phe Lys Ala Phe Tyr Glu Lys Trp Ala Glu Val Phe Lys Asp
1               5                   10                  15

Ala Phe

<210> SEQ ID NO 235
<211> LENGTH: 18
<212> TYPE: PRT
<213> ORGANISM: Artificial
<220> FEATURE:
<223> OTHER INFORMATION: Recombinant peptide

<400> SEQUENCE: 235

Asp Lys Phe Lys Ala Phe Tyr Asp Lys Val Ala Glu Phe Trp Lys Glu
1               5                   10                  15

Ala Phe

<210> SEQ ID NO 236
<211> LENGTH: 18
<212> TYPE: PRT
<213> ORGANISM: Artificial
<220> FEATURE:
<223> OTHER INFORMATION: Recombinant peptide

<400> SEQUENCE: 236

Glu Lys Phe Lys Ala Phe Tyr Glu Lys Val Ala Asp Phe Trp Lys Asp
1               5                   10                  15

Ala Phe

<210> SEQ ID NO 237
<211> LENGTH: 18
<212> TYPE: PRT
<213> ORGANISM: Artificial
<220> FEATURE:
<223> OTHER INFORMATION: Recombinant peptide

<400> SEQUENCE: 237

Glu Lys Phe Lys Ala Phe Tyr Asp Lys Val Ala Asp Phe Trp Lys Glu
1               5                   10                  15

Ala Phe

<210> SEQ ID NO 238
<211> LENGTH: 18
<212> TYPE: PRT
<213> ORGANISM: Artificial
<220> FEATURE:
<223> OTHER INFORMATION: Recombinant peptide

<400> SEQUENCE: 238

Asp Lys Phe Lys Ala Phe Tyr Glu Lys Val Ala Asp Phe Trp Lys Glu
1               5                   10                  15

Ala Phe

<210> SEQ ID NO 239
<211> LENGTH: 18
<212> TYPE: PRT
<213> ORGANISM: Artificial
<220> FEATURE:
<223> OTHER INFORMATION: Recombinant peptide

<400> SEQUENCE: 239

Asp Lys Phe Lys Ala Phe Tyr Glu Lys Val Ala Glu Phe Trp Lys Asp
1               5                   10                  15

Ala Phe

<210> SEQ ID NO 240
<211> LENGTH: 18
<212> TYPE: PRT
<213> ORGANISM: Artificial
<220> FEATURE:
<223> OTHER INFORMATION: Recombinant peptide

<400> SEQUENCE: 240

Phe Ala Glu Lys Phe Lys Glu Ala Val Lys Asp Tyr Phe Ala Lys Phe
1               5                   10                  15

Trp Asp

<210> SEQ ID NO 241
<211> LENGTH: 18
<212> TYPE: PRT
<213> ORGANISM: Artificial
<220> FEATURE:
<223> OTHER INFORMATION: Recombinant peptide

<400> SEQUENCE: 241

Phe Ala Asp Lys Phe Lys Asp Ala Val Lys Glu Tyr Phe Ala Lys Phe
1               5                   10                  15

Trp Glu

<210> SEQ ID NO 242
<211> LENGTH: 18
<212> TYPE: PRT
<213> ORGANISM: Artificial
<220> FEATURE:
<223> OTHER INFORMATION: Recombinant peptide

<400> SEQUENCE: 242

Phe Ala Asp Lys Phe Lys Glu Ala Val Lys Asp Tyr Phe Ala Lys Phe
1               5                   10                  15

Trp Glu

<210> SEQ ID NO 243
<211> LENGTH: 18
<212> TYPE: PRT
<213> ORGANISM: Artificial
<220> FEATURE:
<223> OTHER INFORMATION: Recombinant peptide

<400> SEQUENCE: 243

Phe Ala Glu Lys Phe Lys Asp Ala Val Lys Glu Tyr Phe Ala Lys Phe

```
1               5                   10                  15

Trp Asp

<210> SEQ ID NO 244
<211> LENGTH: 18
<212> TYPE: PRT
<213> ORGANISM: Artificial
<220> FEATURE:
<223> OTHER INFORMATION: Recombinant peptide

<400> SEQUENCE: 244

Phe Ala Glu Lys Phe Lys Asp Ala Val Lys Asp Tyr Phe Ala Lys Phe
1               5                   10                  15

Trp Glu

<210> SEQ ID NO 245
<211> LENGTH: 18
<212> TYPE: PRT
<213> ORGANISM: Artificial
<220> FEATURE:
<223> OTHER INFORMATION: Recombinant peptide

<400> SEQUENCE: 245

Phe Trp Glu Lys Phe Lys Glu Ala Val Lys Asp Tyr Phe Ala Lys Phe
1               5                   10                  15

Ala Asp

<210> SEQ ID NO 246
<211> LENGTH: 18
<212> TYPE: PRT
<213> ORGANISM: Artificial
<220> FEATURE:
<223> OTHER INFORMATION: Recombinant peptide

<400> SEQUENCE: 246

Phe Trp Asp Lys Phe Lys Asp Ala Val Lys Glu Tyr Phe Ala Lys Phe
1               5                   10                  15

Ala Glu

<210> SEQ ID NO 247
<211> LENGTH: 18
<212> TYPE: PRT
<213> ORGANISM: Artificial
<220> FEATURE:
<223> OTHER INFORMATION: Recombinant peptide

<400> SEQUENCE: 247

Phe Ala Asp Lys Phe Lys Glu Ala Val Lys Asp Tyr Phe Ala Lys Phe
1               5                   10                  15

Trp Glu

<210> SEQ ID NO 248
<211> LENGTH: 18
<212> TYPE: PRT
<213> ORGANISM: Artificial
<220> FEATURE:
<223> OTHER INFORMATION: Recombinant peptide

<400> SEQUENCE: 248

Phe Ala Glu Lys Phe Lys Asp Ala Val Lys Glu Tyr Phe Ala Lys Phe
1               5                   10                  15

Trp Asp
```

<210> SEQ ID NO 249
<211> LENGTH: 18
<212> TYPE: PRT
<213> ORGANISM: Artificial
<220> FEATURE:
<223> OTHER INFORMATION: Recombinant peptide

<400> SEQUENCE: 249

Phe Ala Glu Lys Phe Lys Asp Ala Val Lys Asp Tyr Phe Ala Lys Phe
1               5                   10                  15

Trp Glu

<210> SEQ ID NO 250
<211> LENGTH: 18
<212> TYPE: PRT
<213> ORGANISM: Artificial
<220> FEATURE:
<223> OTHER INFORMATION: Recombinant peptide

<400> SEQUENCE: 250

Phe Phe Glu Lys Phe Lys Glu Ala Val Lys Asp Tyr Phe Ala Lys Ala
1               5                   10                  15

Trp Asp

<210> SEQ ID NO 251
<211> LENGTH: 18
<212> TYPE: PRT
<213> ORGANISM: Artificial
<220> FEATURE:
<223> OTHER INFORMATION: Recombinant peptide

<400> SEQUENCE: 251

Phe Phe Asp Lys Phe Lys Asp Ala Val Lys Glu Tyr Phe Ala Lys Ala
1               5                   10                  15

Trp Glu

<210> SEQ ID NO 252
<211> LENGTH: 18
<212> TYPE: PRT
<213> ORGANISM: Artificial
<220> FEATURE:
<223> OTHER INFORMATION: Recombinant peptide

<400> SEQUENCE: 252

Phe Phe Asp Lys Phe Lys Glu Ala Val Lys Asp Tyr Phe Ala Lys Ala
1               5                   10                  15

Trp Glu

<210> SEQ ID NO 253
<211> LENGTH: 18
<212> TYPE: PRT
<213> ORGANISM: Artificial
<220> FEATURE:
<223> OTHER INFORMATION: Recombinant peptide

<400> SEQUENCE: 253

Phe Phe Glu Lys Phe Lys Asp Ala Val Lys Glu Tyr Phe Ala Lys Ala
1               5                   10                  15

Trp Asp

<210> SEQ ID NO 254
<211> LENGTH: 18
<212> TYPE: PRT

```
<213> ORGANISM: Artificial
<220> FEATURE:
<223> OTHER INFORMATION: Recombinant peptide

<400> SEQUENCE: 254

Phe Phe Glu Lys Phe Lys Asp Ala Val Lys Asp Tyr Phe Ala Lys Ala
1               5                   10                  15

Trp Glu

<210> SEQ ID NO 255
<211> LENGTH: 18
<212> TYPE: PRT
<213> ORGANISM: Artificial
<220> FEATURE:
<223> OTHER INFORMATION: Recombinant peptide

<400> SEQUENCE: 255

Phe Ala Glu Lys Ala Lys Glu Phe Val Lys Asp Tyr Phe Ala Lys Phe
1               5                   10                  15

Trp Asp

<210> SEQ ID NO 256
<211> LENGTH: 18
<212> TYPE: PRT
<213> ORGANISM: Artificial
<220> FEATURE:
<223> OTHER INFORMATION: Recombinant peptide

<400> SEQUENCE: 256

Phe Ala Asp Lys Ala Lys Asp Phe Val Lys Glu Tyr Phe Ala Lys Phe
1               5                   10                  15

Trp Glu

<210> SEQ ID NO 257
<211> LENGTH: 18
<212> TYPE: PRT
<213> ORGANISM: Artificial
<220> FEATURE:
<223> OTHER INFORMATION: Recombinant peptide

<400> SEQUENCE: 257

Phe Ala Asp Lys Ala Lys Glu Phe Val Lys Asp Tyr Phe Ala Lys Phe
1               5                   10                  15

Trp Glu

<210> SEQ ID NO 258
<211> LENGTH: 18
<212> TYPE: PRT
<213> ORGANISM: Artificial
<220> FEATURE:
<223> OTHER INFORMATION: Recombinant peptide

<400> SEQUENCE: 258

Phe Ala Glu Lys Ala Lys Asp Phe Val Lys Glu Tyr Phe Ala Lys Phe
1               5                   10                  15

Trp Asp

<210> SEQ ID NO 259
<211> LENGTH: 18
<212> TYPE: PRT
<213> ORGANISM: Artificial
<220> FEATURE:
<223> OTHER INFORMATION: Recombinant peptide
```

```
<400> SEQUENCE: 259

Phe Ala Glu Lys Ala Lys Asp Phe Val Lys Asp Tyr Phe Ala Lys Phe
1               5                   10                  15

Trp Glu

<210> SEQ ID NO 260
<211> LENGTH: 18
<212> TYPE: PRT
<213> ORGANISM: Artificial
<220> FEATURE:
<223> OTHER INFORMATION: Recombinant peptide

<400> SEQUENCE: 260

Phe Ala Glu Lys Phe Lys Glu Val Ala Lys Asp Tyr Phe Ala Lys Phe
1               5                   10                  15

Trp Asp

<210> SEQ ID NO 261
<211> LENGTH: 18
<212> TYPE: PRT
<213> ORGANISM: Artificial
<220> FEATURE:
<223> OTHER INFORMATION: Recombinant peptide

<400> SEQUENCE: 261

Phe Ala Asp Lys Phe Lys Asp Val Ala Lys Glu Tyr Phe Ala Lys Phe
1               5                   10                  15

Trp Glu

<210> SEQ ID NO 262
<211> LENGTH: 18
<212> TYPE: PRT
<213> ORGANISM: Artificial
<220> FEATURE:
<223> OTHER INFORMATION: Recombinant peptide

<400> SEQUENCE: 262

Phe Ala Asp Lys Phe Lys Glu Val Ala Lys Asp Tyr Phe Ala Lys Phe
1               5                   10                  15

Trp Glu

<210> SEQ ID NO 263
<211> LENGTH: 18
<212> TYPE: PRT
<213> ORGANISM: Artificial
<220> FEATURE:
<223> OTHER INFORMATION: Recombinant peptide

<400> SEQUENCE: 263

Phe Ala Glu Lys Phe Lys Asp Val Ala Lys Glu Tyr Phe Ala Lys Phe
1               5                   10                  15

Trp Asp

<210> SEQ ID NO 264
<211> LENGTH: 18
<212> TYPE: PRT
<213> ORGANISM: Artificial
<220> FEATURE:
<223> OTHER INFORMATION: Recombinant peptide

<400> SEQUENCE: 264

Phe Ala Glu Lys Phe Lys Asp Val Ala Lys Asp Tyr Phe Ala Lys Phe
1               5                   10                  15
```

Trp Glu

<210> SEQ ID NO 265
<211> LENGTH: 18
<212> TYPE: PRT
<213> ORGANISM: Artificial
<220> FEATURE:
<223> OTHER INFORMATION: Recombinant peptide

<400> SEQUENCE: 265

Phe Ala Glu Lys Phe Lys Glu Ala Tyr Lys Asp Val Phe Ala Lys Phe
1               5                   10                  15

Trp Asp

<210> SEQ ID NO 266
<211> LENGTH: 18
<212> TYPE: PRT
<213> ORGANISM: Artificial
<220> FEATURE:
<223> OTHER INFORMATION: Recombinant peptide

<400> SEQUENCE: 266

Phe Ala Asp Lys Phe Lys Asp Ala Tyr Lys Glu Val Phe Ala Lys Phe
1               5                   10                  15

Trp Glu

<210> SEQ ID NO 267
<211> LENGTH: 18
<212> TYPE: PRT
<213> ORGANISM: Artificial
<220> FEATURE:
<223> OTHER INFORMATION: Recombinant peptide

<400> SEQUENCE: 267

Phe Ala Asp Lys Phe Lys Glu Ala Tyr Lys Asp Val Phe Ala Lys Phe
1               5                   10                  15

Trp Glu

<210> SEQ ID NO 268
<211> LENGTH: 18
<212> TYPE: PRT
<213> ORGANISM: Artificial
<220> FEATURE:
<223> OTHER INFORMATION: Recombinant peptide

<400> SEQUENCE: 268

Phe Ala Glu Lys Phe Lys Asp Ala Tyr Lys Glu Val Phe Ala Lys Phe
1               5                   10                  15

Trp Asp

<210> SEQ ID NO 269
<211> LENGTH: 18
<212> TYPE: PRT
<213> ORGANISM: Artificial
<220> FEATURE:
<223> OTHER INFORMATION: Recombinant peptide

<400> SEQUENCE: 269

Phe Ala Glu Lys Phe Lys Asp Ala Tyr Lys Asp Val Phe Ala Lys Phe
1               5                   10                  15

Trp Glu

```
<210> SEQ ID NO 270
<211> LENGTH: 18
<212> TYPE: PRT
<213> ORGANISM: Artificial
<220> FEATURE:
<223> OTHER INFORMATION: Recombinant peptide

<400> SEQUENCE: 270

Phe Ala Glu Lys Phe Lys Glu Ala Val Lys Asp Phe Tyr Ala Lys Phe
1               5                   10                  15

Trp Asp

<210> SEQ ID NO 271
<211> LENGTH: 18
<212> TYPE: PRT
<213> ORGANISM: Artificial
<220> FEATURE:
<223> OTHER INFORMATION: Recombinant peptide

<400> SEQUENCE: 271

Phe Ala Asp Lys Phe Lys Asp Ala Val Lys Glu Phe Tyr Ala Lys Phe
1               5                   10                  15

Trp Glu

<210> SEQ ID NO 272
<211> LENGTH: 18
<212> TYPE: PRT
<213> ORGANISM: Artificial
<220> FEATURE:
<223> OTHER INFORMATION: Recombinant peptide

<400> SEQUENCE: 272

Phe Ala Asp Lys Phe Lys Glu Ala Val Lys Asp Phe Tyr Ala Lys Phe
1               5                   10                  15

Trp Glu

<210> SEQ ID NO 273
<211> LENGTH: 18
<212> TYPE: PRT
<213> ORGANISM: Artificial
<220> FEATURE:
<223> OTHER INFORMATION: Recombinant peptide

<400> SEQUENCE: 273

Phe Ala Glu Lys Phe Lys Asp Ala Val Lys Glu Phe Tyr Ala Lys Phe
1               5                   10                  15

Trp Asp

<210> SEQ ID NO 274
<211> LENGTH: 18
<212> TYPE: PRT
<213> ORGANISM: Artificial
<220> FEATURE:
<223> OTHER INFORMATION: Recombinant peptide

<400> SEQUENCE: 274

Phe Ala Glu Lys Phe Lys Asp Ala Val Lys Asp Phe Tyr Ala Lys Phe
1               5                   10                  15

Trp Glu

<210> SEQ ID NO 275
<211> LENGTH: 18
<212> TYPE: PRT
<213> ORGANISM: Artificial
```

```
<220> FEATURE:
<223> OTHER INFORMATION: Recombinant peptide

<400> SEQUENCE: 275

Phe Ala Glu Lys Phe Trp Glu Ala Val Lys Asp Tyr Phe Ala Lys Phe
1               5                   10                  15

Lys Asp

<210> SEQ ID NO 276
<211> LENGTH: 18
<212> TYPE: PRT
<213> ORGANISM: Artificial
<220> FEATURE:
<223> OTHER INFORMATION: Recombinant peptide

<400> SEQUENCE: 276

Phe Ala Asp Lys Phe Trp Asp Ala Val Lys Glu Tyr Phe Ala Lys Phe
1               5                   10                  15

Lys Glu

<210> SEQ ID NO 277
<211> LENGTH: 18
<212> TYPE: PRT
<213> ORGANISM: Artificial
<220> FEATURE:
<223> OTHER INFORMATION: Recombinant peptide

<400> SEQUENCE: 277

Phe Ala Asp Lys Phe Trp Glu Ala Val Lys Asp Tyr Phe Ala Lys Phe
1               5                   10                  15

Lys Glu

<210> SEQ ID NO 278
<211> LENGTH: 18
<212> TYPE: PRT
<213> ORGANISM: Artificial
<220> FEATURE:
<223> OTHER INFORMATION: Recombinant peptide

<400> SEQUENCE: 278

Phe Ala Glu Lys Phe Trp Asp Ala Val Lys Glu Tyr Phe Ala Lys Phe
1               5                   10                  15

Lys Asp

<210> SEQ ID NO 279
<211> LENGTH: 18
<212> TYPE: PRT
<213> ORGANISM: Artificial
<220> FEATURE:
<223> OTHER INFORMATION: Recombinant peptide

<400> SEQUENCE: 279

Phe Ala Glu Lys Phe Trp Asp Ala Val Lys Asp Tyr Phe Ala Lys Phe
1               5                   10                  15

Lys Glu

<210> SEQ ID NO 280
<211> LENGTH: 18
<212> TYPE: PRT
<213> ORGANISM: Artificial
<220> FEATURE:
<223> OTHER INFORMATION: Recombinant peptide

<400> SEQUENCE: 280
```

```
Ala Phe Glu Lys Phe Lys Glu Ala Val Lys Asp Tyr Phe Ala Lys Phe
1               5                   10                  15

Trp Asp

<210> SEQ ID NO 281
<211> LENGTH: 18
<212> TYPE: PRT
<213> ORGANISM: Artificial
<220> FEATURE:
<223> OTHER INFORMATION: Recombinant peptide

<400> SEQUENCE: 281

Ala Phe Asp Lys Phe Lys Asp Ala Val Lys Glu Tyr Phe Ala Lys Phe
1               5                   10                  15

Trp Glu

<210> SEQ ID NO 282
<211> LENGTH: 18
<212> TYPE: PRT
<213> ORGANISM: Artificial
<220> FEATURE:
<223> OTHER INFORMATION: Recombinant peptide

<400> SEQUENCE: 282

Ala Phe Asp Lys Phe Lys Glu Ala Val Lys Asp Tyr Phe Ala Lys Phe
1               5                   10                  15

Trp Glu

<210> SEQ ID NO 283
<211> LENGTH: 18
<212> TYPE: PRT
<213> ORGANISM: Artificial
<220> FEATURE:
<223> OTHER INFORMATION: Recombinant peptide

<400> SEQUENCE: 283

Ala Phe Glu Lys Phe Lys Asp Ala Val Lys Glu Tyr Phe Ala Lys Phe
1               5                   10                  15

Trp Asp

<210> SEQ ID NO 284
<211> LENGTH: 18
<212> TYPE: PRT
<213> ORGANISM: Artificial
<220> FEATURE:
<223> OTHER INFORMATION: Recombinant peptide

<400> SEQUENCE: 284

Ala Phe Glu Lys Phe Lys Asp Ala Val Lys Asp Tyr Phe Ala Lys Phe
1               5                   10                  15

Trp Glu

<210> SEQ ID NO 285
<211> LENGTH: 18
<212> TYPE: PRT
<213> ORGANISM: Artificial
<220> FEATURE:
<223> OTHER INFORMATION: Recombinant peptide

<400> SEQUENCE: 285

Val Ala Glu Lys Phe Lys Glu Ala Phe Lys Asp Tyr Phe Ala Lys Phe
1               5                   10                  15
```

Trp Asp

<210> SEQ ID NO 286
<211> LENGTH: 18
<212> TYPE: PRT
<213> ORGANISM: Artificial
<220> FEATURE:
<223> OTHER INFORMATION: Recombinant peptide

<400> SEQUENCE: 286

Val Ala Asp Lys Phe Lys Asp Ala Phe Lys Glu Tyr Phe Ala Lys Phe
1               5                   10                  15

Trp Glu

<210> SEQ ID NO 287
<211> LENGTH: 18
<212> TYPE: PRT
<213> ORGANISM: Artificial
<220> FEATURE:
<223> OTHER INFORMATION: Recombinant peptide

<400> SEQUENCE: 287

Val Ala Asp Lys Phe Lys Glu Ala Phe Lys Asp Tyr Phe Ala Lys Phe
1               5                   10                  15

Trp Glu

<210> SEQ ID NO 288
<211> LENGTH: 18
<212> TYPE: PRT
<213> ORGANISM: Artificial
<220> FEATURE:
<223> OTHER INFORMATION: Recombinant peptide

<400> SEQUENCE: 288

Val Ala Glu Lys Phe Lys Asp Ala Phe Lys Glu Tyr Phe Ala Lys Phe
1               5                   10                  15

Trp Asp

<210> SEQ ID NO 289
<211> LENGTH: 18
<212> TYPE: PRT
<213> ORGANISM: Artificial
<220> FEATURE:
<223> OTHER INFORMATION: Recombinant peptide

<400> SEQUENCE: 289

Val Ala Glu Lys Phe Lys Asp Ala Phe Lys Asp Tyr Phe Ala Lys Phe
1               5                   10                  15

Trp Glu

<210> SEQ ID NO 290
<211> LENGTH: 18
<212> TYPE: PRT
<213> ORGANISM: Artificial
<220> FEATURE:
<223> OTHER INFORMATION: Recombinant peptide

<400> SEQUENCE: 290

Tyr Ala Glu Lys Phe Lys Glu Ala Val Lys Asp Phe Phe Ala Lys Phe
1               5                   10                  15

Trp Asp

<210> SEQ ID NO 291

```
<211> LENGTH: 18
<212> TYPE: PRT
<213> ORGANISM: Artificial
<220> FEATURE:
<223> OTHER INFORMATION: Recombinant peptide

<400> SEQUENCE: 291

Tyr Ala Asp Lys Phe Lys Asp Ala Val Lys Glu Phe Phe Ala Lys Phe
1               5                   10                  15

Trp Glu

<210> SEQ ID NO 292
<211> LENGTH: 18
<212> TYPE: PRT
<213> ORGANISM: Artificial
<220> FEATURE:
<223> OTHER INFORMATION: Recombinant peptide

<400> SEQUENCE: 292

Tyr Ala Asp Lys Phe Lys Glu Ala Val Lys Asp Phe Phe Ala Lys Phe
1               5                   10                  15

Trp Glu

<210> SEQ ID NO 293
<211> LENGTH: 18
<212> TYPE: PRT
<213> ORGANISM: Artificial
<220> FEATURE:
<223> OTHER INFORMATION: Recombinant peptide

<400> SEQUENCE: 293

Tyr Ala Glu Lys Phe Lys Asp Ala Val Lys Glu Phe Phe Ala Lys Phe
1               5                   10                  15

Trp Asp

<210> SEQ ID NO 294
<211> LENGTH: 18
<212> TYPE: PRT
<213> ORGANISM: Artificial
<220> FEATURE:
<223> OTHER INFORMATION: Recombinant peptide

<400> SEQUENCE: 294

Tyr Ala Glu Lys Phe Lys Asp Ala Val Lys Asp Phe Phe Ala Lys Phe
1               5                   10                  15

Trp Glu

<210> SEQ ID NO 295
<211> LENGTH: 18
<212> TYPE: PRT
<213> ORGANISM: Artificial
<220> FEATURE:
<223> OTHER INFORMATION: Recombinant peptide

<400> SEQUENCE: 295

Ala Ala Glu Lys Phe Lys Glu Phe Val Lys Asp Tyr Phe Ala Lys Phe
1               5                   10                  15

Trp Asp

<210> SEQ ID NO 296
<211> LENGTH: 18
<212> TYPE: PRT
<213> ORGANISM: Artificial
<220> FEATURE:
```

<223> OTHER INFORMATION: Recombinant peptide

<400> SEQUENCE: 296

Ala Ala Asp Lys Phe Lys Asp Phe Val Lys Glu Tyr Phe Ala Lys Phe
1               5                   10                  15

Trp Glu

<210> SEQ ID NO 297
<211> LENGTH: 18
<212> TYPE: PRT
<213> ORGANISM: Artificial
<220> FEATURE:
<223> OTHER INFORMATION: Recombinant peptide

<400> SEQUENCE: 297

Ala Ala Asp Lys Phe Lys Glu Phe Val Lys Asp Tyr Phe Ala Lys Phe
1               5                   10                  15

Trp Glu

<210> SEQ ID NO 298
<211> LENGTH: 18
<212> TYPE: PRT
<213> ORGANISM: Artificial
<220> FEATURE:
<223> OTHER INFORMATION: Recombinant peptide

<400> SEQUENCE: 298

Ala Ala Glu Lys Phe Lys Asp Phe Val Lys Glu Tyr Phe Ala Lys Phe
1               5                   10                  15

Trp Asp

<210> SEQ ID NO 299
<211> LENGTH: 18
<212> TYPE: PRT
<213> ORGANISM: Artificial
<220> FEATURE:
<223> OTHER INFORMATION: Recombinant peptide

<400> SEQUENCE: 299

Ala Ala Glu Lys Phe Lys Asp Phe Val Lys Asp Tyr Phe Ala Lys Phe
1               5                   10                  15

Trp Glu

<210> SEQ ID NO 300
<211> LENGTH: 18
<212> TYPE: PRT
<213> ORGANISM: Artificial
<220> FEATURE:
<223> OTHER INFORMATION: Recombinant peptide

<400> SEQUENCE: 300

Phe Phe Glu Lys Ala Lys Glu Ala Val Lys Asp Tyr Phe Ala Lys Phe
1               5                   10                  15

Trp Asp

<210> SEQ ID NO 301
<211> LENGTH: 18
<212> TYPE: PRT
<213> ORGANISM: Artificial
<220> FEATURE:
<223> OTHER INFORMATION: Recombinant peptide

<400> SEQUENCE: 301

Phe Phe Asp Lys Ala Lys Asp Ala Val Lys Glu Tyr Phe Ala Lys Phe
1               5                   10                  15

Trp Glu

<210> SEQ ID NO 302
<211> LENGTH: 18
<212> TYPE: PRT
<213> ORGANISM: Artificial
<220> FEATURE:
<223> OTHER INFORMATION: Recombinant peptide

<400> SEQUENCE: 302

Phe Phe Asp Lys Ala Lys Glu Ala Val Lys Asp Tyr Phe Ala Lys Phe
1               5                   10                  15

Trp Glu

<210> SEQ ID NO 303
<211> LENGTH: 18
<212> TYPE: PRT
<213> ORGANISM: Artificial
<220> FEATURE:
<223> OTHER INFORMATION: Recombinant peptide

<400> SEQUENCE: 303

Phe Glu Lys Ala Lys Asp Ala Val Lys Glu Tyr Phe Ala Lys Phe
1               5                   10                  15

Trp Asp

<210> SEQ ID NO 304
<211> LENGTH: 18
<212> TYPE: PRT
<213> ORGANISM: Artificial
<220> FEATURE:
<223> OTHER INFORMATION: Recombinant peptide

<400> SEQUENCE: 304

Phe Phe Glu Lys Ala Lys Asp Ala Val Lys Asp Tyr Phe Ala Lys Phe
1               5                   10                  15

Trp Glu

<210> SEQ ID NO 305
<211> LENGTH: 18
<212> TYPE: PRT
<213> ORGANISM: Artificial
<220> FEATURE:
<223> OTHER INFORMATION: Recombinant peptide

<400> SEQUENCE: 305

Phe Tyr Glu Lys Phe Lys Glu Ala Val Lys Asp Ala Phe Ala Lys Phe
1               5                   10                  15

Trp Asp

<210> SEQ ID NO 306
<211> LENGTH: 18
<212> TYPE: PRT
<213> ORGANISM: Artificial
<220> FEATURE:
<223> OTHER INFORMATION: Recombinant peptide

<400> SEQUENCE: 306

Phe Tyr Asp Lys Phe Lys Asp Ala Val Lys Glu Ala Phe Ala Lys Phe
1               5                   10                  15

Trp Glu

<210> SEQ ID NO 307
<211> LENGTH: 18
<212> TYPE: PRT
<213> ORGANISM: Artificial
<220> FEATURE:
<223> OTHER INFORMATION: Recombinant peptide

<400> SEQUENCE: 307

Phe Tyr Asp Lys Phe Lys Glu Ala Val Lys Asp Ala Phe Ala Lys Phe
1               5                   10                  15

Trp Glu

<210> SEQ ID NO 308
<211> LENGTH: 18
<212> TYPE: PRT
<213> ORGANISM: Artificial
<220> FEATURE:
<223> OTHER INFORMATION: Recombinant peptide

<400> SEQUENCE: 308

Phe Tyr Glu Lys Phe Lys Asp Ala Val Lys Glu Ala Phe Ala Lys Phe
1               5                   10                  15

Trp Asp

<210> SEQ ID NO 309
<211> LENGTH: 18
<212> TYPE: PRT
<213> ORGANISM: Artificial
<220> FEATURE:
<223> OTHER INFORMATION: Recombinant peptide

<400> SEQUENCE: 309

Phe Tyr Glu Lys Phe Lys Asp Ala Val Lys Asp Ala Phe Ala Lys Phe
1               5                   10                  15

Trp Glu

<210> SEQ ID NO 310
<211> LENGTH: 18
<212> TYPE: PRT
<213> ORGANISM: Artificial
<220> FEATURE:
<223> OTHER INFORMATION: Recombinant peptide

<400> SEQUENCE: 310

Phe Val Glu Lys Phe Lys Glu Ala Ala Lys Asp Tyr Phe Ala Lys Phe
1               5                   10                  15

Trp Asp

<210> SEQ ID NO 311
<211> LENGTH: 18
<212> TYPE: PRT
<213> ORGANISM: Artificial
<220> FEATURE:
<223> OTHER INFORMATION: Recombinant peptide

<400> SEQUENCE: 311

Phe Val Asp Lys Phe Lys Asp Ala Ala Lys Glu Tyr Phe Ala Lys Phe
1               5                   10                  15

Trp Glu

<210> SEQ ID NO 312
<211> LENGTH: 18

<212> TYPE: PRT
<213> ORGANISM: Artificial
<220> FEATURE:
<223> OTHER INFORMATION: Recombinant peptide

<400> SEQUENCE: 312

Phe Val Asp Lys Phe Lys Glu Ala Ala Lys Asp Tyr Phe Ala Lys Phe
1               5                   10                  15

Trp Glu

<210> SEQ ID NO 313
<211> LENGTH: 18
<212> TYPE: PRT
<213> ORGANISM: Artificial
<220> FEATURE:
<223> OTHER INFORMATION: Recombinant peptide

<400> SEQUENCE: 313

Phe Val Glu Lys Phe Lys Asp Ala Ala Lys Glu Tyr Phe Ala Lys Phe
1               5                   10                  15

Trp Asp

<210> SEQ ID NO 314
<211> LENGTH: 18
<212> TYPE: PRT
<213> ORGANISM: Artificial
<220> FEATURE:
<223> OTHER INFORMATION: Recombinant peptide

<400> SEQUENCE: 314

Phe Val Glu Lys Phe Lys Asp Ala Ala Lys Asp Tyr Phe Ala Lys Phe
1               5                   10                  15

Trp Glu

<210> SEQ ID NO 315
<211> LENGTH: 18
<212> TYPE: PRT
<213> ORGANISM: Artificial
<220> FEATURE:
<223> OTHER INFORMATION: Recombinant peptide

<400> SEQUENCE: 315

Phe Ala Glu Lys Tyr Lys Glu Ala Val Lys Asp Phe Phe Ala Lys Phe
1               5                   10                  15

Trp Asp

<210> SEQ ID NO 316
<211> LENGTH: 18
<212> TYPE: PRT
<213> ORGANISM: Artificial
<220> FEATURE:
<223> OTHER INFORMATION: Recombinant peptide

<400> SEQUENCE: 316

Phe Ala Asp Lys Tyr Lys Asp Ala Val Lys Glu Phe Phe Ala Lys Phe
1               5                   10                  15

Trp Glu

<210> SEQ ID NO 317
<211> LENGTH: 18
<212> TYPE: PRT
<213> ORGANISM: Artificial
<220> FEATURE:
<223> OTHER INFORMATION: Recombinant peptide

<400> SEQUENCE: 317

Phe Ala Asp Lys Tyr Lys Glu Ala Val Lys Asp Phe Phe Ala Lys Phe
1               5                   10                  15

Trp Glu

<210> SEQ ID NO 318
<211> LENGTH: 18
<212> TYPE: PRT
<213> ORGANISM: Artificial
<220> FEATURE:
<223> OTHER INFORMATION: Recombinant peptide

<400> SEQUENCE: 318

Phe Ala Glu Lys Tyr Lys Asp Ala Val Lys Glu Phe Phe Ala Lys Phe
1               5                   10                  15

Trp Asp

<210> SEQ ID NO 319
<211> LENGTH: 18
<212> TYPE: PRT
<213> ORGANISM: Artificial
<220> FEATURE:
<223> OTHER INFORMATION: Recombinant peptide

<400> SEQUENCE: 319

Phe Ala Glu Lys Tyr Lys Asp Ala Val Lys Asp Phe Phe Ala Lys Phe
1               5                   10                  15

Trp Glu

<210> SEQ ID NO 320
<211> LENGTH: 18
<212> TYPE: PRT
<213> ORGANISM: Artificial
<220> FEATURE:
<223> OTHER INFORMATION: Recombinant peptide

<400> SEQUENCE: 320

Phe Ala Glu Lys Val Lys Glu Ala Phe Lys Asp Tyr Phe Ala Lys Phe
1               5                   10                  15

Trp Asp

<210> SEQ ID NO 321
<211> LENGTH: 18
<212> TYPE: PRT
<213> ORGANISM: Artificial
<220> FEATURE:
<223> OTHER INFORMATION: Recombinant peptide

<400> SEQUENCE: 321

Phe Ala Asp Lys Val Lys Asp Ala Phe Lys Glu Tyr Phe Ala Lys Phe
1               5                   10                  15

Trp Glu

<210> SEQ ID NO 322
<211> LENGTH: 18
<212> TYPE: PRT
<213> ORGANISM: Artificial
<220> FEATURE:
<223> OTHER INFORMATION: Recombinant peptide

<400> SEQUENCE: 322

Phe Ala Asp Lys Val Lys Glu Ala Phe Lys Asp Tyr Phe Ala Lys Phe

```
1               5                   10                  15

Trp Glu

<210> SEQ ID NO 323
<211> LENGTH: 18
<212> TYPE: PRT
<213> ORGANISM: Artificial
<220> FEATURE:
<223> OTHER INFORMATION: Recombinant peptide

<400> SEQUENCE: 323

Phe Ala Glu Lys Val Lys Asp Ala Phe Lys Glu Tyr Phe Ala Lys Phe
1               5                   10                  15

Trp Asp

<210> SEQ ID NO 324
<211> LENGTH: 18
<212> TYPE: PRT
<213> ORGANISM: Artificial
<220> FEATURE:
<223> OTHER INFORMATION: Recombinant peptide

<400> SEQUENCE: 324

Phe Ala Glu Lys Val Lys Asp Ala Phe Lys Asp Tyr Phe Ala Lys Phe
1               5                   10                  15

Trp Glu

<210> SEQ ID NO 325
<211> LENGTH: 18
<212> TYPE: PRT
<213> ORGANISM: Artificial
<220> FEATURE:
<223> OTHER INFORMATION: Recombinant peptide

<400> SEQUENCE: 325

Phe Ala Glu Lys Phe Lys Glu Tyr Val Lys Asp Ala Phe Ala Lys Phe
1               5                   10                  15

Trp Asp

<210> SEQ ID NO 326
<211> LENGTH: 18
<212> TYPE: PRT
<213> ORGANISM: Artificial
<220> FEATURE:
<223> OTHER INFORMATION: Recombinant peptide

<400> SEQUENCE: 326

Phe Ala Asp Lys Phe Lys Asp Tyr Val Lys Glu Ala Phe Ala Lys Phe
1               5                   10                  15

Trp Glu

<210> SEQ ID NO 327
<211> LENGTH: 18
<212> TYPE: PRT
<213> ORGANISM: Artificial
<220> FEATURE:
<223> OTHER INFORMATION: Recombinant peptide

<400> SEQUENCE: 327

Phe Ala Asp Lys Phe Lys Glu Tyr Val Lys Asp Ala Phe Ala Lys Phe
1               5                   10                  15

Trp Glu
```

```
<210> SEQ ID NO 328
<211> LENGTH: 18
<212> TYPE: PRT
<213> ORGANISM: Artificial
<220> FEATURE:
<223> OTHER INFORMATION: Recombinant peptide

<400> SEQUENCE: 328

Phe Ala Glu Lys Phe Lys Asp Tyr Val Lys Glu Ala Phe Ala Lys Phe
1               5                   10                  15

Trp Asp

<210> SEQ ID NO 329
<211> LENGTH: 18
<212> TYPE: PRT
<213> ORGANISM: Artificial
<220> FEATURE:
<223> OTHER INFORMATION: Recombinant peptide

<400> SEQUENCE: 329

Phe Ala Glu Lys Phe Lys Asp Tyr Val Lys Asp Ala Phe Ala Lys Phe
1               5                   10                  15

Trp Glu

<210> SEQ ID NO 330
<211> LENGTH: 18
<212> TYPE: PRT
<213> ORGANISM: Artificial
<220> FEATURE:
<223> OTHER INFORMATION: Recombinant peptide

<400> SEQUENCE: 330

Phe Ala Glu Lys Phe Lys Glu Ala Phe Lys Asp Tyr Val Ala Lys Phe
1               5                   10                  15

Trp Asp

<210> SEQ ID NO 331
<211> LENGTH: 18
<212> TYPE: PRT
<213> ORGANISM: Artificial
<220> FEATURE:
<223> OTHER INFORMATION: Recombinant peptide

<400> SEQUENCE: 331

Phe Ala Asp Lys Phe Lys Asp Ala Phe Lys Glu Tyr Val Ala Lys Phe
1               5                   10                  15

Trp Glu

<210> SEQ ID NO 332
<211> LENGTH: 18
<212> TYPE: PRT
<213> ORGANISM: Artificial
<220> FEATURE:
<223> OTHER INFORMATION: Recombinant peptide

<400> SEQUENCE: 332

Phe Ala Asp Lys Phe Lys Glu Ala Phe Lys Asp Tyr Val Ala Lys Phe
1               5                   10                  15

Trp Glu

<210> SEQ ID NO 333
<211> LENGTH: 18
<212> TYPE: PRT
```

```
<213> ORGANISM: Artificial
<220> FEATURE:
<223> OTHER INFORMATION: Recombinant peptide

<400> SEQUENCE: 333

Phe Ala Glu Lys Phe Lys Asp Ala Phe Lys Glu Tyr Val Ala Lys Phe
1               5                   10                  15

Trp Asp

<210> SEQ ID NO 334
<211> LENGTH: 18
<212> TYPE: PRT
<213> ORGANISM: Artificial
<220> FEATURE:
<223> OTHER INFORMATION: Recombinant peptide

<400> SEQUENCE: 334

Phe Ala Glu Lys Phe Lys Asp Ala Phe Lys Asp Tyr Val Ala Lys Phe
1               5                   10                  15

Trp Glu

<210> SEQ ID NO 335
<211> LENGTH: 18
<212> TYPE: PRT
<213> ORGANISM: Artificial
<220> FEATURE:
<223> OTHER INFORMATION: Recombinant peptide

<400> SEQUENCE: 335

Phe Ala Glu Lys Phe Lys Glu Ala Phe Lys Asp Tyr Phe Ala Lys Val
1               5                   10                  15

Trp Asp

<210> SEQ ID NO 336
<211> LENGTH: 18
<212> TYPE: PRT
<213> ORGANISM: Artificial
<220> FEATURE:
<223> OTHER INFORMATION: Recombinant peptide

<400> SEQUENCE: 336

Phe Ala Asp Lys Phe Lys Asp Ala Phe Lys Glu Tyr Phe Ala Lys Val
1               5                   10                  15

Trp Glu

<210> SEQ ID NO 337
<211> LENGTH: 18
<212> TYPE: PRT
<213> ORGANISM: Artificial
<220> FEATURE:
<223> OTHER INFORMATION: Recombinant peptide

<400> SEQUENCE: 337

Phe Ala Asp Lys Phe Lys Glu Ala Phe Lys Asp Tyr Phe Ala Lys Val
1               5                   10                  15

Trp Glu

<210> SEQ ID NO 338
<211> LENGTH: 18
<212> TYPE: PRT
<213> ORGANISM: Artificial
<220> FEATURE:
<223> OTHER INFORMATION: Recombinant peptide
```

<400> SEQUENCE: 338

Phe Ala Glu Lys Phe Lys Asp Ala Phe Lys Glu Tyr Phe Ala Lys Val
1               5                   10                  15

Trp Asp

<210> SEQ ID NO 339
<211> LENGTH: 18
<212> TYPE: PRT
<213> ORGANISM: Artificial
<220> FEATURE:
<223> OTHER INFORMATION: Recombinant peptide

<400> SEQUENCE: 339

Phe Ala Glu Lys Phe Lys Asp Ala Phe Lys Asp Tyr Phe Ala Lys Val
1               5                   10                  15

Trp Glu

<210> SEQ ID NO 340
<211> LENGTH: 18
<212> TYPE: PRT
<213> ORGANISM: Artificial
<220> FEATURE:
<223> OTHER INFORMATION: Recombinant peptide

<400> SEQUENCE: 340

Phe Ala Glu Lys Phe Lys Glu Ala Val Lys Asp Phe Phe Ala Lys Tyr
1               5                   10                  15

Trp Asp

<210> SEQ ID NO 341
<211> LENGTH: 18
<212> TYPE: PRT
<213> ORGANISM: Artificial
<220> FEATURE:
<223> OTHER INFORMATION: Recombinant peptide

<400> SEQUENCE: 341

Phe Ala Asp Lys Phe Lys Asp Ala Val Lys Glu Phe Phe Ala Lys Tyr
1               5                   10                  15

Trp Glu

<210> SEQ ID NO 342
<211> LENGTH: 18
<212> TYPE: PRT
<213> ORGANISM: Artificial
<220> FEATURE:
<223> OTHER INFORMATION: Recombinant peptide

<400> SEQUENCE: 342

Phe Ala Asp Lys Phe Lys Glu Ala Val Lys Asp Phe Phe Ala Lys Tyr
1               5                   10                  15

Trp Glu

<210> SEQ ID NO 343
<211> LENGTH: 18
<212> TYPE: PRT
<213> ORGANISM: Artificial
<220> FEATURE:
<223> OTHER INFORMATION: Recombinant peptide

<400> SEQUENCE: 343

Phe Ala Glu Lys Phe Lys Asp Ala Val Lys Glu Phe Phe Ala Lys Tyr
1               5                   10                  15

Trp Asp

<210> SEQ ID NO 344
<211> LENGTH: 18
<212> TYPE: PRT
<213> ORGANISM: Artificial
<220> FEATURE:
<223> OTHER INFORMATION: Recombinant peptide

<400> SEQUENCE: 344

Phe Ala Glu Lys Phe Lys Asp Ala Val Lys Asp Phe Phe Ala Lys Tyr
1               5                   10                  15

Trp Glu

<210> SEQ ID NO 345
<211> LENGTH: 18
<212> TYPE: PRT
<213> ORGANISM: Artificial
<220> FEATURE:
<223> OTHER INFORMATION: Recombinant peptide

<400> SEQUENCE: 345

Trp Ala Glu Lys Phe Phe Glu Ala Val Lys Asp Tyr Phe Ala Lys Phe
1               5                   10                  15

Lys Asp

<210> SEQ ID NO 346
<211> LENGTH: 18
<212> TYPE: PRT
<213> ORGANISM: Artificial
<220> FEATURE:
<223> OTHER INFORMATION: Recombinant peptide

<400> SEQUENCE: 346

Trp Ala Asp Lys Phe Phe Asp Ala Val Lys Glu Tyr Phe Ala Lys Phe
1               5                   10                  15

Lys Glu

<210> SEQ ID NO 347
<211> LENGTH: 18
<212> TYPE: PRT
<213> ORGANISM: Artificial
<220> FEATURE:
<223> OTHER INFORMATION: Recombinant peptide

<400> SEQUENCE: 347

Trp Ala Asp Lys Phe Phe Glu Ala Val Lys Asp Tyr Phe Ala Lys Phe
1               5                   10                  15

Lys Glu

<210> SEQ ID NO 348
<211> LENGTH: 18
<212> TYPE: PRT
<213> ORGANISM: Artificial
<220> FEATURE:
<223> OTHER INFORMATION: Recombinant peptide

<400> SEQUENCE: 348

Trp Ala Glu Lys Phe Phe Asp Ala Val Lys Glu Tyr Phe Ala Lys Phe
1               5                   10                  15

Lys Asp

```
<210> SEQ ID NO 349
<211> LENGTH: 18
<212> TYPE: PRT
<213> ORGANISM: Artificial
<220> FEATURE:
<223> OTHER INFORMATION: Recombinant peptide

<400> SEQUENCE: 349

Trp Ala Glu Lys Phe Phe Asp Ala Val Lys Asp Tyr Phe Ala Lys Phe
1               5                   10                  15

Lys Glu

<210> SEQ ID NO 350
<211> LENGTH: 18
<212> TYPE: PRT
<213> ORGANISM: Artificial
<220> FEATURE:
<223> OTHER INFORMATION: Recombinant peptide

<400> SEQUENCE: 350

Phe Ala Glu Lys Trp Phe Glu Ala Val Lys Asp Tyr Phe Ala Lys Phe
1               5                   10                  15

Lys Asp

<210> SEQ ID NO 351
<211> LENGTH: 18
<212> TYPE: PRT
<213> ORGANISM: Artificial
<220> FEATURE:
<223> OTHER INFORMATION: Recombinant peptide

<400> SEQUENCE: 351

Phe Ala Asp Lys Trp Phe Asp Ala Val Lys Glu Tyr Phe Ala Lys Phe
1               5                   10                  15

Lys Glu

<210> SEQ ID NO 352
<211> LENGTH: 18
<212> TYPE: PRT
<213> ORGANISM: Artificial
<220> FEATURE:
<223> OTHER INFORMATION: Recombinant peptide

<400> SEQUENCE: 352

Phe Ala Asp Lys Trp Phe Glu Ala Val Lys Asp Tyr Phe Ala Lys Phe
1               5                   10                  15

Lys Glu

<210> SEQ ID NO 353
<211> LENGTH: 18
<212> TYPE: PRT
<213> ORGANISM: Artificial
<220> FEATURE:
<223> OTHER INFORMATION: Recombinant peptide

<400> SEQUENCE: 353

Phe Ala Glu Lys Trp Phe Asp Ala Val Lys Glu Tyr Phe Ala Lys Phe
1               5                   10                  15

Lys Asp

<210> SEQ ID NO 354
<211> LENGTH: 18
<212> TYPE: PRT
<213> ORGANISM: Artificial
```

<220> FEATURE:
<223> OTHER INFORMATION: Recombinant peptide

<400> SEQUENCE: 354

Phe Ala Glu Lys Trp Phe Asp Ala Val Lys Asp Tyr Phe Ala Lys Phe
1               5                   10                  15

Lys Glu

<210> SEQ ID NO 355
<211> LENGTH: 18
<212> TYPE: PRT
<213> ORGANISM: Artificial
<220> FEATURE:
<223> OTHER INFORMATION: Recombinant peptide

<400> SEQUENCE: 355

Phe Ala Glu Lys Phe Val Glu Ala Trp Lys Asp Tyr Phe Ala Lys Phe
1               5                   10                  15

Lys Asp

<210> SEQ ID NO 356
<211> LENGTH: 18
<212> TYPE: PRT
<213> ORGANISM: Artificial
<220> FEATURE:
<223> OTHER INFORMATION: Recombinant peptide

<400> SEQUENCE: 356

Phe Ala Asp Lys Phe Val Asp Ala Trp Lys Glu Tyr Phe Ala Lys Phe
1               5                   10                  15

Lys Glu

<210> SEQ ID NO 357
<211> LENGTH: 18
<212> TYPE: PRT
<213> ORGANISM: Artificial
<220> FEATURE:
<223> OTHER INFORMATION: Recombinant peptide

<400> SEQUENCE: 357

Phe Ala Asp Lys Phe Val Glu Ala Trp Lys Asp Tyr Phe Ala Lys Phe
1               5                   10                  15

Lys Glu

<210> SEQ ID NO 358
<211> LENGTH: 18
<212> TYPE: PRT
<213> ORGANISM: Artificial
<220> FEATURE:
<223> OTHER INFORMATION: Recombinant peptide

<400> SEQUENCE: 358

Phe Ala Glu Lys Phe Val Asp Ala Trp Lys Glu Tyr Phe Ala Lys Phe
1               5                   10                  15

Lys Asp

<210> SEQ ID NO 359
<211> LENGTH: 18
<212> TYPE: PRT
<213> ORGANISM: Artificial
<220> FEATURE:
<223> OTHER INFORMATION: Recombinant peptide

<400> SEQUENCE: 359

-continued

Phe Ala Glu Lys Phe Val Asp Ala Trp Lys Asp Tyr Phe Ala Lys Phe
1               5                   10                  15

Lys Glu

<210> SEQ ID NO 360
<211> LENGTH: 18
<212> TYPE: PRT
<213> ORGANISM: Artificial
<220> FEATURE:
<223> OTHER INFORMATION: Recombinant peptide

<400> SEQUENCE: 360

Phe Tyr Glu Lys Phe Ala Glu Ala Val Lys Asp Trp Phe Ala Lys Phe
1               5                   10                  15

Lys Asp

<210> SEQ ID NO 361
<211> LENGTH: 18
<212> TYPE: PRT
<213> ORGANISM: Artificial
<220> FEATURE:
<223> OTHER INFORMATION: Recombinant peptide

<400> SEQUENCE: 361

Phe Tyr Asp Lys Phe Ala Asp Ala Val Lys Glu Trp Phe Ala Lys Phe
1               5                   10                  15

Lys Glu

<210> SEQ ID NO 362
<211> LENGTH: 18
<212> TYPE: PRT
<213> ORGANISM: Artificial
<220> FEATURE:
<223> OTHER INFORMATION: Recombinant peptide

<400> SEQUENCE: 362

Phe Tyr Asp Lys Phe Ala Glu Ala Val Lys Asp Trp Phe Ala Lys Phe
1               5                   10                  15

Lys Glu

<210> SEQ ID NO 363
<211> LENGTH: 18
<212> TYPE: PRT
<213> ORGANISM: Artificial
<220> FEATURE:
<223> OTHER INFORMATION: Recombinant peptide

<400> SEQUENCE: 363

Phe Tyr Glu Lys Phe Ala Asp Ala Val Lys Glu Trp Phe Ala Lys Phe
1               5                   10                  15

Lys Asp

<210> SEQ ID NO 364
<211> LENGTH: 18
<212> TYPE: PRT
<213> ORGANISM: Artificial
<220> FEATURE:
<223> OTHER INFORMATION: Recombinant peptide

<400> SEQUENCE: 364

Phe Tyr Glu Lys Phe Ala Asp Ala Val Lys Asp Trp Phe Ala Lys Phe
1               5                   10                  15

Lys Glu

<210> SEQ ID NO 365
<211> LENGTH: 18
<212> TYPE: PRT
<213> ORGANISM: Artificial
<220> FEATURE:
<223> OTHER INFORMATION: Recombinant peptide

<400> SEQUENCE: 365

Asp Trp Phe Lys His Phe Tyr Asp Lys Val Ala Glu Lys Phe Lys Glu
1               5                   10                  15

Ala Phe

<210> SEQ ID NO 366
<211> LENGTH: 18
<212> TYPE: PRT
<213> ORGANISM: Artificial
<220> FEATURE:
<223> OTHER INFORMATION: Recombinant peptide

<400> SEQUENCE: 366

Glu Trp Phe Lys His Phe Tyr Glu Lys Val Ala Asp Lys Phe Lys Asp
1               5                   10                  15

Ala Phe

<210> SEQ ID NO 367
<211> LENGTH: 18
<212> TYPE: PRT
<213> ORGANISM: Artificial
<220> FEATURE:
<223> OTHER INFORMATION: Recombinant peptide

<400> SEQUENCE: 367

Glu Trp Phe Lys His Phe Tyr Asp Lys Val Ala Glu Lys Phe Lys Glu
1               5                   10                  15

Ala Phe

<210> SEQ ID NO 368
<211> LENGTH: 18
<212> TYPE: PRT
<213> ORGANISM: Artificial
<220> FEATURE:
<223> OTHER INFORMATION: Recombinant peptide

<400> SEQUENCE: 368

Asp Trp Phe Lys His Phe Tyr Glu Lys Val Ala Glu Lys Phe Lys Glu
1               5                   10                  15

Ala Phe

<210> SEQ ID NO 369
<211> LENGTH: 18
<212> TYPE: PRT
<213> ORGANISM: Artificial
<220> FEATURE:
<223> OTHER INFORMATION: Recombinant peptide

<400> SEQUENCE: 369

Asp Trp Phe Lys His Phe Tyr Asp Lys Val Ala Asp Lys Phe Lys Glu
1               5                   10                  15

Ala Phe

<210> SEQ ID NO 370

```
<211> LENGTH: 18
<212> TYPE: PRT
<213> ORGANISM: Artificial
<220> FEATURE:
<223> OTHER INFORMATION: Recombinant peptide

<400> SEQUENCE: 370

Asp Trp Phe Lys His Phe Tyr Asp Lys Val Ala Glu Lys Phe Lys Asp
1               5                   10                  15

Ala Phe

<210> SEQ ID NO 371
<211> LENGTH: 18
<212> TYPE: PRT
<213> ORGANISM: Artificial
<220> FEATURE:
<223> OTHER INFORMATION: Recombinant peptide

<400> SEQUENCE: 371

Asp Trp His Lys Phe Phe Tyr Asp Lys Val Ala Glu Lys Phe Lys Glu
1               5                   10                  15

Ala Phe

<210> SEQ ID NO 372
<211> LENGTH: 18
<212> TYPE: PRT
<213> ORGANISM: Artificial
<220> FEATURE:
<223> OTHER INFORMATION: Recombinant peptide

<400> SEQUENCE: 372

Glu Trp His Lys Phe Phe Tyr Glu Lys Val Ala Asp Lys Phe Lys Asp
1               5                   10                  15

Ala Phe

<210> SEQ ID NO 373
<211> LENGTH: 18
<212> TYPE: PRT
<213> ORGANISM: Artificial
<220> FEATURE:
<223> OTHER INFORMATION: Recombinant peptide

<400> SEQUENCE: 373

Glu Trp His Lys Phe Phe Tyr Asp Lys Val Ala Glu Lys Phe Lys Glu
1               5                   10                  15

Ala Phe

<210> SEQ ID NO 374
<211> LENGTH: 18
<212> TYPE: PRT
<213> ORGANISM: Artificial
<220> FEATURE:
<223> OTHER INFORMATION: Recombinant peptide

<400> SEQUENCE: 374

Asp Trp His Lys Phe Phe Tyr Glu Lys Val Ala Glu Lys Phe Lys Glu
1               5                   10                  15

Ala Phe

<210> SEQ ID NO 375
<211> LENGTH: 18
<212> TYPE: PRT
<213> ORGANISM: Artificial
<220> FEATURE:
```

<223> OTHER INFORMATION: Recombinant peptide

<400> SEQUENCE: 375

Asp Trp His Lys Phe Phe Tyr Asp Lys Val Ala Asp Lys Phe Lys Glu
1               5                   10                  15

Ala Phe

<210> SEQ ID NO 376
<211> LENGTH: 18
<212> TYPE: PRT
<213> ORGANISM: Artificial
<220> FEATURE:
<223> OTHER INFORMATION: Recombinant peptide

<400> SEQUENCE: 376

Asp Trp His Lys Phe Phe Tyr Asp Lys Val Ala Glu Lys Phe Lys Asp
1               5                   10                  15

Ala Phe

<210> SEQ ID NO 377
<211> LENGTH: 18
<212> TYPE: PRT
<213> ORGANISM: Artificial
<220> FEATURE:
<223> OTHER INFORMATION: Recombinant peptide

<400> SEQUENCE: 377

Asp Trp Phe Lys Phe His Tyr Asp Lys Val Ala Glu Lys Phe Lys Glu
1               5                   10                  15

Ala Phe

<210> SEQ ID NO 378
<211> LENGTH: 18
<212> TYPE: PRT
<213> ORGANISM: Artificial
<220> FEATURE:
<223> OTHER INFORMATION: Recombinant peptide

<400> SEQUENCE: 378

Glu Trp Phe Lys Phe His Tyr Glu Lys Val Ala Asp Lys Phe Lys Asp
1               5                   10                  15

Ala Phe

<210> SEQ ID NO 379
<211> LENGTH: 18
<212> TYPE: PRT
<213> ORGANISM: Artificial
<220> FEATURE:
<223> OTHER INFORMATION: Recombinant peptide

<400> SEQUENCE: 379

Glu Trp Phe Lys Phe His Tyr Asp Lys Val Ala Glu Lys Phe Lys Glu
1               5                   10                  15

Ala Phe

<210> SEQ ID NO 380
<211> LENGTH: 18
<212> TYPE: PRT
<213> ORGANISM: Artificial
<220> FEATURE:
<223> OTHER INFORMATION: Recombinant peptide

<400> SEQUENCE: 380

Asp Trp Phe Lys Phe His Tyr Glu Lys Val Ala Glu Lys Phe Lys Glu
1               5                   10                  15

Ala Phe

<210> SEQ ID NO 381
<211> LENGTH: 18
<212> TYPE: PRT
<213> ORGANISM: Artificial
<220> FEATURE:
<223> OTHER INFORMATION: Recombinant peptide

<400> SEQUENCE: 381

Asp Trp Phe Lys Phe His Tyr Asp Lys Val Ala Asp Lys Phe Lys Glu
1               5                   10                  15

Ala Phe

<210> SEQ ID NO 382
<211> LENGTH: 18
<212> TYPE: PRT
<213> ORGANISM: Artificial
<220> FEATURE:
<223> OTHER INFORMATION: Recombinant peptide

<400> SEQUENCE: 382

Asp Trp Phe Lys Phe His Tyr Asp Lys Val Ala Glu Lys Phe Lys Asp
1               5                   10                  15

Ala Phe

<210> SEQ ID NO 383
<211> LENGTH: 18
<212> TYPE: PRT
<213> ORGANISM: Artificial
<220> FEATURE:
<223> OTHER INFORMATION: Recombinant peptide

<400> SEQUENCE: 383

Asp Trp Phe Lys Val Phe Tyr Asp Lys His Ala Glu Lys Phe Lys Glu
1               5                   10                  15

Ala Phe

<210> SEQ ID NO 384
<211> LENGTH: 18
<212> TYPE: PRT
<213> ORGANISM: Artificial
<220> FEATURE:
<223> OTHER INFORMATION: Recombinant peptide

<400> SEQUENCE: 384

Glu Trp Phe Lys Val Phe Tyr Glu Lys His Ala Asp Lys Phe Lys Asp
1               5                   10                  15

Ala Phe

<210> SEQ ID NO 385
<211> LENGTH: 18
<212> TYPE: PRT
<213> ORGANISM: Artificial
<220> FEATURE:
<223> OTHER INFORMATION: Recombinant peptide

<400> SEQUENCE: 385

Glu Trp Phe Lys Val Phe Tyr Asp Lys His Ala Glu Lys Phe Lys Glu
1               5                   10                  15

Ala Phe

<210> SEQ ID NO 386
<211> LENGTH: 18
<212> TYPE: PRT
<213> ORGANISM: Artificial
<220> FEATURE:
<223> OTHER INFORMATION: Recombinant peptide

<400> SEQUENCE: 386

Asp Trp Phe Lys Val Phe Tyr Glu Lys His Ala Glu Lys Phe Lys Glu
1               5                   10                  15

Ala Phe

<210> SEQ ID NO 387
<211> LENGTH: 18
<212> TYPE: PRT
<213> ORGANISM: Artificial
<220> FEATURE:
<223> OTHER INFORMATION: Recombinant peptide

<400> SEQUENCE: 387

Asp Trp Phe Lys Val Phe Tyr Asp Lys His Ala Asp Lys Phe Lys Glu
1               5                   10                  15

Ala Phe

<210> SEQ ID NO 388
<211> LENGTH: 18
<212> TYPE: PRT
<213> ORGANISM: Artificial
<220> FEATURE:
<223> OTHER INFORMATION: Recombinant peptide

<400> SEQUENCE: 388

Asp Trp Phe Lys Val Phe Tyr Asp Lys His Ala Glu Lys Phe Lys Asp
1               5                   10                  15

Ala Phe

<210> SEQ ID NO 389
<211> LENGTH: 18
<212> TYPE: PRT
<213> ORGANISM: Artificial
<220> FEATURE:
<223> OTHER INFORMATION: Recombinant peptide

<400> SEQUENCE: 389

Asp Trp Phe Lys Ala Phe Tyr Asp Lys Val Ala Glu Lys Phe Lys Glu
1               5                   10                  15

His Phe

<210> SEQ ID NO 390
<211> LENGTH: 18
<212> TYPE: PRT
<213> ORGANISM: Artificial
<220> FEATURE:
<223> OTHER INFORMATION: Recombinant peptide

<400> SEQUENCE: 390

Glu Trp Phe Lys Ala Phe Tyr Glu Lys Val Ala Asp Lys Phe Lys Asp
1               5                   10                  15

His Phe

<210> SEQ ID NO 391
<211> LENGTH: 18

```
<212> TYPE: PRT
<213> ORGANISM: Artificial
<220> FEATURE:
<223> OTHER INFORMATION: Recombinant peptide

<400> SEQUENCE: 391

Glu Trp Phe Lys Ala Phe Tyr Asp Lys Val Ala Glu Lys Phe Lys Glu
1               5                   10                  15

His Phe

<210> SEQ ID NO 392
<211> LENGTH: 18
<212> TYPE: PRT
<213> ORGANISM: Artificial
<220> FEATURE:
<223> OTHER INFORMATION: Recombinant peptide

<400> SEQUENCE: 392

Asp Trp Phe Lys Ala Phe Tyr Glu Lys Val Ala Glu Lys Phe Lys Glu
1               5                   10                  15

His Phe

<210> SEQ ID NO 393
<211> LENGTH: 18
<212> TYPE: PRT
<213> ORGANISM: Artificial
<220> FEATURE:
<223> OTHER INFORMATION: Recombinant peptide

<400> SEQUENCE: 393

Asp Trp Phe Lys Ala Phe Tyr Asp Lys Val Ala Asp Lys Phe Lys Glu
1               5                   10                  15

His Phe

<210> SEQ ID NO 394
<211> LENGTH: 18
<212> TYPE: PRT
<213> ORGANISM: Artificial
<220> FEATURE:
<223> OTHER INFORMATION: Recombinant peptide

<400> SEQUENCE: 394

Asp Trp Phe Lys Ala Phe Tyr Asp Lys Val Ala Glu Lys Phe Lys Asp
1               5                   10                  15

His Phe

<210> SEQ ID NO 395
<211> LENGTH: 18
<212> TYPE: PRT
<213> ORGANISM: Artificial
<220> FEATURE:
<223> OTHER INFORMATION: Recombinant peptide

<400> SEQUENCE: 395

Asp Trp Phe Lys Ala Phe Tyr Asp Lys Val Ala Glu Lys Phe Lys Glu
1               5                   10                  15

Phe His

<210> SEQ ID NO 396
<211> LENGTH: 18
<212> TYPE: PRT
<213> ORGANISM: Artificial
<220> FEATURE:
<223> OTHER INFORMATION: Recombinant peptide
```

```
<400> SEQUENCE: 396

Glu Trp Phe Lys Ala Phe Tyr Glu Lys Val Ala Asp Lys Phe Lys Asp
1               5                   10                  15

Phe His

<210> SEQ ID NO 397
<211> LENGTH: 18
<212> TYPE: PRT
<213> ORGANISM: Artificial
<220> FEATURE:
<223> OTHER INFORMATION: Recombinant peptide

<400> SEQUENCE: 397

Glu Trp Phe Lys Ala Phe Tyr Asp Lys Val Ala Glu Lys Phe Lys Glu
1               5                   10                  15

Phe His

<210> SEQ ID NO 398
<211> LENGTH: 18
<212> TYPE: PRT
<213> ORGANISM: Artificial
<220> FEATURE:
<223> OTHER INFORMATION: Recombinant peptide

<400> SEQUENCE: 398

Asp Trp Phe Lys Ala Phe Tyr Asp Lys Val Ala Glu Lys Phe Lys Glu
1               5                   10                  15

Phe His

<210> SEQ ID NO 399
<211> LENGTH: 18
<212> TYPE: PRT
<213> ORGANISM: Artificial
<220> FEATURE:
<223> OTHER INFORMATION: Recombinant peptide

<400> SEQUENCE: 399

Asp Trp Phe Lys Ala Phe Tyr Glu Lys Val Ala Glu Lys Phe Lys Glu
1               5                   10                  15

Phe His

<210> SEQ ID NO 400
<211> LENGTH: 18
<212> TYPE: PRT
<213> ORGANISM: Artificial
<220> FEATURE:
<223> OTHER INFORMATION: Recombinant peptide

<400> SEQUENCE: 400

Asp Trp Phe Lys Ala Phe Tyr Asp Lys Val Ala Glu Lys Phe Lys Glu
1               5                   10                  15

Phe His

<210> SEQ ID NO 401
<211> LENGTH: 18
<212> TYPE: PRT
<213> ORGANISM: Artificial
<220> FEATURE:
<223> OTHER INFORMATION: Recombinant peptide

<400> SEQUENCE: 401

Asp Trp Phe Lys Ala Phe Tyr Asp Lys Val Ala Glu Lys Phe Lys Asp
```

-continued

```
1               5                   10                  15

Phe His

<210> SEQ ID NO 402
<211> LENGTH: 18
<212> TYPE: PRT
<213> ORGANISM: Artificial
<220> FEATURE:
<223> OTHER INFORMATION: Recombinant peptide

<400> SEQUENCE: 402

Phe Ala Glu Lys Phe Lys Glu Ala Val Lys Asp Tyr Phe Ala Lys Phe
1               5                   10                  15

Trp Asp

<210> SEQ ID NO 403
<211> LENGTH: 18
<212> TYPE: PRT
<213> ORGANISM: Artificial
<220> FEATURE:
<223> OTHER INFORMATION: Recombinant peptide

<400> SEQUENCE: 403

Phe His Glu Lys Phe Lys Glu Ala Val Lys Asp Tyr Phe Ala Lys Phe
1               5                   10                  15

Trp Asp

<210> SEQ ID NO 404
<211> LENGTH: 18
<212> TYPE: PRT
<213> ORGANISM: Artificial
<220> FEATURE:
<223> OTHER INFORMATION: Recombinant peptide

<400> SEQUENCE: 404

Phe His Glu Lys Phe Lys Glu Ala Val Lys Glu Tyr Phe Ala Lys Phe
1               5                   10                  15

Trp Glu

<210> SEQ ID NO 405
<211> LENGTH: 18
<212> TYPE: PRT
<213> ORGANISM: Artificial
<220> FEATURE:
<223> OTHER INFORMATION: Recombinant peptide

<400> SEQUENCE: 405

Phe His Asp Lys Phe Lys Asp Ala Val Lys Asp Tyr Phe Ala Lys Phe
1               5                   10                  15

Trp Asp

<210> SEQ ID NO 406
<211> LENGTH: 18
<212> TYPE: PRT
<213> ORGANISM: Artificial
<220> FEATURE:
<223> OTHER INFORMATION: Recombinant peptide

<400> SEQUENCE: 406

Phe His Asp Lys Phe Lys Asp Ala Val Lys Glu Tyr Phe Ala Lys Phe
1               5                   10                  15

Trp Glu
```

```
<210> SEQ ID NO 407
<211> LENGTH: 18
<212> TYPE: PRT
<213> ORGANISM: Artificial
<220> FEATURE:
<223> OTHER INFORMATION: Recombinant peptide

<400> SEQUENCE: 407

Phe His Asp Lys Phe Lys Glu Ala Val Lys Asp Tyr Phe Ala Lys Phe
1               5                   10                  15

Trp Asp

<210> SEQ ID NO 408
<211> LENGTH: 18
<212> TYPE: PRT
<213> ORGANISM: Artificial
<220> FEATURE:
<223> OTHER INFORMATION: Recombinant peptide

<400> SEQUENCE: 408

Phe His Glu Lys Phe Lys Asp Ala Val Lys Asp Tyr Phe Ala Lys Phe
1               5                   10                  15

Trp Asp

<210> SEQ ID NO 409
<211> LENGTH: 18
<212> TYPE: PRT
<213> ORGANISM: Artificial
<220> FEATURE:
<223> OTHER INFORMATION: Recombinant peptide

<400> SEQUENCE: 409

Phe His Glu Lys Phe Lys Glu Ala Val Lys Glu Tyr Phe Ala Lys Phe
1               5                   10                  15

Trp Asp

<210> SEQ ID NO 410
<211> LENGTH: 18
<212> TYPE: PRT
<213> ORGANISM: Artificial
<220> FEATURE:
<223> OTHER INFORMATION: Recombinant peptide

<400> SEQUENCE: 410

Phe His Glu Lys Phe Lys Glu Ala Val Lys Asp Tyr Phe Ala Lys Phe
1               5                   10                  15

Trp Glu

<210> SEQ ID NO 411
<211> LENGTH: 18
<212> TYPE: PRT
<213> ORGANISM: Artificial
<220> FEATURE:
<223> OTHER INFORMATION: Recombinant peptide

<400> SEQUENCE: 411

His Phe Glu Lys Phe Lys Glu Ala Val Lys Asp Tyr Phe Ala Lys Phe
1               5                   10                  15

Trp Asp

<210> SEQ ID NO 412
<211> LENGTH: 18
<212> TYPE: PRT
```

```
<213> ORGANISM: Artificial
<220> FEATURE:
<223> OTHER INFORMATION: Recombinant peptide

<400> SEQUENCE: 412

His Phe Asp Lys Phe Lys Asp Ala Val Lys Glu Tyr Phe Ala Lys Phe
1               5                   10                  15

Trp Glu

<210> SEQ ID NO 413
<211> LENGTH: 18
<212> TYPE: PRT
<213> ORGANISM: Artificial
<220> FEATURE:
<223> OTHER INFORMATION: Recombinant peptide

<400> SEQUENCE: 413

His Phe Glu Lys Phe Lys Glu Ala Val Lys Glu Tyr Phe Ala Lys Phe
1               5                   10                  15

Trp Glu

<210> SEQ ID NO 414
<211> LENGTH: 18
<212> TYPE: PRT
<213> ORGANISM: Artificial
<220> FEATURE:
<223> OTHER INFORMATION: Recombinant peptide

<400> SEQUENCE: 414

His Phe Asp Lys Phe Lys Glu Ala Val Lys Asp Tyr Phe Ala Lys Phe
1               5                   10                  15

Trp Asp

<210> SEQ ID NO 415
<211> LENGTH: 18
<212> TYPE: PRT
<213> ORGANISM: Artificial
<220> FEATURE:
<223> OTHER INFORMATION: Recombinant peptide

<400> SEQUENCE: 415

His Phe Glu Lys Phe Lys Asp Ala Val Lys Asp Tyr Phe Ala Lys Phe
1               5                   10                  15

Trp Asp

<210> SEQ ID NO 416
<211> LENGTH: 18
<212> TYPE: PRT
<213> ORGANISM: Artificial
<220> FEATURE:
<223> OTHER INFORMATION: Recombinant peptide

<400> SEQUENCE: 416

His Phe Glu Lys Phe Lys Glu Ala Val Lys Glu Tyr Phe Ala Lys Phe
1               5                   10                  15

Trp Asp

<210> SEQ ID NO 417
<211> LENGTH: 18
<212> TYPE: PRT
<213> ORGANISM: Artificial
<220> FEATURE:
<223> OTHER INFORMATION: Recombinant peptide
```

<400> SEQUENCE: 417

His Phe Glu Lys Phe Lys Glu Ala Val Lys Asp Tyr Phe Ala Lys Phe
1               5                   10                  15

Trp Glu

<210> SEQ ID NO 418
<211> LENGTH: 18
<212> TYPE: PRT
<213> ORGANISM: Artificial
<220> FEATURE:
<223> OTHER INFORMATION: Recombinant peptide

<400> SEQUENCE: 418

Phe Phe Glu Lys His Lys Glu Ala Val Lys Asp Tyr Phe Ala Lys Phe
1               5                   10                  15

Trp Asp

<210> SEQ ID NO 419
<211> LENGTH: 18
<212> TYPE: PRT
<213> ORGANISM: Artificial
<220> FEATURE:
<223> OTHER INFORMATION: Recombinant peptide

<400> SEQUENCE: 419

Phe Phe Asp Lys His Lys Asp Ala Val Lys Glu Tyr Phe Ala Lys Phe
1               5                   10                  15

Trp Glu

<210> SEQ ID NO 420
<211> LENGTH: 18
<212> TYPE: PRT
<213> ORGANISM: Artificial
<220> FEATURE:
<223> OTHER INFORMATION: Recombinant peptide

<400> SEQUENCE: 420

Phe Phe Glu Lys His Lys Glu Ala Val Lys Glu Tyr Phe Ala Lys Phe
1               5                   10                  15

Trp Glu

<210> SEQ ID NO 421
<211> LENGTH: 18
<212> TYPE: PRT
<213> ORGANISM: Artificial
<220> FEATURE:
<223> OTHER INFORMATION: Recombinant peptide

<400> SEQUENCE: 421

Phe Phe Asp Lys His Lys Asp Ala Val Lys Asp Tyr Phe Ala Lys Phe
1               5                   10                  15

Trp Asp

<210> SEQ ID NO 422
<211> LENGTH: 18
<212> TYPE: PRT
<213> ORGANISM: Artificial
<220> FEATURE:
<223> OTHER INFORMATION: Recombinant peptide

<400> SEQUENCE: 422

Phe Phe Asp Lys His Lys Glu Ala Val Lys Asp Tyr Phe Ala Lys Phe
1               5                   10                  15

Trp Asp

<210> SEQ ID NO 423
<211> LENGTH: 18
<212> TYPE: PRT
<213> ORGANISM: Artificial
<220> FEATURE:
<223> OTHER INFORMATION: Recombinant peptide

<400> SEQUENCE: 423

Phe Phe Glu Lys His Lys Glu Ala Val Lys Glu Tyr Phe Ala Lys Phe
1               5                   10                  15
Trp Asp

<210> SEQ ID NO 424
<211> LENGTH: 18
<212> TYPE: PRT
<213> ORGANISM: Artificial
<220> FEATURE:
<223> OTHER INFORMATION: Recombinant peptide

<400> SEQUENCE: 424

Phe Phe Glu Lys His Lys Glu Ala Val Lys Asp Tyr Phe Ala Lys Phe
1               5                   10                  15
Trp Glu

<210> SEQ ID NO 425
<211> LENGTH: 18
<212> TYPE: PRT
<213> ORGANISM: Artificial
<220> FEATURE:
<223> OTHER INFORMATION: Recombinant peptide

<400> SEQUENCE: 425

Phe Val Glu Lys Phe Lys Glu Ala His Lys Asp Tyr Phe Ala Lys Phe
1               5                   10                  15
Trp Asp

<210> SEQ ID NO 426
<211> LENGTH: 18
<212> TYPE: PRT
<213> ORGANISM: Artificial
<220> FEATURE:
<223> OTHER INFORMATION: Recombinant peptide

<400> SEQUENCE: 426

Phe Val Asp Lys Phe Lys Asp Ala His Lys Glu Tyr Phe Ala Lys Phe
1               5                   10                  15
Trp Glu

<210> SEQ ID NO 427
<211> LENGTH: 18
<212> TYPE: PRT
<213> ORGANISM: Artificial
<220> FEATURE:
<223> OTHER INFORMATION: Recombinant peptide

<400> SEQUENCE: 427

Phe Val Glu Lys Phe Lys Glu Ala His Lys Glu Tyr Phe Ala Lys Phe
1               5                   10                  15
Trp Glu

```
<210> SEQ ID NO 428
<211> LENGTH: 18
<212> TYPE: PRT
<213> ORGANISM: Artificial
<220> FEATURE:
<223> OTHER INFORMATION: Recombinant peptide

<400> SEQUENCE: 428

Phe Val Asp Lys Phe Lys Asp Ala His Lys Asp Tyr Phe Ala Lys Phe
1               5                   10                  15

Trp Asp

<210> SEQ ID NO 429
<211> LENGTH: 18
<212> TYPE: PRT
<213> ORGANISM: Artificial
<220> FEATURE:
<223> OTHER INFORMATION: Recombinant peptide

<400> SEQUENCE: 429

Phe Val Asp Lys Phe Lys Glu Ala His Lys Asp Tyr Phe Ala Lys Phe
1               5                   10                  15

Trp Asp

<210> SEQ ID NO 430
<211> LENGTH: 18
<212> TYPE: PRT
<213> ORGANISM: Artificial
<220> FEATURE:
<223> OTHER INFORMATION: Recombinant peptide

<400> SEQUENCE: 430

Phe Val Glu Lys Phe Lys Asp Ala His Lys Asp Tyr Phe Ala Lys Phe
1               5                   10                  15

Trp Asp

<210> SEQ ID NO 431
<211> LENGTH: 18
<212> TYPE: PRT
<213> ORGANISM: Artificial
<220> FEATURE:
<223> OTHER INFORMATION: Recombinant peptide

<400> SEQUENCE: 431

Phe Val Glu Lys Phe Lys Glu Ala His Lys Glu Tyr Phe Ala Lys Phe
1               5                   10                  15

Trp Asp

<210> SEQ ID NO 432
<211> LENGTH: 18
<212> TYPE: PRT
<213> ORGANISM: Artificial
<220> FEATURE:
<223> OTHER INFORMATION: Recombinant peptide

<400> SEQUENCE: 432

Phe Val Glu Lys Phe Lys Glu Ala His Lys Asp Tyr Phe Ala Lys Phe
1               5                   10                  15

Trp Glu

<210> SEQ ID NO 433
<211> LENGTH: 18
<212> TYPE: PRT
<213> ORGANISM: Artificial
```

<220> FEATURE:
<223> OTHER INFORMATION: Recombinant peptide

<400> SEQUENCE: 433

Phe Ala Glu Lys Phe Lys Glu His Val Lys Asp Tyr Phe Ala Lys Phe
1               5                   10                  15

Trp Asp

<210> SEQ ID NO 434
<211> LENGTH: 18
<212> TYPE: PRT
<213> ORGANISM: Artificial
<220> FEATURE:
<223> OTHER INFORMATION: Recombinant peptide

<400> SEQUENCE: 434

Phe Ala Asp Lys Phe Lys Asp His Val Lys Glu Tyr Phe Ala Lys Phe
1               5                   10                  15

Trp Glu

<210> SEQ ID NO 435
<211> LENGTH: 18
<212> TYPE: PRT
<213> ORGANISM: Artificial
<220> FEATURE:
<223> OTHER INFORMATION: Recombinant peptide

<400> SEQUENCE: 435

Phe Ala Glu Lys Phe Lys Glu His Val Lys Glu Tyr Phe Ala Lys Phe
1               5                   10                  15

Trp Glu

<210> SEQ ID NO 436
<211> LENGTH: 18
<212> TYPE: PRT
<213> ORGANISM: Artificial
<220> FEATURE:
<223> OTHER INFORMATION: Recombinant peptide

<400> SEQUENCE: 436

Phe Ala Asp Lys Phe Lys Asp His Val Lys Asp Tyr Phe Ala Lys Phe
1               5                   10                  15

Trp Asp

<210> SEQ ID NO 437
<211> LENGTH: 18
<212> TYPE: PRT
<213> ORGANISM: Artificial
<220> FEATURE:
<223> OTHER INFORMATION: Recombinant peptide

<400> SEQUENCE: 437

Phe Ala Asp Lys Phe Lys Glu His Val Lys Asp Tyr Phe Ala Lys Phe
1               5                   10                  15

Trp Asp

<210> SEQ ID NO 438
<211> LENGTH: 18
<212> TYPE: PRT
<213> ORGANISM: Artificial
<220> FEATURE:
<223> OTHER INFORMATION: Recombinant peptide

<400> SEQUENCE: 438

Phe Ala Glu Lys Phe Lys Asp His Val Lys Asp Tyr Phe Ala Lys Phe
1               5                   10                  15

Trp Asp

<210> SEQ ID NO 439
<211> LENGTH: 18
<212> TYPE: PRT
<213> ORGANISM: Artificial
<220> FEATURE:
<223> OTHER INFORMATION: Recombinant peptide

<400> SEQUENCE: 439

Phe Ala Glu Lys Phe Lys Glu His Val Lys Glu Tyr Phe Ala Lys Phe
1               5                   10                  15

Trp Asp

<210> SEQ ID NO 440
<211> LENGTH: 18
<212> TYPE: PRT
<213> ORGANISM: Artificial
<220> FEATURE:
<223> OTHER INFORMATION: Recombinant peptide

<400> SEQUENCE: 440

Phe Ala Glu Lys Phe Lys Glu His Val Lys Asp Tyr Phe Ala Lys Phe
1               5                   10                  15

Trp Glu

<210> SEQ ID NO 441
<211> LENGTH: 18
<212> TYPE: PRT
<213> ORGANISM: Artificial
<220> FEATURE:
<223> OTHER INFORMATION: Recombinant peptide

<400> SEQUENCE: 441

Phe Ala Glu Lys Phe Lys Glu Phe Val Lys Asp Tyr His Ala Lys Phe
1               5                   10                  15

Trp Asp

<210> SEQ ID NO 442
<211> LENGTH: 18
<212> TYPE: PRT
<213> ORGANISM: Artificial
<220> FEATURE:
<223> OTHER INFORMATION: Recombinant peptide

<400> SEQUENCE: 442

Phe Ala Asp Lys Phe Lys Asp Phe Val Lys Glu Tyr His Ala Lys Phe
1               5                   10                  15

Trp Glu

<210> SEQ ID NO 443
<211> LENGTH: 18
<212> TYPE: PRT
<213> ORGANISM: Artificial
<220> FEATURE:
<223> OTHER INFORMATION: Recombinant peptide

<400> SEQUENCE: 443

Phe Ala Asp Lys Phe Lys Glu Phe Val Lys Asp Tyr His Ala Lys Phe
1               5                   10                  15

Trp Asp

<210> SEQ ID NO 444
<211> LENGTH: 18
<212> TYPE: PRT
<213> ORGANISM: Artificial
<220> FEATURE:
<223> OTHER INFORMATION: Recombinant peptide

<400> SEQUENCE: 444

Phe Ala Glu Lys Phe Lys Asp Phe Val Lys Asp Tyr His Ala Lys Phe
1               5                   10                  15

Trp Asp

<210> SEQ ID NO 445
<211> LENGTH: 18
<212> TYPE: PRT
<213> ORGANISM: Artificial
<220> FEATURE:
<223> OTHER INFORMATION: Recombinant peptide

<400> SEQUENCE: 445

Phe Ala Asp Lys Phe Lys Asp Phe Val Lys Asp Tyr His Ala Lys Phe
1               5                   10                  15

Trp Asp

<210> SEQ ID NO 446
<211> LENGTH: 18
<212> TYPE: PRT
<213> ORGANISM: Artificial
<220> FEATURE:
<223> OTHER INFORMATION: Recombinant peptide

<400> SEQUENCE: 446

Phe Ala Glu Lys Phe Lys Glu Phe Val Lys Glu Tyr His Ala Lys Phe
1               5                   10                  15

Trp Glu

<210> SEQ ID NO 447
<211> LENGTH: 18
<212> TYPE: PRT
<213> ORGANISM: Artificial
<220> FEATURE:
<223> OTHER INFORMATION: Recombinant peptide

<400> SEQUENCE: 447

Phe Ala Glu Lys Phe Lys Glu Phe Val Lys Glu Tyr His Ala Lys Phe
1               5                   10                  15

Trp Asp

<210> SEQ ID NO 448
<211> LENGTH: 18
<212> TYPE: PRT
<213> ORGANISM: Artificial
<220> FEATURE:
<223> OTHER INFORMATION: Recombinant peptide

<400> SEQUENCE: 448

Phe Ala Glu Lys Phe Lys Glu Phe Val Lys Asp Tyr His Ala Lys Phe
1               5                   10                  15

Trp Glu

<210> SEQ ID NO 449

```
<211> LENGTH: 18
<212> TYPE: PRT
<213> ORGANISM: Artificial
<220> FEATURE:
<223> OTHER INFORMATION: Recombinant peptide

<400> SEQUENCE: 449

Phe Ala Glu Lys Phe Lys Glu Phe Val Lys Asp Tyr Phe Ala Lys His
1               5                   10                  15

Trp Asp

<210> SEQ ID NO 450
<211> LENGTH: 18
<212> TYPE: PRT
<213> ORGANISM: Artificial
<220> FEATURE:
<223> OTHER INFORMATION: Recombinant peptide

<400> SEQUENCE: 450

Phe Ala Asp Lys Phe Lys Asp Phe Val Lys Glu Tyr Phe Ala Lys His
1               5                   10                  15

Trp Glu

<210> SEQ ID NO 451
<211> LENGTH: 18
<212> TYPE: PRT
<213> ORGANISM: Artificial
<220> FEATURE:
<223> OTHER INFORMATION: Recombinant peptide

<400> SEQUENCE: 451

Phe Ala Glu Lys Phe Lys Glu Phe Val Lys Glu Tyr Phe Ala Lys His
1               5                   10                  15

Trp Glu

<210> SEQ ID NO 452
<211> LENGTH: 18
<212> TYPE: PRT
<213> ORGANISM: Artificial
<220> FEATURE:
<223> OTHER INFORMATION: Recombinant peptide

<400> SEQUENCE: 452

Phe Ala Asp Lys Phe Lys Asp Phe Val Lys Asp Tyr Phe Ala Lys His
1               5                   10                  15

Trp Asp

<210> SEQ ID NO 453
<211> LENGTH: 18
<212> TYPE: PRT
<213> ORGANISM: Artificial
<220> FEATURE:
<223> OTHER INFORMATION: Recombinant peptide

<400> SEQUENCE: 453

Phe Ala Asp Lys Phe Lys Glu Phe Val Lys Asp Tyr Phe Ala Lys His
1               5                   10                  15

Trp Asp

<210> SEQ ID NO 454
<211> LENGTH: 18
<212> TYPE: PRT
<213> ORGANISM: Artificial
<220> FEATURE:
```

<223> OTHER INFORMATION: Recombinant peptide

<400> SEQUENCE: 454

Phe Ala Glu Lys Phe Lys Asp Phe Val Lys Asp Tyr Phe Ala Lys His
1               5                   10                  15

Trp Asp

<210> SEQ ID NO 455
<211> LENGTH: 18
<212> TYPE: PRT
<213> ORGANISM: Artificial
<220> FEATURE:
<223> OTHER INFORMATION: Recombinant peptide

<400> SEQUENCE: 455

Phe Ala Glu Lys Phe Lys Glu Phe Val Lys Glu Tyr Phe Ala Lys His
1               5                   10                  15

Trp Asp

<210> SEQ ID NO 456
<211> LENGTH: 18
<212> TYPE: PRT
<213> ORGANISM: Artificial
<220> FEATURE:
<223> OTHER INFORMATION: Recombinant peptide

<400> SEQUENCE: 456

Phe Ala Glu Lys Phe Lys Glu Phe Val Lys Asp Tyr Phe Ala Lys His
1               5                   10                  15

Trp Glu

<210> SEQ ID NO 457
<211> LENGTH: 18
<212> TYPE: PRT
<213> ORGANISM: Artificial
<220> FEATURE:
<223> OTHER INFORMATION: Recombinant peptide

<400> SEQUENCE: 457

Phe Ala Glu Lys Phe Lys Glu Ala Val Lys Glu Tyr Phe Ala Lys Phe
1               5                   10                  15

Trp Glu

<210> SEQ ID NO 458
<211> LENGTH: 18
<212> TYPE: PRT
<213> ORGANISM: Artificial
<220> FEATURE:
<223> OTHER INFORMATION: Recombinant peptide

<400> SEQUENCE: 458

Phe Ala Asp Lys Phe Lys Asp Ala Val Lys Asp Tyr Phe Ala Lys Phe
1               5                   10                  15

Trp Asp

<210> SEQ ID NO 459
<211> LENGTH: 18
<212> TYPE: PRT
<213> ORGANISM: Artificial
<220> FEATURE:
<223> OTHER INFORMATION: Recombinant peptide

<400> SEQUENCE: 459

```
Phe Ala Glu Arg Phe Arg Glu Ala Val Lys Asp Tyr Phe Ala Lys Phe
1               5                   10                  15

Trp Asp

<210> SEQ ID NO 460
<211> LENGTH: 18
<212> TYPE: PRT
<213> ORGANISM: Artificial
<220> FEATURE:
<223> OTHER INFORMATION: Recombinant peptide

<400> SEQUENCE: 460

Phe Ala Glu Lys Phe Arg Glu Ala Val Lys Asp Tyr Phe Ala Lys Phe
1               5                   10                  15

Trp Asp

<210> SEQ ID NO 461
<211> LENGTH: 18
<212> TYPE: PRT
<213> ORGANISM: Artificial
<220> FEATURE:
<223> OTHER INFORMATION: Recombinant peptide

<400> SEQUENCE: 461

Phe Ala Glu Lys Phe Lys Glu Ala Val Arg Asp Tyr Phe Ala Lys Phe
1               5                   10                  15

Trp Asp

<210> SEQ ID NO 462
<211> LENGTH: 18
<212> TYPE: PRT
<213> ORGANISM: Artificial
<220> FEATURE:
<223> OTHER INFORMATION: Recombinant peptide

<400> SEQUENCE: 462

Phe Ala Glu Lys Phe Lys Glu Ala Val Lys Asp Tyr Phe Ala Arg Phe
1               5                   10                  15

Trp Asp

<210> SEQ ID NO 463
<211> LENGTH: 18
<212> TYPE: PRT
<213> ORGANISM: Artificial
<220> FEATURE:
<223> OTHER INFORMATION: Recombinant peptide

<400> SEQUENCE: 463

Phe Ala Glu Lys Phe Lys Glu Ala Val Lys Glu Tyr Phe Ala Lys Phe
1               5                   10                  15

Trp Glu

<210> SEQ ID NO 464
<211> LENGTH: 18
<212> TYPE: PRT
<213> ORGANISM: Artificial
<220> FEATURE:
<223> OTHER INFORMATION: Recombinant peptide

<400> SEQUENCE: 464

Phe Ala Asp Lys Phe Lys Asp Ala Val Lys Asp Tyr Phe Ala Lys Phe
1               5                   10                  15

Trp Asp
```

<210> SEQ ID NO 465
<211> LENGTH: 18
<212> TYPE: PRT
<213> ORGANISM: Artificial
<220> FEATURE:
<223> OTHER INFORMATION: Recombinant peptide

<400> SEQUENCE: 465

Phe Ala Glu Arg Phe Arg Glu Ala Val Lys Asp Tyr Phe Ala Lys Phe
1               5                   10                  15

Trp Asp

<210> SEQ ID NO 466
<211> LENGTH: 18
<212> TYPE: PRT
<213> ORGANISM: Artificial
<220> FEATURE:
<223> OTHER INFORMATION: Recombinant peptide

<400> SEQUENCE: 466

Phe Ala Glu Lys Phe Arg Glu Ala Val Lys Asp Tyr Phe Ala Lys Phe
1               5                   10                  15

Trp Asp

<210> SEQ ID NO 467
<211> LENGTH: 18
<212> TYPE: PRT
<213> ORGANISM: Artificial
<220> FEATURE:
<223> OTHER INFORMATION: Recombinant peptide

<400> SEQUENCE: 467

Phe Ala Glu Lys Phe Lys Glu Ala Val Arg Asp Tyr Phe Ala Lys Phe
1               5                   10                  15

Trp Asp

<210> SEQ ID NO 468
<211> LENGTH: 18
<212> TYPE: PRT
<213> ORGANISM: Artificial
<220> FEATURE:
<223> OTHER INFORMATION: Recombinant peptide

<400> SEQUENCE: 468

Phe Ala Glu Lys Phe Lys Glu Ala Val Lys Asp Tyr Phe Ala Arg Phe
1               5                   10                  15

Trp Asp

<210> SEQ ID NO 469
<211> LENGTH: 18
<212> TYPE: PRT
<213> ORGANISM: Artificial
<220> FEATURE:
<223> OTHER INFORMATION: Recombinant peptide

<400> SEQUENCE: 469

Phe Ala Glu Lys Phe Lys Glu Ala Val Lys Glu Tyr Phe Ala Lys Phe
1               5                   10                  15

Trp Glu

<210> SEQ ID NO 470
<211> LENGTH: 18

<212> TYPE: PRT
<213> ORGANISM: Artificial
<220> FEATURE:
<223> OTHER INFORMATION: Recombinant peptide

<400> SEQUENCE: 470

Phe Ala Asp Lys Phe Lys Asp Ala Val Lys Asp Tyr Phe Ala Lys Phe
1               5                   10                  15

Trp Asp

<210> SEQ ID NO 471
<211> LENGTH: 18
<212> TYPE: PRT
<213> ORGANISM: Artificial
<220> FEATURE:
<223> OTHER INFORMATION: Recombinant peptide

<400> SEQUENCE: 471

Phe Ala Glu Arg Phe Arg Glu Ala Val Lys Asp Tyr Phe Ala Lys Phe
1               5                   10                  15

Trp Asp

<210> SEQ ID NO 472
<211> LENGTH: 18
<212> TYPE: PRT
<213> ORGANISM: Artificial
<220> FEATURE:
<223> OTHER INFORMATION: Recombinant peptide

<400> SEQUENCE: 472

Phe Ala Glu Lys Phe Arg Glu Ala Val Lys Asp Tyr Phe Ala Lys Phe
1               5                   10                  15

Trp Asp

<210> SEQ ID NO 473
<211> LENGTH: 18
<212> TYPE: PRT
<213> ORGANISM: Artificial
<220> FEATURE:
<223> OTHER INFORMATION: Recombinant peptide

<400> SEQUENCE: 473

Phe Ala Glu Lys Phe Lys Glu Ala Val Arg Asp Tyr Phe Ala Lys Phe
1               5                   10                  15

Trp Asp

<210> SEQ ID NO 474
<211> LENGTH: 18
<212> TYPE: PRT
<213> ORGANISM: Artificial
<220> FEATURE:
<223> OTHER INFORMATION: Recombinant peptide

<400> SEQUENCE: 474

Phe Ala Glu Lys Phe Lys Glu Ala Val Lys Asp Tyr Phe Ala Arg Phe
1               5                   10                  15

Trp Asp

<210> SEQ ID NO 475
<211> LENGTH: 18
<212> TYPE: PRT
<213> ORGANISM: Artificial
<220> FEATURE:
<223> OTHER INFORMATION: Recombinant peptide -continued

```
<400> SEQUENCE: 475

Phe Ala Glu Arg Phe Arg Glu Ala Val Lys Asp Tyr Phe Ala Lys Phe
1               5                   10                  15

Trp Asp

<210> SEQ ID NO 476
<211> LENGTH: 18
<212> TYPE: PRT
<213> ORGANISM: Artificial
<220> FEATURE:
<223> OTHER INFORMATION: Recombinant peptide

<400> SEQUENCE: 476

Phe Ala Glu Lys Phe Arg Glu Ala Val Lys Asp Tyr Phe Ala Lys Phe
1               5                   10                  15

Trp Asp

<210> SEQ ID NO 477
<211> LENGTH: 18
<212> TYPE: PRT
<213> ORGANISM: Artificial
<220> FEATURE:
<223> OTHER INFORMATION: Recombinant peptide

<400> SEQUENCE: 477

Phe Ala Glu Lys Phe Lys Glu Ala Val Arg Asp Tyr Phe Ala Lys Phe
1               5                   10                  15

Trp Asp

<210> SEQ ID NO 478
<211> LENGTH: 18
<212> TYPE: PRT
<213> ORGANISM: Artificial
<220> FEATURE:
<223> OTHER INFORMATION: Recombinant peptide

<400> SEQUENCE: 478

Phe Ala Glu Lys Phe Lys Glu Ala Val Lys Asp Tyr Phe Ala Arg Phe
1               5                   10                  15

Trp Asp

<210> SEQ ID NO 479
<211> LENGTH: 18
<212> TYPE: PRT
<213> ORGANISM: Artificial
<220> FEATURE:
<223> OTHER INFORMATION: Recombinant peptide

<400> SEQUENCE: 479

Phe Ala Glu Lys Phe Lys Glu Ala Val Lys Glu Tyr Phe Ala Lys Phe
1               5                   10                  15

Trp Glu

<210> SEQ ID NO 480
<211> LENGTH: 18
<212> TYPE: PRT
<213> ORGANISM: Artificial
<220> FEATURE:
<223> OTHER INFORMATION: Recombinant peptide

<400> SEQUENCE: 480

Phe Ala Asp Lys Phe Lys Asp Ala Val Lys Asp Tyr Phe Ala Lys Phe
```

```
1               5                  10                  15
Trp Asp

<210> SEQ ID NO 481
<211> LENGTH: 18
<212> TYPE: PRT
<213> ORGANISM: Artificial
<220> FEATURE:
<223> OTHER INFORMATION: Recombinant peptide

<400> SEQUENCE: 481

Phe Ala Glu Arg Phe Arg Glu Ala Val Lys Asp Tyr Phe Ala Lys Phe
1               5                  10                  15

Trp Asp

<210> SEQ ID NO 482
<211> LENGTH: 18
<212> TYPE: PRT
<213> ORGANISM: Artificial
<220> FEATURE:
<223> OTHER INFORMATION: Recombinant peptide

<400> SEQUENCE: 482

Phe Ala Glu Lys Phe Arg Glu Ala Val Lys Asp Tyr Phe Ala Lys Phe
1               5                  10                  15

Trp Asp

<210> SEQ ID NO 483
<211> LENGTH: 18
<212> TYPE: PRT
<213> ORGANISM: Artificial
<220> FEATURE:
<223> OTHER INFORMATION: Recombinant peptide

<400> SEQUENCE: 483

Phe Ala Glu Lys Phe Lys Glu Ala Val Arg Asp Tyr Phe Ala Lys Phe
1               5                  10                  15

Trp Asp

<210> SEQ ID NO 484
<211> LENGTH: 18
<212> TYPE: PRT
<213> ORGANISM: Artificial
<220> FEATURE:
<223> OTHER INFORMATION: Recombinant peptide

<400> SEQUENCE: 484

Phe Ala Glu Lys Phe Lys Glu Ala Val Lys Asp Tyr Phe Ala Arg Phe
1               5                  10                  15

Trp Asp

<210> SEQ ID NO 485
<211> LENGTH: 18
<212> TYPE: PRT
<213> ORGANISM: Artificial
<220> FEATURE:
<223> OTHER INFORMATION: Recombinant peptide

<400> SEQUENCE: 485

Leu Phe Glu Lys Phe Ala Glu Ala Phe Lys Asp Tyr Val Ala Lys Trp
1               5                  10                  15

Lys Asp
```

```
<210> SEQ ID NO 486
<211> LENGTH: 18
<212> TYPE: PRT
<213> ORGANISM: Artificial
<220> FEATURE:
<223> OTHER INFORMATION: Recombinant peptide

<400> SEQUENCE: 486

Leu Phe Glu Arg Phe Ala Glu Ala Phe Lys Asp Tyr Val Ala Lys Trp
1               5                   10                  15

Lys Asp

<210> SEQ ID NO 487
<211> LENGTH: 18
<212> TYPE: PRT
<213> ORGANISM: Artificial
<220> FEATURE:
<223> OTHER INFORMATION: Recombinant peptide

<400> SEQUENCE: 487

Leu Phe Glu Lys Phe Ala Glu Ala Phe Arg Asp Tyr Val Ala Lys Trp
1               5                   10                  15

Lys Asp

<210> SEQ ID NO 488
<211> LENGTH: 18
<212> TYPE: PRT
<213> ORGANISM: Artificial
<220> FEATURE:
<223> OTHER INFORMATION: Recombinant peptide

<400> SEQUENCE: 488

Leu Phe Glu Lys Phe Ala Glu Ala Phe Lys Asp Tyr Val Ala Arg Trp
1               5                   10                  15

Lys Asp

<210> SEQ ID NO 489
<211> LENGTH: 18
<212> TYPE: PRT
<213> ORGANISM: Artificial
<220> FEATURE:
<223> OTHER INFORMATION: Recombinant peptide

<400> SEQUENCE: 489

Leu Phe Glu Lys Phe Ala Glu Ala Phe Lys Asp Tyr Val Ala Lys Trp
1               5                   10                  15

Arg Asp

<210> SEQ ID NO 490
<211> LENGTH: 18
<212> TYPE: PRT
<213> ORGANISM: Artificial
<220> FEATURE:
<223> OTHER INFORMATION: Recombinant peptide

<400> SEQUENCE: 490

Leu Phe Glu Lys Phe Ala Glu Ala Phe Lys Glu Tyr Val Ala Lys Trp
1               5                   10                  15

Lys Glu

<210> SEQ ID NO 491
<211> LENGTH: 18
<212> TYPE: PRT
```

<213> ORGANISM: Artificial
<220> FEATURE:
<223> OTHER INFORMATION: Recombinant peptide

<400> SEQUENCE: 491

Leu Phe Asp Lys Phe Ala Asp Ala Phe Lys Asp Tyr Val Ala Lys Trp
1               5                   10                  15

Lys Asp

<210> SEQ ID NO 492
<211> LENGTH: 18
<212> TYPE: PRT
<213> ORGANISM: Artificial
<220> FEATURE:
<223> OTHER INFORMATION: Recombinant peptide

<400> SEQUENCE: 492

Leu Phe Asp Lys Phe Ala Glu Ala Phe Lys Asp Tyr Val Ala Lys Trp
1               5                   10                  15

Lys Asp

<210> SEQ ID NO 493
<211> LENGTH: 18
<212> TYPE: PRT
<213> ORGANISM: Artificial
<220> FEATURE:
<223> OTHER INFORMATION: Recombinant peptide

<400> SEQUENCE: 493

Leu Phe Glu Lys Phe Ala Asp Ala Phe Lys Asp Tyr Val Ala Lys Trp
1               5                   10                  15

Lys Asp

<210> SEQ ID NO 494
<211> LENGTH: 18
<212> TYPE: PRT
<213> ORGANISM: Artificial
<220> FEATURE:
<223> OTHER INFORMATION: Recombinant peptide

<400> SEQUENCE: 494

Leu Phe Glu Lys Phe Ala Glu Ala Phe Lys Glu Tyr Val Ala Lys Trp
1               5                   10                  15

Lys Asp

<210> SEQ ID NO 495
<211> LENGTH: 18
<212> TYPE: PRT
<213> ORGANISM: Artificial
<220> FEATURE:
<223> OTHER INFORMATION: Recombinant peptide

<400> SEQUENCE: 495

Leu Phe Glu Lys Phe Ala Glu Ala Phe Lys Asp Tyr Val Ala Lys Trp
1               5                   10                  15

Lys Glu

<210> SEQ ID NO 496
<211> LENGTH: 18
<212> TYPE: PRT
<213> ORGANISM: Artificial
<220> FEATURE:
<223> OTHER INFORMATION: Recombinant peptide

<400> SEQUENCE: 496

Phe Ala Glu Lys Ala Trp Glu Phe Val Lys Asp Tyr Phe Ala Lys Leu
1               5                   10                  15

Lys Asp

<210> SEQ ID NO 497
<211> LENGTH: 18
<212> TYPE: PRT
<213> ORGANISM: Artificial
<220> FEATURE:
<223> OTHER INFORMATION: Recombinant peptide

<400> SEQUENCE: 497

Phe Ala Glu Arg Ala Trp Glu Phe Val Lys Asp Tyr Phe Ala Lys Leu
1               5                   10                  15

Lys Asp

<210> SEQ ID NO 498
<211> LENGTH: 18
<212> TYPE: PRT
<213> ORGANISM: Artificial
<220> FEATURE:
<223> OTHER INFORMATION: Recombinant peptide

<400> SEQUENCE: 498

Phe Ala Glu Lys Ala Trp Glu Phe Val Lys Asp Tyr Phe Ala Lys Leu
1               5                   10                  15

Lys Asp

<210> SEQ ID NO 499
<211> LENGTH: 18
<212> TYPE: PRT
<213> ORGANISM: Artificial
<220> FEATURE:
<223> OTHER INFORMATION: Recombinant peptide

<400> SEQUENCE: 499

Phe Ala Glu Lys Ala Trp Glu Phe Val Lys Asp Tyr Phe Ala Lys Leu
1               5                   10                  15

Lys Asp

<210> SEQ ID NO 500
<211> LENGTH: 18
<212> TYPE: PRT
<213> ORGANISM: Artificial
<220> FEATURE:
<223> OTHER INFORMATION: Recombinant peptide

<400> SEQUENCE: 500

Phe Ala Glu Lys Ala Trp Glu Phe Val Lys Asp Tyr Phe Ala Lys Leu
1               5                   10                  15

Arg Asp

<210> SEQ ID NO 501
<211> LENGTH: 18
<212> TYPE: PRT
<213> ORGANISM: Artificial
<220> FEATURE:
<223> OTHER INFORMATION: Recombinant peptide

<400> SEQUENCE: 501

Phe Ala Glu Lys Ala Trp Glu Phe Val Lys Glu Tyr Phe Ala Lys Leu
1               5                   10                  15

Lys Glu

<210> SEQ ID NO 502
<211> LENGTH: 18
<212> TYPE: PRT
<213> ORGANISM: Artificial
<220> FEATURE:
<223> OTHER INFORMATION: Recombinant peptide

<400> SEQUENCE: 502

Phe Ala Asp Lys Ala Trp Asp Phe Val Lys Asp Tyr Phe Ala Lys Leu
1               5                   10                  15
Lys Asp

<210> SEQ ID NO 503
<211> LENGTH: 18
<212> TYPE: PRT
<213> ORGANISM: Artificial
<220> FEATURE:
<223> OTHER INFORMATION: Recombinant peptide

<400> SEQUENCE: 503

Phe Ala Asp Lys Ala Trp Glu Phe Val Lys Asp Tyr Phe Ala Lys Leu
1               5                   10                  15
Lys Asp

<210> SEQ ID NO 504
<211> LENGTH: 18
<212> TYPE: PRT
<213> ORGANISM: Artificial
<220> FEATURE:
<223> OTHER INFORMATION: Recombinant peptide

<400> SEQUENCE: 504

Phe Ala Glu Lys Ala Trp Asp Phe Val Lys Asp Tyr Phe Ala Lys Leu
1               5                   10                  15
Lys Asp

<210> SEQ ID NO 505
<211> LENGTH: 18
<212> TYPE: PRT
<213> ORGANISM: Artificial
<220> FEATURE:
<223> OTHER INFORMATION: Recombinant peptide

<400> SEQUENCE: 505

Phe Ala Glu Lys Ala Trp Glu Phe Val Lys Glu Tyr Phe Ala Lys Leu
1               5                   10                  15
Lys Asp

<210> SEQ ID NO 506
<211> LENGTH: 18
<212> TYPE: PRT
<213> ORGANISM: Artificial
<220> FEATURE:
<223> OTHER INFORMATION: Recombinant peptide

<400> SEQUENCE: 506

Phe Ala Glu Lys Ala Trp Glu Phe Val Lys Asp Tyr Phe Ala Lys Leu
1               5                   10                  15
Lys Glu

<210> SEQ ID NO 507
<211> LENGTH: 18
<212> TYPE: PRT
<213> ORGANISM: Artificial
<220> FEATURE:
<223> OTHER INFORMATION: Recombinant peptide

<400> SEQUENCE: 507

Phe Phe Glu Lys Phe Lys Glu Phe Val Lys Asp Tyr Phe Ala Lys Leu
1               5                   10                  15

Trp Asp

<210> SEQ ID NO 508
<211> LENGTH: 18
<212> TYPE: PRT
<213> ORGANISM: Artificial
<220> FEATURE:
<223> OTHER INFORMATION: Recombinant peptide

<400> SEQUENCE: 508

Phe Phe Glu Lys Phe Lys Glu Phe Val Lys Glu Tyr Phe Ala Lys Leu
1               5                   10                  15

Trp Glu

<210> SEQ ID NO 509
<211> LENGTH: 18
<212> TYPE: PRT
<213> ORGANISM: Artificial
<220> FEATURE:
<223> OTHER INFORMATION: Recombinant peptide

<400> SEQUENCE: 509

Phe Phe Asp Lys Phe Lys Asp Phe Val Lys Asp Tyr Phe Ala Lys Leu
1               5                   10                  15

Trp Asp

<210> SEQ ID NO 510
<211> LENGTH: 18
<212> TYPE: PRT
<213> ORGANISM: Artificial
<220> FEATURE:
<223> OTHER INFORMATION: Recombinant peptide

<400> SEQUENCE: 510

Phe Phe Glu Arg Phe Lys Glu Phe Val Lys Asp Tyr Phe Ala Lys Leu
1               5                   10                  15

Trp Asp

<210> SEQ ID NO 511
<211> LENGTH: 18
<212> TYPE: PRT
<213> ORGANISM: Artificial
<220> FEATURE:
<223> OTHER INFORMATION: Recombinant peptide

<400> SEQUENCE: 511

Phe Phe Glu Lys Phe Arg Glu Phe Val Lys Asp Tyr Phe Ala Lys Leu
1               5                   10                  15

Trp Asp

<210> SEQ ID NO 512
<211> LENGTH: 18
<212> TYPE: PRT
<213> ORGANISM: Artificial

<220> FEATURE:
<223> OTHER INFORMATION: Recombinant peptide

<400> SEQUENCE: 512

Phe Phe Glu Lys Phe Lys Glu Phe Val Arg Asp Tyr Phe Ala Lys Leu
1               5                   10                  15

Trp Asp

<210> SEQ ID NO 513
<211> LENGTH: 18
<212> TYPE: PRT
<213> ORGANISM: Artificial
<220> FEATURE:
<223> OTHER INFORMATION: Recombinant peptide

<400> SEQUENCE: 513

Phe Phe Glu Lys Phe Lys Glu Phe Val Lys Asp Tyr Phe Ala Arg Leu
1               5                   10                  15

Trp Asp

<210> SEQ ID NO 514
<211> LENGTH: 18
<212> TYPE: PRT
<213> ORGANISM: Artificial
<220> FEATURE:
<223> OTHER INFORMATION: Recombinant peptide

<400> SEQUENCE: 514

Phe Phe Asp Lys Phe Lys Glu Phe Val Lys Asp Tyr Phe Ala Lys Leu
1               5                   10                  15

Trp Asp

<210> SEQ ID NO 515
<211> LENGTH: 18
<212> TYPE: PRT
<213> ORGANISM: Artificial
<220> FEATURE:
<223> OTHER INFORMATION: Recombinant peptide

<400> SEQUENCE: 515

Phe Phe Glu Lys Phe Lys Asp Phe Val Lys Asp Tyr Phe Ala Lys Leu
1               5                   10                  15

Trp Asp

<210> SEQ ID NO 516
<211> LENGTH: 18
<212> TYPE: PRT
<213> ORGANISM: Artificial
<220> FEATURE:
<223> OTHER INFORMATION: Recombinant peptide

<400> SEQUENCE: 516

Phe Phe Glu Lys Phe Lys Glu Phe Val Lys Glu Tyr Phe Ala Lys Leu
1               5                   10                  15

Trp Asp

<210> SEQ ID NO 517
<211> LENGTH: 18
<212> TYPE: PRT
<213> ORGANISM: Artificial
<220> FEATURE:
<223> OTHER INFORMATION: Recombinant peptide

<400> SEQUENCE: 517

```
Phe Phe Glu Lys Phe Lys Glu Phe Val Lys Asp Tyr Phe Ala Lys Leu
1               5                   10                  15

Trp Glu

<210> SEQ ID NO 518
<211> LENGTH: 18
<212> TYPE: PRT
<213> ORGANISM: Artificial
<220> FEATURE:
<223> OTHER INFORMATION: Recombinant peptide

<400> SEQUENCE: 518

Phe Leu Glu Lys Phe Lys Glu Phe Val Lys Asp Tyr Phe Ala Lys Phe
1               5                   10                  15

Trp Asp

<210> SEQ ID NO 519
<211> LENGTH: 18
<212> TYPE: PRT
<213> ORGANISM: Artificial
<220> FEATURE:
<223> OTHER INFORMATION: Recombinant peptide

<400> SEQUENCE: 519

Phe Leu Glu Lys Phe Lys Glu Phe Val Lys Glu Tyr Phe Ala Lys Phe
1               5                   10                  15

Trp Glu

<210> SEQ ID NO 520
<211> LENGTH: 18
<212> TYPE: PRT
<213> ORGANISM: Artificial
<220> FEATURE:
<223> OTHER INFORMATION: Recombinant peptide

<400> SEQUENCE: 520

Phe Leu Asp Lys Phe Lys Glu Phe Val Lys Asp Tyr Phe Ala Lys Phe
1               5                   10                  15

Trp Asp

<210> SEQ ID NO 521
<211> LENGTH: 18
<212> TYPE: PRT
<213> ORGANISM: Artificial
<220> FEATURE:
<223> OTHER INFORMATION: Recombinant peptide

<400> SEQUENCE: 521

Phe Leu Asp Lys Phe Lys Glu Phe Val Lys Asp Tyr Phe Ala Lys Phe
1               5                   10                  15

Trp Asp

<210> SEQ ID NO 522
<211> LENGTH: 18
<212> TYPE: PRT
<213> ORGANISM: Artificial
<220> FEATURE:
<223> OTHER INFORMATION: Recombinant peptide

<400> SEQUENCE: 522

Phe Leu Glu Lys Phe Lys Asp Phe Val Lys Asp Tyr Phe Ala Lys Phe
1               5                   10                  15
```

Trp Asp

<210> SEQ ID NO 523
<211> LENGTH: 18
<212> TYPE: PRT
<213> ORGANISM: Artificial
<220> FEATURE:
<223> OTHER INFORMATION: Recombinant peptide

<400> SEQUENCE: 523

Phe Leu Glu Lys Phe Lys Glu Phe Val Lys Glu Tyr Phe Ala Lys Phe
1               5                   10                  15

Trp Asp

<210> SEQ ID NO 524
<211> LENGTH: 18
<212> TYPE: PRT
<213> ORGANISM: Artificial
<220> FEATURE:
<223> OTHER INFORMATION: Recombinant peptide

<400> SEQUENCE: 524

Phe Leu Glu Lys Phe Lys Glu Phe Val Lys Asp Tyr Phe Ala Lys Phe
1               5                   10                  15

Trp Glu

<210> SEQ ID NO 525
<211> LENGTH: 18
<212> TYPE: PRT
<213> ORGANISM: Artificial
<220> FEATURE:
<223> OTHER INFORMATION: Recombinant peptide

<400> SEQUENCE: 525

Phe Leu Glu Arg Phe Lys Glu Phe Val Lys Asp Tyr Phe Ala Lys Phe
1               5                   10                  15

Trp Asp

<210> SEQ ID NO 526
<211> LENGTH: 18
<212> TYPE: PRT
<213> ORGANISM: Artificial
<220> FEATURE:
<223> OTHER INFORMATION: Recombinant peptide

<400> SEQUENCE: 526

Phe Leu Glu Lys Phe Arg Glu Phe Val Lys Asp Tyr Phe Ala Lys Phe
1               5                   10                  15

Trp Asp

<210> SEQ ID NO 527
<211> LENGTH: 18
<212> TYPE: PRT
<213> ORGANISM: Artificial
<220> FEATURE:
<223> OTHER INFORMATION: Recombinant peptide

<400> SEQUENCE: 527

Phe Leu Glu Lys Phe Lys Glu Phe Val Arg Asp Tyr Phe Ala Lys Phe
1               5                   10                  15

Trp Asp

<210> SEQ ID NO 528

```
<211> LENGTH: 18
<212> TYPE: PRT
<213> ORGANISM: Artificial
<220> FEATURE:
<223> OTHER INFORMATION: Recombinant peptide

<400> SEQUENCE: 528

Phe Leu Glu Lys Phe Lys Glu Phe Val Lys Asp Tyr Phe Ala Arg Phe
1               5                   10                  15

Trp Asp

<210> SEQ ID NO 529
<211> LENGTH: 18
<212> TYPE: PRT
<213> ORGANISM: Artificial
<220> FEATURE:
<223> OTHER INFORMATION: Recombinant peptide

<400> SEQUENCE: 529

Phe Phe Glu Lys Phe Lys Glu Phe Phe Lys Asp Tyr Phe Ala Lys Leu
1               5                   10                  15

Trp Asp

<210> SEQ ID NO 530
<211> LENGTH: 18
<212> TYPE: PRT
<213> ORGANISM: Artificial
<220> FEATURE:
<223> OTHER INFORMATION: Recombinant peptide

<400> SEQUENCE: 530

Phe Phe Glu Lys Phe Lys Glu Phe Phe Lys Glu Tyr Phe Ala Lys Leu
1               5                   10                  15

Trp Glu

<210> SEQ ID NO 531
<211> LENGTH: 18
<212> TYPE: PRT
<213> ORGANISM: Artificial
<220> FEATURE:
<223> OTHER INFORMATION: Recombinant peptide

<400> SEQUENCE: 531

Phe Phe Asp Lys Phe Lys Asp Phe Phe Lys Asp Tyr Phe Ala Lys Leu
1               5                   10                  15

Trp Asp

<210> SEQ ID NO 532
<211> LENGTH: 18
<212> TYPE: PRT
<213> ORGANISM: Artificial
<220> FEATURE:
<223> OTHER INFORMATION: Recombinant peptide

<400> SEQUENCE: 532

Phe Phe Glu Arg Phe Lys Glu Phe Phe Lys Asp Tyr Phe Ala Lys Leu
1               5                   10                  15

Trp Asp

<210> SEQ ID NO 533
<211> LENGTH: 18
<212> TYPE: PRT
<213> ORGANISM: Artificial
<220> FEATURE:
```

<223> OTHER INFORMATION: Recombinant peptide

<400> SEQUENCE: 533

Phe Phe Glu Lys Phe Arg Glu Phe Phe Lys Asp Tyr Phe Ala Lys Leu
1               5                   10                  15

Trp Asp

<210> SEQ ID NO 534
<211> LENGTH: 18
<212> TYPE: PRT
<213> ORGANISM: Artificial
<220> FEATURE:
<223> OTHER INFORMATION: Recombinant peptide

<400> SEQUENCE: 534

Phe Phe Glu Lys Phe Lys Glu Phe Phe Arg Asp Tyr Phe Ala Lys Leu
1               5                   10                  15

Trp Asp

<210> SEQ ID NO 535
<211> LENGTH: 18
<212> TYPE: PRT
<213> ORGANISM: Artificial
<220> FEATURE:
<223> OTHER INFORMATION: Recombinant peptide

<400> SEQUENCE: 535

Phe Phe Glu Arg Phe Lys Glu Phe Phe Lys Asp Tyr Phe Ala Arg Leu
1               5                   10                  15

Trp Asp

<210> SEQ ID NO 536
<211> LENGTH: 18
<212> TYPE: PRT
<213> ORGANISM: Artificial
<220> FEATURE:
<223> OTHER INFORMATION: Recombinant peptide

<400> SEQUENCE: 536

Phe Phe Asp Lys Phe Lys Glu Phe Phe Lys Asp Tyr Phe Ala Lys Leu
1               5                   10                  15

Trp Asp

<210> SEQ ID NO 537
<211> LENGTH: 18
<212> TYPE: PRT
<213> ORGANISM: Artificial
<220> FEATURE:
<223> OTHER INFORMATION: Recombinant peptide

<400> SEQUENCE: 537

Phe Phe Glu Lys Phe Lys Asp Phe Phe Lys Asp Tyr Phe Ala Lys Leu
1               5                   10                  15

Trp Asp

<210> SEQ ID NO 538
<211> LENGTH: 18
<212> TYPE: PRT
<213> ORGANISM: Artificial
<220> FEATURE:
<223> OTHER INFORMATION: Recombinant peptide

<400> SEQUENCE: 538

Phe Phe Glu Lys Phe Lys Glu Phe Phe Lys Glu Tyr Phe Ala Lys Leu
1               5                   10                  15

Trp Asp

<210> SEQ ID NO 539
<211> LENGTH: 18
<212> TYPE: PRT
<213> ORGANISM: Artificial
<220> FEATURE:
<223> OTHER INFORMATION: Recombinant peptide

<400> SEQUENCE: 539

Phe Phe Glu Lys Phe Lys Glu Phe Phe Lys Asp Tyr Phe Ala Lys Leu
1               5                   10                  15

Trp Glu

<210> SEQ ID NO 540
<211> LENGTH: 18
<212> TYPE: PRT
<213> ORGANISM: Artificial
<220> FEATURE:
<223> OTHER INFORMATION: Recombinant peptide

<400> SEQUENCE: 540

Phe Ala Glu Lys Phe Lys Glu Ala Val Lys Asp Tyr Phe Ala Lys Phe
1               5                   10                  15

Trp Asp

<210> SEQ ID NO 541
<211> LENGTH: 18
<212> TYPE: PRT
<213> ORGANISM: Artificial
<220> FEATURE:
<223> OTHER INFORMATION: Recombinant peptide

<400> SEQUENCE: 541

Phe Ala Glu Lys Phe Lys Glu Ala Val Lys Glu Tyr Phe Ala Lys Phe
1               5                   10                  15

Trp Glu

<210> SEQ ID NO 542
<211> LENGTH: 18
<212> TYPE: PRT
<213> ORGANISM: Artificial
<220> FEATURE:
<223> OTHER INFORMATION: Recombinant peptide

<400> SEQUENCE: 542

Phe Ala Asp Lys Phe Lys Asp Ala Val Lys Asp Tyr Phe Ala Lys Phe
1               5                   10                  15

Trp Asp

<210> SEQ ID NO 543
<211> LENGTH: 18
<212> TYPE: PRT
<213> ORGANISM: Artificial
<220> FEATURE:
<223> OTHER INFORMATION: Recombinant peptide

<400> SEQUENCE: 543

Phe Ala Glu Arg Phe Arg Glu Ala Val Lys Asp Tyr Phe Ala Lys Phe
1               5                   10                  15

Trp Asp

<210> SEQ ID NO 544
<211> LENGTH: 18
<212> TYPE: PRT
<213> ORGANISM: Artificial
<220> FEATURE:
<223> OTHER INFORMATION: Recombinant peptide

<400> SEQUENCE: 544

Phe Ala Glu Lys Phe Arg Glu Ala Val Lys Asp Tyr Phe Ala Lys Phe
1               5                   10                  15

Trp Asp

<210> SEQ ID NO 545
<211> LENGTH: 18
<212> TYPE: PRT
<213> ORGANISM: Artificial
<220> FEATURE:
<223> OTHER INFORMATION: Recombinant peptide

<400> SEQUENCE: 545

Phe Ala Glu Lys Phe Lys Glu Ala Val Arg Asp Tyr Phe Ala Lys Phe
1               5                   10                  15

Trp Asp

<210> SEQ ID NO 546
<211> LENGTH: 18
<212> TYPE: PRT
<213> ORGANISM: Artificial
<220> FEATURE:
<223> OTHER INFORMATION: Recombinant peptide

<400> SEQUENCE: 546

Phe Ala Glu Lys Phe Lys Glu Ala Val Lys Asp Tyr Phe Ala Arg Phe
1               5                   10                  15

Trp Asp

<210> SEQ ID NO 547
<211> LENGTH: 18
<212> TYPE: PRT
<213> ORGANISM: Artificial
<220> FEATURE:
<223> OTHER INFORMATION: Recombinant peptide

<400> SEQUENCE: 547

Asp Lys Trp Lys Ala Val Tyr Asp Lys Phe Ala Glu Ala Phe Lys Glu
1               5                   10                  15

Phe Phe

<210> SEQ ID NO 548
<211> LENGTH: 18
<212> TYPE: PRT
<213> ORGANISM: Artificial
<220> FEATURE:
<223> OTHER INFORMATION: Recombinant peptide

<400> SEQUENCE: 548

Glu Lys Trp Lys Ala Val Tyr Glu Lys Phe Ala Glu Ala Phe Lys Glu
1               5                   10                  15

Phe Phe

<210> SEQ ID NO 549
<211> LENGTH: 18

<212> TYPE: PRT
<213> ORGANISM: Artificial
<220> FEATURE:
<223> OTHER INFORMATION: Recombinant peptide

<400> SEQUENCE: 549

Asp Lys Trp Lys Ala Val Tyr Asp Lys Phe Ala Asp Ala Phe Lys Asp
1               5                   10                  15

Phe Phe

<210> SEQ ID NO 550
<211> LENGTH: 18
<212> TYPE: PRT
<213> ORGANISM: Artificial
<220> FEATURE:
<223> OTHER INFORMATION: Recombinant peptide

<400> SEQUENCE: 550

Asp Arg Trp Lys Ala Val Tyr Asp Lys Phe Ala Glu Ala Phe Lys Glu
1               5                   10                  15

Phe Phe

<210> SEQ ID NO 551
<211> LENGTH: 18
<212> TYPE: PRT
<213> ORGANISM: Artificial
<220> FEATURE:
<223> OTHER INFORMATION: Recombinant peptide

<400> SEQUENCE: 551

Asp Lys Trp Arg Ala Val Tyr Asp Lys Phe Ala Glu Ala Phe Lys Glu
1               5                   10                  15

Phe Phe

<210> SEQ ID NO 552
<211> LENGTH: 18
<212> TYPE: PRT
<213> ORGANISM: Artificial
<220> FEATURE:
<223> OTHER INFORMATION: Recombinant peptide

<400> SEQUENCE: 552

Asp Lys Trp Lys Ala Val Tyr Asp Arg Phe Ala Glu Ala Phe Lys Glu
1               5                   10                  15

Phe Phe

<210> SEQ ID NO 553
<211> LENGTH: 18
<212> TYPE: PRT
<213> ORGANISM: Artificial
<220> FEATURE:
<223> OTHER INFORMATION: Recombinant peptide

<400> SEQUENCE: 553

Asp Lys Trp Lys Ala Val Tyr Asp Lys Phe Ala Glu Ala Phe Arg Glu
1               5                   10                  15

Phe Phe

<210> SEQ ID NO 554
<211> LENGTH: 18
<212> TYPE: PRT
<213> ORGANISM: Artificial
<220> FEATURE:
<223> OTHER INFORMATION: Recombinant peptide

```
<400> SEQUENCE: 554

Phe Phe Glu Lys Phe Ala Glu Ala Phe Lys Asp Tyr Val Ala Lys Trp
1               5                   10                  15

Lys Asp

<210> SEQ ID NO 555
<211> LENGTH: 18
<212> TYPE: PRT
<213> ORGANISM: Artificial
<220> FEATURE:
<223> OTHER INFORMATION: Recombinant peptide

<400> SEQUENCE: 555

Phe Phe Glu Lys Phe Ala Glu Ala Phe Lys Glu Tyr Val Ala Lys Trp
1               5                   10                  15

Lys Glu

<210> SEQ ID NO 556
<211> LENGTH: 18
<212> TYPE: PRT
<213> ORGANISM: Artificial
<220> FEATURE:
<223> OTHER INFORMATION: Recombinant peptide

<400> SEQUENCE: 556

Phe Phe Asp Lys Phe Ala Asp Ala Phe Lys Asp Tyr Val Ala Lys Trp
1               5                   10                  15

Lys Asp

<210> SEQ ID NO 557
<211> LENGTH: 18
<212> TYPE: PRT
<213> ORGANISM: Artificial
<220> FEATURE:
<223> OTHER INFORMATION: Recombinant peptide

<400> SEQUENCE: 557

Phe Phe Glu Arg Phe Ala Glu Ala Phe Lys Asp Tyr Val Ala Lys Trp
1               5                   10                  15

Lys Asp

<210> SEQ ID NO 558
<211> LENGTH: 18
<212> TYPE: PRT
<213> ORGANISM: Artificial
<220> FEATURE:
<223> OTHER INFORMATION: Recombinant peptide

<400> SEQUENCE: 558

Phe Phe Glu Arg Phe Ala Glu Ala Phe Arg Asp Tyr Val Ala Lys Trp
1               5                   10                  15

Lys Asp

<210> SEQ ID NO 559
<211> LENGTH: 18
<212> TYPE: PRT
<213> ORGANISM: Artificial
<220> FEATURE:
<223> OTHER INFORMATION: Recombinant peptide

<400> SEQUENCE: 559

Phe Phe Glu Lys Phe Ala Glu Ala Phe Lys Asp Tyr Val Ala Arg Trp
```

<210> SEQ ID NO 560
<211> LENGTH: 18
<212> TYPE: PRT
<213> ORGANISM: Artificial
<220> FEATURE:
<223> OTHER INFORMATION: Recombinant peptide

<400> SEQUENCE: 560

Phe Phe Glu Arg Phe Ala Glu Ala Phe Lys Asp Tyr Val Ala Lys Trp
1               5                   10                  15

Arg Asp

<210> SEQ ID NO 561
<211> LENGTH: 18
<212> TYPE: PRT
<213> ORGANISM: Artificial
<220> FEATURE:
<223> OTHER INFORMATION: Recombinant peptide

<400> SEQUENCE: 561

Phe Phe Asp Lys Phe Ala Glu Ala Phe Lys Asp Tyr Val Ala Lys Trp
1               5                   10                  15

Lys Asp

<210> SEQ ID NO 562
<211> LENGTH: 18
<212> TYPE: PRT
<213> ORGANISM: Artificial
<220> FEATURE:
<223> OTHER INFORMATION: Recombinant peptide

<400> SEQUENCE: 562

Phe Phe Glu Lys Phe Ala Asp Ala Phe Lys Asp Tyr Val Ala Lys Trp
1               5                   10                  15

Lys Asp

<210> SEQ ID NO 563
<211> LENGTH: 18
<212> TYPE: PRT
<213> ORGANISM: Artificial
<220> FEATURE:
<223> OTHER INFORMATION: Recombinant peptide

<400> SEQUENCE: 563

Phe Phe Glu Arg Phe Ala Glu Ala Phe Lys Glu Tyr Val Ala Lys Trp
1               5                   10                  15

Lys Asp

<210> SEQ ID NO 564
<211> LENGTH: 18
<212> TYPE: PRT
<213> ORGANISM: Artificial
<220> FEATURE:
<223> OTHER INFORMATION: Recombinant peptide

<400> SEQUENCE: 564

Phe Phe Glu Arg Phe Ala Glu Ala Phe Lys Asp Tyr Val Ala Lys Trp
1               5                   10                  15

Lys Glu

<210> SEQ ID NO 565
<211> LENGTH: 18
<212> TYPE: PRT
<213> ORGANISM: Artificial
<220> FEATURE:
<223> OTHER INFORMATION: Recombinant peptide

<400> SEQUENCE: 565

Phe Phe Glu Lys Phe Lys Glu Phe Phe Lys Asp Tyr Phe Ala Lys Phe
1               5                   10                  15

Trp Asp

<210> SEQ ID NO 566
<211> LENGTH: 18
<212> TYPE: PRT
<213> ORGANISM: Artificial
<220> FEATURE:
<223> OTHER INFORMATION: Recombinant peptide

<400> SEQUENCE: 566

Phe Phe Asp Lys Phe Lys Asp Phe Phe Lys Asp Tyr Phe Ala Lys Phe
1               5                   10                  15

Trp Asp

<210> SEQ ID NO 567
<211> LENGTH: 18
<212> TYPE: PRT
<213> ORGANISM: Artificial
<220> FEATURE:
<223> OTHER INFORMATION: Recombinant peptide

<400> SEQUENCE: 567

Phe Phe Glu Lys Phe Lys Glu Phe Phe Lys Glu Tyr Phe Ala Lys Phe
1               5                   10                  15

Trp Glu

<210> SEQ ID NO 568
<211> LENGTH: 18
<212> TYPE: PRT
<213> ORGANISM: Artificial
<220> FEATURE:
<223> OTHER INFORMATION: Recombinant peptide

<400> SEQUENCE: 568

Phe Phe Glu Arg Phe Lys Glu Phe Phe Lys Asp Tyr Phe Ala Lys Phe
1               5                   10                  15

Trp Asp

<210> SEQ ID NO 569
<211> LENGTH: 18
<212> TYPE: PRT
<213> ORGANISM: Artificial
<220> FEATURE:
<223> OTHER INFORMATION: Recombinant peptide

<400> SEQUENCE: 569

Phe Phe Glu Lys Phe Arg Glu Phe Phe Lys Asp Tyr Phe Ala Lys Phe
1               5                   10                  15

Trp Asp

<210> SEQ ID NO 570
<211> LENGTH: 18
<212> TYPE: PRT

<213> ORGANISM: Artificial
<220> FEATURE:
<223> OTHER INFORMATION: Recombinant peptide

<400> SEQUENCE: 570

Phe Phe Glu Lys Phe Lys Glu Phe Phe Arg Asp Tyr Phe Ala Lys Phe
1               5                   10                  15

Trp Asp

<210> SEQ ID NO 571
<211> LENGTH: 18
<212> TYPE: PRT
<213> ORGANISM: Artificial
<220> FEATURE:
<223> OTHER INFORMATION: Recombinant peptide

<400> SEQUENCE: 571

Phe Phe Glu Lys Phe Lys Glu Phe Phe Lys Asp Tyr Phe Ala Arg Phe
1               5                   10                  15

Trp Asp

<210> SEQ ID NO 572
<211> LENGTH: 18
<212> TYPE: PRT
<213> ORGANISM: Artificial
<220> FEATURE:
<223> OTHER INFORMATION: Recombinant peptide

<400> SEQUENCE: 572

Phe Phe Asp Lys Phe Lys Glu Phe Phe Lys Asp Tyr Phe Ala Lys Phe
1               5                   10                  15

Trp Asp

<210> SEQ ID NO 573
<211> LENGTH: 18
<212> TYPE: PRT
<213> ORGANISM: Artificial
<220> FEATURE:
<223> OTHER INFORMATION: Recombinant peptide

<400> SEQUENCE: 573

Phe Phe Glu Lys Phe Lys Asp Phe Phe Lys Asp Tyr Phe Ala Lys Phe
1               5                   10                  15

Trp Asp

<210> SEQ ID NO 574
<211> LENGTH: 18
<212> TYPE: PRT
<213> ORGANISM: Artificial
<220> FEATURE:
<223> OTHER INFORMATION: Recombinant peptide

<400> SEQUENCE: 574

Phe Phe Glu Lys Phe Lys Glu Phe Phe Lys Glu Tyr Phe Ala Lys Phe
1               5                   10                  15

Trp Asp

<210> SEQ ID NO 575
<211> LENGTH: 18
<212> TYPE: PRT
<213> ORGANISM: Artificial
<220> FEATURE:
<223> OTHER INFORMATION: Recombinant peptide

```
<400> SEQUENCE: 575

Phe Phe Glu Lys Phe Lys Glu Phe Phe Lys Asp Tyr Phe Ala Lys Phe
1               5                   10                  15

Trp Glu

<210> SEQ ID NO 576
<211> LENGTH: 33
<212> TYPE: PRT
<213> ORGANISM: Artificial
<220> FEATURE:
<223> OTHER INFORMATION: Recombinant peptide

<400> SEQUENCE: 576

Glu Val Arg Ala Lys Leu Glu Glu Gln Ala Gln Gln Ile Arg Leu Gln
1               5                   10                  15

Ala Glu Ala Phe Gln Ala Arg Leu Lys Ser Trp Phe Glu Pro Leu Val
                20                  25                  30

Glu

<210> SEQ ID NO 577
<211> LENGTH: 29
<212> TYPE: PRT
<213> ORGANISM: Artificial
<220> FEATURE:
<223> OTHER INFORMATION: Recombinant peptide

<400> SEQUENCE: 577

Glu Val Arg Ala Lys Leu Glu Glu Gln Ala Gln Gln Ile Arg Leu Gln
1               5                   10                  15

Ala Glu Ala Phe Gln Ala Arg Leu Lys Ser Trp Phe Glu
                20                  25

<210> SEQ ID NO 578
<211> LENGTH: 26
<212> TYPE: PRT
<213> ORGANISM: Artificial
<220> FEATURE:
<223> OTHER INFORMATION: Recombinant peptide

<400> SEQUENCE: 578

Glu Val Arg Ser Lys Leu Glu Glu Trp Phe Ala Ala Phe Arg Glu Phe
1               5                   10                  15

Ala Glu Glu Phe Leu Ala Arg Leu Lys Ser
                20                  25

<210> SEQ ID NO 579
<211> LENGTH: 22
<212> TYPE: PRT
<213> ORGANISM: Artificial
<220> FEATURE:
<223> OTHER INFORMATION: Recombinant peptide

<400> SEQUENCE: 579

Pro Val Leu Asp Leu Phe Arg Glu Leu Leu Asn Glu Leu Leu Glu Ala
1               5                   10                  15

Leu Lys Gln Lys Leu Lys
                20

<210> SEQ ID NO 580
<211> LENGTH: 37
<212> TYPE: PRT
<213> ORGANISM: Artificial
<220> FEATURE:
```

<223> OTHER INFORMATION: Recombinant peptide

<400> SEQUENCE: 580

Asp Trp Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
        35

<210> SEQ ID NO 581
<211> LENGTH: 37
<212> TYPE: PRT
<213> ORGANISM: Artificial
<220> FEATURE:
<223> OTHER INFORMATION: Recombinant peptide

<400> SEQUENCE: 581

Glu Glu Leu Lys Glu Lys Leu Glu Glu Leu Lys Glu Lys Leu Glu Glu
1               5                   10                  15

Lys Leu Pro Glu Glu Leu Lys Glu Lys Leu Glu Glu Leu Lys Glu Lys
            20                  25                  30

Leu Glu Glu Lys Leu
        35

<210> SEQ ID NO 582
<211> LENGTH: 37
<212> TYPE: PRT
<213> ORGANISM: Artificial
<220> FEATURE:
<223> OTHER INFORMATION: Recombinant peptide

<400> SEQUENCE: 582

Glu Glu Leu Lys Ala Lys Leu Glu Glu Leu Lys Ala Lys Leu Glu Glu
1               5                   10                  15

Lys Leu Pro Glu Glu Leu Lys Ala Lys Leu Glu Glu Leu Lys Ala Lys
            20                  25                  30

Leu Glu Glu Lys Leu
        35

<210> SEQ ID NO 583
<211> LENGTH: 37
<212> TYPE: PRT
<213> ORGANISM: Artificial
<220> FEATURE:
<223> OTHER INFORMATION: Recombinant peptide

<400> SEQUENCE: 583

Glu Lys Leu Lys Ala Leu Leu Glu Lys Leu Leu Ala Lys Leu Lys Glu
1               5                   10                  15

Leu Leu Pro Glu Lys Leu Lys Ala Leu Leu Glu Lys Leu Leu Ala Lys
            20                  25                  30

Leu Lys Glu Leu Leu
        35

<210> SEQ ID NO 584
<211> LENGTH: 37
<212> TYPE: PRT
<213> ORGANISM: Artificial
<220> FEATURE:
<223> OTHER INFORMATION: Recombinant peptide

<400> SEQUENCE: 584

```
Glu Trp Leu Lys Glu Leu Leu Glu Lys Leu Leu Glu Lys Leu Lys Glu
1               5                   10                  15

Leu Leu Pro Glu Trp Leu Lys Glu Leu Leu Glu Lys Leu Leu Glu Lys
            20                  25                  30

Leu Lys Glu Leu Leu
        35

<210> SEQ ID NO 585
<211> LENGTH: 37
<212> TYPE: PRT
<213> ORGANISM: Artificial
<220> FEATURE:
<223> OTHER INFORMATION: Recombinant peptide

<400> SEQUENCE: 585

Glu Lys Phe Lys Glu Leu Leu Glu Lys Phe Leu Glu Lys Phe Lys Glu
1               5                   10                  15

Leu Leu Pro Glu Lys Phe Lys Glu Leu Leu Glu Lys Phe Leu Glu Lys
            20                  25                  30

Phe Lys Glu Leu Leu
        35

<210> SEQ ID NO 586
<211> LENGTH: 37
<212> TYPE: PRT
<213> ORGANISM: Artificial
<220> FEATURE:
<223> OTHER INFORMATION: Recombinant peptide

<400> SEQUENCE: 586

Glu Lys Leu Lys Glu Leu Leu Glu Lys Leu Leu Glu Leu Leu Lys Lys
1               5                   10                  15

Leu Leu Pro Glu Lys Leu Lys Glu Leu Leu Glu Lys Leu Leu Glu Leu
            20                  25                  30

Leu Lys Lys Leu Leu
        35

<210> SEQ ID NO 587
<211> LENGTH: 37
<212> TYPE: PRT
<213> ORGANISM: Artificial
<220> FEATURE:
<223> OTHER INFORMATION: Recombinant peptide

<400> SEQUENCE: 587

Glu Lys Leu Lys Glu Leu Leu Glu Lys Leu Lys Ala Lys Leu Glu Glu
1               5                   10                  15

Leu Leu Pro Glu Lys Leu Lys Glu Leu Leu Glu Lys Leu Lys Ala Lys
            20                  25                  30

Leu Glu Glu Leu Leu
        35

<210> SEQ ID NO 588
<211> LENGTH: 37
<212> TYPE: PRT
<213> ORGANISM: Artificial
<220> FEATURE:
<223> OTHER INFORMATION: Recombinant peptide

<400> SEQUENCE: 588

Glu Lys Leu Lys Glu Leu Leu Glu Lys Leu Leu Ala Lys Leu Lys Glu
1               5                   10                  15
```

```
Leu Leu Pro Glu Lys Leu Lys Glu Leu Leu Glu Lys Leu Leu Ala Lys
            20                  25                  30

Leu Lys Glu Leu Leu
        35

<210> SEQ ID NO 589
<211> LENGTH: 37
<212> TYPE: PRT
<213> ORGANISM: Artificial
<220> FEATURE:
<223> OTHER INFORMATION: Recombinant peptide

<400> SEQUENCE: 589

Glu Lys Phe Lys Glu Leu Leu Glu Lys Leu Leu Glu Lys Leu Lys Glu
1               5                   10                  15

Leu Leu Pro Glu Lys Phe Lys Glu Leu Leu Glu Lys Leu Leu Glu Lys
            20                  25                  30

Leu Lys Glu Leu Leu
        35

<210> SEQ ID NO 590
<211> LENGTH: 37
<212> TYPE: PRT
<213> ORGANISM: Artificial
<220> FEATURE:
<223> OTHER INFORMATION: Recombinant peptide

<400> SEQUENCE: 590

Glu Lys Leu Lys Ala Lys Leu Glu Glu Leu Lys Ala Lys Leu Glu Glu
1               5                   10                  15

Leu Leu Pro Glu Lys Leu Lys Ala Lys Leu Glu Glu Leu Lys Ala Lys
            20                  25                  30

Leu Glu Glu Leu Leu
        35

<210> SEQ ID NO 591
<211> LENGTH: 36
<212> TYPE: PRT
<213> ORGANISM: Artificial
<220> FEATURE:
<223> OTHER INFORMATION: Recombinant peptide

<400> SEQUENCE: 591

Glu Glu Leu Lys Glu Leu Leu Lys Glu Leu Leu Lys Lys Leu Glu Lys
1               5                   10                  15

Leu Leu Pro Glu Leu Lys Glu Leu Leu Lys Glu Leu Leu Lys Lys Leu
            20                  25                  30

Glu Lys Leu Leu
        35

<210> SEQ ID NO 592
<211> LENGTH: 37
<212> TYPE: PRT
<213> ORGANISM: Artificial
<220> FEATURE:
<223> OTHER INFORMATION: Recombinant peptide

<400> SEQUENCE: 592

Glu Glu Leu Lys Lys Leu Leu Glu Glu Leu Leu Lys Lys Leu Lys Glu
1               5                   10                  15

Leu Leu Pro Glu Glu Leu Lys Lys Leu Leu Glu Glu Leu Leu Lys Lys
            20                  25                  30
```

Leu Lys Glu Leu Leu
        35

<210> SEQ ID NO 593
<211> LENGTH: 37
<212> TYPE: PRT
<213> ORGANISM: Artificial
<220> FEATURE:
<223> OTHER INFORMATION: Recombinant peptide

<400> SEQUENCE: 593

Glu Lys Leu Lys Glu Leu Leu Glu Lys Leu Leu Glu Lys Leu Lys Glu
1               5                   10                  15

Leu Leu Ala Glu Lys Leu Lys Glu Leu Leu Glu Lys Leu Leu Glu Lys
            20                  25                  30

Leu Lys Glu Leu Leu
        35

<210> SEQ ID NO 594
<211> LENGTH: 38
<212> TYPE: PRT
<213> ORGANISM: Artificial
<220> FEATURE:
<223> OTHER INFORMATION: Recombinant peptide

<400> SEQUENCE: 594

Glu Lys Leu Lys Glu Leu Leu Glu Lys Leu Leu Glu Lys Leu Lys Glu
1               5                   10                  15

Leu Leu Ala Ala Glu Lys Leu Lys Glu Leu Leu Glu Lys Leu Leu Glu
            20                  25                  30

Lys Leu Lys Glu Leu Leu
        35

<210> SEQ ID NO 595
<211> LENGTH: 37
<212> TYPE: PRT
<213> ORGANISM: Artificial
<220> FEATURE:
<223> OTHER INFORMATION: Recombinant peptide

<400> SEQUENCE: 595

Glu Lys Leu Lys Ala Lys Leu Glu Glu Leu Lys Ala Lys Leu Glu Glu
1               5                   10                  15

Leu Leu Pro Glu Lys Ala Lys Ala Ala Leu Glu Glu Ala Lys Ala Lys
            20                  25                  30

Ala Glu Glu Leu Ala
        35

<210> SEQ ID NO 596
<211> LENGTH: 37
<212> TYPE: PRT
<213> ORGANISM: Artificial
<220> FEATURE:
<223> OTHER INFORMATION: Recombinant peptide

<400> SEQUENCE: 596

Glu Lys Leu Lys Ala Lys Leu Glu Glu Leu Lys Ala Lys Leu Glu Glu
1               5                   10                  15

Leu Leu Pro Glu His Ala Lys Ala Ala Leu Glu Glu Ala Lys Cys Lys
            20                  25                  30

Ala Glu Glu Leu Ala
        35

<210> SEQ ID NO 597
<211> LENGTH: 37
<212> TYPE: PRT
<213> ORGANISM: Artificial
<220> FEATURE:
<223> OTHER INFORMATION: Recombinant peptide

<400> SEQUENCE: 597

Asp His Leu Lys Ala Phe Tyr Asp Lys Val Ala Cys Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
        35

<210> SEQ ID NO 598
<211> LENGTH: 37
<212> TYPE: PRT
<213> ORGANISM: Artificial
<220> FEATURE:
<223> OTHER INFORMATION: Recombinant peptide

<400> SEQUENCE: 598

Asp Trp Leu Lys Ala Phe Tyr Asp Lys Val Ala Glu Lys Leu Lys Glu
1               5                   10                  15

Ala Phe Pro Asp His Ala Lys Ala Ala Tyr Asp Lys Ala Ala Cys Lys
            20                  25                  30

Ala Lys Glu Ala Ala
        35

<210> SEQ ID NO 599
<211> LENGTH: 37
<212> TYPE: PRT
<213> ORGANISM: Artificial
<220> FEATURE:
<223> OTHER INFORMATION: Recombinant peptide

<400> SEQUENCE: 599

Asp Trp Leu Lys Ala Phe Tyr Asp Lys Val Ala Cys Lys Leu Lys Glu
1               5                   10                  15

Ala Phe Pro Asp Trp Ala Lys Ala Ala Tyr Asn Lys Ala Ala Glu Lys
            20                  25                  30

Ala Lys Glu Ala Ala
        35

<210> SEQ ID NO 600
<211> LENGTH: 37
<212> TYPE: PRT
<213> ORGANISM: Artificial
<220> FEATURE:
<223> OTHER INFORMATION: Recombinant peptide

<400> SEQUENCE: 600

Asp His Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
        35

<210> SEQ ID NO 601

<211> LENGTH: 23
<212> TYPE: PRT
<213> ORGANISM: Artificial
<220> FEATURE:
<223> OTHER INFORMATION: Recombinant peptide

<400> SEQUENCE: 601

Val Leu Glu Ser Phe Lys Val Ser Phe Leu Ser Ala Leu Glu Glu Tyr
1               5                   10                  15

Thr Lys Lys Leu Asn Thr Gln
            20

<210> SEQ ID NO 602
<211> LENGTH: 18
<212> TYPE: PRT
<213> ORGANISM: Artificial
<220> FEATURE:
<223> OTHER INFORMATION: Recombinant peptide

<400> SEQUENCE: 602

Asp Lys Trp Lys Ala Val Tyr Asp Lys Phe Ala Glu Ala Phe Lys Glu
1               5                   10                  15

Phe Leu

<210> SEQ ID NO 603
<211> LENGTH: 18
<212> TYPE: PRT
<213> ORGANISM: Artificial
<220> FEATURE:
<223> OTHER INFORMATION: Recombinant peptide

<400> SEQUENCE: 603

Asp Lys Leu Lys Ala Phe Tyr Asp Lys Val Phe Glu Trp Ala Lys Glu
1               5                   10                  15

Ala Phe

<210> SEQ ID NO 604
<211> LENGTH: 11
<212> TYPE: PRT
<213> ORGANISM: Artificial
<220> FEATURE:
<223> OTHER INFORMATION: Recombinant peptide

<400> SEQUENCE: 604

Ala Val Thr Thr Val Arg Leu Tyr Tyr Gln Asp
1               5                   10

<210> SEQ ID NO 605
<211> LENGTH: 11
<212> TYPE: PRT
<213> ORGANISM: Artificial
<220> FEATURE:
<223> OTHER INFORMATION: Recombinant peptide

<400> SEQUENCE: 605

Asp Gln Tyr Tyr Leu Arg Val Thr Thr Val Ala
1               5                   10

<210> SEQ ID NO 606
<211> LENGTH: 19
<212> TYPE: PRT
<213> ORGANISM: Artificial
<220> FEATURE:
<223> OTHER INFORMATION: Recombinant peptide

<400> SEQUENCE: 606

```
Glu Cys Lys Pro Cys Leu Lys Gln Thr Cys Met Lys Phe Tyr Ala Arg
1               5                   10                  15

Val Cys Arg

<210> SEQ ID NO 607
<211> LENGTH: 14
<212> TYPE: PRT
<213> ORGANISM: Artificial
<220> FEATURE:
<223> OTHER INFORMATION: Recombinant peptide

<400> SEQUENCE: 607

Phe Ser Arg Ala Ser Ser Ile Ile Asp Glu Leu Phe Gln Asp
1               5                   10

<210> SEQ ID NO 608
<211> LENGTH: 21
<212> TYPE: PRT
<213> ORGANISM: Artificial
<220> FEATURE:
<223> OTHER INFORMATION: Recombinant peptide

<400> SEQUENCE: 608

Ile Gln Asn Ala Val Asn Gly Val Lys Gln Ile Lys Thr Leu Ile Glu
1               5                   10                  15

Lys Thr Asn Glu Glu
            20

<210> SEQ ID NO 609
<211> LENGTH: 18
<212> TYPE: PRT
<213> ORGANISM: Artificial
<220> FEATURE:
<223> OTHER INFORMATION: Recombinant peptide

<400> SEQUENCE: 609

Leu Leu Glu Gln Leu Asn Glu Gln Phe Asn Trp Val Ser Arg Leu Ala
1               5                   10                  15

Asn Leu

<210> SEQ ID NO 610
<211> LENGTH: 22
<212> TYPE: PRT
<213> ORGANISM: Artificial
<220> FEATURE:
<223> OTHER INFORMATION: Recombinant peptide

<400> SEQUENCE: 610

Leu Leu Glu Gln Leu Asn Glu Gln Phe Asn Trp Val Ser Arg Leu Ala
1               5                   10                  15

Asn Leu Thr Glu Gly Glu
            20

<210> SEQ ID NO 611
<211> LENGTH: 22
<212> TYPE: PRT
<213> ORGANISM: Artificial
<220> FEATURE:
<223> OTHER INFORMATION: Recombinant peptide

<400> SEQUENCE: 611

Leu Leu Glu Gln Leu Asn Glu Gln Phe Asn Trp Val Ser Arg Leu Ala
1               5                   10                  15
```

Asn Leu Thr Gln Gly Glu
          20

<210> SEQ ID NO 612
<211> LENGTH: 10
<212> TYPE: PRT
<213> ORGANISM: Artificial
<220> FEATURE:
<223> OTHER INFORMATION: Recombinant peptide

<400> SEQUENCE: 612

Leu Val Gly Arg Gln Leu Glu Glu Phe Leu
1               5                   10

<210> SEQ ID NO 613
<211> LENGTH: 12
<212> TYPE: PRT
<213> ORGANISM: Artificial
<220> FEATURE:
<223> OTHER INFORMATION: Recombinant peptide

<400> SEQUENCE: 613

Met Asn Gly Asp Arg Ile Asp Ser Leu Leu Glu Asn
1               5                   10

<210> SEQ ID NO 614
<211> LENGTH: 25
<212> TYPE: PRT
<213> ORGANISM: Artificial
<220> FEATURE:
<223> OTHER INFORMATION: Recombinant peptide

<400> SEQUENCE: 614

Asn Glu Leu Gln Glu Met Ser Asn Gln Gly Ser Lys Tyr Val Asn Lys
1               5                   10                  15

Glu Ile Gln Asn Ala Val Asn Gly Val
            20                  25

<210> SEQ ID NO 615
<211> LENGTH: 16
<212> TYPE: PRT
<213> ORGANISM: Artificial
<220> FEATURE:
<223> OTHER INFORMATION: Recombinant peptide

<400> SEQUENCE: 615

Pro Cys Leu Lys Gln Thr Cys Met Lys Phe Tyr Ala Arg Val Cys Arg
1               5                   10                  15

<210> SEQ ID NO 616
<211> LENGTH: 15
<212> TYPE: PRT
<213> ORGANISM: Artificial
<220> FEATURE:
<223> OTHER INFORMATION: Recombinant peptide

<400> SEQUENCE: 616

Pro Phe Leu Glu Met Ile His Glu Ala Gln Gln Ala Met Asp Ile
1               5                   10                  15

<210> SEQ ID NO 617
<211> LENGTH: 16
<212> TYPE: PRT
<213> ORGANISM: Artificial
<220> FEATURE:
<223> OTHER INFORMATION: Recombinant peptide

```
<400> SEQUENCE: 617

Pro Gly Val Cys Asn Glu Thr Met Met Ala Leu Trp Glu Glu Cys Lys
1               5                   10                  15

<210> SEQ ID NO 618
<211> LENGTH: 21
<212> TYPE: PRT
<213> ORGANISM: Artificial
<220> FEATURE:
<223> OTHER INFORMATION: Recombinant peptide

<400> SEQUENCE: 618

Pro Lys Phe Met Glu Thr Val Ala Glu Lys Ala Leu Gln Glu Tyr Arg
1               5                   10                  15

Lys Lys His Arg Glu
            20

<210> SEQ ID NO 619
<211> LENGTH: 14
<212> TYPE: PRT
<213> ORGANISM: Artificial
<220> FEATURE:
<223> OTHER INFORMATION: Recombinant peptide

<400> SEQUENCE: 619

Pro Ser Gly Val Thr Glu Val Val Val Lys Leu Phe Asp Ser
1               5                   10

<210> SEQ ID NO 620
<211> LENGTH: 32
<212> TYPE: PRT
<213> ORGANISM: Artificial
<220> FEATURE:
<223> OTHER INFORMATION: Recombinant peptide

<400> SEQUENCE: 620

Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
            20                  25                  30

<210> SEQ ID NO 621
<211> LENGTH: 11
<212> TYPE: PRT
<213> ORGANISM: Artificial
<220> FEATURE:
<223> OTHER INFORMATION: Recombinant peptide

<400> SEQUENCE: 621

Pro Thr Glu Phe Ile Arg Glu Gly Asp Asp Asp
1               5                   10

<210> SEQ ID NO 622
<211> LENGTH: 11
<212> TYPE: PRT
<213> ORGANISM: Artificial
<220> FEATURE:
<223> OTHER INFORMATION: Recombinant peptide

<400> SEQUENCE: 622

Gln Gln Thr His Met Leu Asp Val Met Gln Asp
1               5                   10

<210> SEQ ID NO 623
<211> LENGTH: 32
```

<212> TYPE: PRT
<213> ORGANISM: Artificial
<220> FEATURE:
<223> OTHER INFORMATION: Recombinant peptide

<400> SEQUENCE: 623

Arg Lys Thr Leu Leu Ser Asn Leu Glu Glu Ala Lys Lys Lys Glu
1               5                   10                  15

Asp Ala Leu Asn Glu Thr Arg Glu Ser Glu Thr Lys Leu Lys Glu Leu
            20                  25                  30

<210> SEQ ID NO 624
<211> LENGTH: 15
<212> TYPE: PRT
<213> ORGANISM: Artificial
<220> FEATURE:
<223> OTHER INFORMATION: Recombinant peptide

<400> SEQUENCE: 624

Arg Met Lys Asp Gln Cys Asp Lys Cys Arg Glu Ile Leu Ser Val
1               5                   10                  15

<210> SEQ ID NO 625
<211> LENGTH: 18
<212> TYPE: PRT
<213> ORGANISM: Artificial
<220> FEATURE:
<223> OTHER INFORMATION: Recombinant peptide

<400> SEQUENCE: 625

Gly Val Phe Ala Lys Ile Phe Lys Trp Ile Ser Gly Leu Phe Lys Lys
1               5                   10                  15

Ile Gly

<210> SEQ ID NO 626
<211> LENGTH: 18
<212> TYPE: PRT
<213> ORGANISM: Artificial
<220> FEATURE:
<223> OTHER INFORMATION: Recombinant peptide

<400> SEQUENCE: 626

Gly Ile Lys Lys Phe Leu Gly Ser Ile Trp Lys Phe Ile Lys Ala Phe
1               5                   10                  15

Val Gly

<210> SEQ ID NO 627
<211> LENGTH: 18
<212> TYPE: PRT
<213> ORGANISM: Artificial
<220> FEATURE:
<223> OTHER INFORMATION: Recombinant peptide

<400> SEQUENCE: 627

Gly Phe Lys Lys Phe Leu Gly Ser Trp Ala Lys Ile Tyr Lys Ala Phe
1               5                   10                  15

Val Gly

<210> SEQ ID NO 628
<211> LENGTH: 18
<212> TYPE: PRT
<213> ORGANISM: Artificial
<220> FEATURE:
<223> OTHER INFORMATION: Recombinant peptide

```
<400> SEQUENCE: 628

Gly Phe Arg Arg Phe Leu Gly Ser Trp Ala Arg Ile Tyr Arg Ala Phe
1               5                   10                  15

Val Gly

<210> SEQ ID NO 629
<211> LENGTH: 20
<212> TYPE: PRT
<213> ORGANISM: Artificial
<220> FEATURE:
<223> OTHER INFORMATION: Recombinant peptide

<400> SEQUENCE: 629

Thr Glu Glu Leu Arg Val Arg Leu Ala Ser His Leu Arg Lys Leu Arg
1               5                   10                  15

Lys Arg Leu Leu
            20

<210> SEQ ID NO 630
<211> LENGTH: 17
<212> TYPE: PRT
<213> ORGANISM: Artificial
<220> FEATURE:
<223> OTHER INFORMATION: Recombinant peptide

<400> SEQUENCE: 630

Thr Glu Glu Leu Arg Val Arg Leu Ala Ser His Leu Arg Lys Leu Arg
1               5                   10                  15

Lys

<210> SEQ ID NO 631
<211> LENGTH: 17
<212> TYPE: PRT
<213> ORGANISM: Artificial
<220> FEATURE:
<223> OTHER INFORMATION: Recombinant peptide

<400> SEQUENCE: 631

Leu Arg Val Arg Leu Ala Ser His Leu Arg Lys Leu Arg Lys Arg Leu
1               5                   10                  15

Leu

<210> SEQ ID NO 632
<211> LENGTH: 14
<212> TYPE: PRT
<213> ORGANISM: Artificial
<220> FEATURE:
<223> OTHER INFORMATION: Recombinant peptide

<400> SEQUENCE: 632

Arg Leu Ala Ser His Leu Arg Lys Leu Arg Lys Arg Leu Leu
1               5                   10

<210> SEQ ID NO 633
<211> LENGTH: 11
<212> TYPE: PRT
<213> ORGANISM: Artificial
<220> FEATURE:
<223> OTHER INFORMATION: Recombinant peptide

<400> SEQUENCE: 633

Ser His Leu Arg Lys Leu Arg Lys Arg Leu Leu
1               5                   10
```

-continued

<210> SEQ ID NO 634
<211> LENGTH: 9
<212> TYPE: PRT
<213> ORGANISM: Artificial
<220> FEATURE:
<223> OTHER INFORMATION: Recombinant peptide

<400> SEQUENCE: 634

Leu Arg Lys Leu Arg Lys Arg Leu Leu
1               5

<210> SEQ ID NO 635
<211> LENGTH: 18
<212> TYPE: PRT
<213> ORGANISM: Artificial
<220> FEATURE:
<223> OTHER INFORMATION: Recombinant peptide

<400> SEQUENCE: 635

Leu Arg Lys Leu Arg Lys Arg Leu Leu Leu Arg Lys Leu Arg Lys Arg
1               5                   10                  15

Leu Leu

<210> SEQ ID NO 636
<211> LENGTH: 27
<212> TYPE: PRT
<213> ORGANISM: Artificial
<220> FEATURE:
<223> OTHER INFORMATION: Recombinant peptide

<400> SEQUENCE: 636

Leu Arg Lys Leu Arg Lys Arg Leu Leu Leu Arg Lys Leu Arg Lys Arg
1               5                   10                  15

Leu Leu Leu Arg Lys Leu Arg Lys Arg Leu Leu
            20                  25

<210> SEQ ID NO 637
<211> LENGTH: 34
<212> TYPE: PRT
<213> ORGANISM: Artificial
<220> FEATURE:
<223> OTHER INFORMATION: Recombinant peptide

<400> SEQUENCE: 637

Arg Gln Ile Lys Ile Trp Phe Gln Asn Arg Arg Met Lys Trp Lys Lys
1               5                   10                  15

Cys Leu Arg Val Arg Leu Ala Ser His Leu Arg Lys Leu Arg Lys Arg
            20                  25                  30

Leu Leu

<210> SEQ ID NO 638
<211> LENGTH: 17
<212> TYPE: PRT
<213> ORGANISM: Artificial
<220> FEATURE:
<223> OTHER INFORMATION: Recombinant peptide

<400> SEQUENCE: 638

Leu Arg Val Arg Leu Ala Ser His Leu Arg Lys Leu Arg Lys Arg Leu
1               5                   10                  15

Leu

<210> SEQ ID NO 639

```
<211> LENGTH: 61
<212> TYPE: PRT
<213> ORGANISM: Artificial
<220> FEATURE:
<223> OTHER INFORMATION: Recombinant peptide

<400> SEQUENCE: 639

Glu Glu Leu Arg Val Arg Leu Ala Ser His Leu Arg Lys Leu Arg Lys
1               5                   10                  15

Arg Leu Leu Arg Asp Ala Asp Asp Leu Gln Lys Arg Leu Ala Val Tyr
            20                  25                  30

Glu Glu Gln Ala Gln Gln Ile Arg Leu Gln Ala Glu Ala Phe Gln Ala
        35                  40                  45

Arg Leu Lys Ser Trp Phe Glu Pro Leu Val Glu Asp Met
    50                  55                  60

<210> SEQ ID NO 640
<211> LENGTH: 33
<212> TYPE: PRT
<213> ORGANISM: Artificial
<220> FEATURE:
<223> OTHER INFORMATION: Recombinant peptide

<400> SEQUENCE: 640

Cys Glu Glu Leu Arg Val Arg Leu Ala Ser His Leu Arg Lys Leu Arg
1               5                   10                  15

Lys Arg Leu Leu Arg Asp Ala Asp Asp Leu Gln Lys Arg Leu Ala Val
            20                  25                  30

Tyr

<210> SEQ ID NO 641
<211> LENGTH: 30
<212> TYPE: PRT
<213> ORGANISM: Artificial
<220> FEATURE:
<223> OTHER INFORMATION: Recombinant peptide

<400> SEQUENCE: 641

Leu Arg Lys Leu Arg Lys Arg Leu Leu Arg Asp Ala Asp Asp Leu Leu
1               5                   10                  15

Arg Lys Leu Arg Lys Arg Leu Leu Arg Asp Ala Asp Asp Leu
            20                  25                  30

<210> SEQ ID NO 642
<211> LENGTH: 20
<212> TYPE: PRT
<213> ORGANISM: Artificial
<220> FEATURE:
<223> OTHER INFORMATION: Recombinant peptide

<400> SEQUENCE: 642

Thr Glu Glu Leu Arg Val Arg Leu Ala Ser His Leu Arg Lys Leu Arg
1               5                   10                  15

Lys Arg Leu Leu
            20

<210> SEQ ID NO 643
<211> LENGTH: 20
<212> TYPE: PRT
<213> ORGANISM: Artificial
<220> FEATURE:
<223> OTHER INFORMATION: Recombinant peptide

<400> SEQUENCE: 643
```

```
Thr Glu Glu Leu Arg Val Arg Leu Ala Ser His Leu Glu Lys Leu Arg
1               5                   10                  15

Lys Arg Leu Leu
            20

<210> SEQ ID NO 644
<211> LENGTH: 20
<212> TYPE: PRT
<213> ORGANISM: Artificial
<220> FEATURE:
<223> OTHER INFORMATION: Recombinant peptide

<400> SEQUENCE: 644

Thr Glu Glu Leu Arg Val Arg Leu Ala Ser His Leu Arg Glu Leu Arg
1               5                   10                  15

Lys Arg Leu Leu
            20

<210> SEQ ID NO 645
<211> LENGTH: 20
<212> TYPE: PRT
<213> ORGANISM: Artificial
<220> FEATURE:
<223> OTHER INFORMATION: Recombinant peptide

<400> SEQUENCE: 645

Leu Arg Glu Lys Lys Leu Arg Val Ser Ala Leu Arg Thr His Arg Leu
1               5                   10                  15

Glu Leu Arg Leu
            20

<210> SEQ ID NO 646
<211> LENGTH: 28
<212> TYPE: PRT
<213> ORGANISM: Artificial
<220> FEATURE:
<223> OTHER INFORMATION: Recombinant peptide

<400> SEQUENCE: 646

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 647
<211> LENGTH: 28
<212> TYPE: PRT
<213> ORGANISM: Artificial
<220> FEATURE:
<223> OTHER INFORMATION: Recombinant peptide

<400> SEQUENCE: 647

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 648
<211> LENGTH: 28
<212> TYPE: PRT
<213> ORGANISM: Artificial
<220> FEATURE:
<223> OTHER INFORMATION: Recombinant peptide
```

```
<400> SEQUENCE: 648

Arg Arg Arg Arg Arg Arg Arg Arg Arg Asp Trp Leu Lys Ala Phe
1               5                   10                  15

Tyr Asp Lys Val Ala Glu Lys Leu Lys Glu Ala Phe
                20                  25

<210> SEQ ID NO 649
<211> LENGTH: 14
<212> TYPE: PRT
<213> ORGANISM: Artificial
<220> FEATURE:
<223> OTHER INFORMATION: Recombinant peptide
<220> FEATURE:
<221> NAME/KEY: misc_feature
<222> LOCATION: (3)..(3)
<223> OTHER INFORMATION: Xaa is 3,3'-diphenyl alanine, Trp, Phe, or Ala

<400> SEQUENCE: 649

Arg Glu Xaa Thr Gly Leu Ala Trp Glu Trp Trp Arg Thr Val
1               5                   10

<210> SEQ ID NO 650
<211> LENGTH: 18
<212> TYPE: DNA
<213> ORGANISM: Artificial
<220> FEATURE:
<223> OTHER INFORMATION: PCR primer

<400> SEQUENCE: 650
tgatatctcc actgacgt                                                    18

<210> SEQ ID NO 651
<211> LENGTH: 21
<212> TYPE: DNA
<213> ORGANISM: Artificial
<220> FEATURE:
<223> OTHER INFORMATION: PCR primer

<400> SEQUENCE: 651
cgagaaagga agggaagaaa g                                                21

<210> SEQ ID NO 652
<211> LENGTH: 18
<212> TYPE: DNA
<213> ORGANISM: Artificial
<220> FEATURE:
<223> OTHER INFORMATION: PCR primer

<400> SEQUENCE: 652
tgatatctcc actgacgt                                                    18

<210> SEQ ID NO 653
<211> LENGTH: 21
<212> TYPE: DNA
<213> ORGANISM: Artificial
<220> FEATURE:
<223> OTHER INFORMATION: PCR primer

<400> SEQUENCE: 653
cgagaaagga agggaagaaa g                                                21

<210> SEQ ID NO 654
<211> LENGTH: 33
<212> TYPE: DNA
<213> ORGANISM: Artificial
<220> FEATURE:
```

```
<223> OTHER INFORMATION: Portion of plasmid

<400> SEQUENCE: 654
tctagaggat ccccgggtgg tcagtccctt atg                    33
```